US012371503B2

(12) United States Patent
Gromada et al.

(10) Patent No.: US 12,371,503 B2
(45) **Date of Patent: *Jul. 29, 2025**

(54) METHODS OF TREATMENT USING A LEPTIN RECEPTOR AGONIST ANTIBODY

(71) Applicant: Regeneron Pharmaceuticals, Inc., Tarrytown, NY (US)

(72) Inventors: Jesper Gromada, Scarsdale, NY (US); Panayiotis Stevis, West Orange, NJ (US); Judith Altarejos, Chappaqua, NY (US); Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/737,965

(22) Filed: May 5, 2022

(65) Prior Publication Data

US 2022/0280641 A1 Sep. 8, 2022

Related U.S. Application Data

(62) Division of application No. 16/377,089, filed on Apr. 5, 2019, now Pat. No. 11,608,381.

(60) Provisional application No. 62/653,731, filed on Apr. 6, 2018.

(51) Int. Cl.

| | |
|---|---|
| ***A61K 39/395*** | (2006.01) |
| ***A61K 9/00*** | (2006.01) |
| ***A61K 45/06*** | (2006.01) |
| ***A61P 3/00*** | (2006.01) |
| ***A61P 3/04*** | (2006.01) |
| ***A61P 3/06*** | (2006.01) |
| ***A61P 3/10*** | (2006.01) |
| ***C07K 14/00*** | (2006.01) |
| ***C07K 16/28*** | (2006.01) |
| *A61K 38/22* | (2006.01) |
| *A61K 39/00* | (2006.01) |
| *C07K 14/575* | (2006.01) |

(52) U.S. Cl.

CPC ........ *C07K 16/2869* (2013.01); *A61K 9/0019* (2013.01); *A61K 39/3955* (2013.01); *A61K 45/06* (2013.01); *A61P 3/00* (2018.01); *A61P 3/04* (2018.01); *A61P 3/06* (2018.01); *A61P 3/10* (2018.01); *A61K 38/2264* (2013.01); *A61K 2039/505* (2013.01); *A61K 2039/54* (2013.01); *A61K 2039/545* (2013.01); *C07K 14/5759* (2013.01); *C07K 2317/21* (2013.01); *C07K 2317/33* (2013.01); *C07K 2317/34* (2013.01); *C07K 2317/565* (2013.01); *C07K 2317/75* (2013.01); *C07K 2317/76* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | |
|---|---|---|---|
| 4,596,556 | A | 6/1986 | Morrow et al. |
| 4,790,824 | A | 12/1988 | Morrow et al. |
| 4,941,880 | A | 7/1990 | Burns |
| 4,946,778 | A | 8/1990 | Ladner et al. |
| 5,064,413 | A | 11/1991 | McKinnon et al. |
| 5,312,335 | A | 5/1994 | McKinnon et al. |
| 5,383,851 | A | 1/1995 | McKinnon, et al. |
| 5,399,163 | A | 3/1995 | Peterson et al. |
| 5,717,073 | A | 2/1998 | Wijdenes et al. |
| 5,932,448 | A | 8/1999 | Tso et al. |
| 5,965,521 | A | 10/1999 | Stephens et al. |
| 6,005,080 | A | 12/1999 | Snodgrass et al. |
| 6,096,002 | A | 8/2000 | Landau |
| 6,096,506 | A | 8/2000 | Lee et al. |
| 6,129,914 | A | 10/2000 | Weinert et al. |
| 6,329,511 | B1 | 12/2001 | Vasquez et al. |
| 6,380,363 | B1 | 4/2002 | Tartaglia et al. |
| 6,620,135 | B1 | 9/2003 | Weston et al. |
| 6,977,240 | B1 | 12/2005 | Tartaglia et al. |
| 7,067,472 | B1 | 6/2006 | Feng et al. |

(Continued)

FOREIGN PATENT DOCUMENTS

| | | |
|---|---|---|
| AU | 2004201496 C1 | 8/2018 |
| CN | 107 760 761 | 3/2018 |

(Continued)

OTHER PUBLICATIONS

Haque et al. Serum adiponectin and leptin levels in patients with lipodystrophies. The Journal of Clinical Endocrinology and Metabolism. vol. 87(5):2395-2398 (2002). (Year: 2002).*

(Continued)

*Primary Examiner* — Elizabeth C. Kemmerer

*Assistant Examiner* — Regina M DeBerry

(74) *Attorney, Agent, or Firm* — FisherBroyles, LLP; Christy G. Rothwell; Gabriele Amodeo

(57) ABSTRACT

Provided herein are therapeutic methods of treatment using agonist leptin receptor (LEPR) antibodies, antigen-binding fragments thereof, or compositions comprising the LEPR antibodies or antigen-binding fragments thereof. Such therapeutic methods include treatment for conditions related to metabolic dysfunction, including for example, lipodystrophy, adiposity or obesity, reducing body weight, non-alcoholic fatty liver disease, hyperphagia, hyperglycemia, insulin resistance, dyslipidemia, hepatic steatosis, and infertility.

12 Claims, 34 Drawing Sheets

Specification includes a Sequence Listing.

(56) References Cited

U.S. PATENT DOCUMENTS

| | | | |
|---|---|---|---|
| 7,067,477 | B2 | 6/2006 | MacLeod |
| 7,183,254 | B2 | 2/2007 | DePaoli et al. |
| 7,261,893 | B2 | 8/2007 | Veldman et al. |
| 7,294,754 | B2 | 11/2007 | Poueymirou et al. |
| 7,307,142 | B2 | 12/2007 | Gertler et al. |
| 7,320,789 | B2 | 1/2008 | Aghahanian et al. |
| 7,521,048 | B2 | 4/2009 | Gliniak et al. |
| 7,524,937 | B2 | 4/2009 | Carter et al. |
| 7,575,878 | B2 | 8/2009 | Tavernier et al. |
| 7,576,259 | B2 | 8/2009 | Poueymirou et al. |
| 7,632,499 | B2 | 12/2009 | Davies et al. |
| 7,635,760 | B2 | 12/2009 | Han et al. |
| 7,659,442 | B2 | 2/2010 | Poueymirou et al. |
| 7,807,159 | B2 | 10/2010 | Chin et al. |
| 7,863,240 | B2 | 1/2011 | Ilan et al. |
| 7,888,486 | B2 | 2/2011 | Walsh et al. |
| 8,017,634 | B2 | 9/2011 | Sinclair et al. |
| 8,318,666 | B2 | 11/2012 | DePaoli et al. |
| 8,697,396 | B2 | 4/2014 | Dall'Acqua et al. |
| 8,840,894 | B2 | 9/2014 | Stitt et al. |
| 8,846,724 | B2 | 9/2014 | Sinclair et al. |
| 8,871,209 | B2 | 10/2014 | Stitt et al. |
| 8,969,291 | B2 | 3/2015 | Ilan et al. |
| 9,221,902 | B2 | 12/2015 | Smider et al. |
| 9,260,515 | B2 | 2/2016 | Stitt et al. |
| 9,332,742 | B2 | 5/2016 | McWhirter et al. |
| 9,334,331 | B2 | 5/2016 | Igawa et al. |
| 9,421,257 | B2 | 8/2016 | Ilan et al. |
| 9,718,881 | B2 | 8/2017 | Gromada et al. |
| 9,890,212 | B2 | 2/2018 | Stitt et al. |
| 10,023,644 | B2 | 7/2018 | Gromada et al. |
| 10,253,102 | B2 | 4/2019 | Gromada et al. |
| 10,400,036 | B2 | 9/2019 | Stitt et al. |
| 10,421,807 | B2 | 9/2019 | Gonzales et al. |
| 10,526,403 | B2 | 1/2020 | Gromada et al. |
| 10,550,192 | B2 | 2/2020 | Gromada et al. |
| 10,618,968 | B2 | 4/2020 | Gromada et al. |
| 10,934,249 | B2 | 3/2021 | Pordy et al. |
| 11,248,044 | B2 | 2/2022 | Donahue et al. |
| 11,535,675 | B2 | 12/2022 | Gromada et al. |
| 11,608,381 | B2 | 3/2023 | Gromada et al. |
| 11,834,500 | B2 | 12/2023 | Gromada et al. |
| 2002/0182676 | A1 | 12/2002 | Tartaglia et al. |
| 2004/0202652 | A1 | 10/2004 | Karsenty et al. |
| 2004/0253242 | A1 | 12/2004 | Bowdish et al. |
| 2006/0068429 | A1 | 3/2006 | Bailleul et al. |
| 2007/0178095 | A1 | 8/2007 | Smith et al. |
| 2008/0078000 | A1 | 3/2008 | Poueymirou et al. |
| 2009/0148436 | A1 | 6/2009 | Lavallie et al. |
| 2009/0234106 | A1 | 9/2009 | Han et al. |
| 2010/0166764 | A1 | 7/2010 | Sayers et al. |
| 2010/0260772 | A1 | 10/2010 | Karsenty |
| 2011/0092417 | A1 | 4/2011 | Artymiuk et al. |
| 2011/0293630 | A1 | 12/2011 | Stitt et al. |
| 2012/0204278 | A1 | 8/2012 | Bradley et al. |
| 2012/0258073 | A1 | 10/2012 | Gerdes et al. |
| 2013/0122007 | A1 | 5/2013 | Stitt et al. |
| 2014/0134162 | A1 | 5/2014 | Stavenhagen et al. |
| 2014/0171623 | A1 | 6/2014 | Dall'Acqua et al. |
| 2014/0243504 | A1 | 8/2014 | Davis et al. |
| 2017/0101477 | A1 | 4/2017 | Gromada |
| 2018/0037648 | A1 | 2/2018 | Ilan et al. |
| 2018/0127508 | A1 | 5/2018 | Gromada et al. |
| 2019/0002569 | A1 | 1/2019 | Belaid-Choucair et al. |
| 2019/0185562 | A1 | 6/2019 | Gromada et al. |
| 2019/0309079 | A1 | 10/2019 | Gromada |
| 2020/0031946 | A1 | 1/2020 | Gromada et al. |
| 2020/0123264 | A1 | 4/2020 | Gromada et al. |
| 2022/0098313 | A1 | 3/2022 | Oral et al. |
| 2022/0112293 | A1 | 4/2022 | Gromada et al. |
| 2023/0235068 | A1 | 7/2023 | Gromada et al. |
| 2024/0158497 | A1 | 5/2024 | Gromada et al. |

FOREIGN PATENT DOCUMENTS

| | | | |
|---|---|---|---|
| EP | 981365 | B1 | 12/2004 |
| EP | 885299 | B1 | 10/2005 |
| EP | 0730606 | B1 | 11/2005 |
| EP | 0879286 | B1 | 4/2008 |
| EP | 1619250 | B1 | 11/2009 |
| EP | 1444516 | B1 | 7/2010 |
| EP | 1019432 | B1 | 1/2012 |
| EP | 2219031 | B1 | 4/2013 |
| EP | 2780368 | | 9/2014 |
| EP | 2649184 | B1 | 7/2015 |
| EP | 3298889 | A1 | 3/2018 |
| EP | 3538554 | | 9/2019 |
| EP | 2989894 | B1 | 8/2020 |
| EP | 3362477 | B1 | 1/2022 |
| JP | 1991219894 | | 9/1991 |
| WO | WO 1996/005309 | | 2/1996 |
| WO | WO 1996/08510 | | 3/1996 |
| WO | WO 1997/019952 | | 6/1997 |
| WO | WO 1997/025425 | | 7/1997 |
| WO | WO 1997/26272 | | 7/1997 |
| WO | WO 1997/26335 | | 7/1997 |
| WO | WO 1997/26370 | | 7/1997 |
| WO | WO 1997/26523 | | 7/1997 |
| WO | WO 1997/27286 | | 7/1997 |
| WO | WO 1997/41263 | | 11/1997 |
| WO | WO 199822128 | A1 | 5/1998 |
| WO | WO 1998/48831 | | 11/1998 |
| WO | WO 2002/36789 | | 5/2002 |
| WO | WO 2002/66630 | | 8/2002 |
| WO | WO 2005/049655 | | 6/2005 |
| WO | WO 2006/053883 | | 5/2006 |
| WO | WO 2010070094 | | 6/2010 |
| WO | WO 2011/004192 | | 1/2011 |
| WO | WO 2011/097603 | | 8/2011 |
| WO | WO 2011130499 | A1 | 10/2011 |
| WO | WO 2012/141798 | | 10/2012 |
| WO | WO 2012/148873 | | 11/2012 |
| WO | WO 2013/022782 | | 2/2013 |
| WO | WO 2013/184761 | | 12/2013 |
| WO | WO 2014/043361 | | 3/2014 |
| WO | WO 2015/124588 | | 8/2015 |
| WO | WO 2016039796 | A2 | 3/2016 |
| WO | WO 2016168613 | A1 | 10/2016 |
| WO | WO 2017/66204 | | 4/2017 |
| WO | WO 2018089532 | | 5/2018 |
| WO | WO 2019195796 | | 10/2019 |
| WO | WO 2020131910 | A1 | 6/2020 |
| WO | WO 2022/060827 | A2 | 3/2022 |
| WO | WO 2022060827 | A3 | 4/2022 |

OTHER PUBLICATIONS

Simha et al. Effect of subcutaneous leptin replacement therapy on bone metabolism in patients with generalized lipodystrophy. The Journal of Clinical Endocrinology and Metabolism. vol. 87(11):4942-4945; (2002). (Year: 2002).*

Christensen et al. Increased bone mineral content in patients with congenital generalized lipodystrophy is unaffected by metreleptin replacement therapy. Endocrine Reviews, vol. 35, Supp. Suppl. 3. Abstract No. OR43-6. 96th Annual Meeting and Expo of the Endocrine Society, Endo Chicago, IL (2014) (Year: 2014).*

Park et al. Long term of leptin replacement in patients with Dunnigan-type familial partial lipodystrophy. Metabolism Clinical and Experimental 56:508-516; (2007). (Year: 2007).*

2008 Guidance Document Ethical Considerations for Clinical Trials on Medicinal Products Conducted with the Pediatric Population.

Addy et al. (2008) ""Safety, tolerability, pharmacokinetics, and pharmacodynamic properties of taranabant, a novel selective cannabinoid-1 receptor inverseagonist, for the treatment of obesity: results from a double-blind, placebo-controlled, single oral dose study in healthy volunteers"" J Clin Pharmacol. 48(4):418-27.

Aijluni (2017) "Efficacy and Safety of Metreleptin in Patients with Partial Lipodystrophy: Lessons from an Expanded Access Program" Journal of Diabetes & metabolism 7(3):1000659, 7 pages.

(56) References Cited

OTHER PUBLICATIONS

Al-Attar et al. (2007) "Quantitative and qualitative differences in subcutaneous adipose tissue stores across lipodystrophy types shown by magnetic resonance imaging" BMC Med Imaging. 7:3.
Al-Lazikani et al. (1997) "Standard Conformations for the Canonical Structures of Immunoglobulins" J. Mol. Biol. 273:927-948.
Allen, Loyd V. Jr. Ph.D. "The Art, Science and Technology of Pharmaceutical Compounding" in American Pharmacists Association (Washington, D.C., 1999), Introduction pp. xxxii-xxxvii.
Allison et al. (2014) ""Connecting leptin signaling tobiological function"" J Endocrinol 223(1):T25-35.
Altschul et al. (1990) "Basic Local Alignment Search Tool" J. Mol. Biol. 215:403-410.
Altschul et al. (1997) "Gapped BLAST and PSI-BLAST: a New Generation of Protein Database Search Programs" Nucleic Acids Res. 25:3389-402.
Angrisani et al. (2017) "Bariatric Surgery and Endoluminal Procedures: IFSO Worldwide Survey 2014" Obes Surg. 27(9):2279-2289.
Aronis, et al. (2011) "Preadipocyte Factor-1 Levels Are Higher in Women with Hypothalamic Amenorrhea and Are Associated with Bone Mineral Content and Bone Mineral Density through a Mechanism Independent of Leptin", J. Clin. Endocrinol. Metab. 96(10):E1634-E1639.
Barash et al. (1996) "Leptin is a metabolic signal to the reproductive system" Endocrinology 137(7): 3144-3147.
Baumann et al. (1996) "The full-length leptin receptor has signaling capabilities of interleukin 6-type cytokine receptors" Proc Natl Acad Sci U S A 93:8374-8378.
Boden et al. (1996) "Effect of Fasting on Serum Leptin in Nomal Human Subjects", J Clin Endocrinol Metab. 81(9): 3419-3423.
Brown et al. (2016) "The Diagnosis and Management of Lipodystrophy Syndromes: A Multi-Society Practice Guideline" J Clin Endocrinol Metab. 101(12):4500-4511.
Buettner et al. (2002) "Definition and characterization of relative hypo- andhyperleptinemia in a large Caucasian population"J Endocrinol. 175(3): 745-756.
Burakiewicz et al. (2017) "Quantifying fat replacement of muscle by quantitative MRI in muscular dystrophy" J Neurol. 264(10):2053-2067.
Campfield et al. (1995) "Recombinant mouse OB protein: evidence for a peripheral signal linking adiposity and central neural networks" Science 269:546-549.
Carpenter et al. (2012) "Structure of the Human Obesity Receptor Leptin-Binding Domain Reveals the Mechanism of Leptin Antagonism by a Monoclonal Antibody" Structure 20(3):487-97.
Chan et al. (2003) "The role of falling leptin levels in the neuroendocrine and metabolic adaptation to short-term starvation in healthy men" J Clin Invest. 111(9): 1409-1421.
Chan et al. (2016) "Immunogenicity associated with Metreleptin treatment in patients with obesity or lipodystrophy" Clin Endocrinol. 85(1):137-149.
Chehab et al. (1996) "Correction of the sterility defect in homozygous obese female mice by treatment with the human recombinant leptin" Nat Genet 12:318-320.
Ciofi et al. (2009) "Brain-endocrine interactions: a microvascular route in the mediobasal hypothalamus" Endocrinology 150:5509-5519.
Clement et al. (1998) "A mutation in the human leptin receptor gene causes obesity and pituitary dysfunction" Nature 392(6674):398-401.
Cohen et al. (2001) "Selective deletion of leptin receptor in neurons leads to obesity" J Clin Invest 108:1113-1121.
Considine et al. (1996) "Serum Immunoreactive-Leptin Concentrations in Normal-Weight and Obese Humans" N. Engl. J. Med. 334(5): 292-295.
Coppari et al. (2005) "The hypothalamic arcuate nucleus: a key site for mediating leptin's effects on glucose homeostasis and locomotor activity" Cell Metab 1:63-72.
Courteix, et al. (2007) "Preserved Bone Health in Adolescent Elite Rhythmic Gymnasts Despite Hypoleptinemia", Hormone Research, 68:20-27.
Cowley et al. (2001) "Leptin activates anorexigenic POMC neurons through a neural network in the arcuate nucleus" Nature 411:480-484.
Dalton et al. (2015) "Preliminary validation and principal components analysis ofthe Control of Eating Questionnaire (CoEQ) for the experience of food craving" Eur J Clin Nutr. Nature Publishing Group 69(12):1313-7.
Dardeno, et al. (2010) "Leptin in Human Physiology and Therapeutics", Front Neuroendocrinol., 31(3):377-393.
De Luca et al. (2005) "Complete rescue of obesity, diabetes, and infertility in db/db mice by neuron-specific LEPR-B transgenes" J Clin Invest 115:3484-3493.
Deddish et al. (1990 "Carboxypeptidase M in Madin-Darby Canin Kidney Cells" J. Biological Chemistry 265:25:15083-89.
Denroche et al. (2013) "Leptin administration enhances islet transplant performance in diabetic mice" Diabetes 62:2738-2746.
Dubern et al. (2012) "Leptin and leptin receptor-related monogenic obesity." Biochimie 94(10): 2111-5.
Ducy et al. (2000) "Leptin Inhibits Bone Formation Through a Hypothalamic Relay:A Central Control of Bone Mass" Cell, 100:197-207.
Ebihara et al. (2007) "Efficacy and Safety of Leptin-Replacement Therapy and Possible Mechanisms of Leptin Actions in Patients with Generalized Lipodystrophy" J Clin Endocrinol Metab 92(2):532-541.
Edwards et al. (2003) "The Remarkable Flexibility of the Human antibody Repertoire; Isolation of Over One Thousand Different Antibodies to a Single Protein", BLYS. Journal of Molecular Biology, 334:103-118.
Ehring (1999) Analytical Biochemistry 267(2):252-259 "Hydrogen Exchange/Electrospray Ionization Mass Spectrometry Studies of Structural Features of Proteins and Protein/Protein Interactions".
El-Zayadi (2008) "Hepatic steatosis: a benign disease or a silent killer" World J Gastroenterol 14(26):4120-4126.
Engen and Smith (2001) Anal. Chem. 73:256A-265A "The Basics of Ion Chromatography".
Farooqi et al. (1999) "Effects of Recombinant Leptin Therapy in a Child with Congenital Leptin Deficiency" The New England Journal of Medicine 341(12):879-884.
Farooqi et al. (2002) "Beneficial effects of leptin on obesity, T cell hyporesponsiveness, and neuroendocrine/metabolic dysfunction of human congenital leptin deficiency." J Clin Invest. 110(8): 1093-1103.
Farooqi et al. (2007) N Engl J Med 356(3): 237-247 "Clinical and Molecular Genetic Spectrum of Congeintal Deficiency of the Leptin Receptor".
Federico et al. (2006) "Treatment of patients with non-alcoholic fatty liver disease: Current views and perspectives" Digestive & Liver Disease 38(11):789-801.
Feng et al. (2018) "Roles and Mechanisms of Leptin in Osteogenic Stimulation in Cervical Ossification of the Posterior longitudinal Ligament", Journal of Orthopaedic Surgery and Research, 13:165, 8 pages.
Fenton et al. (2020) "Rheostat Positions: A New Classification of Protein Positions Relevant to Pharmacogenomics Medicinal Chemistry Research", 29:1133-1146.
Festi et al. (2004) "Hepatic steatosis in obese patients: clinical aspects and prognostic significance" Obes Rev. 5(1):27-42.
Flak and Myers (2016) "Minireview: CNS Mechanisms of Leptin Action" Mol Endocrinol. 30: 3-12.
Flegal et al. (2016) "Trends in Obesity Among Adults in the United States,2005 to 2014" JAMA. American Medical Association. 315(21):2284-2291.
Flint et al. (2000) "Reproducibility, power and validity of visual analogue scalesin assessment of appetite sensations in single test meal studies" Int. J. Obes. Relat. Metab. Disord. 24(1):38-48.
Friedman et al. (2014) "Leptin at 20" an Overview J Endocrinol 223(1):T1-8.
Funcke et al. (2014) "Monogenic forms of childhood obesity due to mutations in the leptin gene" Mol Cell Pediatr. 1(1):3.

(56) References Cited

OTHER PUBLICATIONS

Gavrila et al. (2003) "Diurnal and Ultradian Dynamics of Serum Adiponectin in Healthy Men: Comparison with Leptin, Circulating Soluble Leptin Receptor, and Cortisol Patterns" J Clin Endocrinol Metab. 88(6):2838-2843.
Ghazali et al. (2003) "Bone Mineral Density Directly Correlates With Elevated SerumLeptin in Haemodialysis Patients", Nephrology Dialysis Transplantation, 18:1882-1890.
Ghorban-Sabbagh et al. (2016) "Correlation Between Serum Leptin and Bone Mineral Density in Hemodialysis Patients", J. Renal Inj. Prev. 5(3):112-117.
Gibson et al. (2004) "Congenital Leptin Deficiency Due to Homozygosity for the Delta133G Mutation: Report of Another Case and Evaluation of Response to Four Years of Leptin Therapy" J Clin Endocrin. & Metab. 2004; 89(10):4821-4826.
Gonnet et al. (1992) "Exhaustive Matching of the Entire Protein Sequence Database" Science 256: 1443-1445.
Goodson (1984) in Medical Applications of Controlled Release, supra, vol. 2, pp. 115-138.
Halaas et al. (1995) "Weight-reducing effects of the plasma protein encoded by the obese gene" Science 269:543-546.
Halaas et al. (1997) "Physiological response to long-term peripheral and central leptin infusion in lean and obese mice" Proc Natl Acad Sci USA 94:8878-8883.
Haniu et al. (1998) "Human Leptin Receptor" J Biol Chem 273(44): 28691-699.
Harris et al. (1998) "A leptin dose-response study in obese (ob/ob) and lean (+/?) mice" Endocrinology 139:8-19.
Herrick et al. (2016) "Leptin, Leptin Soluble Receptor, and the Free LeptinIndex following a Diet and Physical Activity LifestyleIntervention in Obese Males and Females" J Obes. Hindawi. 2016(2): 8375828-5.
Heymsfield et al. (1999) "Recombinant Leptin for Weight Loss in Obese and Lean Adults, A Randomized, Controlled, Dose-Escalation Trial" JAMA. 282(16): 1568-1575.
Hochleitner et al. (2000) "Characterization of a Discontinuous Epitope of the Human Immunodeficiency Virus (HIV) Core Protein p24 by Epitope Excision and Differential Chmeical modification Followed by Mass Psectrometric Peptide Mapping Analysis" Protein Science 9:487-496.
International Search Report from PCT/US2019/026173 dated Jul. 30, 2019, 15 pages.
Jing et al. (2016) "Mechanical Vibration Mitigates the Decrease of Bone Quantity and Bone Quality of Leptin Receptor-Deficient Db/Db Mice by Promoting Bone Formation and Inhibiting Bone Resorption", Journal of Bone and Minearl Research, 31(9):1713-1724.
Junghans et al. (1990) "Anti-Tac-H, a Humanized Antibody to the Interluekin 2 Receptor with new Features for Immunotherapy in Malignant and Immune Disorders" Cancer Res. 50:1495-1502.
Kazane et al. (2013) "Self-Assembled Antibody Multimers through Peptide Nucleic Acid Conjugation" J. Am. Chem. Soc. [Epub: Dec. 4, 2012], 135:340-346.
Klein et al. (2012) "Progress in Overcoming the Chaim Association Issue in Bispecific Heterodimeric IgG Antibodies" mAbs 4:6, 1-11.
Klopfenstein et al. (2012) "Comparison of 3 T MRI and CT for the measurementof visceral and subcutaneous adipose tissue in humans" Br J Radiol. 85(1018):e826-30.
Krishna et al. (2009) "Potent and selective agonism of the melanocortinreceptor 4 with MK-0493 does not induce weight loss in obese human subjects: energy intake predicts lack of weight loss efficacy" Clin Pharmacol Ther. 86(6):659-66.
Kufer et al. (2004) "A Revival of Bispecific Antibodies" Trends Biotechnol. 22:238-244.
Lammert et al. (2001) "Soluble leptin receptor represents the main leptin bindingactivity in human blood" Biochem Biophys Res Commun 283(4):982-988.
Langer (1990) "New Methods of Drug Delivery" Science 249:1527-1533.
Licinio et al. (2004) "Phenotypic effects of leptin replacement on morbid obesity, diabetes mellitus, hypogonadism, and behavior in leptin-deficient adults." Proc Natl Acad Sci USA. 101(13): 4531-4536.
Lou et al. (2010) "Reduced body weight and increased energy expenditure intransgenic mice over-expressing soluble eptin receptor" PLoS One 5(7):e11669.
Mantzoros et al. (2011) "Leptin in Human Physiology and Pathophysiology", Am J. Physiol. Endocrinol. Metab., 301(4):E567-584.
Martin et al. (1989) "Modeling Antibody Hypervariable Loops: A Combined Algorithm" Proc. Natl. Acad. Sci. USA 86:9268-9272.
Mazen et al. (2011) "Homozygosity for a novel missense mutation in the leptin receptor gene (P316T) in two Egyptian cousins with severe early onset obesity" Mol Genet Metab 102:461-464.
McDuffie et al. (2004) "Effects of exogenous leptin on satiety and satiation inpatients with lipodystrophy and leptin insufficiency" J. Clin. Endocrinol. Metab. 89(9):4258-63.
Minicocci et al. (2012) "Mutations in the ANGPTL3 gene and familial combined hypolipidemia: a clinical and biochemical characterization" J Clin Endocrinol Metab 97(7):E1266-1275.
Montague et al. (1997) "Congenital leptin deficiency is associated with severe early-onset obesity in humans" Nature 387(6636):903-908.
Mordenti et al. (1991) "Interspecies Scaling of Clearance and Volume of Distribution Data for Five Therapeutic Proteins" Pharmaceut. Res. 8:1351.
Muniyappa et al. (2017) "Metreleptin therapy lowers plasma angiopoietin-likeprotein 3 in patients with generalized lipodystrophy" Journal of Clin Lipidol 11(2):543-550.
Muzzin et al. (1996) "Correction of obesity and diabetes in genetically obese mice by leptin gene therapy" Proc Natl Acad Sci USA 93:14804-14808.
Ng et al. (2014) "Global, regional, and national prevalence of overweight and obesity in children and adults during 1980-2013: a systematic analysis for the Global Burden of Disease Study 2013" Lancet 384(9945):766-781.
Nidhina Haridas (2015) "Regulation of Angiopoietin-Like Proteins(ANGPTLs) 3 and 8 by Insulin" J Clin Endocrinol Metab 100(10):E1299-1307.
Norsted et al. (2008) "Protein components of the blood-brain barrier (BBB) in the mediobasal hypothalamus" Journal of chemical neuroanatomy 36:107-121.
Oral et al. (2002) "Leptin-Replacement Therapy for Lipodystrophy" N Engl J Med. 346(8):570-578.
Oral, E., "Clinical Protocol to Investigate the Efficacy of Recombinant Human Leptin (Metreleptin) in Nonalcoholic Steatohepatitis (NASH) or Nonalcoholic Fatty Liver Disease (NAFLD) Associated With Lipodystrophy", University of Michigan, Oct. 8, 2012, 12 pages, [online]: U.S. National Library of Medicine, retrieved on Oct. 7, 2019, ClinicalTrials.gov Identified NCT01679197.
Oral, E., "Clinical Protocol to Investigate the Long-term Safety and Efficacy of Metreleptin in Various Forms of Partial Lipodystrophy", Unviersity of Michigan, Sep. 29, 2015, 8 pages, [online] U.S. National Library of Medicine, retrieved on Oct. 28, 2021, ClinicalTrials.gov Identifier: NCT02654977.
Özsu, et al. (2017) "Early-onset severe obesity due to complete deletion of the leptin gene in a boy." J Pediatr Endocrinol Metab. 30(11): 1227-1230.
Patni and Gard (2015) "Congenital generalized lipodystrophies—new insights into metabolic dysfunction" Nat Rev Endocrinol 11:522-534.
Paz-Filho et al. (2011) "Ten years of leptin replacement therapy" Obesity reviews 12: e315-e323.
Pearson (1994) "Using the FASTA Program to Search Protein and DNA Sequence Databases"Methods Mol. Biol. 24: 307-331.
Pelleymounter et al. (1995) "Effects of the obese gene product on body weight regulation in ob/ob mice" Science 269:540-543.
Powell et al. (1998) "Compendium of excipients for parenteral formulations" PDA J Pharm Sci Technol 52:238-311.
Ravussin et al. (2009) "Enhanced Weight Loss With Pramlintide/Metreleptin: An Integrated Neurohormonal Approach to Obesity Pharmacotherapy" Obesity 17(9):1736-1743.

(56) References Cited

OTHER PUBLICATIONS

Reddy et al. (2000) J. Immunol. 164:1925-1933 "Elimination of Fc Receptor-Dependent Effector Functions of a Modified IgG4 Monoclonal Antibody to Human CD4".
Roemmich et al. (2003) "Relationship of Leptin to Bone Mineralization inChildren and Adolescents", J. Clin. Endocrinol. Metab., 88(2):599-604.
Ruhl and Everhart (2001) "Leptin concentrations in the United States: relations with demographic and anthropometric measures" Am J Clin Nutr. 74(3):295-301.
Sienkiewicz et al. (2011) "Long-term Metreleptin Treatment Increases Bone MineralDensity and Content at the Lumbar Spine of Lean Hypoleptinemic Women", Metabolism Clinical and Experimental, 60:1211-1221.
Simha (2014) "Metreleptin for Metabolic Disorders Associated with Generalized or Partial Lipodystrophy" Expert Rev. Endorinol. Metab., 9(3):205-212.
Schoeller et al. (1997) "Entrainment of the diurnal rhythm of plasma leptin to meal timing" J Clin Invest. 100(7):1882-1887.
Schurgin et al. (2004) "Endocrine and Metabolic Effects of Physiologic r-metHuLeptin Administration during Acute Caloric Deprivation in Normal-Weight Women" J Clin Endocrinol Metab, 89(11): 5402-5409.
Sefton (1987) "Implantable Pumps" CRC Crit. Ref. Biomed. Eng. 14:201.
Shimomura et al. (1998) "Insulin resistance and diabetes mellitus in transgenic mice expressing nuclear SREBP-1c in adipose tissue: model for congenital generalized lipodystrophy" Genes Dev 12:3182-3194.
Shimomura et al. (1999) "Leptin reverses insulinresistance anddiabetesmellitus in mice with congenital lipodystrophy" Letters to Nature 401:73-76.
Sinha et al. (1996) "Evidence of free and bound leptin in human circulation. Studies in lean and obese subjects and during short-term fasting" J Clin Invest 98(6):1277-1282.
Sjöström (1998) "Randomised placebo-controlled trial of orlistat for weight loss and prevention of weight regain in obese patients" Lancet 352(9123):167-172.
Smith et al. (2010) "Multicenter, Placebo-Controlled Trial of Lorcaserin for Weight Management" N. Engl. J. Med. 363(3):245-256.
Stoner, L., "Setemelanotide in a Single Patient With Partial Lipodystrophy", Rhythm Pharmaceuticals, Inc., Ann Arbor, MI, Aug. 25, 2017, 5 pages, [online] U.S. National Library of Medicine, retrieved on Oct. 28, 2021, ClinicalTrials.gov Identifier: NCT03262610.
Tartaglia et al. (1995) "Identification and Expression Cloning of a Leptin Receptor, OB-R" Cell 83:1263-1271.
Tartaglia et al. (1996) "The full-length leptin receptor has signaling capabilities of interleukin 6-type cytokine receptors" Proc Natl Acad Sci USA 93:8374-8378.
Tartaglia et al. (1997) "The Leptin Receptor" J Biol Chem 7:272(10):6093-6.
Taylor et al. (1992) "A transgenic mouse that expresses a diversity of human sequence heavy and light chain Immunoglobulins" Nucl. Acids Res. 20:6287-6295.
Tikka (2016) "The role of ANGPTL3 in controlling lipoprotein metabolism" Endocrine 52(2):187-93.
Tokuriki et al. (2009) "Stability Effects of Mutations and Protein Evolvability" Current Opinion Struc. Biol., 19:596-604.
"Trial of Leptin Replacement Therapy in Patients with Lipodystrophy" [online] Mar. 11, 2009 (retrieved on Aug. 4, 2021), Retrieved from ClinicalTrials.gov, identifier: NCTO0896289 (Year:2009).
Tutt et al. (1991) "Trispecific F(ab')3 Derivatives that Use Cooperative Signaling Via the TCR/CD3 Complex and CD2 to Activate and Redirect Resting Cytotoxic T Cells", J. Immunol. 147:60-69.
Upadhyay (2015) "The Role of Leptin in Regulating Bone Metabolism", Metabolism, 64(1):105-113.
Valenzuela et al. (2003) "High-throughput Engineering of the Mouse Genome Coupled with High-Resolution Expression Analysis" Nature Biotechnology, 21(6):652-659.
Wabitsch et al. (2015) "Severe Early-Onset Obesity Due to Bioinactive Leptin Caused by a p.N103K Mutation in the Leptin Gene." J Clin Endocrinol Metab. 100(9): 3227-3230).
Warren et al. (1999) "Functional Hypothalamic Amenorrhea: Hypoleptinemiaand Disordered Eating", The Journal of Clinical Endocrinology & Metabolism, 84(3):873-877.
Welt et al. (2004) "Recombinant Human Leptin in Women with Hypothalamic Amenorrhea", N. Engl. J. Med., 351:987-997.
White and Tartaglia (1996) "Leptin and OB-R: body weight regulation by a cytokine receptor" Cytokine & growth factor reviews 7:303-309.
Wu et al. (1987) "Receptor-Mediated in Vitro Gene Transformation by a Soluble DNA Carrier System" J. Biol. Chem. 262:4429-4432.
Yadav and Pitchumoni (2003) "Issues in Hyperlipidemic Pancreatitis" J Clinical Gastroenterol 36(1):54-62.
Zhang et al. (1994) "Positional cloning of the mouse obese gene and its human homologue", Nature 372: 425-432.
Zhang et al. (2016) "Characteristics of patients potentially eligible for pharmacotherapy for weight loss in primary care practice in the United States" Obes Sci Pract. 2(2): 104-114.
Zuchero et al. (2016) "Discovery of Novel Blood-Brain Barrier Targets to Enhance Brain Uptake of Therapeutic Antibodies" Neuron 89:70-82.
European Publication Notice received for EP Application No. 21207469.4, dated Sep. 14, 2022, 1 page.
Mould and Green (2010) "Pharmacokinetics and Pharmacodynamics of Monoclonal Antibodies," BioDrugs, 24(1):29-39.
Tyagi and Gupta (1998) "Chemical Modification and Chemical Crosslinking for Protein/Engzyme Stabilization," Biochmistry, 63(3):395-407, Abstract Only.
Ahmann, et al. (2015) "Efficacy and safety of liraglutide versus placebo added to basal insulin analogues (with or without metformin) in patients with type 2 diabetes: a randomized, placebo-controlled trial," Diabetes, Obesity and Metabolism 17(11):1056-1064.
Bhaskar, et al. (2016) "An Allosteric Antibody to the Leptin Receptor Reduces Body Weight and Reverses the Diabetic Phenotype in the $Lep^{ob}/Lep^{ob}$ Mouse," Obesity 00:(00) 1-8.
Bray and Wadden (2015) "Improving Long-Term Weight Loss Maintenance: Can We Do It?", Obesity 23:2-3.
Chagnon et al. (2000) "Associations Between the Leptin Receptor Gene and Adiposity in Middle-Aged Caucasian Males from the Heritage Family Study", Journal of Clinical Endocrinology & Metabolism 85(1):29-34.
Ehring (1999) "Hydrogen Exchange/Electrospray Ionization Mass Spectrometry Studies of Structural Features of Proteins and Protein/Protein Interactions" Analytical Biochemistry 267(2):252-259.
Farooqi, et al. (2007) "Clinical and Molecular Genetic Spectrum of Congenital Deficiency of the Leptin Receptor," N. Engl. J. Med. 356:237-247.
Friedman and Halaas (1998) "Leptin and the regulation of body weight in mammals" Nature 395(6704):763-70.
Garg (2011) "Lipodystrophies: Genetic and Acquired Body Fat Disorders", Journal of Clinical Endocrinology and Metabolism, 96(11):3313-3325.
Goel, et al. (2004) "Plasticity Within The Antigen-Combining Site May Manifest as Molecular Mimicry in the Humoral Immune Response", J. Immunol., 173:7358-7367.
Goodson (1984) in Medical Applications of Controlled Release, vol. 2, pp. 115-138.
Gorska, et al. (2010) "Leptin Receptors", European Journal of Medical Research, 15(Supplemental II):50-54.
Halpern, et al. (2010) "Combinations of Drugs in the Treatment of Obesity", Pharmaceuticals, 3:2398-2415.
Iepsen, et al. (2014) "Treatment With a GLP-1 Receptor Agonist Diminishes the Decrease in Free Plasma Leptin During Maintenance of Weight Loss," International Journal of Obesity, 39(5):834-841.
Justice, et al. (2016) "Using the Mouse to Model Human Disease: Increasing Validity and Reproducibility", Disease, Models & Mechanisms 9:101-103.
Kazane et al., (2012) "Synthesis of Bispecific Antibodies using Genetically Encoded Unnatural Amino Acids", J. Am. Chem. Soc., 134:9918-9921 [Epub: Dec. 4, 2012].

(56) References Cited

OTHER PUBLICATIONS

Khan, et al. (2014) "Adjustable Locks and Flexible Keys: Plasticity of Epitope-Paratope Interactions in Germline Antibodies", J. Immunol. 192:5398-5405.
Li, et al. (2016) "The Role of Leptin in Central Nervous System Diseases", NeuroReport 27(5):350-355.
Lin, et al. (2018) "Leptin signaling axis specifically associates with clinical prognosis and is multifunctional in regulating cancer progression", Oncontarget 9(24):17210-17219.
Lloyd, et al. (2009) "Modeling the Human Immune Response: Performance of a 10(11) Human Antibody Repertoire Against a Broad Panel of Therapeutically Relevant Antigens." Protein Engineering & Selection 22(3):159-168.
Mancour, et al. (2012) "Ligand-Induced Architecture of the Leptin Receptor Signaling Complex," Molecular Cell 48:655-661.
Marcic et al. (2000) "Replacement of the Transmembrane Anchor in Angiotensin I-converting Enzyme (ACE) with a Glycosylphosphatidylinositol Tail Affects Activation of the $B_2$ Bradykinin Receptor by ACE Inhibitors", J. Biol Chem. 275(21):16110-8.
Mak, et al. (2014) "Exploiting the therapeutic potential of leptin signaling in cachexia", Current Opinion in Supportive and Palliative Care 8(4):352-357.
Mayo Clinic (2015) "Lipodystrophy Syndromes: New Treatment, Newer Questions", Published online Sep. 1, 2015, 4 pages.
McMurphy et al., (2014) "The Anti-Tumor Activity of a Neutralizing Nanobody Targeting Leptin Receptor in a Mouse Model of Melanoma", PLOS One (2014) 9(2):e89895.
Meehan, et al. (2016) "Metreleptin for Injection to Treat the Complications of Leptin Efficiency in Patients with Congenital or Acquired Generalized Lipodystrophy," Clinical Pharmacology 9(1):59-68.
Molek, et al. ( 2014) "Screening of synthetic phage display scFv libraries yields competitive ligands of human leptin receptor", Biochemical and Biophysical Research Communications 452(3):479-483.
Moon et al. (2013) "Leptin's Role in Lipodystrophic and Nonlipodystrophic Insulin-Resistant and Diabetic Individuals", Endocrine Reviews, 34(3):377-412.
Morris, et al. (1996) "Epitope Mapping of Protein Antigens by Competition ELISA", The Protein Protocols Handbook, Humana Press, pp. 595-600.
Osorio (2014) "Leptin and Leptin Receptor Expressions in Prostate Tumors May Predict Disease Aggressiveness?", Acta Cirurgica Brasileira, 29(supl.3), 5pages.
Padlan (1994) "Anatomy of the Antibody Molecule", Molecular Immunology, 31(3):169-217.
Park and Ahima (2014) "Leptin Signaling", F1000Prime Reports, 73(6), 8 pages.
Paz-Filho, et al. (2014) "Leptin treatment: Facts and expectations," Metabolism, pp. 1-11, http://dx.doi.org/10.1016/j.metabol.2014.07.014.
International Search Report and Written Opinion received for PCT/US2017/060690 on Jan. 10, 2018, 17 pages.
PCT International Search Report and Written Opinion received for PCT/US2016/056465, on Jan. 10, 2017.
Peelman, et al. (2014) "Insights into signaling assemblies of the leptin receptor," Journal of Endocrinology 223:T9-T23.
Poosarla, et al. (2017) "Computational De Novo Design of Antibodies Binding to a Peptide With High Affinity", Biotechn. Bioeng., 114(6):1331-1342.
Procaccini, et al. (2015) "Leptin in autoimmune diseases," Metabolism Clinical and Experimental 64:92-104.
Rabia, et al. (2018) "Understanding and Overcoming Trade-Offs Between Antibody Affinity, Specificity, Stability and Solubility," Biochemical Engineer Journal, 137:365-374.
Rosenbaum, et al. (2002) "Low Dose Leptin Administration Reverse Effects of Sustained Weight-Reduction on Energy Expenditure and Circulating Concentrations of Thyroid Hormones," The Journal of Clinical Endocrinology & Metabolism 87(5):2391-2394.
Rosenbaum, et al. (2005) "Low-dose Leptin Reverses Skeletal Muscle, Autonomic, and Neuroendocrine Adaptations to Maintenance of Reduced Weight" The Journal of Clinical Investigation 115(12):3579-3586.
Sweeney (2002) "Leptin signaling", Cell Signal 14(8):655-663.
Tomer (2000) "Characterization of a discontinuous epitope of the human immunodeficiency virus (HIV) core protein p24 by epitope excision and differential chemical modification followed by mass spectrometric peptide mapping analysis", Protein Science 9:487-496.
University of Utah Healthcare (2014) "Knowing the Difference Between Inherited and Acquired Cancers Can Save Lives", Published online Sep. 5, 2014, 3 pages.
Ussar, et al. (2011) "Receptor Antibodies as Novel Therapeutics for Diabetes," Science Translational Medicine, 3(113):22-24.
Wauman, et al. (2011) "Leptin Receptor Signaling: Pathways to Leptin Resistance", Frontiers in Biosciences 16:2771-2793.
Zabeau et al. (2014) "Antagonizing leptin: current status and future directions" Biol. Chem. 395(5):499-514.
Akinci, et al. (2018) "Update on Therapeutic Options in Lipodystrophy," Current Diabetes Reports 18 :139, pp. 1-12.
Al Qaraghuli, et al. (2020) "Antibody-Protein Binding and Conformational Changes: Identifying Allosteric Signaling Pathways to Engineer a Better Effector Response", Nature Scientific Reports, 10:13969.
Kawaji, et al. (2001) "Anti-leptin Receptor Antibody Mimics the Stimulation of Lipolysis Induced by Leptin in Isolated Mouse Fat Pads", Journal of Lipid Research, 42(10):1671-1677.
Kyratsous et al. (2015) "Reply to Dimitrov et al.:VelociSuite Technologies are a Foundation for Rapid Therapeutic Antibody Development", PNAS 112(37) E5116.
Molina, et al. (2014) "Pressure Ulcers—Burns/Annals of Physical Rehabilitation Medicine," Lipoatrophia Semicircularis: A case report Abstract P159-e, 57S : e212-e217.
Murphy, et al. (2014) "Mice with Megabase Humanization of their Immunoglobulin Genes Generate Antibodies as Efficiently as Normal Mice", PNAS 111(14):5153-5158.
Nolis (2014) "Exploring the Pathophysiology Behind the More Common Genetic and Acquired Lipodystrophies," Journal of Human Genetics, 59 : 16-23.
Phillips (2001) "The Challenge of Gene Therapy and DNA Delivery", J. Pharm. Pharmacology 53:1169-1174.
Purdham, et al. (2008) "A Neutralizing Leptin Receptor Antibody Mitigates Hypertrophy and Hemodynamic Dysfunction in the Postinfarcted Rat Heart", Am. J. Physiol. Heart Circ. Physiol., 295(1):H441-H446.
Accession No. NP_002294.2 TO: Protein [Internet]. Bethesda (MD): National Library of Medicine (US), National Center for Biotechnology Information; [2016]—Accession No. NP_002294.2, "Leptin Receptor Isoform 1 Precursor [*Homo Sapiens*]," cited on Oct. 16, 2016, [online], [retrieved on Feb. 15, 2017]. Retrieved from: https://www.ncbi.nlm.nih.gov/protein/NP_002294.2, 5 pages.
Accession No. XP_005543194.1 TO: Protein [Internet]. Bethesda (MD): National Library of Medicine (US), National Center for Biotechnology Information; [2016]—Accession No. XP_005543194.1, "Predicted: Leptin Receptor Isoform X1 [Macaca Fascicularis]," cited on Jan. 25, 2016, [online], [retrieved on Feb. 15, 2017]. Retrieved from: https://www.ncbi.nlm.nih.gov/protein/XP_005543194.1, 2 pages.
Fazeli et al. (2006) "Identification of a Monoclonal Antibody Against the Leptin Receptor That Acts as an Antagonist and Blocks Human Monocyte and T Cell Activation," J Immunol. Methods, 312:190-200.
Hukshorn et al. (2000) "Weekly Subcutaneous Pegylated Recombinant Native Human Leptin (PEG-OB) Administration in Obese Men," J Clin Endocrinol Metab., 85(11): 4003-4009.
Jakubke et al. (1985) "Amino Acids, Peptides, Proteins," M. Mir., pp. 93-94 (Russian reference).
Jakubke et al. (1985) "Amino Acids, Peptides, Proteins," M. Mir., pp. 93-94 (English translation of the Russian reference).
Kabat et al. (1991) "Sequences of Proteins of Immunological Interest," 5th Edition (Bethesda, MD), U.S. Department of Health

(56) References Cited

OTHER PUBLICATIONS and Human Services, Public Health Service National Institutes of Health, NIH Publication No. 91-3242, pp. 661-696.
Klein et al. (2012) "Progress in Overcoming the Chain Association Issue in Bispecific Heterodimeric IgG Antibodies," mAbs 4(6): 653-663.
Mashkovsky (2012) "Drugs," 16th ed., revised, corrected and supplemented, M.:New Wave pp. 12-13 (Russian reference).
Mashkovsky (2012) "Drugs," 16th ed., revised, corrected and supplemented, M.:New Wave pp. 12-13 (English translation of the Russian reference).
Mironov et al. (2012) "Guidelines for Conducting Preclinical Studies of Drugs, Part One," M.:Grif and K, pp. 858-860, table 2 (Russian reference).
Mironov et al. (2012) "Guidelines for Conducting Preclinical Studies of Drugs, Part One," M.:Grif and K, pp. 858-860, table 2 (English translation of the Russian reference).
Ravussin et al. (2014) "A Missing Link in Bodyweight Homeostasis: The Catabolic Signal of the Overfed State," Cell Metab., 20(4): 565-572.
Selezneva et al. (2015) "Complex Approach to Study Pharmacological Agents In Vitro, Ex Vivo, In Vivo," International Research Journal, 6(37): 125-127 In Russian with English Abstract.
Van Dielen et al. (2002) "Leptin and Soluble Leptin Receptor Levels in Obese and Weight-Losing Individuals," J Clin Endocrinol Metab., 87(4): 1708-1716.
Yue et al. (2016) "Leptin Receptor Promotes Adipogenesis and Reduces Osteogenesis by Regulating Mesenchymal Stromal Cells in Adult Bone Marrow," Cell Stem Cell, 18(6): 782-796.
Horiuchi (2010) "Regulation of Bone Metabolism by Leptin, a Product of the Obese Gene", The Journal of the Tokyo Dental College Society, 110(4): 448-451.
Accession No. NP_001003679.1 TO: Protein [Internet]. Bethesda (MD): National Library of Medicine (US), National Center for Biotechnology Information; [2019]—Accession No. NP_001003679.1, "Leptin Receptor Isoform 3 Precursor [*Homo sapiens*]", cited on Mar. 12, 2019, [online], [retrieved on Mar. 20, 2019]. Retrieved from: https://www.ncbi.nlm.nih.gov/protein/51093379/, 6 pages.
Accession No. NP_002175.2 TO: Protein [Internet]. Bethesda (MD): National Library of Medicine (US), National Center for Biotechnology Information; [2019]—Accession No. NP_002175.2, "Interleukin-6 Receptor Subunit Beta Isoform 1 Precursor [*Homo sapiens*]", cited on Mar. 12, 2019, [online], [retrieved on Mar. 20, 2019]. Retrieved from: https://www.ncbi.nlm.nih.gov/protein/NP_002175.2, 6 pages.
Ajluni et al. (2017) "Spectrum of Disease Associated with Partial Lipodystrophy: Lessons from A Trial Cohort", Clin Endocrinol (Oxf), 86(5): 698-707.
Akinci et al. (2020) "Adipose Tissue, Appetite, and Obesity, Mechanisms and Treatment of Obesity in Humans, The Treatment of Partial Lipodystrophy in the Setting of Neutralizing Antibody Against Metreleptin with Leptin Receptor Agonist REGN4461", Journal of the Endocrine Society, vol. 4, Abstract Supplement, A544 (OR33-02).
Akinci et al. (2020) "The Complicated Clinical Course in A Case of Atypical Lipodystrophy After Development of Neutralizing Antibody to Metreleptin: Treatment with Setmelanotide", Endocrinol Diabetes Metab Case Rep., 1-9.
Akinci et al. (2018) "Phenotypic and Genetic Characteristics of Lipodystrophy: Pathophysiology, Metabolic Abnormalities, and Comorbidities", Curr Diab Rep., 18(12):143, 1-12.
Akinci et al. (2018) "Renal Complications of Lipodystrophy: A Closer Look at The Natural History of Kidney Disease", Clin Endocrinol (Oxf), 89(1):65-75.
Akinci et al. (2017) "Clinical Presentations, Metabolic Abnormalities and End-Organ Complications in Patients with Familial Partial Lipodystrophy", Metabolism-Clin and Exp., 72: 109-119.
Altschul (1993) "A Protein Alignment Scoring System Sensitive at all Evolutionary Distances", J. Mol. Evol., 36:290-300.
ALTSCHUL (1991) "Amino Acid Substitution Matrices from an Information Theoretic Perspective", J. Mol. Biol., 219: 555-565.
Altschul et al. (2005) "Protein Database Searches Using Compositionally Adjusted Substitution Matrices", FEBS J., 272(20): 5101-5109.
Anonymus (2019) "Study of REGN4461, a Leptin Receptor Agonist Antibody, in Patient with Generalized Lipodystrophy", Full Text View, ClinicalTrials.gov, Nov. 12, 2019, 10 pages.
Anthony (2008) "Nutrition Screening Tools for Hospitalized Patients", Nutr. Clin. Pract. 23: 373-382.
Aslam et al. (2013) "Acquired Generalized Lipodystrophy Associated with Peripheral Tcell Lymphoma with Cutaneous Infiltration", International J. Dermatol., 54: 827-829.
Baca et al. (1997) "Antibody Humanization Using Monovalent Phage Display," J Biol Chem., 272(16): 10678-10684.
Bahrenberg et al. (2002) "Identification of the Critical Sequence Elements in the Cytoplasmic Domain of Leptin Receptor Isoforms Required for Janus Kinase/Signal Transducer and Activator of Transcription Activation by Receptor Heterodimers", Molecular Endocrinology, 16(4): 859-872.
Barbas (1995) "Synthetic Human Antibodies", Nat Med., 1(8): 837-839.
Barr et al. (1999) "Subcellular Localization and Internalization of the Four Human Leptin Receptor Isoforms", J Biol Chem., 274(30): 21416-21424.
Barsh & Schwartz (2002) "Genetic Approaches to Studying Energy Balance: Perception and Integration", Nat Rev Genet., 3(8): 589-600.
Bates & Myers (2003) "The Role of Leptin Receptor Signaling in Feeding and Neuroendocrine Function", Trends in Endocrinology and Metabolism, 14(10): 447-452.
Bates et al. (2003) "STAT3 Signaling is Required for Leptin Regulation of Energy Balance but not Reproduction", Nature 421: 856-859.
Bendig (1995) "Humanization of Rodent Monoclonal Antibodies by CDR Grafting", Method3: A Companion to Methods in Enzymology, 8: 83-93.
Bingham et al. (2008) "Predictors of Acquired Lipodystrophy in Juvenile-Onset Dermatomyositis and A Gradient Of Severity", Medicine (Baltimore), 87(2): 70-86.
Bjornholm et al. (2007) "Mice Lacking Inhibitory Leptin Receptor Signals are Lean with Normal Endocrine Function", J. Clin. Invest., 117: 1354-1360.
Boersma and Pluckthun (2011) "DARPins and Other Repeat Protein Scaffolds: Advances in Engineering and Applications", Curr. Opin. Biotechnol., 22: 849-857.
Bolan et al. (2002) "Intensive, Long-Term Plasma Exchange Therapy for Severe Hypertriglyceridemia in Acquired Generalized Lipoatrophy", J Clin Endocrinol Metab., 87(1): 380-384.
Brennan et al. (1985) "Preparation of Bispecific Antibodies by Chemical Recombination of Monoclonal Immunoglobulin G1 Fragments," Science, 229: 81-83.
Brown et al. (2018) "Long-Term Effectiveness and Safety of Metreleptin in The Treatment of Patients with Generalized Lipodystrophy", Endocrine, 60(3): 479-489.
Brown et al. (2016) "Lymphoma in Acquired Generalized Lipodystrophy", Leuk Lymphoma, 57(1): 45-50.
Bülbül et al. (2001) "Acute Pancreatitis in A Patient with Partial Lipodystrophy and Membranoproliferative Glomerulonephritis", Nephrol Dial Transplant., 16(9): 1930-1931.
Carpenter et al. (2000) "Non-Fc Receptor-Binding Humanized Anti-CD3 Antibodies Induce Apoptosis of Activated Human T Cells," J Immunol. 165(11): 6205-6213.
Carpenter et al. (1998) "Enhancing Leptin Response by Preventing SH2-containing Phosphate 2 Interaction with Ob Receptor", Proc. Natl. Acad. Sci. USA, 95: 6061-6066.
Carter (2001) "Bispecific Human IgG by Design", J Immunol Meth., 248: 7-15.
CAsset et al. (2003) "A Peptide Mimetic of an Anti-CD4 Monoclonal Antibody by Rational Design", Biochemical and Biophysical Research Communications, 307: 198-205.
Ceddia (2005) "Direct Metabolic Regulation in Skeletal Muscle and Fat Tissue by Leptin: Implications for Glucose and Fatty Acids Homeostasis", Int J Obes., 29(10): 1175-1183.

(56) References Cited

OTHER PUBLICATIONS

Chen et al. (1996) "Evidence That the Diabetes Gene Encodes the Leptin Receptor: Identification of a Mutation in the Leptin Receptor Gene in db/db Mice", Cell, 84(3): 491-495.
Cheung (2014) "A Pegylated Leptin Antagonist Ameliorates CKD-Associated Cachexia in Mice", J Am Soc Nephrol., 25(1): 119-128.
Chothia et al. (1989) "Conformations of Immunoglobulin Hypervariable Regions", Nature, 342: 877-883.
Chothia et al. (1987) "Canonical Structures for The Hypervariable Regions of Immunoglobulins", J. Mol. Biol., 196: 901-917.
"A Study to Examine the Safety, Tolerability and Biological Effects of REGN4461 in Healthy Volunteers [ClinicalTrials.gov posting, identifier NCT03530514]. Accessed May 21, 2018."
"A Study to Examine the Safety, Tolerability and Biological Effects of REGN4461 in Healthy Volunteers [ClinicalTrials.gov posting, identifier NCT03530514]. Accessed Jul. 9, 2018."
"A Study to Examine the Safety, Tolerability and Biological Effects of REGN4461 in Healthy Volunteers [ClinicalTrials.gov posting, identifier NCT03530514]. Accessed Nov. 15, 2019."
"A Study to Examine the Safety, Tolerability and Biological Effects of REGN4461 in Healthy Volunteers [ClinicalTrials.gov posting, identifier NCT03530514]. Accessed Mar. 9, 2020."
"Study of REGN4461, a Leptin Receptor Agonist Antibody, in Patients with Generalized Lipodystrophy [ClinicalTrials.gov posting, identifier NCT04159415]. Accessed Nov. 12, 2019."
"Study of REGN4461, a Leptin Receptor Agonist Antibody, in Patients with Generalized Lipodystrophy [ClinicalTrials.gov posting, identifier NCT04159415]. Accessed Jan. 29, 2020."
"Study of REGN4461, a Leptin Receptor Agonist Antibody, in Patients with Generalized Lipodystrophy [ClinicalTrials.gov posting, identifier NCT04159415]. Accessed Apr. 28, 2020."
"Study of REGN4461, a Leptin Receptor Agonist Antibody, in Patients with Generalized Lipodystrophy [ClinicalTrials.gov posting, identifier NCT04159415]. Accessed May 21, 2020."
"Study of REGN4461, a Leptin Receptor Agonist Antibody, in Patients with Generalized Lipodystrophy [ClinicalTrials.gov posting, identifier NCT04159415]. Accessed Aug. 12, 2021."
"Expanded Access to REGN4461 for Patients With 1) Generalized Lipodystrophy, 2) Partial Lipodystrophy or 3) Monogenic Obesity Due to LEP or LEPR Loss of Function [ClinicalTrials.gov posting, identifier NCT04710056]. Accessed Jan. 13, 2021."
Conrath et al. (2001) "Camel Single-Domain Antibodies as Modular Building Units in Bispecific and Bivalent Antibody Constructs", J Biol Chem., 276(10): 7346-7350.
Coppari & Bjørbæk (2012) "The Potential of Leptin for Treating Diabetes and Its Mechanism of Action", Nat Rev Drug Discov., 11(9): 692-708.
Cron et al. (2016) "The Role of gp130 Receptor Cytokines in The Regulation of Metabolic Homeostasis", Journal of Experimental Biology, 219(2): 259-265.
De Bruin et al. (1999) "Selection of High-Affinity Phage Antibodies from Phage Display Libraries", Nat Biotech. 17: 397-399.
Dechiara et al. (2010) "Producing Fully ES Cell-Derived Mice from Eight-Cell Stage Embryo Injections", Meth Enzymol., 476: 285-94.
Dechiara et al. (2009) "VelociMouse: Fully ES Cell-Derived FO-Generation Mice Obtained from the Injection of ES Cells into Eight-Cell-Stage Embryos", Meth Mol Biol., 530: 311-24.
Dembo et al. (1994) "Limit Distribution of Maximal Non-Aligned Two-Sequence Segmental Score", Ann. Prob., 22(4): 2022-2039.
Desmyter et al. (2001) "Antigen Specificity and High Affinity Binding Provided by One Single Loop of a Camel Single-Domain Antibody", J Biol Chem., 276(28): 26285-26290.
Detsky et al. (1987) "What is Subjective Global Assessment of Nutritional Status?" J Parent Enteral Nutr., 11(1): 8-13.
Dewall et al. (2008) "Collective and Individual Functions of Leptin Receptor Modulated Neurons Controlling Metabolism and Ingestion", Endocrinology, 149(4): 1773-1785.
Eldin et al. (2020) "Healthcare Delivery and Education, Expanding Clinical Considerations for Patient Testing and Care-Pain is a Major Driver of Quality of Life and Psychoemotional Health in Lipodystrophy Syndromes", Journal of the Endocrine Society, MON-121, vol. 4, Abstract Supplementation, A571.
Everts et al. (2002) "Selective Intracellular Delivery of Dexamethasone into Activated Endothelial Cells Using an E-Selection-Directed Immunoconjugate", J Immunol., 168: 883-889.
Fearon et al. (2011) "Definition and Classification of Cancer Cachexia: An International Consensus", Lancet Oncol., 12: 489-495.
Febbraio (2007) "gp130 Receptor Ligands as Potential Therapeutic Targets for Obesity", Journal of Clinical Investigation, 117(4): 841-849.
Ferguson et al. (1999) "Validation of a Malnutrition Screening Tool for Patients Receiving Radiotherapy", Australas Radio., 43: 325-327.
Foote and Winter (1992) "Antibody Framework Residues Affecting the Conformation of the Hypervariable Loops", J Mol Biol., 224: 487-499.
Foss-Freitas et al. (2020) "Diagnostic Strategies and Clinical Management of Lipodystrophy", Expert Rev Endocrinol Metab, 15(2): 95-114.
Foster et al. (2003) "Body Weight Regulation by Selective MC4 Receptor Agonists and Antagonists", Ann N.Y. Acad Sci., 994: 103-110.
Franceschini et al. (1995) "Pre-B Acute Lymphoblastic Leukemia in A Patient with Partial Lipodystrophy and Acanthosis Nigricans", Panminerva Med., 37(4): 248-251.
Garg (2000) "Gender Differences in The Prevalence of Metabolic Complications in Familial Partial Lipodystrophy (Dunnigan Variety)", J Clin Endocrinol Metab., 85(5): 1776-1782.
Ge et al. (2018) "Leptin in Depression: A Potential Therapeutic Agent", Cell Death & Disease, 9(11): 1096, 10 pages.
Gibellini et al. (1998) "Extracellular HIV-1 Tat Protein Induces the Rapid Ser133 Phosphorylation and Activation of CREB Transcription Factor in Both Jurkat Lymphoblastoid T Cells and Primary Peripheral Blood Mononuclear Cells", J Immunol., 160: 3891-3898.
Gish & States (1993) "Identification of Protein Coding Regions by Database Similarity Search", Nature Genet., 3: 266-272.
Greenfield et al. (2009) "Modulation of Blood Pressure by Central Melanocortinergic Pathways", N Engl J Med., 360: 44-52.
Gromada et al. (2017) "New Isolated Antibody That Binds Human Leptin Receptor (LEPR) and Activates LEPR Signaling Used to Treat Disease Associated with or Caused by Leptin Deficiency or Leptin Resistance e.g. Lipodystrophy, Metabolic Syndrome, and Diabetes", XP55865322, Database Accession No. 2017-288676 Abstract and & US2017/101477 A1, Database WPI [Online Apr. 13, 2017], 3 pages.
Hall et al. (1978) "Generalised Lipodystrophy, Scleroderma, And Hodgkin's Disease", Arch Intern Med., 138(8): 1303-1304.
Hancock et al. (1994) "SIMPLE34: An Improved and Enhanced Implementation for VAX and Sun Computers of the SIMPLE Algorithm for Analysis of Clustered Repetitive Motifs in Nucleotide Sequences", Comput. Appl. Biosci., 10(1): 67-70.
Handelsman et al. (2013) "The Clinical Approach to The Detection of Lipodystrophy—An AACE Consensus Statement", Endocr Pract., 19(1): 107-16.
Haque et al. (2002) "Post-Mortem Findings in Familial Partial Lipodystrophy", Dunnigan Variety. Diabet Med., 19(12): 1022-1025.
He et al. (1998) "Humanization and Pharmacokinetics of a Monoclonal Antibody with Specificity for Both E- and P-Selectin", J Immunol., 160: 1029-1035.
Hegele (2001) "Premature Atherosclerosis Associated with Monogenic Insulin Resistance", Circulation, 103(18): 2225-2229.
Henikoff et al. (1992) "Amino Acid Substitution Matrices from Protein Blocks", Proc. Natl. Acad. Sci. USA, 89: 10915-10919.
Hoogenboom and Chames (2000) "Natural and Designer Binding Sites Made By Phage Display Technology", Immunol Today, 21(8): 371-377.
Hsing and Bishop (1999) "Requirement for Nuclear Factor-KB Activation by a Distinct Subset of CD40-Mediated Effector Functions in B Lymphocytes", J Immunol., 162: 2804-2811.
Hudson and Kortt (1999) "High Avidity scFv Multimers; Diabodies and Triabodies", J Immunol Meth., 231: 177-189.

(56) References Cited

OTHER PUBLICATIONS

Hukshorn et al. (2003) "Pegylated Human Recombinant Leptin (PEG-OB) Causes Additional Weight Loss in Severely Energy-Restricted, Overweight Men", Am J Clin Nutr., 77: 771-776.
International Search Report and Written Opinion for PCT/US2019/066908 mailed Mar. 25, 2020.
Janoschek et al. (2006) "gp130 Signaling in Proopiomelanocortin Neurons Mediates the Acute Anorectic Response to Centrally Applied Ciliary Neurotrophic Factor", PNAS, 103(28): 10707-10712.
Javor et al. (2004) "Proteinuric Nephropathy in Acquired and Congenital Generalized Lipodystrophy: Baseline Characteristics and Course During Recombinant Leptin Therapy", J Clin Endocrinol Metab., 89(7): 3199-3207.
Kabat (1978) "The Structural Basis for Antibody Complementary", Adv. Prot. Chem., 32: 1-75.
Kabat et al. (1977) "Unusual Distributions of Amino Acids in Complementarity-Determining (Hypervariable) Segments of Heavy and Light Chains of Immunoglobulins and Their Possible Roles in Specificity of Antibody-Combining Sites", J. Biol. Chem., 252: 6609-6616.
Kaithamana et al. (1999) "Induction of Experimental Autoimmune Graves' Disease in BALB/c Mice", J Immunol., 163: 5157-5164.
Karlin et al. (1990) "Methods for Assessing the Statistical Significance of Molecular Sequence Features by Using General Scoring Schemes", Proc. Natl. Acad. Sci. USA, 87: 2264-2268.
Karlin et al. (1993) "Applications and Statistics for Multiple High-Scoring Segments in Molecular Sequences", Proc. Natl. Acad. Sci. USA, 90: 5873-5877.
Kawahara et al. (2003) "Bypassing Antibiotic Selection: Positive Screening of Genetically Modified Cells with an Antigen-Dependent Proliferation Switch", Nucleic Acids Research, 31(No. 7 e32): 1-8.
Kievet et al. (2013) "Chronic Treatment with A Melanocortin-4 Receptor Agonist Causes Weight Loss, Reduces Insulin Resistance, And Improves Cardiovascular Function in Diet-Induced Obese Rhesus Macaques", Diabetes, 62: 490-497.
Kruizenga et al. (2005) "Development and Validation of a Hospital Screening Tool for Malnutriton: The Short Nutritional Assessment Questionnaire (SNAQ)", Clin Nutr 24: 75-82.
Kruizenga et al. (2010) "The SNAQRC, An Easy Traffic Light System as a First Step in the Recognition of Undernutrition in Residential Care", J Nutr Health Aging, 14(2): 83-89.
Kühnen et al. (2016) "Proopiomelanocortin Deficiency Treated with a Melanocortin-4 Receptor Agonist", N Engl J Med, 375: 240-246.
Lambert et al. (2001) "Ciliary Neurotrophic Factor Activates Leptin-like Pathways and Reduces Body Fat, Without Cachexia or Rebound Weight Gain, Even in Leptin-Resistant Obesity", PNAS, 98(8): 4652-4657.
Le Doussal et al. (1991) "Enhanced In Vivo Targeting of an Asymmetric Bivalent Hapten to Double-Antigen-Positive Mouse B Cells with Monoclonal Antibody Conjugate Cocktails", J Immunol., 146(1): 169-175.
Liu et al. (2010) "Acute Administration of Leptin Produces Anxiolytic-like Effects: A Comparison with Fluoxetine", Psychopharmacology, Springer, Berlin, DE, 207(4): 535-545.
Lüdtke, et al. (2005) "Hepatic Steatosis in Dunnigan-Type Familial Partial Lipodystrophy", Am J Gastroenterol., 100(10): 2218-2224.
MacCallum et al. (1996) "Antibody-Antigen Interactions: Contact Analysis and Binding Site Topography", J. Mol. Biol., 262: 732-745.
Mack et al. (1995) "A Small Bispecific Antibody Construct Expressed as a Functional Single-Chain Molecule with High Tumor Cell Cytotoxicity", Proc Natl Acad Sci., 92: 7021-7025.
Madden et al. (1996) "Applications of Network BLAST Server", Meth. Enzymol., 266: 131-141.
Malecki et al. (2002) "Molecular Immunolabeling with Recombinant Single-Chain Variable Fragment (scFv) Antibodies Designed with Metal-Binding Domains", Proc Natl Acad Sci., 99(1): 213-218.
Marks & Cone (2001) "Central Melanocortins and The Regulation of Weight During Acute and Chronic Disease", Recent Prog Horm Res., 56: 359-375.
Marsh et al. (1999) "Effects of Neuropeptide Y Deficiency on Hypothalamic Agouti-Related Protein Expression and Responsiveness to Melanocortin Analogues", Brain Research, 848: 66-77.
Marsh et al. (1999) "Response of Melanocortin-4 Receptor-Deficient Mice to Anorectic and Orexigenic Peptides", Nature Genetics, 21: 119-122.
Martin et al. (1991) "Molecular Modeling of Antibody Combining Sites", Methods Enzymol., 203: 121-153.
Mendez et al. (1997) "Functional Transplant of Megabase Human Immunoglobulin Loci Recapitulates Human Antibody Response in Mice", Nat Gen., 15: 146-156.
Menne et al. (2000) "A Comparison of Signal Sequence Prediction Methods Using a Test Set of Signal Peptides", Bioinformatics, 16(8): 741-742.
Meyaard et al. (1997) "LAIR-1, a Novel Inhibitory Receptor Expressed on Human Mononuclear Leukocytes", Immunity, 7: 283-290.
Misra et al. (2004) "Clinical Features and Metabolic and Autoimmune Derangements in Acquired Partial Lipodystrophy: Report Of 35 Cases and Review of The Literature", Medicine (Baltimore), 83(1): 18-34.
Misra et al. (2003) "Clinical Features and Metabolic Derangements in Acquired Generalized Lipodystrophy: Case Reports and Review of The Literature", Medicine (Baltimore), 82(2): 129-146.
Mori et al. (2004) "Socs3 Deficiency in the Brain Elevates Leptin Sensitivity and Confers Resistance to Diet-Induced Obesity", Nature Medicine, 10(7): 739-743.
Morris & Rui (2009) "Recent Advances in Understanding Leptin Signaling and Leptin Resistance", Am J Physiol Endocrinol Metab., 297(6): E1247-59.
Morrison (1985) "Transfectomas Provide Novel Chimeric Antibodies", Science 229: 1202-1207.
Neelemaat et al. (2008) "Screening Malnutrition in Hospital Outpatients. Can the SNAQ Malnutrition Screening Tool Also be Applied to this Population?" Clin Nutr 27:439-446.
Oral & Chan (2010) "Rationale for Leptin-Replacement Therapy for Severe Lipodystrophy", Endocr Pract., 16(2): 324-333.
Oral et al. (2019) "Long-Term Effectiveness and Safety of Metreleptin in The Treatment of Patients with Partial Lipodystrophy", Endocrine, 64(3): 500-511.
O'Sullivan et al. (2007) "Cytokine Receptor Signaling Through the Jak-Stat-Socs Pathway in Disease," Mol. Immunol., 44(10): 2497-2506.
Özen, et al (2020) "Current Diagnosis, Treatment and Clinical Challenges in the Management of Lipodystrophy Syndromes in Children and Young People", J Clin Res Pediatr Endocrinol, 12(1):17-28.
Paul (1993) "Fundamental Immunology", 3rd Edition, Laboratory of Immunology National Institute of Allergy and Infection Diseases National Institutes of Health, pp. 292-295.
PCT International Search Report and Written Opinion for International application No. PCT/US2018/066075 mailed Feb. 25, 2019.
Pearson (2000) "Flexible Sequence Similarity Searching with the FASTA3 Program Package", Methods in Molecular Biology, 132: 185-219.
Pedersen et al. (1992) "Antibody Modeling: Beyond Homology", Immunomethods, 1(2): 126-136.
Powell et al. (2011) "New Drug Targets for the Treatment of Obesity", Clin. Pharmacol. Ther., 90(1): 40-51.
Raso et al. (1997) "Intracellular Targeting with Low pH-Triggered Bispecific Antibodies" J Biol Chem 272(44):27623-27628.
Rebouissou et al. (2009) "Frequent In-Frame Somatic Deletions Activate GP130 in Inflammatory Hepatocellular Tumours," Nature, 457(7226): 200-205.
Reineke (2004) "Antibody Epitope Mapping Ussing Arrays of Synthetic Peptides," Methods Mol. Biol., 248: 443-463.
Rhythm Pharma. Press Release, PRNewswire, Rhythm Presents Cardiovascular Safety Data from Phase 1b/2a Clinical Trials of Setmelanotide in Obesity (Nov. 6, 2015).

(56) References Cited

OTHER PUBLICATIONS

Savage et al. (2009) "Complement Abnormalities in Acquired Lipodystrophy Revisited", J Clin Endocrinol Metab.,94(1): 10-16.
Segal et al. (2001) "Introduction: Bispecific Antibodies" J Immunol Meth., 248: 1-6.
Shetty et al. (2011) "Leptin Administration to Overweight and Obese Subjects for Six Months Increases Free Leptin Concentrations but Does not Alter Circulating Hormones of the Thyroid and IGF Axes During Weight Loss Induced by a Mild Hypocaloric Diet", Eur. J Endocrinol., 165(2): 249-254.
Shields et al. (2002) "Lack of Fucose on Human IgG1 N-Linked Oligosaccharide Improves Binding to Human FcγRIII and Antibody-dependent Cellular Toxicity", JBC, 277: 26733-26740.
Smith et al. (1975) "Lipodystrophy, Pancreatitis, And Eosinophilia", Gut., 16(3): 230-234.
States et al. (1991) "Improved Sensitivity of Nucleic Acid Database Searches Using Application-Specific Scoring Matrices", Methods, 3: 66-70.
Stears et al. (2014) "Diagnosis and Management of Lipodystrophy: a Practical Update", Clinical Lipidology, 9(2): 235-259.
Stefater et al. (2012) "The Anorectic Effect of CNTF Does Not Require Action in Leptin-Responsive Neurons", Endocrinology, 153(6): 2647-54.
Suthaus et al. (2010) "Forced Homo- and Heterodimerization of all gp130-type Receptor Complexes Leads to Constitutive Ligand-Independent Signaling and Cytokine-Independent Growth", Mol. Biol. Cell., 1(15): 2797-807.
Sweeney (2002) "Leptin Signalling", Cell Signal, 14(8): 655-663.
Taga et al. (1997) "Gp130 and the interleukin-6 family of cytokines", Annu. Rev. Immunol, 15: 797-819.
Tang et al. (1999) "Use of a Peptide Mimotope to Guide the Humanization of MRK-16, and Anti-P-Glycoprotein Monoclonal Antibody", J Biol Chem., 274(39): 27371-27378.
Traunecker et al. (1991) "Bispecific Single Chain Molecules (Janusins) Target Cytotoxic Lymphocytes on HIV Infected Cells", EMBO J., 10(12): 3655-3659.
UK Working Party on Acute Pancreatitis (2005) "UK Guidelines for the Management of Acute Pancreatitis", Gut.; 54 (Suppl 3): iii1-iii9.
Vajdos et al. (2002) "Comprehensive Functional Maps of the Antigen-binding Site of an Anti-ErbB2 Antibody Obtained with Shotgun Scanning Mutagenesis", J. Mol. Biol., 320: 415-428.
Van Der Klaauw & Farooqi (2015) "The Hunger Genes: Pathways to Obesity", Cell., 161(1): 119-132.
Van Maldergem et al. (2002) "Genotype-Phenotype Relationships in Berardinelli-Seip Congenital Lipodystrophy", J Med Genet., 39(10): 722-733.
Vaughan et al. (1996) "Human Antibodies with Sub-Nanomolar Affinities Isolated from a Large Non-Immunized Phage Display Library", Nat Biotechnol., 14: 309-314.
Villanueva and Myers (2008) "Leptin Receptor Signaling and the Regulation of Mammalian Physiology", Int J Obes., 32: S8-S12.
Volkel et al. (2001) "Optimized Linker Sequences for the Expression of Monomeric and Dimeric Bispecific Single-Chain Diabodies", Prot Eng. 14(10): 815-823.
Von Heijne (1983) "Patterns of Amino Acids Near Signal-Sequence Cleavage Sites", Eur J Biochem., 133: 17-21.
Von Heijne (1986) "A New Method for Predicting Signal Sequence Cleavage Sites", Nucl Acids Res., 14(11): 4683-4690.
Wikberg & Mutulis (2008) "Targeting Melanocortin Receptors: An Approach to Treat Weight Disorders and Sexual Dysfunction", Nat Rev Drug Discov., 7(4): 307-323.
Wootton et al. (1993) "Statistics of Local Complexity in Amino Acid Sequences and Sequence Databases", Comput. Chem., 17:149-163.
Wren et al. (2002) "SIGNAL-Sequence Information and GeNomic Analysis", Comp Meth Prog Biomed., 68: 177-181.
Wright et al. (2000) "Lymphoid/Neuronal Cell Surface OX2 Glycoprotein Recognizes a Novel Receptor on Macrophages Implicated in the Control of Their Function", Immunity, 13: 233-242.
Wu et al. (1999) "Humanization of a Murine Monoclonal Antibody by Simultaneous Optimization of Framework and CDR Residues", J. Mol. Biol., 294: 151-162.
Yiannias et al. (2006) "Peripheral T-Cell Lymphoma Presenting as Lipoatrophy and Nodules", Int J Dermatol., 45(12): 1415-1419.
Zabeau et al. (2015) "Leptin: From Structural Insights to the Design of Antagonists", Life Sciences, 140: 49-56.
Zabeau et al. (2003) "The Ins and Outs of Leptin Receptor Activation", FEBS Letters, 546: 45-50.
Zadeh et al. (2013) "The Liver Diseases of Lipodystrophy: The Long-term Effect of Leptin Treatment", J Hepatol., 59(1): 131-137.
Zhang et al. (1997) "PowerBLAST: A New Network BLAST Application for Interactive or Automated Sequence Analysis and Annotation", Genome Res., 7: 649-656.
Zhao et al. (2014) "Leptin and IL-6 Family Cytokines Synergize to Stimulate Müller Glia Reprogramming and Retina Regeneration," Cell Reports, 9(1): 272-284.

* cited by examiner

*P<0.05, Isotype Control vs H4H18482P2
@P<0.05, Isotype Control vs H4H18487P2
!P<0.05, Isotype Control vs H4H18492P2
#P<0.05, H4H18492P2 vs H4H18482P2
$P<0.05, H4H18492P2 vs H4H18487P2

Fat Mass Pre-mAb Dosing
(Day -19)

Fat Mass Post mAb Dosing
(Day 17)

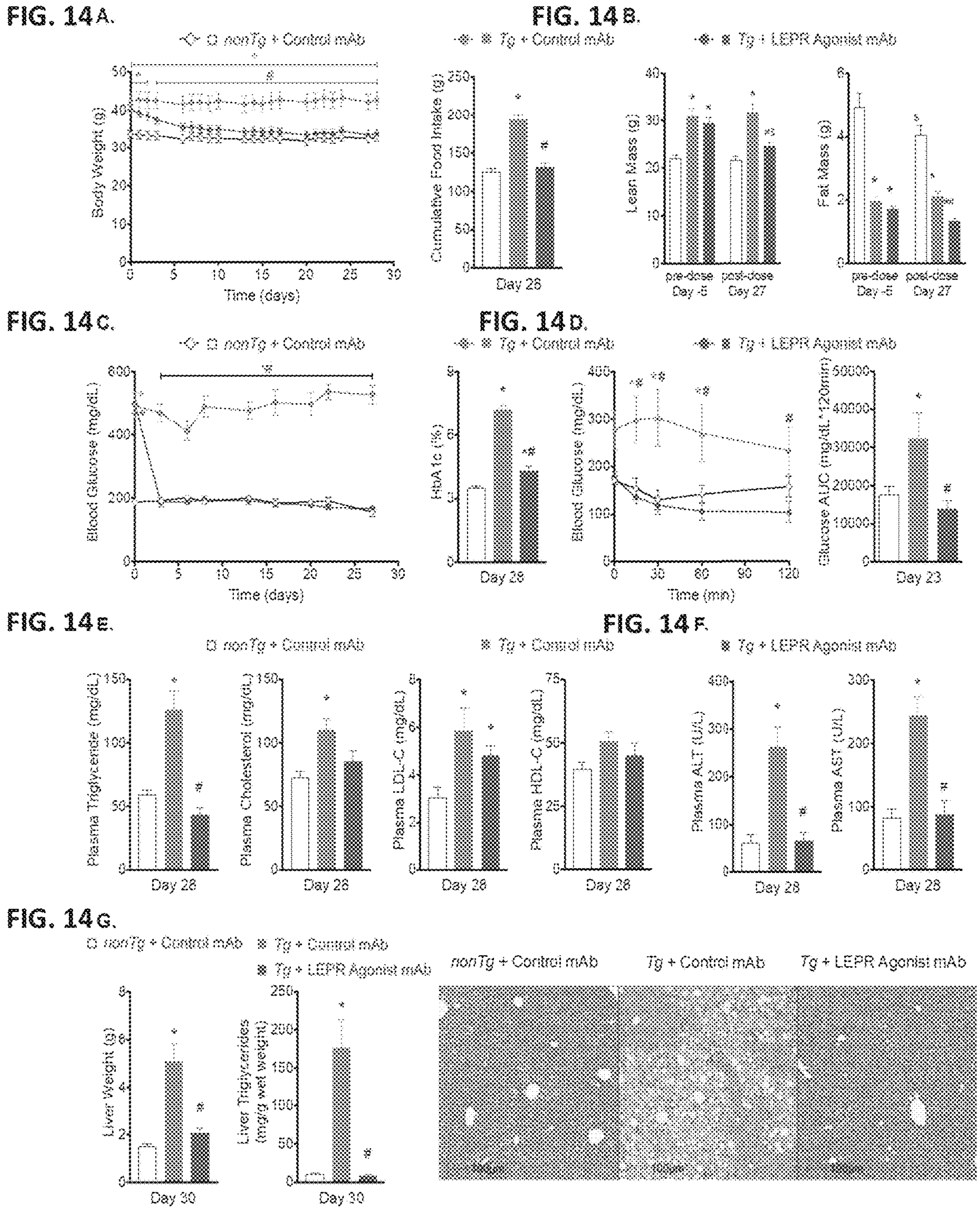
FIG. 14A.
FIG. 14B.
nonTg + Control mAb
Tg + Control mAb
Tg + LEPR Agonist mAb
Body Weight (g)
Time (days)
Cumulative Food Intake (g)
Day 28
Lean Mass (g)
Fat Mass (g)
pre-dose Day -5
post-dose Day 27
FIG. 14C.
FIG. 14D.
Blood Glucose (mg/dL)
Time (days)
HbA1c (%)
Day 28
Blood Glucose (mg/dL)
Time (min)
Glucose AUC (mg/dL*120min)
Day 23
FIG. 14E.
FIG. 14F.
Plasma Triglyceride (mg/dL)
Plasma Cholesterol (mg/dL)
Plasma LDL-C (mg/dL)
Plasma HDL-C (mg/dL)
Plasma ALT (U/L)
Plasma AST (U/L)
Day 28
FIG. 14G.
Liver Weight (g)
Liver Triglycerides (mg/g wet weight)
Day 30
nonTg + Control mAb
Tg + Control mAb
Tg + LEPR Agonist mAb Schedule of Assessments for Treatment Period 1

| **Study Period** | **Screening Period** | **Treatment Period 1** | | | | | | | | | | | |
|---|---|---|---|---|---|---|---|---|---|---|---|---|---|
| **Study Week** | **-2 to 0** | **1** | **2** | **3** | **4** | **5** | **6** | **7** | **8** | **9** | **10** | **11** | **12** |
| Informed consent/assent | X | | | | | | | | | | | | |
| Inclusion/Exclusion | X | X | | | | | | | | | | | |
| Medical history | X | X | | | | | | | | | | | |
| Pregnancy test | X | X | | | X | | | | X | | | | X |
| Physical examination | X | | | | | | | | | | | | X |
| Weight | X | | X | | X | | | | X | | | | X |
| Waist | X | | X | | X | | | | X | | | | X |
| Hip | X | | X | | X | | | | X | | | | X |
| Height | X | | | | | | | | | | | | X |
| Patient photos | X | | | | | | | | | | | | X |
| PHQ-9 & C-SSRS | X | | | | X | | | | X | | | | X |
| H4H17319P2 IV loading dose administration | | X | | | | | | | | | | | |
| H4H17319P2 SC administrations | | X | X | X | X | X | X | X | X | X | X | X | X |
| Injection site inspection | | X | X | X | X | X | X | X | X | X | X | X | X |
| Vital signs | X | X | X | X | X | X | X | X | X | X | X | X | X |
| ECG (12-lead) | X | X | | | | | | | | | | | |
| Safety laboratory tests | X | X | X | X | X | X | X | X | X | X | X | X | X |

FIG. 20A

| Study Period | Screening Period | Treatment Period 1 | | | | | | | | | | | |
|---|---|---|---|---|---|---|---|---|---|---|---|---|---|
| **Study Week** | **-2 to 0** | **1** | **2** | **3** | **4** | **5** | **6** | **7** | **8** | **9** | **10** | **11** | **12** |
| Hunger Questionnaire | X | X | X | X | X | X | X | X | X | X | X | X | X |
| Global Hunger Questions | X | X | | | | | | | | | | | X |
| DEXA fat distribution | X | | | | | | | | | | | | X |
| Liver MRI | X | | | | | | | | | | | | X |
| REE | X | | | | | | | | | | | | X |
| SF-36 | X | | | | | | | | | | | | X |
| H4H17319P2 concentration samples | | X | X | | X | | X | | X | | X | | X |
| ADA samples | | X | | | | | | | | | | | X |
| Adverse events | X | X | X | X | X | X | X | X | X | X | X | X | X |
| Concomitant meds | X | X | X | X | X | X | X | X | X | X | X | X | X |

FIG. 20A CONTINUED

Schedule of Assessments for Treatment Period 2 and Extended Treatment Period

| Study Period | Treatment Period 2 | | | | | | | | | | | | Extended Treatment Period | | | | | | |
|---|---|---|---|---|---|---|---|---|---|---|---|---|---|---|---|---|---|---|---|
| **Study Week** | **13** | **14** | **15** | **16** | **17** | **18** | **19** | **20** | **21** | **22** | **23** | **24** | **28** | **32** | **36** | **40** | **44** | **48** | **52** |
| Informed consent/assent | X | | | | | | | | | | | X | | | | | | | |
| Inclusion/ Exclusion | X | | | | | | | | | | | | | | | | | | |
| Medical history | X | | | | | | | | | | | | | | | | | | |
| Pregnancy test | X | | | X | | | | X | | | | X | X | X | X | X | X | X | X |
| Physical examination | X | | | | | | | | | | | X | | | | | | | X |
| Weight | X | X | | X | | X | | X | | X | | X | X | X | X | X | X | X | X |
| Waist | X | X | | X | | X | | X | | X | | X | X | X | X | X | X | X | X |
| Hip | X | X | | X | | X | | X | | X | | X | X | X | X | X | X | X | X |
| Height | X | | | | | | | | | | | X | | | | | | | X |
| Patient photos | X | | | | | | | | | | | X | | | | | | | X |
| PHQ-9 & C-SSRS | X | X | X | X | X | X | X | X | X | X | X | X | X | X | X | X | X | X | X |
| H4H17319P2 SC administrations | X | X | X | X | X | X | X | X | X | X | X | X | X | X | X | X | X | X | X |
| Injection site inspection | | X | X | X | X | X | X | X | X | X | X | X | X | X | X | X | X | X | X |
| Vital signs | X | X | X | X | X | X | X | X | X | X | X | X | X | X | X | X | X | X | X |

FIG. 20B

| **Study Period** | **Treatment Period 2** | | | | | | | | | | | | **Extended Treatment Period** | | | | | | |
|---|---|---|---|---|---|---|---|---|---|---|---|---|---|---|---|---|---|---|---|
| **Study Week** | **13** | **14** | **15** | **16** | **17** | **18** | **19** | **20** | **21** | **22** | **23** | **24** | **28** | **32** | **36** | **40** | **44** | **48** | **52** |
| ECG (12-lead) | X | | | | | | | | | | | X | | | | | | | X |
| Safety laboratory tests | X | X | X | X | X | X | X | X | X | X | X | X | X | X | X | X | X | X | X |
| Hunger Questionnaire | X | X | X | X | X | X | X | X | X | X | X | X | X | X | X | X | X | X | X |
| Global Hunger Questions | X | | | | | | | | | | | X | | | | | | | X |
| DEXA fat distribution | X | | | | | | | | | | | X | | | | | | | X |
| Liver MRI | X | | | | | | | | | | | X | | | | | | | X |
| REE | X | | | | | | | | | | | X | | | | | | | X |
| SF-36 | X | | | | | | | | | | | X | | | | | | | X |
| H4H17319P2 concentration samples | X | | X | | X | | X | | | X | | X | X | X | X | X | X | X | X |
| ADA samples | | | | | | | | | | | | X | | | | | | | X |
| Adverse events | X | X | X | X | X | X | X | X | X | X | X | X | X | X | X | X | X | X | X |
| Concomitant meds | X | X | X | X | X | X | X | X | X | X | X | X | X | X | X | X | X | X | X |

FIG. 20B CONTINUED

Lepr hu/hu + IgG4P Control (N=5)
Lepr hu/hu Lep-/- + IgG4P Control (N=7)
Lepr hu/hu Lep-/- + H4H17319P2 (N=8)

Blood Glucose (mg/dL)
800
600
400
200
0
0 7 14 21 28 35
Study Day
*

Body Weight (g)
80
60
40
20
0
0 7 14 21 28 35
Study Day
*

Cumulative Food Intake (g)
500
400
300
200
100
0
0 7 14 21 28 35
Study Day
*

*Lepr*$^{hu/hu}$ + IgG4$^P$ Control (N=5)
*Lepr*$^{hu/hu}$ *Lep*$^{-/-}$ + IgG4$^P$ Control (N=7)
*Lepr*$^{hu/hu}$ *Lep*$^{-/-}$ + H4H17319P2 (N=8)

Lepr hu/hu + IgG4P Control (N=7-8)
Lepr A409E/A409E + IgG4P Control (N=9-10)
Lepr A409E/A409E + H4H17319P2 (N=10)

Glucose (mg/dL)
Time (days)

Body Weight (g)
Time (days)

Food Intake (g)
Time (days)

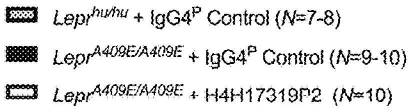
FIG. 24A
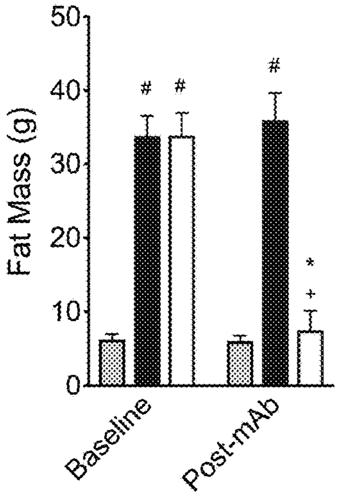
FIG. 24B
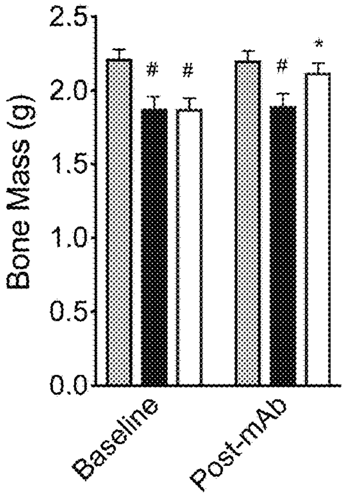
FIG. 24C
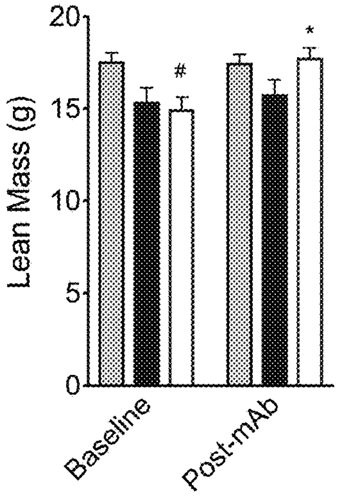

Schedule of Events Part A – Screening, Treatment, and Follow-up Periods

| | Screening | Treatment Period | | | Follow-up | | | | | | | | | |
|---|---|---|---|---|---|---|---|---|---|---|---|---|---|---|
| | | in-clinic stay | | | | | | | | | | | | |
| **Study Procedure** | **Screening Visit 1** | **Visit 2** | **Visit 3** | **Visit 4** | **Visit 5** | **Visit 6** | **Visit 7** | **Visit 8** | **Visit 9** | **Visit 10** | **Visit 11** | **Visit 12** | **Visit 13** | **End of Study Visit 14** |
| Day±window | -21 to -2 | -1 | 1 | 2 | 4±2 | 8±2 | 15±2 | 22±2 | 29±2 | 43±2 | 57±2 | 85±2 | 99±2 | 113±2 |
| Week | -3 | | | | | 1 | 2 | 3 | 4 | 6 | 8 | 12 | 14 | 16 |
| **Screening/Baseline:** | | | | | | | | | | | | | | |
| Inclusion/Exclusion | X | | X | | | | | | | | | | | |
| Informed Consent | X | | | | | | | | | | | | | |
| Medical History | X | | | | | | | | | | | | | |
| Demographics | X | | | | | | | | | | | | | |
| Clinic admission | | X | | | | | | | | | | | | |
| Clinic discharge | | | X[1] | X[2] | | | | | | | | | | |
| HIV and hepatitis testing (HBsAg, HCV) | X | | | | | | | | | | | | | |
| Randomization | | | X | | | | | | | | | | | |
| **Treatment:** | | | | | | | | | | | | | | |
| Administer Study Drug | | | X | | | | | | | | | | | |
| Concomitant Meds and Tx | X | X | X | X | X | X | X | X | X | X | X | X | X | X |
| **Safety:** | | | | | | | | | | | | | | |
| Vital Signs[3] | X | X | X | X | X | X | X | X | X | X | X | X | X | X |
| Physical Examination | X | | X | X | | | X | | X | | | | | X |
| Electrocardiogram | X | | X[18] | | X | | | | | | | | | X |
| Adverse Events | X | X | X | X | X | X | X | X | X | X | X | X | X | X |
| **Laboratory Testing[4]:** | | | | | | | | | | | | | | |
| Hematology | X | | X | | | X | X | X | X | X | X | X | X | X |
| Blood Chemistry | X | | X | | | X | X | X | X | X | X | X | X | X |
| Pregnancy Test | Serum | Urine | | | | | Urine | | Urine | | Urine | Urine | | Serum |
| FSH (women only) | X | | | | | | | | | | | | | |
| Urinalysis | X | X | | | | X | X | | X | | X | X | X | X |
| Drug screening | X | X | | | | | | | | | | | | |
| HbA1c | X | | X | | | | | | | | X | | | X |

FIG. 25

| | Screening | Treatment Period | | | Follow-up | | | | | | | | | |
|---|---|---|---|---|---|---|---|---|---|---|---|---|---|---|
| | | in-clinic stay | | | | | | | | | | | | |
| **Study Procedure** | **Screening Visit 1** | **Visit 2** | **Visit 3** | **Visit 4** | **Visit 5** | **Visit 6** | **Visit 7** | **Visit 8** | **Visit 9** | **Visit 10** | **Visit 11** | **Visit 12** | **Visit 13** | **End of Study Visit 14** |
| Day±window | -21 to -2 | -1 | 1 | 2 | 4±2 | 8±2 | 15±2 | 22±2 | 29±2 | 43±2 | 57±2 | 85±2 | 99±2 | 113±2 |
| Week | -3 | | | | | 1 | 2 | 3 | 4 | 6 | 8 | 12 | 14 | 16 |
| **Efficacy:** | | | | | | | | | | | | | | |
| Weight[5] | X | | X | X | | X | X | X | X | X | X | X | X | X |
| Height | X | | | | | | | | | | | | | |
| Waist circumference | | X | X | | | | | X | | X | | X | | X |
| Skin fold thickness[6] | | | X | | | | | X | | X | | X | | X |
| **PK/Drug Concentration and ADA Samples:** | | | | | | | | | | | | | | |
| PK/Drug conc. Sample and sLEPR, ANGPTL3 | | | X[7] | X | X | X | X | X | X | X | X | X | | X |
| ADA sample | | | X | | | | | | | | | | | X |
| **Biomarkers[4]:** | | | | | | | | | | | | | | |
| Leptin | | | X | | | X | X | | X | | | | | X |
| Insulin | | | X | | | X | X | | X | | | | | |
| Endocrine Hormones | | | X | | | X | X | | X | | | | | X |
| Biomarker samples | | | X | | | X | X | | X | | | | | X |
| Future Biomedical Research Serum and Plasma Samples | | | X | | | X | X | | X | | | | | X |
| **Genomic DNA sample[8]** | | | | | | | | | | | | | | |
| Blood sample for DNA isolation | | | X | | | | | | | | | | | |

FIG. 25 CONTINUED

Schedule of Events Part B –Prescreening, Screening, Baseline

| | Prescreening | Screening | | Baseline | |
|---|---|---|---|---|---|
| | | | | 2 Day In-clinic Stay | |
| **Study Procedure/Visit** | **0** | **1** | **2** | **3** | **4[9]** |
| Day | -60 to -14 | -32 to -14 | -29 to -14 | -14 to -2 | -13 to -1 |
| Window | | | | | |
| Week | -8 to -2 | -5 | -4 | -2 | -2 |
| **Screening/Baseline:** | | | | | |
| Inclusion/Exclusion | | X | | | |
| Informed Consent | X | | | | |
| Medical History | | X | | | |
| Demographics | | X | | | |
| Clinic admission | | | | X | |
| Clinic discharge | | | | | X |
| HIV and Hepatitis testing (HBsAg, HCV) | | X | | | |
| **Treatment:** | | | | | |
| Administer Study Drug | | | | | |
| Concomitant Meds and Tx | | X | | X | X |
| Standardized breakfast | | | | X | |
| Standardized lunch | | | | X | |
| Standardized dinner | | | | X | |
| **Safety:** | | | | | |
| Vital Signs[3] | | X | | X | X |
| Physical Examination | | X | | | |
| Electrocardiogram | | X | | | |
| Adverse Events | | X | X | X | X |

FIG. 26

| | | | | | | |
|---|---|---|---|---|---|---|
| **Laboratory Testing[4]:** | | | | | | |
| Hematology | | X | | | | |
| Blood Chemistry | | X | | | | |
| Pregnancy Test | | Serum | | | | |
| FSH (women only) | | X | | | | |
| Urinalysis | | X | | | | |
| Drug screening | | X | | | X | |
| HbA1c | | X | | | | |
| **Efficacy:** | | | | | | |
| Weight[5] | X | | | | X | |
| Height | X | | | | | |
| Waist circumference | | X | | | | |
| Skin fold thickness[6] | | X | | | | |
| Food intake measure (ad-lib breakfast) | | | | | | X |
| Food intake measure (ad-lib lunch) | | | | | | X |
| Food intake measure (ad-lib dinner) | | | | | | X |
| In-clinic appetite assessment[16] | | | | | X | |
| Daily appetite questionnaire[17] | | | | | X | |
| Subject training on in-clinic appetite assessment and daily appetite questionnaire | | | X | | | |
| DXA | | | X[13] | X | | |
| MRI | | | X[13] | X | | |
| **Biomarkers[4]:** | | | | | | |
| Endocrine Hormones | | | | | | X |
| Leptin | X | X | | | | X |

FIG. 26 CONTINUED

| | Prescreening | Screening | Baseline | | |
|---|---|---|---|---|---|
| | | | | 2 Day In-clinic Stay | |
| **Study Procedure/Visit** | **0** | **1** | **2** | **3** | **4**[9] |
| Day | -60 to -14 | -32 to -14 | -29 to -14 | -14 to -2 | -13 to -1 |
| Window | | | | | |
| Week | -8 to -2 | -5 | -4 | -2 | -2 |
| ANGPTL3 | | | | | X |
| Biomarker samples (to be specified) | | | | | X |
| Future Biomedical Research Serum and Plasma Samples | | | | | X |

FIG. 26 CONTINUED

Schedule of Events Part B – Treatment and Follow-up Periods

| | Treatment Period | | | | | | | | | | | | | | | | Follow-up | | | |
|---|---|---|---|---|---|---|---|---|---|---|---|---|---|---|---|---|---|---|---|---|
| | In-clinic[9] | | | | | In-clinic | | | | | | | | | In-clinic | | | | | |
| | | | | | | | | | | | | | | | EOT | | | | | EOS |
| Study Procedure/Visit | 5[9] | 6 | 7 | 8 | 9 | 10 | 11[9] | 12 | 13 | 14 | 15 | 16 | 17 | 18 | 19 | 20[9] | 21 | 22 | 23 | 24 |
| Day | 1 | 2 | 8 | 15 | 22 | 29[10] | 30[10] | 36 | 43 | 50 | 57 | 64 | 71 | 78 | 84[11] | 85[11] | 107 | 135 | 163 | 191 |
| Window | | | ±2 | ±2 | ±2 | ±2 | | ±2 | ±2 | ±2 | ±2 | ±2 | ±2 | ±2 | ±2 | | ±4 | ±4 | ±4 | ±4 |
| Week | | | 1 | 2 | 3 | 4 | | 5 | 6 | 7 | 8 | 9 | 10 | 11 | 12 | | 15 | 19 | 23 | 27 |
| **Screening/Baseline:** | | | | | | | | | | | | | | | | | | | | |
| Inclusion/Exclusion | X | | | | | | | | | | | | | | | | | | | |
| Clinic admission | | | | | | X | | | | | | | | | X | | | | | |
| Clinic discharge | | X | | | | | X | | | | | | | | | X | | | | |
| Randomization and cohort assignment | X | | | | | | | | | | | | | | | | | | | |
| **Treatment:** | | | | | | | | | | | | | | | | | | | | |
| Administer Study Drug[12] | X | | X | X | X | X | | X | X | X | X | X | X | X | | | | | | |
| Concomitant Meds and Tx | X | X | X | X | X | X | X | X | X | X | X | X | X | X | X | X | X | X | X | X |
| Standardized breakfast | | | | | | X | | | | | | | | | X | | | | | |
| Standardized lunch | | | | | | X | | | | | | | | | X | | | | | |
| Standardized dinner | | | | | | X | | | | | | | | | X | | | | | |
| **Safety:** | | | | | | | | | | | | | | | | | | | | |
| Vital Signs[3] | X | X | X | X | X | X | X | X | X | X | X | X | X | X | X | X | X | X | X | X |
| Physical Examination | X | | | | X | | | | X | | | | | | X | | | | | X |
| Electrocardiogram[18] | X | X | | | | | | | X | | | | | | X | | | | | X |
| Adverse Events | X | X | X | X | X | X | X | X | X | X | X | X | X | X | X | X | X | X | X | X |
| **Laboratory Testing[4]:** | | | | | | | | | | | | | | | | | | | | |
| Hematology | X | | X | X | X | X | | X | X | X | X | X | X | X | X | | X | X | X | X |
| Blood Chemistry | X | | X | X | X | X | | X | X | X | X | X | X | X | X | | X | X | X | X |
| Pregnancy Test | U | | U | U | U | U | | U | U | U | U | U | U | U | U | | U | U | U | U |
| Urinalysis | X | | X | X | | X | | | X | | X | | X | | X | | | X | | X |
| Drug screening | X | | | | | X | | | | | | | | | X | | | | | |
| HbA1c | X | | | | | | | | X | | | | | | X | | | | | X |
| **Efficacy:** | | | | | | | | | | | | | | | | | | | | |
| Weight[5] | X | | X | X | X | X | | X | X | X | X | X | X | X | X | | X | X | X | X |
| Waist circumference | X | | | | | | | | | | X | | | | X | | | | | X |

FIG. 27

| | Treatment Period | | | | | | | | | | | | | | | | Follow-up | | | |
|---|---|---|---|---|---|---|---|---|---|---|---|---|---|---|---|---|---|---|---|---|
| | In-clinic[9] | | | | | In-clinic | | | | | | | | | In-clinic | | | | | |
| **Study Procedure/Visit** | **5[9]** | **6** | **7** | **8** | **9** | **10** | **11[9]** | **12** | **13** | **14** | **15** | **16** | **17** | **18** | **EOT 19** | **20[9]** | **21** | **22** | **23** | **EOS 24** |
| Day | 1 | 2 | 8 | 15 | 22 | 29[10] | 30[10] | 36 | 43 | 50 | 57 | 64 | 71 | 78 | 84[11] | 85[11] | 107 | 135 | 163 | 191 |
| Window | | | ±2 | ±2 | ±2 | ±2 | | ±2 | ±2 | ±2 | ±2 | ±2 | ±2 | ±2 | ±2 | | ±4 | ±4 | ±4 | ±4 |
| Week | | | 1 | 2 | 3 | 4 | | 5 | 6 | 7 | 8 | 9 | 10 | 11 | 12 | | 15 | 19 | 23 | 27 |
| Skin fold thickness[6] | X | | | | | | | | | | X | | | | X | | | | | X |
| Food intake measure (ad-lib breakfast) | | | | | | | X | | | | | | | | | X | | | | |
| Food intake measure (ad-lib lunch) | | | | | | | X | | | | | | | | | X | | | | |
| Food intake measure (ad-lib dinner) | | | | | | | X | | | | | | | | | X | | | | |
| In-clinic appetite assessment[16] | | | | | | X | | | | | | | | | X | | | | | |
| Daily appetite questionnaire[17] | X | | X | X | X | X | | X | X | X | X | X | X | X | X | | X | X | X | X |
| DXA | | | | | | | | | | | | | | X[14] | | | | | | X[14] |
| MRI | | | | | | | | | | | | | | X[14] | | | | | | X[14] |
| **PK/Drug Concentration and ADA Samples:** | | | | | | | | | | | | | | | | | | | | |
| PK/Drug conc. Sample and sLEPR, ANGPTL3[15] | X[7] | X | X | X | X | X | X | X | X | X | X | X | X | X | X | | X | X | X | X |
| ADA sample | X | | | | | | | | | | | | | | X | | | | | X |
| **Biomarkers[4]:** | | | | | | | | | | | | | | | | | | | | |
| Endocrine Hormones | X | | | | | X | | | | | | | | | X | | | | | X |
| Leptin | X | | | X | X | X | | X | X | X | | X | | | X | | | | | X |
| Insulin | X | | X | X | X | X | | X | X | X | | X | | | X | | | | | X |
| Biomarker samples (to be specified) | X | | | X | | X | | | | | X | | | | X | | | X | | X |
| Future Biomedical Research Serum and Plasma Samples | X | | | X | | X | X | | | | X | | | | X | | | X | | X |
| **Optional Genomic DNA sample[8]:** | | | | | | | | | | | | | | | | | | | | |
| Blood-sample for DNA isolation | X | | | | | | | | | | | | | | | | | | | |

S = Serum; U = Urine

FIG. 27 CONTINUED

SEQUENCE LISTING

```
<160> NUMBER OF SEQ ID NOS: 120

<210> SEQ ID NO 1
<211> LENGTH: 357
<212> TYPE: DNA
<213> ORGANISM: Artificial Sequence
<220> FEATURE:
<223> OTHER INFORMATION: synthetic

<400> SEQUENCE: 1

caggtgcagc tggtggagtc tgggggaggc gtggtccagc ctgggaagtc cctgagactc      60

tcctgtgtag cgtctggatt caccttcagt tccgatgcca tgtactgggt ccgccaggct     120

ccaggcaagg ggctggaatg ggtggcagtt atttattatg atggaaatta tcaatactat     180

gaagactccg ttaagggtcg attcaccatc tccagagaca attcccagaa cacgctggat     240

ctgcaaatga acagcctgag agtcgacgac acggctgtat atttctgtgc gcgtctcaac     300

tgggattact ggtatctcga tctctggggc cgtggcaccc tggtcactgt ctcctca        357


<210> SEQ ID NO 2
<211> LENGTH: 119
<212> TYPE: PRT
<213> ORGANISM: Artificial Sequence
<220> FEATURE:
<223> OTHER INFORMATION: synthetic

<400> SEQUENCE: 2

Gln Val Gln Leu Val Glu Ser Gly Gly Gly Val Val Gln Pro Gly Lys
1               5                   10                  15

Ser Leu Arg Leu Ser Cys Val Ala Ser Gly Phe Thr Phe Ser Ser Asp
            20                  25                  30

Ala Met Tyr Trp Val Arg Gln Ala Pro Gly Lys Gly Leu Glu Trp Val
        35                  40                  45

Ala Val Ile Tyr Tyr Asp Gly Asn Tyr Gln Tyr Tyr Glu Asp Ser Val
    50                  55                  60

Lys Gly Arg Phe Thr Ile Ser Arg Asp Asn Ser Gln Asn Thr Leu Asp
65                  70                  75                  80

Leu Gln Met Asn Ser Leu Arg Val Asp Asp Thr Ala Val Tyr Phe Cys
                85                  90                  95

Ala Arg Leu Asn Trp Asp Tyr Trp Tyr Leu Asp Leu Trp Gly Arg Gly
            100                 105                 110

Thr Leu Val Thr Val Ser Ser
        115
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcacct tcagttccga tgcc 24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Ser Asp Ala
1 5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atttattatg atggaaatta tcaa 24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Tyr Tyr Asp Gly Asn Tyr Gln
1 5

<210> SEQ ID NO 7
<211> LENGTH: 36
<212> TYPE: DNA
<213> ORGANISM: Artificial Sequence
<220> FEATURE:
<223> OTHER INFORMATION: synthetic

<400> SEQUENCE: 7
gcgcgtctca actgggatta ctggtatctc gatctc 36

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Ala Arg Leu Asn Trp Asp Tyr Trp Tyr Leu Asp Leu
1 5 10

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccgtca 180
aggttcagtg gcagtggatc tgggacagat ttcactctca ccatcagcag tctgcaacct 240
gaagattttg caacttacta ctgtcaacag agttacagta cccctccgat caccttcggc 300
caagggacac gactggagat taaa 324

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Pro
85 90 95

Ile Thr Phe Gly Gln Gly Thr Arg Leu Glu Ile Lys
100 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
cagagcatta gcagctat 18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ser Ile Ser Ser Tyr
1 5

<210> SEQ ID NO 13
<211> LENGTH: 9
<212> TYPE: DNA
<213> ORGANISM: Artificial Sequence
<220> FEATURE:

<223> OTHER INFORMATION: synthetic

<400> SEQUENCE: 13 gctgcatcc 9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: synthetic

<400> SEQUENCE: 15
caacagagtt acagtacccc tccgatcacc 30

<210> SEQ ID NO 16
<211> LENGTH: 10
<212> TYPE: PRT
<213> ORGANISM: Artificial Sequence
<220> FEATURE:
<223> OTHER INFORMATION: synthetic

<400> SEQUENCE: 16

Gln Gln Ser Tyr Ser Thr Pro Pro Ile Thr
1 5 10

<210> SEQ ID NO 17
<211> LENGTH: 357
<212> TYPE: DNA
<213> ORGANISM: Artificial Sequence
<220> FEATURE:
<223> OTHER INFORMATION: synthetic

<400> SEQUENCE: 17
caggtgcagc tggtggagtc cgggggaggc gtggtccagc ctgggaggtc cctgagactc 60
tcctgtacag cgtctggatt caccttcagt agttatgcca tgtactgggt ccgccaggct 120
ccaggcaagg ggctggagtg ggtgtcagtt atatactatg atggaagtta taaatactat 180
gcagactccg tgaagggccg attcaccatc tccagagaca attccaagaa cacgctgtat 240
ctgcaaatgg acagcctgag agccgaggac acggctgtct attactgtgc gagttataac 300
tggaactact ggtacttcga tttctggggc cgtggcaccc tggtcactgt ctcctca 357

<210> SEQ ID NO 18
<211> LENGTH: 119
<212> TYPE: PRT
<213> ORGANISM: Artificial Sequence
<220> FEATURE:
<223> OTHER INFORMATION: synthetic

<400> SEQUENCE: 18

Gln Val Gln Leu Val Glu Ser Gly Gly Gly Val Val Gln Pro Gly Arg
1 5 10 15

```
Ser Leu Arg Leu Ser Cys Thr Ala Ser Gly Phe Thr Phe Ser Ser Tyr
            20                  25                  30

Ala Met Tyr Trp Val Arg Gln Ala Pro Gly Lys Gly Leu Glu Trp Val
        35                  40                  45

Ser Val Ile Tyr Tyr Asp Gly Ser Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Ser Tyr Asn Trp Asn Tyr Trp Tyr Phe Asp Phe Trp Gly Arg Gly
            100                 105                 110

Thr Leu Val Thr Val Ser Ser
        115


<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19

ggattcacct tcagtagtta tgcc                                            24


<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Ser Ser Tyr Ala
1               5


<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21

atatactatg atggaagtta taaa                                            24


<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Tyr Tyr Asp Gly Ser Tyr Lys
1               5


<210> SEQ ID NO 23
<211> LENGTH: 36
<212> TYPE: DNA
<213> ORGANISM: Artificial Sequence
<220> FEATURE:
<223> OTHER INFORMATION: synthetic
```

<400> SEQUENCE: 23
gcgagttata actggaacta ctggtacttc gatttc 36

<210> SEQ ID NO 24
<211> LENGTH: 12
<212> TYPE: PRT
<213> ORGANISM: Artificial Sequence
<220> FEATURE:
<223> OTHER INFORMATION: synthetic

<400> SEQUENCE: 24

Ala Ser Tyr Asn Trp Asn Tyr Trp Tyr Phe Asp Phe
1 5 10

<210> SEQ ID NO 25
<211> LENGTH: 357
<212> TYPE: DNA
<213> ORGANISM: Artificial Sequence
<220> FEATURE:
<223> OTHER INFORMATION: synthetic

<400> SEQUENCE: 25
caggtgcagc tggtggagtc tgggggaagc gtggtccagc ctgggaggtc cctgagactc 60
tcctgtgcag cgtctggatt caccttcagt acatatgcca tgtactgggt ccgccagact 120
ccaggcaagg ggctggagtg ggtggctgtt ttatactctg atggaagtaa taaatactat 180
atagactccg tgaagggccg attcaccatc tccagagaca cttccacgaa cactctgtat 240
ctgcaaatga gcagcctgcg agccgacgac tcggctctat attactgtgc gcgtctcaac 300
tgggattact ggtacttcga tctctggggc cgtggcaccc tggtcactgt ctcctca 357

<210> SEQ ID NO 26
<211> LENGTH: 119
<212> TYPE: PRT
<213> ORGANISM: Artificial Sequence
<220> FEATURE:
<223> OTHER INFORMATION: synthetic

<400> SEQUENCE: 26

Gln Val Gln Leu Val Glu Ser Gly Gly Ser Val Val Gln Pro Gly Arg
1 5 10 15

Ser Leu Arg Leu Ser Cys Ala Ala Ser Gly Phe Thr Phe Ser Thr Tyr
20 25 30

Ala Met Tyr Trp Val Arg Gln Thr Pro Gly Lys Gly Leu Glu Trp Val
35 40 45

Ala Val Leu Tyr Ser Asp Gly Ser Asn Lys Tyr Tyr Ile Asp Ser Val
50 55 60

Lys Gly Arg Phe Thr Ile Ser Arg Asp Thr Ser Thr Asn Thr Leu Tyr
65 70 75 80

Leu Gln Met Ser Ser Leu Arg Ala Asp Asp Ser Ala Leu Tyr Tyr Cys
85 90 95

Ala Arg Leu Asn Trp Asp Tyr Trp Tyr Phe Asp Leu Trp Gly Arg Gly
100 105 110

Thr Leu Val Thr Val Ser Ser
115

<210> SEQ ID NO 27
<211> LENGTH: 24
<212> TYPE: DNA
<213> ORGANISM: Artificial Sequence
<220> FEATURE:

<223> OTHER INFORMATION: synthetic

<400> SEQUENCE: 27
ggattcacct tcagtacata tgcc 24

<210> SEQ ID NO 28
<211> LENGTH: 8
<212> TYPE: PRT
<213> ORGANISM: Artificial Sequence
<220> FEATURE:
<223> OTHER INFORMATION: synthetic

<400> SEQUENCE: 28

Gly Phe Thr Phe Ser Thr Tyr Ala
1 5

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
ttatactctg atggaagtaa taaa 24

<210> SEQ ID NO 30
<211> LENGTH: 8
<212> TYPE: PRT
<213> ORGANISM: Artificial Sequence
<220> FEATURE:
<223> OTHER INFORMATION: synthetic

<400> SEQUENCE: 30

Leu Tyr Ser Asp Gly Ser Asn Lys
1 5

<210> SEQ ID NO 31
<211> LENGTH: 36
<212> TYPE: DNA
<213> ORGANISM: Artificial Sequence
<220> FEATURE:
<223> OTHER INFORMATION: synthetic

<400> SEQUENCE: 31
gcgcgtctca actgggatta ctggtacttc gatctc 36

<210> SEQ ID NO 32
<211> LENGTH: 12
<212> TYPE: PRT
<213> ORGANISM: Artificial Sequence
<220> FEATURE:
<223> OTHER INFORMATION: synthetic

<400> SEQUENCE: 32

Ala Arg Leu Asn Trp Asp Tyr Trp Tyr Phe Asp Leu
1 5 10

<210> SEQ ID NO 33
<211> LENGTH: 357
<212> TYPE: DNA
<213> ORGANISM: Artificial Sequence
<220> FEATURE:
<223> OTHER INFORMATION: synthetic

<400> SEQUENCE: 33

```
caggtgcagc tggtggagtc tgggggaggc gtggtccagc ctgggaggtc cctgagactc      60

tcctgtgaag cgtctggatt cagcagcagt gacaatgcca tgtactgggt ccgccaggct     120

ccaggcaagg ggctggagtg ggtgtcagtt atatatcatg atggaagtta taaatactat     180

gaagactccg tgaagggccg attcaccatc gccagagaca attccaagaa cacgctttat     240

ttgcaaatga acagcctgag agccgaggac acggctgtat attactgtgc gaggtataac     300

tggaaccact ggtacttcga tgtctggggc cgtggcaccc tggtcactgt ctcctca        357
```

<210> SEQ ID NO 34
<211> LENGTH: 119
<212> TYPE: PRT
<213> ORGANISM: Artificial Sequence
<220> FEATURE:
<223> OTHER INFORMATION: synthetic

<400> SEQUENCE: 34

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Ser Ser Ser Asp Asn
            20                  25                  30

Ala Met Tyr Trp Val Arg Gln Ala Pro Gly Lys Gly Leu Glu Trp Val
        35                  40                  45

Ser Val Ile Tyr His Asp Gly Ser Tyr Lys Tyr Tyr Glu Asp Ser Val
    50                  55                  60

Lys Gly Arg Phe Thr Ile Ala Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Trp Asn His Trp Tyr Phe Asp Val Trp Gly Arg Gly
            100                 105                 110

Thr Leu Val Thr Val Ser Ser
        115
```

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35

```
ggattcagca gcagtgacaa tgcc                                             24
```

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

```
Gly Phe Ser Ser Ser Asp Asn Ala
1               5
```

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37
atatatcatg atggaagtta taaa 24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Tyr His Asp Gly Ser Tyr Lys
1 5

<210> SEQ ID NO 39
<211> LENGTH: 36
<212> TYPE: DNA
<213> ORGANISM: Artificial Sequence
<220> FEATURE:
<223> OTHER INFORMATION: synthetic

<400> SEQUENCE: 39
gcgaggtata actggaacca ctggtacttc gatgtc 36

<210> SEQ ID NO 40
<211> LENGTH: 12
<212> TYPE: PRT
<213> ORGANISM: Artificial Sequence
<220> FEATURE:
<223> OTHER INFORMATION: synthetic

<400> SEQUENCE: 40

Ala Arg Tyr Asn Trp Asn His Trp Tyr Phe Asp Val
1 5 10

<210> SEQ ID NO 41
<211> LENGTH: 366
<212> TYPE: DNA
<213> ORGANISM: Artificial Sequence
<220> FEATURE:
<223> OTHER INFORMATION: synthetic

<400> SEQUENCE: 41
caggtgcagc tggtggagtc tgggggaggc gtggtccagc ctgggaggtc cctgagactc 60
tcctgtgcag cctctggatt caccttcagt acctatggca tgcactgggt ccgccaggct 120
ccaggcaagg ggctggagtg ggtgtcagtt atatcatatg acgaaagtaa taagtactat 180
gcagactccg tgaagggccg attcaccatt tctagagaca attccaagaa cgcgctgtat 240
ttacaaatga acagcctgag aaatgaggac acggctgtgt attactgtgc gagagatcgg 300
ccttttggat tggttaccgg atggttcgac ccctggggcc agggaaccct ggtcaccgtc 360
tcctca 366

<210> SEQ ID NO 42
<211> LENGTH: 122
<212> TYPE: PRT
<213> ORGANISM: Artificial Sequence
<220> FEATURE:
<223> OTHER INFORMATION: synthetic

<400> SEQUENCE: 42

Gln Val Gln Leu Val Glu Ser Gly Gly Gly Val Val Gln Pro Gly Arg
1 5 10 15

```
Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ser Val Ile Ser Tyr Asp Glu Ser Asn Lys Tyr Tyr Ala Asp Ser Val
    50                  55                  60

Lys Gly Arg Phe Thr Ile Ser Arg Asp Asn Ser Lys Asn Ala Leu Tyr
65                  70                  75                  80

Leu Gln Met Asn Ser Leu Arg Asn Glu Asp Thr Ala Val Tyr Tyr Cys
                85                  90                  95

Ala Arg Asp Arg Pro Phe Gly Leu Val Thr Gly Trp Phe Asp Pro Trp
            100                 105                 110

Gly Gln Gly Thr Leu Val Thr Val Ser Ser
        115                 120


<210> SEQ ID NO 43
<211> LENGTH: 24
<212> TYPE: DNA
<213> ORGANISM: Artificial Sequence
<220> FEATURE:
<223> OTHER INFORMATION: synthetic

<400> SEQUENCE: 43

ggattcacct tcagtaccta tggc                                            24


<210> SEQ ID NO 44
<211> LENGTH: 8
<212> TYPE: PRT
<213> ORGANISM: Artificial Sequence
<220> FEATURE:
<223> OTHER INFORMATION: synthetic

<400> SEQUENCE: 44

Gly Phe Thr Phe Ser Thr Tyr Gly
1               5


<210> SEQ ID NO 45
<211> LENGTH: 24
<212> TYPE: DNA
<213> ORGANISM: Artificial Sequence
<220> FEATURE:
<223> OTHER INFORMATION: synthetic

<400> SEQUENCE: 45

atatcatatg acgaaagtaa taag                                            24


<210> SEQ ID NO 46
<211> LENGTH: 8
<212> TYPE: PRT
<213> ORGANISM: Artificial Sequence
<220> FEATURE:
<223> OTHER INFORMATION: synthetic

<400> SEQUENCE: 46

Ile Ser Tyr Asp Glu Ser Asn Lys
1               5


<210> SEQ ID NO 47
<211> LENGTH: 45
<212> TYPE: DNA
<213> ORGANISM: Artificial Sequence
<220> FEATURE:
<223> OTHER INFORMATION: synthetic
```

<400> SEQUENCE: 47
gcgagagatc ggccttttgg attggttacc ggatggttcg acccc 45

<210> SEQ ID NO 48
<211> LENGTH: 15
<212> TYPE: PRT
<213> ORGANISM: Artificial Sequence
<220> FEATURE:
<223> OTHER INFORMATION: synthetic

<400> SEQUENCE: 48

Ala Arg Asp Arg Pro Phe Gly Leu Val Thr Gly Trp Phe Asp Pro
1 5 10 15

<210> SEQ ID NO 49
<211> LENGTH: 360
<212> TYPE: DNA
<213> ORGANISM: Artificial Sequence
<220> FEATURE:
<223> OTHER INFORMATION: synthetic

<400> SEQUENCE: 49
caggtgcagc tggtggagtc tgggggaggc gtggtccagc ctgggaggtc cctgagactc 60
tcctgtgcag cgtctggatt cagtttcaat acctatggca tgcactgggt ccgccaggct 120
ccaggcaagg ggctggagtg ggtgacaatt atatggtatg atggaagtat taaatactat 180
gcagactccg tgaagggccg attcaccatc tccagagaca attccaagaa cacgctgtat 240
ctgcaaatga acagcctgag agccgaggac acggctgtgt attattgtgc gagaggtgga 300
tatagtggct acctctactt tgactactgg ggccagggaa ccctggtcac cgtctcctca 360

<210> SEQ ID NO 50
<211> LENGTH: 120
<212> TYPE: PRT
<213> ORGANISM: Artificial Sequence
<220> FEATURE:
<223> OTHER INFORMATION: synthetic

<400> SEQUENCE: 50

Gln Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Asn Thr Tyr
20 25 30

Gly Met His Trp Val Arg Gln Ala Pro Gly Lys Gly Leu Glu Trp Val
35 40 45

Thr Ile Ile Trp Tyr Asp Gly Ser Ile Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Gly Tyr Ser Gly Tyr Leu Tyr Phe Asp Tyr Trp Gly Gln
100 105 110

Gly Thr Leu Val Thr Val Ser Ser
115 120

<210> SEQ ID NO 51
<211> LENGTH: 24
<212> TYPE: DNA
<213> ORGANISM: Artificial Sequence
<220> FEATURE:

<223> OTHER INFORMATION: synthetic

<400> SEQUENCE: 51
ggattcagtt tcaataccta tggc 24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Ser Phe Asn Thr Tyr Gly
1 5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
atatggtatg atggaagtat taaa 24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Ile Trp Tyr Asp Gly Ser Ile Lys
1 5

<210> SEQ ID NO 55
<211> LENGTH: 39
<212> TYPE: DNA
<213> ORGANISM: Artificial Sequence
<220> FEATURE:
<223> OTHER INFORMATION: synthetic

<400> SEQUENCE: 55
gcgagaggtg gatatagtgg ctacctctac tttgactac 39

<210> SEQ ID NO 56
<211> LENGTH: 13
<212> TYPE: PRT
<213> ORGANISM: Artificial Sequence
<220> FEATURE:
<223> OTHER INFORMATION: synthetic

<400> SEQUENCE: 56

Ala Arg Gly Gly Tyr Ser Gly Tyr Leu Tyr Phe Asp Tyr
1 5 10

<210> SEQ ID NO 57
<211> LENGTH: 372
<212> TYPE: DNA
<213> ORGANISM: Artificial Sequence
<220> FEATURE:
<223> OTHER INFORMATION: synthetic

<400> SEQUENCE: 57

```
caggtgcagc tgcaggagtc gggcccagga ctggtgaagc cttcacagac cctgtccctc      60

acctgcactg tctctggtgg ctccatcagc agcggtggtg actactggag ctggatccgc     120

cagctcccag ggaagggcct ggagtggatt gggtacatct attacagtgg gagcgcctac     180

tataatccgt ccctcaagag tcgaggtacc atatcaatag acacgtctaa gaaccagttc     240

tccctgaagc tgacctctgt gactgccgcg gacacggccg tatatttctg tgtgaaatta     300

cgatttttgg agtggttctt ggggggctgg ttcggcccct ggggccaggg aaccctggtc     360

accgtctcct ca                                                          372


<210> SEQ ID NO 58
<211> LENGTH: 124
<212> TYPE: PRT
<213> ORGANISM: Artificial Sequence
<220> FEATURE:
<223> OTHER INFORMATION: synthetic

<400> SEQUENCE: 58

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Asp Tyr Trp Ser Trp Ile Arg Gln Leu Pro Gly Lys Gly Leu Glu
        35                  40                  45

Trp Ile Gly Tyr Ile Tyr Tyr Ser Gly Ser Ala Tyr Tyr Asn Pro Ser
    50                  55                  60

Leu Lys Ser Arg Gly Thr Ile Ser Ile Asp Thr Ser Lys Asn Gln Phe
65                  70                  75                  80

Ser Leu Lys Leu Thr Ser Val Thr Ala Ala Asp Thr Ala Val Tyr Phe
                85                  90                  95

Cys Val Lys Leu Arg Phe Leu Glu Trp Phe Leu Gly Gly Trp Phe Gly
            100                 105                 110

Pro Trp Gly Gln Gly Thr Leu Val Thr Val Ser Ser
        115                 120


<210> SEQ ID NO 59
<211> LENGTH: 30
<212> TYPE: DNA
<213> ORGANISM: Artificial Sequence
<220> FEATURE:
<223> OTHER INFORMATION: synthetic

<400> SEQUENCE: 59

ggtggctcca tcagcagcgg tggtgactac                                       30


<210> SEQ ID NO 60
<211> LENGTH: 10
<212> TYPE: PRT
<213> ORGANISM: Artificial Sequence
<220> FEATURE:
<223> OTHER INFORMATION: synthetic

<400> SEQUENCE: 60

Gly Gly Ser Ile Ser Ser Gly Gly Asp Tyr
1               5                   10


<210> SEQ ID NO 61
<211> LENGTH: 21
<212> TYPE: DNA
<213> ORGANISM: Artificial Sequence
<220> FEATURE:
```

<223> OTHER INFORMATION: synthetic

<400> SEQUENCE: 61
atctattaca gtgggagcgc c 21

<210> SEQ ID NO 62
<211> LENGTH: 7
<212> TYPE: PRT
<213> ORGANISM: Artificial Sequence
<220> FEATURE:
<223> OTHER INFORMATION: synthetic

<400> SEQUENCE: 62

Ile Tyr Tyr Ser Gly Ser Ala
1 5

<210> SEQ ID NO 63
<211> LENGTH: 48
<212> TYPE: DNA
<213> ORGANISM: Artificial Sequence
<220> FEATURE:
<223> OTHER INFORMATION: synthetic

<400> SEQUENCE: 63
gtgaaattac gatttttgga gtggttcttg gggggctggt tcggcccc 48

<210> SEQ ID NO 64
<211> LENGTH: 16
<212> TYPE: PRT
<213> ORGANISM: Artificial Sequence
<220> FEATURE:
<223> OTHER INFORMATION: synthetic

<400> SEQUENCE: 64

Val Lys Leu Arg Phe Leu Glu Trp Phe Leu Gly Gly Trp Phe Gly Pro
1 5 10 15

<210> SEQ ID NO 65
<211> LENGTH: 351
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tgggggaggc ttggtacagc cgggggggtc cctgagactc 60
tcctgtgcag cctctggatt cacctttagc aactatggca tgacctgggt ccgccaggct 120
ccagggaagg gcctggaatg ggtctcagct attactggtg gtggtggtag cacatactac 180
tcaaactccg tgaagggccg gttcaccatc tccagagaca attccaagaa cacggtgtat 240
ctgcgaatga acagtgtgag agccgaggac acggccgtat attactgtgc gaaatataag 300
tggaacttcg tggacgactg gggccaggga accacggtca ccgtctcctc a 351

<210> SEQ ID NO 66
<211> LENGTH: 117
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Gly
1 5 10 15

-continued

```
Ser Leu Arg Leu Ser Cys Ala Ala Ser Gly Phe Thr Phe Ser Asn Tyr
            20                  25                  30

Gly Met Thr Trp Val Arg Gln Ala Pro Gly Lys Gly Leu Glu Trp Val
        35                  40                  45

Ser Ala Ile Thr Gly Gly Gly Gly Ser Thr Tyr Tyr Ser Asn Ser Val
    50                  55                  60

Lys Gly Arg Phe Thr Ile Ser Arg Asp Asn Ser Lys Asn Thr Val Tyr
65                  70                  75                  80

Leu Arg Met Asn Ser Val Arg Ala Glu Asp Thr Ala Val Tyr Tyr Cys
                85                  90                  95

Ala Lys Tyr Lys Trp Asn Phe Val Asp Asp Trp Gly Gln Gly Thr Thr
            100                 105                 110

Val Thr Val Ser Ser
        115


<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67

ggattcacct ttagcaacta tggc                                            24


<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Ser Asn Tyr Gly
1               5


<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69

attactggtg gtggtggtag caca                                            24


<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Thr Gly Gly Gly Gly Ser Thr
1               5


<210> SEQ ID NO 71
<211> LENGTH: 30
<212> TYPE: DNA
<213> ORGANISM: Artificial Sequence
<220> FEATURE:
<223> OTHER INFORMATION: synthetic
```

<400> SEQUENCE: 71
gcgaaatata agtggaactt cgtggacgac 30

<210> SEQ ID NO 72
<211> LENGTH: 10
<212> TYPE: PRT
<213> ORGANISM: Artificial Sequence
<220> FEATURE:
<223> OTHER INFORMATION: synthetic

<400> SEQUENCE: 72

Ala Lys Tyr Lys Trp Asn Phe Val Asp Asp
1 5 10

<210> SEQ ID NO 73
<211> LENGTH: 360
<212> TYPE: DNA
<213> ORGANISM: Artificial Sequence
<220> FEATURE:
<223> OTHER INFORMATION: synthetic

<400> SEQUENCE: 73
gaggtgcagc tggtggagtc tgggggaggc ttggtacagc ctggggggtc cctgagactc 60
tcctgtgttg cctctggatt caccttcaat aaatacgaca tgcactgggt ccgccaaact 120
actggaaaag gtctagagtg ggtctcaggt attgatactg atggtgacac atactatcca 180
ggctccgtga agggccgatt caccatctcc agagaaaatg ccgagaactc cctgtatctt 240
caaatgaacg gcctgagagt cggggacacg gctgtgtatt actgtgcaag atggccttgg 300
agtggtttct atggtgcttt tgatatctgg ggccaaggga caatggtcac cgtctcttca 360

<210> SEQ ID NO 74
<211> LENGTH: 120
<212> TYPE: PRT
<213> ORGANISM: Artificial Sequence
<220> FEATURE:
<223> OTHER INFORMATION: synthetic

<400> SEQUENCE: 74

Glu Val Gln Leu Val Glu Ser Gly Gly Gly Leu Val Gln Pro Gly Gly
1 5 10 15

Ser Leu Arg Leu Ser Cys Val Ala Ser Gly Phe Thr Phe Asn Lys Tyr
20 25 30

Asp Met His Trp Val Arg Gln Thr Thr Gly Lys Gly Leu Glu Trp Val
35 40 45

Ser Gly Ile Asp Thr Asp Gly Asp Thr Tyr Tyr Pro Gly Ser Val Lys
50 55 60

Gly Arg Phe Thr Ile Ser Arg Glu Asn Ala Glu Asn Ser Leu Tyr Leu
65 70 75 80

Gln Met Asn Gly Leu Arg Val Gly Asp Thr Ala Val Tyr Tyr Cys Ala
85 90 95

Arg Trp Pro Trp Ser Gly Phe Tyr Gly Ala Phe Asp Ile Trp Gly Gln
100 105 110

Gly Thr Met Val Thr Val Ser Ser
115 120

<210> SEQ ID NO 75
<211> LENGTH: 24
<212> TYPE: DNA
<213> ORGANISM: Artificial Sequence
<220> FEATURE:

<223> OTHER INFORMATION: synthetic

<400> SEQUENCE: 75
ggattcacct tcaataaata cgac 24

<210> SEQ ID NO 76
<211> LENGTH: 8
<212> TYPE: PRT
<213> ORGANISM: Artificial Sequence
<220> FEATURE:
<223> OTHER INFORMATION: synthetic

<400> SEQUENCE: 76

Gly Phe Thr Phe Asn Lys Tyr Asp
1 5

<210> SEQ ID NO 77
<211> LENGTH: 21
<212> TYPE: DNA
<213> ORGANISM: Artificial Sequence
<220> FEATURE:
<223> OTHER INFORMATION: synthetic

<400> SEQUENCE: 77
attgatactg atggtgacac a 21

<210> SEQ ID NO 78
<211> LENGTH: 7
<212> TYPE: PRT
<213> ORGANISM: Artificial Sequence
<220> FEATURE:
<223> OTHER INFORMATION: synthetic

<400> SEQUENCE: 78

Ile Asp Thr Asp Gly Asp Thr
1 5

<210> SEQ ID NO 79
<211> LENGTH: 42
<212> TYPE: DNA
<213> ORGANISM: Artificial Sequence
<220> FEATURE:
<223> OTHER INFORMATION: synthetic

<400> SEQUENCE: 79
gcaagatggc cttggagtgg tttctatggt gcttttgata tc 42

<210> SEQ ID NO 80
<211> LENGTH: 14
<212> TYPE: PRT
<213> ORGANISM: Artificial Sequence
<220> FEATURE:
<223> OTHER INFORMATION: synthetic

<400> SEQUENCE: 80

Ala Arg Trp Pro Trp Ser Gly Phe Tyr Gly Ala Phe Asp Ile
1 5 10

<210> SEQ ID NO 81
<211> LENGTH: 366
<212> TYPE: DNA
<213> ORGANISM: Artificial Sequence
<220> FEATURE:
<223> OTHER INFORMATION: synthetic

<400> SEQUENCE: 81

-continued

```
caggtgcagc tgcaggagtc gggcccagga ctggtgaagc cttcacagac cctgtccctc      60

acctgcactg tctctggtgg ctccatcagc agtggtaatt actactggaa ctggatccgc     120

caacagccag gagagggcct ggagtggatt gcttacatct atcacaatgg ggtcaccaac     180

ttcaatccgt ccctcaagag tcgacttact atatcagtag acacgtctaa gactcagttc     240

tccctgaagt tgaggtctgt gactgccgcg gacacggccg tttattactg tgcgagatca     300

ggcagctggt tcgagaactg gtacttcgat ctctggggcc gtggcaccct ggtcactgtc     360

tcctca                                                                366
```

<210> SEQ ID NO 82
<211> LENGTH: 122
<212> TYPE: PRT
<213> ORGANISM: Artificial Sequence
<220> FEATURE:
<223> OTHER INFORMATION: synthetic

<400> SEQUENCE: 82

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asn Tyr Tyr Trp Asn Trp Ile Arg Gln Gln Pro Gly Glu Gly Leu Glu
        35                  40                  45

Trp Ile Ala Tyr Ile Tyr His Asn Gly Val Thr Asn Phe Asn Pro Ser
    50                  55                  60

Leu Lys Ser Arg Leu Thr Ile Ser Val Asp Thr Ser Lys Thr Gln Phe
65                  70                  75                  80

Ser Leu Lys Leu Arg Ser Val Thr Ala Ala Asp Thr Ala Val Tyr Tyr
                85                  90                  95

Cys Ala Arg Ser Gly Ser Trp Phe Glu Asn Trp Tyr Phe Asp Leu Trp
            100                 105                 110

Gly Arg Gly Thr Leu Val Thr Val Ser Ser
        115                 120
```

<210> SEQ ID NO 83
<211> LENGTH: 30
<212> TYPE: DNA
<213> ORGANISM: Artificial Sequence
<220> FEATURE:
<223> OTHER INFORMATION: synthetic

<400> SEQUENCE: 83

```
ggtggctcca tcagcagtgg taattactac                                       30
```

<210> SEQ ID NO 84
<211> LENGTH: 10
<212> TYPE: PRT
<213> ORGANISM: Artificial Sequence
<220> FEATURE:
<223> OTHER INFORMATION: synthetic

<400> SEQUENCE: 84

```
Gly Gly Ser Ile Ser Ser Gly Asn Tyr Tyr
1               5                   10
```

<210> SEQ ID NO 85
<211> LENGTH: 21
<212> TYPE: DNA
<213> ORGANISM: Artificial Sequence
<220> FEATURE:

<223> OTHER INFORMATION: synthetic

<400> SEQUENCE: 85
atctatcaca atggggtcac c 21

<210> SEQ ID NO 86
<211> LENGTH: 7
<212> TYPE: PRT
<213> ORGANISM: Artificial Sequence
<220> FEATURE:
<223> OTHER INFORMATION: synthetic

<400> SEQUENCE: 86

Ile Tyr His Asn Gly Val Thr
1 5

<210> SEQ ID NO 87
<211> LENGTH: 42
<212> TYPE: DNA
<213> ORGANISM: Artificial Sequence
<220> FEATURE:
<223> OTHER INFORMATION: synthetic

<400> SEQUENCE: 87
gcgagatcag gcagctggtt cgagaactgg tacttcgatc tc 42

<210> SEQ ID NO 88
<211> LENGTH: 14
<212> TYPE: PRT
<213> ORGANISM: Artificial Sequence
<220> FEATURE:
<223> OTHER INFORMATION: synthetic

<400> SEQUENCE: 88

Ala Arg Ser Gly Ser Trp Phe Glu Asn Trp Tyr Phe Asp Leu
1 5 10

<210> SEQ ID NO 89
<211> LENGTH: 324
<212> TYPE: DNA
<213> ORGANISM: Artificial Sequence
<220> FEATURE:
<223> OTHER INFORMATION: synthetic

<400> SEQUENCE: 89
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcaccttg gacgttcggc 300
caagggacca aggtggaaat caaa 324

<210> SEQ ID NO 90
<211> LENGTH: 108
<212> TYPE: PRT
<213> ORGANISM: Artificial Sequence
<220> FEATURE:
<223> OTHER INFORMATION: synthetic

<400> SEQUENCE: 90

Glu Ile Val Leu Thr Gln Ser Pro Gly Thr Leu Ser Leu Ser Pro Gly
1 5 10 15

-continued

```
Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 91
<211> LENGTH: 21
<212> TYPE: DNA
<213> ORGANISM: Artificial Sequence
<220> FEATURE:
<223> OTHER INFORMATION: synthetic

<400> SEQUENCE: 91
cagagtgtta gcagcagcta c 21

<210> SEQ ID NO 92
<211> LENGTH: 7
<212> TYPE: PRT
<213> ORGANISM: Artificial Sequence
<220> FEATURE:
<223> OTHER INFORMATION: synthetic

<400> SEQUENCE: 92

```
Gln Ser Val Ser Ser Ser Tyr
1               5
```

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 ggtgcatcc 9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

```
Gly Ala Ser
1
```

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
cagcagtatg gtagctcacc ttggacg 27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Gln Gln Tyr Gly Ser Ser Pro Trp Thr
1 5

<210> SEQ ID NO 97
<211> LENGTH: 360
<212> TYPE: DNA
<213> ORGANISM: Artificial Sequence
<220> FEATURE:
<223> OTHER INFORMATION: synthetic

<400> SEQUENCE: 97
caggtgcagc tgcaggagtc gggcccagga ctggtgaagc cttcggagac cctgtccctc 60
acctgcactg tctctggtgg ctccatcagt aattcctact ggagctggat ccggcagccc 120
ccagggaagg gactggagtg gattggatat gtctattccc gtgggaacac caagtacaac 180
ccctccctca cgagtcgagt caccatgtca tttgacacgt ccaagaacca gttctccctg 240
aaactgaggt ctgtgaccgc cgcagacacg gccgtgtatt actgtgcgag aagcagcagc 300
tggtacgagg actggtactt cgatctctgg ggccgtggca ccctggtcac tgtctcctca 360

<210> SEQ ID NO 98
<211> LENGTH: 120
<212> TYPE: PRT
<213> ORGANISM: Artificial Sequence
<220> FEATURE:
<223> OTHER INFORMATION: synthetic

<400> SEQUENCE: 98

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Asn Ser
20 25 30

Tyr Trp Ser Trp Ile Arg Gln Pro Pro Gly Lys Gly Leu Glu Trp Ile
35 40 45

Gly Tyr Val Tyr Ser Arg Gly Asn Thr Lys Tyr Asn Pro Ser Leu Thr
50 55 60

Ser Arg Val Thr Met Ser Phe Asp Thr Ser Lys Asn Gln Phe Ser Leu
65 70 75 80

Lys Leu Arg Ser Val Thr Ala Ala Asp Thr Ala Val Tyr Tyr Cys Ala
85 90 95

Arg Ser Ser Ser Trp Tyr Glu Asp Trp Tyr Phe Asp Leu Trp Gly Arg
100 105 110

Gly Thr Leu Val Thr Val Ser Ser
115 120

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
ggtggctcca tcagtaattc ctac 24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Gly Ser Ile Ser Asn Ser Tyr
1 5

<210> SEQ ID NO 101
<211> LENGTH: 21
<212> TYPE: DNA
<213> ORGANISM: Artificial Sequence
<220> FEATURE:
<223> OTHER INFORMATION: synthetic

<400> SEQUENCE: 101
gtctattccc gtgggaacac c 21

<210> SEQ ID NO 102
<211> LENGTH: 7
<212> TYPE: PRT
<213> ORGANISM: Artificial Sequence
<220> FEATURE:
<223> OTHER INFORMATION: synthetic

<400> SEQUENCE: 102

Val Tyr Ser Arg Gly Asn Thr
1 5

<210> SEQ ID NO 103
<211> LENGTH: 42
<212> TYPE: DNA
<213> ORGANISM: Artificial Sequence
<220> FEATURE:
<223> OTHER INFORMATION: synthetic

<400> SEQUENCE: 103
gcgagaagca gcagctggta cgaggactgg tacttcgatc tc 42

<210> SEQ ID NO 104
<211> LENGTH: 14
<212> TYPE: PRT
<213> ORGANISM: Artificial Sequence
<220> FEATURE:
<223> OTHER INFORMATION: synthetic

<400> SEQUENCE: 104

Ala Arg Ser Ser Ser Trp Tyr Glu Asp Trp Tyr Phe Asp Leu
1 5 10

<210> SEQ ID NO 105
<211> LENGTH: 354
<212> TYPE: DNA
<213> ORGANISM: Artificial Sequence
<220> FEATURE:
<223> OTHER INFORMATION: synthetic

<400> SEQUENCE: 105
caggtgcagc tacagcagtg gggcgcaggg ctgtttaagc cttcggagac cctgtccctc 60
acctgcgatg tctatggtgg gtccttcaga ggttattatt ggagttggat ccgccagccc 120
ccagggaagg ggctggagtg gattggggaa atcagttata gtggtttcac caattacaac 180
ccgtccctca agagtcgagt catcatatca atagatacgt ccaagaacca gttctccctg 240
aagatgagct ctgtgaccgc cgcggacacg gctgtttatt actgtgcgag agttacctat 300
ggttatggga cctttgatta ttggggccag ggaaccctgg tcaccgtctc ctca 354

<210> SEQ ID NO 106
<211> LENGTH: 118
<212> TYPE: PRT
<213> ORGANISM: Artificial Sequence
<220> FEATURE:
<223> OTHER INFORMATION: synthetic

<400> SEQUENCE: 106

Gln Val Gln Leu Gln Gln Trp Gly Ala Gly Leu Phe Lys Pro Ser Glu
1 5 10 15

Thr Leu Ser Leu Thr Cys Asp Val Tyr Gly Gly Ser Phe Arg Gly Tyr
20 25 30

Tyr Trp Ser Trp Ile Arg Gln Pro Pro Gly Lys Gly Leu Glu Trp Ile
35 40 45

Gly Glu Ile Ser Tyr Ser Gly Phe Thr Asn Tyr Asn Pro Ser Leu Lys
50 55 60

Ser Arg Val Ile Ile Ser Ile Asp Thr Ser Lys Asn Gln Phe Ser Leu
65 70 75 80

Lys Met Ser Ser Val Thr Ala Ala Asp Thr Ala Val Tyr Tyr Cys Ala
85 90 95

Arg Val Thr Tyr Gly Tyr Gly Thr Phe Asp Tyr Trp Gly Gln Gly Thr
100 105 110

Leu Val Thr Val Ser Ser
115

<210> SEQ ID NO 107
<211> LENGTH: 24
<212> TYPE: DNA
<213> ORGANISM: Artificial Sequence
<220> FEATURE:
<223> OTHER INFORMATION: synthetic

<400> SEQUENCE: 107
ggtgggtcct tcagaggtta ttat 24

<210> SEQ ID NO 108
<211> LENGTH: 8
<212> TYPE: PRT
<213> ORGANISM: Artificial Sequence
<220> FEATURE:
<223> OTHER INFORMATION: synthetic

<400> SEQUENCE: 108

Gly Gly Ser Phe Arg Gly Tyr Tyr
1 5

<210> SEQ ID NO 109
<211> LENGTH: 21
<212> TYPE: DNA
<213> ORGANISM: Artificial Sequence
<220> FEATURE:
<223> OTHER INFORMATION: synthetic

<400> SEQUENCE: 109
atcagttata gtggtttcac c 21

```
<210> SEQ ID NO 110
<211> LENGTH: 7
<212> TYPE: PRT
<213> ORGANISM: Artificial Sequence
<220> FEATURE:
<223> OTHER INFORMATION: synthetic

<400> SEQUENCE: 110

Ile Ser Tyr Ser Gly Phe Thr
1               5


<210> SEQ ID NO 111
<211> LENGTH: 36
<212> TYPE: DNA
<213> ORGANISM: Artificial Sequence
<220> FEATURE:
<223> OTHER INFORMATION: synthetic

<400> SEQUENCE: 111

gcgagagtta cctatggtta tgggaccttt gattat                               36


<210> SEQ ID NO 112
<211> LENGTH: 12
<212> TYPE: PRT
<213> ORGANISM: Artificial Sequence
<220> FEATURE:
<223> OTHER INFORMATION: synthetic

<400> SEQUENCE: 112

Ala Arg Val Thr Tyr Gly Tyr Gly Thr Phe Asp Tyr
1               5                   10


<210> SEQ ID NO 113
<211> LENGTH: 1165
<212> TYPE: PRT
<213> ORGANISM: Artificial Sequence
<220> FEATURE:
<223> OTHER INFORMATION: hLEPR Accession No P48357

<400> SEQUENCE: 113

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160
```

-continued

```
Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
        515                 520                 525

Val Leu Pro Asp Ser Val Val Lys Pro Leu Pro Pro Ser Ser Val Lys
    530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
```

-continued

```
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
    610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
        675                 680                 685

Gly Thr Trp Ser Glu Asp Val Gly Asn His Thr Lys Phe Thr Phe Leu
    690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
        755                 760                 765

Tyr Phe Ile Ile Glu Trp Lys Asn Leu Asn Glu Asp Gly Glu Ile Lys
    770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
    850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
                885                 890                 895

His Leu Phe Ile Lys His Thr Ala Ser Val Thr Cys Gly Pro Leu Leu
            900                 905                 910

Leu Glu Pro Glu Thr Ile Ser Glu Asp Ile Ser Val Asp Thr Ser Trp
        915                 920                 925

Lys Asn Lys Asp Glu Met Met Pro Thr Thr Val Val Ser Leu Leu Ser
    930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Glu Val Thr Tyr Glu Asp
                965                 970                 975

Glu Ser Gln Arg Gln Pro Phe Val Lys Tyr Ala Thr Leu Ile Ser Asn
            980                 985                 990

Ser Lys Pro Ser Glu Thr Gly Glu  Glu Gln Gly Leu Ile  Asn Ser Ser
        995                 1000                1005
```

```
Val Thr Lys Cys Phe Ser Ser Lys Asn Ser Pro Leu Lys Asp Ser
    1010                1015                1020

Phe Ser Asn Ser Ser Trp Glu Ile Glu Ala Gln Ala Phe Phe Ile
    1025                1030                1035

Leu Ser Asp Gln His Pro Asn Ile Ile Ser Pro His Leu Thr Phe
    1040                1045                1050

Ser Glu Gly Leu Asp Glu Leu Leu Lys Leu Glu Gly Asn Phe Pro
    1055                1060                1065

Glu Glu Asn Asn Asp Lys Lys Ser Ile Tyr Tyr Leu Gly Val Thr
    1070                1075                1080

Ser Ile Lys Lys Arg Glu Ser Gly Val Leu Leu Thr Asp Lys Ser
    1085                1090                1095

Arg Val Ser Cys Pro Phe Pro Ala Pro Cys Leu Phe Thr Asp Ile
    1100                1105                1110

Arg Val Leu Gln Asp Ser Cys Ser His Phe Val Glu Asn Asn Ile
    1115                1120                1125

Asn Leu Gly Thr Ser Ser Lys Lys Thr Phe Ala Ser Tyr Met Pro
    1130                1135                1140

Gln Phe Gln Thr Cys Ser Thr Gln Thr His Lys Ile Met Glu Asn
    1145                1150                1155

Lys Met Cys Asp Leu Thr Val
    1160                1165


<210> SEQ ID NO 114
<211> LENGTH: 846
<212> TYPE: PRT
<213> ORGANISM: Artificial Sequence
<220> FEATURE:
<223> OTHER INFORMATION: hLEPR.mmh aa 1-818: F22-D839 of P48357 aa 819-
      846: myc-myc-hexahistidine tag

<400> SEQUENCE: 114

Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Ser Asn Gly His Tyr Glu Thr Ala Val Glu
        35                  40                  45

Pro Lys Phe Asn Ser Ser Gly Thr His Phe Ser Asn Leu Ser Lys Thr
    50                  55                  60

Thr Phe His Cys Cys Phe Arg Ser Glu Gln Asp Arg Asn Cys Ser Leu
65                  70                  75                  80

Cys Ala Asp Asn Ile Glu Gly Lys Thr Phe Val Ser Thr Val Asn Ser
                85                  90                  95

Leu Val Phe Gln Gln Ile Asp Ala Asn Trp Asn Ile Gln Cys Trp Leu
            100                 105                 110

Lys Gly Asp Leu Lys Leu Phe Ile Cys Tyr Val Glu Ser Leu Phe Lys
        115                 120                 125

Asn Leu Phe Arg Asn Tyr Asn Tyr Lys Val His Leu Leu Tyr Val Leu
    130                 135                 140

Pro Glu Val Leu Glu Asp Ser Pro Leu Val Pro Gln Lys Gly Ser Phe
145                 150                 155                 160

Gln Met Val His Cys Asn Cys Ser Val His Glu Cys Cys Glu Cys Leu
                165                 170                 175

Val Pro Val Pro Thr Ala Lys Leu Asn Asp Thr Leu Leu Met Cys Leu
```

```
        180                 185                 190

Lys Ile Thr Ser Gly Gly Val Ile Phe Gln Ser Pro Leu Met Ser Val
    195                 200                 205

Gln Pro Ile Asn Met Val Lys Pro Asp Pro Pro Leu Gly Leu His Met
    210                 215                 220

Glu Ile Thr Asp Asp Gly Asn Leu Lys Ile Ser Trp Ser Ser Pro Pro
225                 230                 235                 240

Leu Val Pro Phe Pro Leu Gln Tyr Gln Val Lys Tyr Ser Glu Asn Ser
                245                 250                 255

Thr Thr Val Ile Arg Glu Ala Asp Lys Ile Val Ser Ala Thr Ser Leu
            260                 265                 270

Leu Val Asp Ser Ile Leu Pro Gly Ser Ser Tyr Glu Val Gln Val Arg
        275                 280                 285

Gly Lys Arg Leu Asp Gly Pro Gly Ile Trp Ser Asp Trp Ser Thr Pro
    290                 295                 300

Arg Val Phe Thr Thr Gln Asp Val Ile Tyr Phe Pro Pro Lys Ile Leu
305                 310                 315                 320

Thr Ser Val Gly Ser Asn Val Ser Phe His Cys Ile Tyr Lys Lys Glu
                325                 330                 335

Asn Lys Ile Val Pro Ser Lys Glu Ile Val Trp Trp Met Asn Leu Ala
            340                 345                 350

Glu Lys Ile Pro Gln Ser Gln Tyr Asp Val Val Ser Asp His Val Ser
        355                 360                 365

Lys Val Thr Phe Phe Asn Leu Asn Glu Thr Lys Pro Arg Gly Lys Phe
    370                 375                 380

Thr Tyr Asp Ala Val Tyr Cys Cys Asn Glu His Glu Cys His His Arg
385                 390                 395                 400

Tyr Ala Glu Leu Tyr Val Ile Asp Val Asn Ile Asn Ile Ser Cys Glu
                405                 410                 415

Thr Asp Gly Tyr Leu Thr Lys Met Thr Cys Arg Trp Ser Thr Ser Thr
            420                 425                 430

Ile Gln Ser Leu Ala Glu Ser Thr Leu Gln Leu Arg Tyr His Arg Ser
        435                 440                 445

Ser Leu Tyr Cys Ser Asp Ile Pro Ser Ile His Pro Ile Ser Glu Pro
    450                 455                 460

Lys Asp Cys Tyr Leu Gln Ser Asp Gly Phe Tyr Glu Cys Ile Phe Gln
465                 470                 475                 480

Pro Ile Phe Leu Leu Ser Gly Tyr Thr Met Trp Ile Arg Ile Asn His
                485                 490                 495

Ser Leu Gly Ser Leu Asp Ser Pro Pro Thr Cys Val Leu Pro Asp Ser
            500                 505                 510

Val Val Lys Pro Leu Pro Pro Ser Ser Val Lys Ala Glu Ile Thr Ile
        515                 520                 525

Asn Ile Gly Leu Leu Lys Ile Ser Trp Glu Lys Pro Val Phe Pro Glu
    530                 535                 540

Asn Asn Leu Gln Phe Gln Ile Arg Tyr Gly Leu Ser Gly Lys Glu Val
545                 550                 555                 560

Gln Trp Lys Met Tyr Glu Val Tyr Asp Ala Lys Ser Lys Ser Val Ser
                565                 570                 575

Leu Pro Val Pro Asp Leu Cys Ala Val Tyr Ala Val Gln Val Arg Cys
            580                 585                 590

Lys Arg Leu Asp Gly Leu Gly Tyr Trp Ser Asn Trp Ser Asn Pro Ala
        595                 600                 605
```

```
Tyr Thr Val Val Met Asp Ile Lys Val Pro Met Arg Gly Pro Glu Phe
    610                 615                 620

Trp Arg Ile Ile Asn Gly Asp Thr Met Lys Lys Glu Lys Asn Val Thr
625                 630                 635                 640

Leu Leu Trp Lys Pro Leu Met Lys Asn Asp Ser Leu Cys Ser Val Gln
                645                 650                 655

Arg Tyr Val Ile Asn His His Thr Ser Cys Asn Gly Thr Trp Ser Glu
            660                 665                 670

Asp Val Gly Asn His Thr Lys Phe Thr Phe Leu Trp Thr Glu Gln Ala
        675                 680                 685

His Thr Val Thr Val Leu Ala Ile Asn Ser Ile Gly Ala Ser Val Ala
    690                 695                 700

Asn Phe Asn Leu Thr Phe Ser Trp Pro Met Ser Lys Val Asn Ile Val
705                 710                 715                 720

Gln Ser Leu Ser Ala Tyr Pro Leu Asn Ser Ser Cys Val Ile Val Ser
                725                 730                 735

Trp Ile Leu Ser Pro Ser Asp Tyr Lys Leu Met Tyr Phe Ile Ile Glu
            740                 745                 750

Trp Lys Asn Leu Asn Glu Asp Gly Glu Ile Lys Trp Leu Arg Ile Ser
        755                 760                 765

Ser Ser Val Lys Lys Tyr Tyr Ile His Asp His Phe Ile Pro Ile Glu
    770                 775                 780

Lys Tyr Gln Phe Ser Leu Tyr Pro Ile Phe Met Glu Gly Val Gly Lys
785                 790                 795                 800

Pro Lys Ile Ile Asn Ser Phe Thr Gln Asp Asp Ile Glu Lys His Gln
                805                 810                 815

Ser Asp Glu Gln Lys Leu Ile Ser Glu Glu Asp Leu Gly Gly Glu Gln
            820                 825                 830

Lys Leu Ile Ser Glu Glu Asp Leu His His His His His His
        835                 840                 845
```

<210> SEQ ID NO 115
<211> LENGTH: 1051
<212> TYPE: PRT
<213> ORGANISM: Artificial Sequence
<220> FEATURE:
<223> OTHER INFORMATION: hLEPR.mFc aa 1-818: F22-D839 of P48357 aa 819-1051: mouse IgG2a (E98-K330 of P01863)

<400> SEQUENCE: 115

```
Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Ser Asn Gly His Tyr Glu Thr Ala Val Glu
        35                  40                  45

Pro Lys Phe Asn Ser Ser Gly Thr His Phe Ser Asn Leu Ser Lys Thr
    50                  55                  60

Thr Phe His Cys Cys Phe Arg Ser Glu Gln Asp Arg Asn Cys Ser Leu
65                  70                  75                  80

Cys Ala Asp Asn Ile Glu Gly Lys Thr Phe Val Ser Thr Val Asn Ser
                85                  90                  95

Leu Val Phe Gln Gln Ile Asp Ala Asn Trp Asn Ile Gln Cys Trp Leu
            100                 105                 110

Lys Gly Asp Leu Lys Leu Phe Ile Cys Tyr Val Glu Ser Leu Phe Lys
```

-continued

```
        115                 120                 125

Asn Leu Phe Arg Asn Tyr Asn Tyr Lys Val His Leu Leu Tyr Val Leu
    130                 135                 140

Pro Glu Val Leu Glu Asp Ser Pro Leu Val Pro Gln Lys Gly Ser Phe
145                 150                 155                 160

Gln Met Val His Cys Asn Cys Ser Val His Glu Cys Cys Glu Cys Leu
                165                 170                 175

Val Pro Val Pro Thr Ala Lys Leu Asn Asp Thr Leu Leu Met Cys Leu
            180                 185                 190

Lys Ile Thr Ser Gly Gly Val Ile Phe Gln Ser Pro Leu Met Ser Val
        195                 200                 205

Gln Pro Ile Asn Met Val Lys Pro Asp Pro Pro Leu Gly Leu His Met
    210                 215                 220

Glu Ile Thr Asp Asp Gly Asn Leu Lys Ile Ser Trp Ser Ser Pro Pro
225                 230                 235                 240

Leu Val Pro Phe Pro Leu Gln Tyr Gln Val Lys Tyr Ser Glu Asn Ser
                245                 250                 255

Thr Thr Val Ile Arg Glu Ala Asp Lys Ile Val Ser Ala Thr Ser Leu
            260                 265                 270

Leu Val Asp Ser Ile Leu Pro Gly Ser Ser Tyr Glu Val Gln Val Arg
        275                 280                 285

Gly Lys Arg Leu Asp Gly Pro Gly Ile Trp Ser Asp Trp Ser Thr Pro
    290                 295                 300

Arg Val Phe Thr Thr Gln Asp Val Ile Tyr Phe Pro Pro Lys Ile Leu
305                 310                 315                 320

Thr Ser Val Gly Ser Asn Val Ser Phe His Cys Ile Tyr Lys Lys Glu
                325                 330                 335

Asn Lys Ile Val Pro Ser Lys Glu Ile Val Trp Trp Met Asn Leu Ala
            340                 345                 350

Glu Lys Ile Pro Gln Ser Gln Tyr Asp Val Val Ser Asp His Val Ser
        355                 360                 365

Lys Val Thr Phe Phe Asn Leu Asn Glu Thr Lys Pro Arg Gly Lys Phe
    370                 375                 380

Thr Tyr Asp Ala Val Tyr Cys Cys Asn Glu His Glu Cys His His Arg
385                 390                 395                 400

Tyr Ala Glu Leu Tyr Val Ile Asp Val Asn Ile Asn Ile Ser Cys Glu
                405                 410                 415

Thr Asp Gly Tyr Leu Thr Lys Met Thr Cys Arg Trp Ser Thr Ser Thr
            420                 425                 430

Ile Gln Ser Leu Ala Glu Ser Thr Leu Gln Leu Arg Tyr His Arg Ser
        435                 440                 445

Ser Leu Tyr Cys Ser Asp Ile Pro Ser Ile His Pro Ile Ser Glu Pro
    450                 455                 460

Lys Asp Cys Tyr Leu Gln Ser Asp Gly Phe Tyr Glu Cys Ile Phe Gln
465                 470                 475                 480

Pro Ile Phe Leu Leu Ser Gly Tyr Thr Met Trp Ile Arg Ile Asn His
                485                 490                 495

Ser Leu Gly Ser Leu Asp Ser Pro Pro Thr Cys Val Leu Pro Asp Ser
            500                 505                 510

Val Val Lys Pro Leu Pro Pro Ser Ser Val Lys Ala Glu Ile Thr Ile
        515                 520                 525

Asn Ile Gly Leu Leu Lys Ile Ser Trp Glu Lys Pro Val Phe Pro Glu
    530                 535                 540
```

-continued

```
Asn Asn Leu Gln Phe Gln Ile Arg Tyr Gly Leu Ser Gly Lys Glu Val
545                 550                 555                 560

Gln Trp Lys Met Tyr Glu Val Tyr Asp Ala Lys Ser Lys Ser Val Ser
                565                 570                 575

Leu Pro Val Pro Asp Leu Cys Ala Val Tyr Ala Val Gln Val Arg Cys
            580                 585                 590

Lys Arg Leu Asp Gly Leu Gly Tyr Trp Ser Asn Trp Ser Asn Pro Ala
        595                 600                 605

Tyr Thr Val Val Met Asp Ile Lys Val Pro Met Arg Gly Pro Glu Phe
    610                 615                 620

Trp Arg Ile Ile Asn Gly Asp Thr Met Lys Lys Glu Lys Asn Val Thr
625                 630                 635                 640

Leu Leu Trp Lys Pro Leu Met Lys Asn Asp Ser Leu Cys Ser Val Gln
                645                 650                 655

Arg Tyr Val Ile Asn His His Thr Ser Cys Asn Gly Thr Trp Ser Glu
            660                 665                 670

Asp Val Gly Asn His Thr Lys Phe Thr Phe Leu Trp Thr Glu Gln Ala
        675                 680                 685

His Thr Val Thr Val Leu Ala Ile Asn Ser Ile Gly Ala Ser Val Ala
    690                 695                 700

Asn Phe Asn Leu Thr Phe Ser Trp Pro Met Ser Lys Val Asn Ile Val
705                 710                 715                 720

Gln Ser Leu Ser Ala Tyr Pro Leu Asn Ser Ser Cys Val Ile Val Ser
                725                 730                 735

Trp Ile Leu Ser Pro Ser Asp Tyr Lys Leu Met Tyr Phe Ile Ile Glu
            740                 745                 750

Trp Lys Asn Leu Asn Glu Asp Gly Glu Ile Lys Trp Leu Arg Ile Ser
        755                 760                 765

Ser Ser Val Lys Lys Tyr Tyr Ile His Asp His Phe Ile Pro Ile Glu
    770                 775                 780

Lys Tyr Gln Phe Ser Leu Tyr Pro Ile Phe Met Glu Gly Val Gly Lys
785                 790                 795                 800

Pro Lys Ile Ile Asn Ser Phe Thr Gln Asp Asp Ile Glu Lys His Gln
                805                 810                 815

Ser Asp Glu Pro Arg Gly Pro Thr Ile Lys Pro Cys Pro Pro Cys Lys
            820                 825                 830

Cys Pro Ala Pro Asn Leu Leu Gly Gly Pro Ser Val Phe Ile Phe Pro
        835                 840                 845

Pro Lys Ile Lys Asp Val Leu Met Ile Ser Leu Ser Pro Ile Val Thr
    850                 855                 860

Cys Val Val Val Asp Val Ser Glu Asp Asp Pro Asp Val Gln Ile Ser
865                 870                 875                 880

Trp Phe Val Asn Asn Val Glu Val His Thr Ala Gln Thr Gln Thr His
                885                 890                 895

Arg Glu Asp Tyr Asn Ser Thr Leu Arg Val Val Ser Ala Leu Pro Ile
            900                 905                 910

Gln His Gln Asp Trp Met Ser Gly Lys Glu Phe Lys Cys Lys Val Asn
        915                 920                 925

Asn Lys Asp Leu Pro Ala Pro Ile Glu Arg Thr Ile Ser Lys Pro Lys
    930                 935                 940

Gly Ser Val Arg Ala Pro Gln Val Tyr Val Leu Pro Pro Pro Glu Glu
945                 950                 955                 960
```

-continued

```
Glu Met Thr Lys Lys Gln Val Thr Leu Thr Cys Met Val Thr Asp Phe
                965                 970                 975

Met Pro Glu Asp Ile Tyr Val Glu Trp Thr Asn Asn Gly Lys Thr Glu
            980                 985                 990

Leu Asn Tyr Lys Asn Thr Glu Pro  Val Leu Asp Ser Asp  Gly Ser Tyr
        995                 1000                 1005

Phe Met  Tyr Ser Lys Leu Arg  Val Glu Lys Lys Asn  Trp Val Glu
    1010                 1015                 1020

Arg Asn  Ser Tyr Ser Cys Ser  Val Val His Glu Gly  Leu His Asn
    1025                 1030                 1035

His His  Thr Thr Lys Ser Phe  Ser Arg Thr Pro Gly  Lys
    1040                 1045                 1050
```

```
<210> SEQ ID NO 116
<211> LENGTH: 1045
<212> TYPE: PRT
<213> ORGANISM: Artificial Sequence
<220> FEATURE:
<223> OTHER INFORMATION: hLEPR.hFc aa 1-818: F22-D839 of P48357 aa 819-
      1045: human IgG1 tag (D104-K330 of P01857)

<400> SEQUENCE: 116

Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Ser Asn Gly His Tyr Glu Thr Ala Val Glu
        35                  40                  45

Pro Lys Phe Asn Ser Ser Gly Thr His Phe Ser Asn Leu Ser Lys Thr
    50                  55                  60

Thr Phe His Cys Cys Phe Arg Ser Glu Gln Asp Arg Asn Cys Ser Leu
65                  70                  75                  80

Cys Ala Asp Asn Ile Glu Gly Lys Thr Phe Val Ser Thr Val Asn Ser
                85                  90                  95

Leu Val Phe Gln Gln Ile Asp Ala Asn Trp Asn Ile Gln Cys Trp Leu
            100                 105                 110

Lys Gly Asp Leu Lys Leu Phe Ile Cys Tyr Val Glu Ser Leu Phe Lys
        115                 120                 125

Asn Leu Phe Arg Asn Tyr Asn Tyr Lys Val His Leu Leu Tyr Val Leu
    130                 135                 140

Pro Glu Val Leu Glu Asp Ser Pro Leu Val Pro Gln Lys Gly Ser Phe
145                 150                 155                 160

Gln Met Val His Cys Asn Cys Ser Val His Glu Cys Cys Glu Cys Leu
                165                 170                 175

Val Pro Val Pro Thr Ala Lys Leu Asn Asp Thr Leu Leu Met Cys Leu
            180                 185                 190

Lys Ile Thr Ser Gly Gly Val Ile Phe Gln Ser Pro Leu Met Ser Val
        195                 200                 205

Gln Pro Ile Asn Met Val Lys Pro Asp Pro Pro Leu Gly Leu His Met
    210                 215                 220

Glu Ile Thr Asp Asp Gly Asn Leu Lys Ile Ser Trp Ser Ser Pro Pro
225                 230                 235                 240

Leu Val Pro Phe Pro Leu Gln Tyr Gln Val Lys Tyr Ser Glu Asn Ser
                245                 250                 255

Thr Thr Val Ile Arg Glu Ala Asp Lys Ile Val Ser Ala Thr Ser Leu
            260                 265                 270
```

-continued

```
Leu Val Asp Ser Ile Leu Pro Gly Ser Ser Tyr Glu Val Gln Val Arg
        275                 280                 285

Gly Lys Arg Leu Asp Gly Pro Gly Ile Trp Ser Asp Trp Ser Thr Pro
    290                 295                 300

Arg Val Phe Thr Thr Gln Asp Val Ile Tyr Phe Pro Pro Lys Ile Leu
305                 310                 315                 320

Thr Ser Val Gly Ser Asn Val Ser Phe His Cys Ile Tyr Lys Lys Glu
                325                 330                 335

Asn Lys Ile Val Pro Ser Lys Glu Ile Val Trp Trp Met Asn Leu Ala
            340                 345                 350

Glu Lys Ile Pro Gln Ser Gln Tyr Asp Val Val Ser Asp His Val Ser
        355                 360                 365

Lys Val Thr Phe Phe Asn Leu Asn Glu Thr Lys Pro Arg Gly Lys Phe
    370                 375                 380

Thr Tyr Asp Ala Val Tyr Cys Cys Asn Glu His Glu Cys His His Arg
385                 390                 395                 400

Tyr Ala Glu Leu Tyr Val Ile Asp Val Asn Ile Asn Ile Ser Cys Glu
                405                 410                 415

Thr Asp Gly Tyr Leu Thr Lys Met Thr Cys Arg Trp Ser Thr Ser Thr
            420                 425                 430

Ile Gln Ser Leu Ala Glu Ser Thr Leu Gln Leu Arg Tyr His Arg Ser
        435                 440                 445

Ser Leu Tyr Cys Ser Asp Ile Pro Ser Ile His Pro Ile Ser Glu Pro
    450                 455                 460

Lys Asp Cys Tyr Leu Gln Ser Asp Gly Phe Tyr Glu Cys Ile Phe Gln
465                 470                 475                 480

Pro Ile Phe Leu Leu Ser Gly Tyr Thr Met Trp Ile Arg Ile Asn His
                485                 490                 495

Ser Leu Gly Ser Leu Asp Ser Pro Pro Thr Cys Val Leu Pro Asp Ser
            500                 505                 510

Val Val Lys Pro Leu Pro Pro Ser Ser Val Lys Ala Glu Ile Thr Ile
        515                 520                 525

Asn Ile Gly Leu Leu Lys Ile Ser Trp Glu Lys Pro Val Phe Pro Glu
    530                 535                 540

Asn Asn Leu Gln Phe Gln Ile Arg Tyr Gly Leu Ser Gly Lys Glu Val
545                 550                 555                 560

Gln Trp Lys Met Tyr Glu Val Tyr Asp Ala Lys Ser Lys Ser Val Ser
                565                 570                 575

Leu Pro Val Pro Asp Leu Cys Ala Val Tyr Ala Val Gln Val Arg Cys
            580                 585                 590

Lys Arg Leu Asp Gly Leu Gly Tyr Trp Ser Asn Trp Ser Asn Pro Ala
        595                 600                 605

Tyr Thr Val Val Met Asp Ile Lys Val Pro Met Arg Gly Pro Glu Phe
    610                 615                 620

Trp Arg Ile Ile Asn Gly Asp Thr Met Lys Lys Glu Lys Asn Val Thr
625                 630                 635                 640

Leu Leu Trp Lys Pro Leu Met Lys Asn Asp Ser Leu Cys Ser Val Gln
                645                 650                 655

Arg Tyr Val Ile Asn His His Thr Ser Cys Asn Gly Thr Trp Ser Glu
            660                 665                 670

Asp Val Gly Asn His Thr Lys Phe Thr Phe Leu Trp Thr Glu Gln Ala
        675                 680                 685
```

His Thr Val Thr Val Leu Ala Ile Asn Ser Ile Gly Ala Ser Val Ala
690 695 700

Asn Phe Asn Leu Thr Phe Ser Trp Pro Met Ser Lys Val Asn Ile Val
705 710 715 720

Gln Ser Leu Ser Ala Tyr Pro Leu Asn Ser Ser Cys Val Ile Val Ser
725 730 735

Trp Ile Leu Ser Pro Ser Asp Tyr Lys Leu Met Tyr Phe Ile Ile Glu
740 745 750

Trp Lys Asn Leu Asn Glu Asp Gly Glu Ile Lys Trp Leu Arg Ile Ser
755 760 765

Ser Ser Val Lys Lys Tyr Tyr Ile His Asp His Phe Ile Pro Ile Glu
770 775 780

Lys Tyr Gln Phe Ser Leu Tyr Pro Ile Phe Met Glu Gly Val Gly Lys
785 790 795 800

Pro Lys Ile Ile Asn Ser Phe Thr Gln Asp Asp Ile Glu Lys His Gln
805 810 815

Ser Asp Asp Lys Thr His Thr Cys Pro Pro Cys Pro Ala Pro Glu Leu
820 825 830

Leu Gly Gly Pro Ser Val Phe Leu Phe Pro Pro Lys Pro Lys Asp Thr
835 840 845

Leu Met Ile Ser Arg Thr Pro Glu Val Thr Cys Val Val Val Asp Val
850 855 860

Ser His Glu Asp Pro Glu Val Lys Phe Asn Trp Tyr Val Asp Gly Val
865 870 875 880

Glu Val His Asn Ala Lys Thr Lys Pro Arg Glu Glu Gln Tyr Asn Ser
885 890 895

Thr Tyr Arg Val Val Ser Val Leu Thr Val Leu His Gln Asp Trp Leu
900 905 910

Asn Gly Lys Glu Tyr Lys Cys Lys Val Ser Asn Lys Ala Leu Pro Ala
915 920 925

Pro Ile Glu Lys Thr Ile Ser Lys Ala Lys Gly Gln Pro Arg Glu Pro
930 935 940

Gln Val Tyr Thr Leu Pro Pro Ser Arg Asp Glu Leu Thr Lys Asn Gln
945 950 955 960

Val Ser Leu Thr Cys Leu Val Lys Gly Phe Tyr Pro Ser Asp Ile Ala
965 970 975

Val Glu Trp Glu Ser Asn Gly Gln Pro Glu Asn Asn Tyr Lys Thr Thr
980 985 990

Pro Pro Val Leu Asp Ser Asp Gly Ser Phe Phe Leu Tyr Ser Lys Leu
995 1000 1005

Thr Val Asp Lys Ser Arg Trp Gln Gln Gly Asn Val Phe Ser Cys
1010 1015 1020

Ser Val Met His Glu Ala Leu His Asn His Tyr Thr Gln Lys Ser
1025 1030 1035

Leu Ser Leu Ser Pro Gly Lys
1040 1045

<210> SEQ ID NO 117
<211> LENGTH: 844
<212> TYPE: PRT
<213> ORGANISM: Artificial Sequence
<220> FEATURE:
<223> OTHER INFORMATION: MfLEPR.mmh aa 1-816: Macaca fascicularis F22-
D837 with a T827A substitution from XP_005543194.1 aa 817-844:
myc-myc-hexahistidine tag

<400> SEQUENCE: 117

Phe Asn Leu Ser Tyr Pro Ile Thr Pro Trp Arg Phe Lys Leu Ser Cys
1               5                   10                  15

Met Pro Pro Asn Ser Thr Tyr Asp Tyr Phe Leu Leu Pro Ala Gly Leu
            20                  25                  30

Ser Lys Asn Thr Ser Asn Leu Asn Gly His Tyr Glu Thr Ala Val Glu
        35                  40                  45

Phe Asn Ser Ser Asp Thr His Phe Ser Asn Leu Ser Lys Thr Thr Phe
    50                  55                  60

His Cys Cys Phe Arg Ser Glu Gln Asp Arg Asn Cys Ser Leu Cys Ala
65                  70                  75                  80

Asp Asn Ile Glu Gly Lys Thr Phe Val Ser Thr Val Asn Ser Ser Val
                85                  90                  95

Phe Gln Gln Met Gly Ala Asn Trp Asn Ile Gln Cys Trp Leu Lys Gly
            100                 105                 110

Asp Leu Lys Leu Phe Ile Cys Tyr Val Glu Ser Leu Phe Lys Asn Pro
        115                 120                 125

Phe Lys Asn Tyr Lys His Lys Val His Leu Leu Tyr Val Leu Pro Glu
    130                 135                 140

Val Leu Glu Asp Ser Pro Leu Val Pro Gln Lys Gly Ser Phe Gln Met
145                 150                 155                 160

Val His Cys Asn Cys Ser Val His Glu Arg Cys Glu Cys Leu Val Pro
                165                 170                 175

Val Pro Thr Ala Lys Leu Asn Asp Thr Leu Leu Met Cys Leu Lys Ile
            180                 185                 190

Thr Ser Gly Gly Val Ile Phe Gln Ser Pro Leu Met Ser Val Gln Pro
        195                 200                 205

Ile Asn Met Val Lys Pro Asp Pro Pro Leu Gly Leu Arg Met Glu Ile
    210                 215                 220

Thr Asp Asp Gly Asn Leu Lys Ile Ser Trp Ser Ser Pro Pro Leu Val
225                 230                 235                 240

Pro Phe Pro Leu Gln Tyr Glu Val Lys Tyr Ser Glu Asn Ser Thr Thr
                245                 250                 255

Val Ile Arg Glu Ala Asp Lys Ile Val Ser Ala Thr Ser Leu Leu Val
            260                 265                 270

Asp Gly Ile Leu Pro Gly Ser Ser Tyr Glu Val Gln Val Arg Gly Lys
        275                 280                 285

Arg Leu Asp Gly Pro Gly Ile Trp Ser Asp Trp Ser Thr Pro His Val
    290                 295                 300

Phe Thr Thr Gln Asp Val Ile Tyr Phe Pro Pro Lys Ile Leu Thr Ser
305                 310                 315                 320

Val Gly Ser Asn Val Ser Phe His Cys Ile Tyr Lys Asn Glu Asn Lys
                325                 330                 335

Ile Val Ser Ser Lys Lys Ile Val Trp Trp Met Asn Leu Ala Glu Lys
            340                 345                 350

Ile Pro Gln Ser Gln Tyr Asp Val Val Ser Asp His Val Ser Lys Val
        355                 360                 365

Thr Phe Phe Asn Leu Asn Glu Thr Lys Pro Arg Gly Lys Phe Thr Tyr
    370                 375                 380

Asp Ala Val Tyr Cys Cys Asn Glu His Glu Cys His His Arg Tyr Ala
385                 390                 395                 400

Glu Leu Tyr Val Ile Asp Val Asn Ile Asn Ile Ser Cys Glu Thr Asp
                405                 410                 415

```
Gly His Leu Thr Lys Met Thr Cys Arg Trp Ser Thr Asn Thr Ile Gln
            420                 425                 430

Ser Leu Ala Gly Ser Thr Leu Gln Leu Arg Tyr Arg Arg Ser Ser Leu
        435                 440                 445

Tyr Cys Phe Asp Ile Pro Ser Ile His Pro Ile Ser Lys Pro Lys Asp
    450                 455                 460

Cys Tyr Leu Gln Ser Asp Gly Phe Tyr Glu Cys Val Phe Gln Pro Ile
465                 470                 475                 480

Phe Leu Leu Ser Gly Tyr Thr Met Trp Ile Arg Ile Asn His Pro Leu
                485                 490                 495

Gly Ser Leu Asp Ser Pro Pro Thr Cys Val Leu Pro Asp Ser Val Val
            500                 505                 510

Lys Pro Leu Pro Pro Ser Ser Val Lys Ala Glu Ile Ile Lys Asn Ile
        515                 520                 525

Gly Leu Leu Lys Ile Ser Trp Glu Lys Pro Val Phe Pro Glu Asn Asn
    530                 535                 540

Leu Gln Phe Gln Ile Arg Tyr Gly Leu Ser Gly Lys Glu Ile Gln Trp
545                 550                 555                 560

Lys Met Tyr Asp Val Tyr Asp Ala Lys Ser Lys Ser Val Ser Leu Pro
                565                 570                 575

Val Pro Asp Phe Cys Ala Val Tyr Ala Val Gln Val Arg Cys Lys Arg
            580                 585                 590

Ser Asp Gly Leu Gly Leu Trp Ser Asn Trp Ser Asn Pro Ala Tyr Thr
        595                 600                 605

Val Val Met Asp Ile Lys Val Pro Met Arg Gly Pro Glu Phe Trp Arg
    610                 615                 620

Ile Ile Asn Gly Asp Thr Met Lys Lys Glu Lys Asn Val Thr Leu Leu
625                 630                 635                 640

Trp Lys Pro Leu Met Lys Asn Asp Ser Leu Cys Ser Val Gln Arg Tyr
                645                 650                 655

Val Ile Asn His His Thr Ser Cys Asn Gly Thr Trp Ser Glu Asp Val
            660                 665                 670

Gly Asn His Thr Lys Phe Thr Phe Leu Trp Thr Glu Gln Ala His Thr
        675                 680                 685

Val Thr Val Leu Ala Ile Asn Ser Ile Gly Ala Ser Val Ala Asn Phe
    690                 695                 700

Asn Leu Thr Phe Ser Trp Pro Met Ser Lys Val Asn Ile Val Gln Ser
705                 710                 715                 720

Leu Ser Ala Tyr Pro Leu Asn Ser Ser Cys Val Ile Leu Ser Trp Ile
                725                 730                 735

Leu Ser Pro Ser Asp Tyr Lys Leu Met Tyr Phe Ile Ile Glu Trp Lys
            740                 745                 750

Asn Leu Asn Glu Asp Gly Glu Ile Lys Trp Leu Arg Ile Ser Ser Ser
        755                 760                 765

Val Lys Lys Tyr Tyr Ile His Asp His Phe Ile Pro Ile Glu Lys Tyr
    770                 775                 780

Gln Phe Ser Leu Tyr Pro Ile Phe Met Glu Gly Val Gly Lys Pro Lys
785                 790                 795                 800

Ile Ile Asn Ser Phe Ala Gln Asp Asn Thr Glu Lys His Gln Asn Asp
                805                 810                 815

Glu Gln Lys Leu Ile Ser Glu Glu Asp Leu Gly Gly Glu Gln Lys Leu
            820                 825                 830
```

```
Ile Ser Glu Glu Asp Leu His His His His His His
        835                 840


<210> SEQ ID NO 118
<211> LENGTH: 846
<212> TYPE: PRT
<213> ORGANISM: Artificial Sequence
<220> FEATURE:
<223> OTHER INFORMATION: mLEPR.mmh aa 1-818: Mouse LEPR (L22-G839 of
      NP_666258.2) aa 817-846: myc-myc-hexahistidine tag

<400> SEQUENCE: 118

Leu Asn Leu Ala Tyr Pro Ile Ser Pro Trp Lys Phe Lys Leu Phe Cys
1               5                   10                  15

Gly Pro Pro Asn Thr Thr Asp Asp Ser Phe Leu Ser Pro Ala Gly Ala
            20                  25                  30

Pro Asn Asn Ala Ser Ala Leu Lys Gly Ala Ser Glu Ala Ile Val Glu
        35                  40                  45

Ala Lys Phe Asn Ser Ser Gly Ile Tyr Val Pro Glu Leu Ser Lys Thr
    50                  55                  60

Val Phe His Cys Cys Phe Gly Asn Glu Gln Gly Gln Asn Cys Ser Ala
65                  70                  75                  80

Leu Thr Asp Asn Thr Glu Gly Lys Thr Leu Ala Ser Val Val Lys Ala
                85                  90                  95

Ser Val Phe Arg Gln Leu Gly Val Asn Trp Asp Ile Glu Cys Trp Met
            100                 105                 110

Lys Gly Asp Leu Thr Leu Phe Ile Cys His Met Glu Pro Leu Pro Lys
        115                 120                 125

Asn Pro Phe Lys Asn Tyr Asp Ser Lys Val His Leu Leu Tyr Asp Leu
    130                 135                 140

Pro Glu Val Ile Asp Asp Ser Pro Leu Pro Pro Leu Lys Asp Ser Phe
145                 150                 155                 160

Gln Thr Val Gln Cys Asn Cys Ser Leu Arg Gly Cys Glu Cys His Val
                165                 170                 175

Pro Val Pro Arg Ala Lys Leu Asn Tyr Ala Leu Leu Met Tyr Leu Glu
            180                 185                 190

Ile Thr Ser Ala Gly Val Ser Phe Gln Ser Pro Leu Met Ser Leu Gln
        195                 200                 205

Pro Met Leu Val Val Lys Pro Asp Pro Pro Leu Gly Leu His Met Glu
    210                 215                 220

Val Thr Asp Asp Gly Asn Leu Lys Ile Ser Trp Asp Ser Gln Thr Met
225                 230                 235                 240

Ala Pro Phe Pro Leu Gln Tyr Gln Val Lys Tyr Leu Glu Asn Ser Thr
                245                 250                 255

Ile Val Arg Glu Ala Ala Glu Ile Val Ser Ala Thr Ser Leu Leu Val
            260                 265                 270

Asp Ser Val Leu Pro Gly Ser Ser Tyr Glu Val Gln Val Arg Ser Lys
        275                 280                 285

Arg Leu Asp Gly Ser Gly Val Trp Ser Asp Trp Ser Ser Pro Gln Val
    290                 295                 300

Phe Thr Thr Gln Asp Val Val Tyr Phe Pro Pro Lys Ile Leu Thr Ser
305                 310                 315                 320

Val Gly Ser Asn Ala Ser Phe His Cys Ile Tyr Lys Asn Glu Asn Gln
                325                 330                 335

Ile Ile Ser Ser Lys Gln Ile Val Trp Trp Arg Asn Leu Ala Glu Lys
            340                 345                 350
```

-continued

```
Ile Pro Glu Ile Gln Tyr Ser Ile Val Ser Asp Arg Val Ser Lys Val
        355                 360                 365

Thr Phe Ser Asn Leu Lys Ala Thr Arg Pro Arg Gly Lys Phe Thr Tyr
    370                 375                 380

Asp Ala Val Tyr Cys Cys Asn Glu Gln Ala Cys His His Arg Tyr Ala
385                 390                 395                 400

Glu Leu Tyr Val Ile Asp Val Asn Ile Asn Ile Ser Cys Glu Thr Asp
                405                 410                 415

Gly Tyr Leu Thr Lys Met Thr Cys Arg Trp Ser Pro Ser Thr Ile Gln
            420                 425                 430

Ser Leu Val Gly Ser Thr Val Gln Leu Arg Tyr His Arg Arg Ser Leu
        435                 440                 445

Tyr Cys Pro Asp Ser Pro Ser Ile His Pro Thr Ser Glu Pro Lys Asn
    450                 455                 460

Cys Val Leu Gln Arg Asp Gly Phe Tyr Glu Cys Val Phe Gln Pro Ile
465                 470                 475                 480

Phe Leu Leu Ser Gly Tyr Thr Met Trp Ile Arg Ile Asn His Ser Leu
                485                 490                 495

Gly Ser Leu Asp Ser Pro Pro Thr Cys Val Leu Pro Asp Ser Val Val
            500                 505                 510

Lys Pro Leu Pro Pro Ser Asn Val Lys Ala Glu Ile Thr Val Asn Thr
        515                 520                 525

Gly Leu Leu Lys Val Ser Trp Glu Lys Pro Val Phe Pro Glu Asn Asn
    530                 535                 540

Leu Gln Phe Gln Ile Arg Tyr Gly Leu Ser Gly Lys Glu Ile Gln Trp
545                 550                 555                 560

Lys Thr His Glu Val Phe Asp Ala Lys Ser Lys Ser Ala Ser Leu Leu
                565                 570                 575

Val Ser Asp Leu Cys Ala Val Tyr Val Val Gln Val Arg Cys Arg Arg
            580                 585                 590

Leu Asp Gly Leu Gly Tyr Trp Ser Asn Trp Ser Ser Pro Ala Tyr Thr
        595                 600                 605

Leu Val Met Asp Val Lys Val Pro Met Arg Gly Pro Glu Phe Trp Arg
    610                 615                 620

Lys Met Asp Gly Asp Val Thr Lys Lys Glu Arg Asn Val Thr Leu Leu
625                 630                 635                 640

Trp Lys Pro Leu Thr Lys Asn Asp Ser Leu Cys Ser Val Arg Arg Tyr
                645                 650                 655

Val Val Lys His Arg Thr Ala His Asn Gly Thr Trp Ser Glu Asp Val
            660                 665                 670

Gly Asn Arg Thr Asn Leu Thr Phe Leu Trp Thr Glu Pro Ala His Thr
        675                 680                 685

Val Thr Val Leu Ala Val Asn Ser Leu Gly Ala Ser Leu Val Asn Phe
    690                 695                 700

Asn Leu Thr Phe Ser Trp Pro Met Ser Lys Val Ser Ala Val Glu Ser
705                 710                 715                 720

Leu Ser Ala Tyr Pro Leu Ser Ser Ser Cys Val Ile Leu Ser Trp Thr
                725                 730                 735

Leu Ser Pro Asp Asp Tyr Ser Leu Leu Tyr Leu Val Ile Glu Trp Lys
            740                 745                 750

Ile Leu Asn Glu Asp Asp Gly Met Lys Trp Leu Arg Ile Pro Ser Asn
        755                 760                 765
```

-continued

Val Lys Lys Phe Tyr Ile His Asp Asn Phe Ile Pro Ile Glu Lys Tyr
    770                 775                 780

Gln Phe Ser Leu Tyr Pro Val Phe Met Glu Gly Val Gly Lys Pro Lys
785                 790                 795                 800

Ile Ile Asn Gly Phe Thr Lys Asp Ala Ile Asp Lys Gln Gln Asn Asp
                805                 810                 815

Ala Gly Glu Gln Lys Leu Ile Ser Glu Glu Asp Leu Gly Gly Glu Gln
            820                 825                 830

Lys Leu Ile Ser Glu Glu Asp Leu His His His His His His
        835                 840                 845

<210> SEQ ID NO 119
<211> LENGTH: 846
<212> TYPE: PRT
<213> ORGANISM: Artificial Sequence
<220> FEATURE:
<223> OTHER INFORMATION: rLEPR.mmh aa 1-818: Rat LEPR (L22-G839 of
      NP_036728.1) aa 819-846: myc-myc-hexahistidine tag

<400> SEQUENCE: 119

Leu Asn Leu Ala Tyr Pro Thr Ser Pro Trp Arg Phe Lys Leu Phe Cys
1               5                   10                  15

Ala Pro Pro Ser Thr Thr Asp Asp Ser Phe Leu Ser Pro Ala Gly Val
            20                  25                  30

Pro Asn Asn Thr Ser Ser Leu Lys Gly Ala Ser Glu Ala Leu Val Glu
        35                  40                  45

Ala Lys Phe Asn Ser Thr Gly Ile Tyr Val Ser Glu Leu Ser Lys Thr
    50                  55                  60

Ile Phe His Cys Cys Phe Gly Asn Glu Gln Gly Gln Asn Cys Ser Ala
65                  70                  75                  80

Leu Thr Gly Asn Thr Glu Gly Lys Thr Leu Ala Ser Val Val Lys Pro
                85                  90                  95

Leu Val Phe Arg Gln Leu Gly Val Asn Trp Asp Ile Glu Cys Trp Met
            100                 105                 110

Lys Gly Asp Leu Thr Leu Phe Ile Cys His Met Glu Pro Leu Leu Lys
        115                 120                 125

Asn Pro Phe Lys Asn Tyr Asp Ser Lys Val His Leu Leu Tyr Asp Leu
    130                 135                 140

Pro Glu Val Ile Asp Asp Leu Pro Leu Pro Pro Leu Lys Asp Ser Phe
145                 150                 155                 160

Gln Thr Val Gln Cys Asn Cys Ser Val Arg Glu Cys Glu Cys His Val
                165                 170                 175

Pro Val Pro Arg Ala Lys Val Asn Tyr Ala Leu Leu Met Tyr Leu Glu
            180                 185                 190

Ile Thr Ser Ala Gly Val Ser Phe Gln Ser Pro Leu Met Ser Leu Gln
        195                 200                 205

Pro Met Leu Val Val Lys Pro Asp Pro Pro Leu Gly Leu Arg Met Glu
    210                 215                 220

Val Thr Asp Asp Gly Asn Leu Lys Ile Ser Trp Asp Ser Gln Thr Lys
225                 230                 235                 240

Ala Pro Phe Pro Leu Gln Tyr Gln Val Lys Tyr Leu Glu Asn Ser Thr
                245                 250                 255

Ile Val Arg Glu Ala Ala Glu Ile Val Ser Asp Thr Ser Leu Leu Val
            260                 265                 270

Asp Ser Val Leu Pro Gly Ser Ser Tyr Glu Val Gln Val Arg Ser Lys
        275                 280                 285

```
Arg Leu Asp Gly Ser Gly Val Trp Ser Asp Trp Ser Leu Pro Gln Leu
    290                 295                 300

Phe Thr Thr Gln Asp Val Met Tyr Phe Pro Pro Lys Ile Leu Thr Ser
305                 310                 315                 320

Val Gly Ser Asn Ala Ser Phe Cys Cys Ile Tyr Lys Asn Glu Asn Gln
                325                 330                 335

Thr Ile Ser Ser Lys Gln Ile Val Trp Trp Met Asn Leu Ala Glu Lys
            340                 345                 350

Ile Pro Glu Thr Gln Tyr Asn Thr Val Ser Asp His Ile Ser Lys Val
        355                 360                 365

Thr Phe Ser Asn Leu Lys Ala Thr Arg Pro Arg Gly Lys Phe Thr Tyr
    370                 375                 380

Asp Ala Val Tyr Cys Cys Asn Glu Gln Ala Cys His His Arg Tyr Ala
385                 390                 395                 400

Glu Leu Tyr Val Ile Asp Val Asn Ile Asn Ile Ser Cys Glu Thr Asp
                405                 410                 415

Gly Tyr Leu Thr Lys Met Thr Cys Arg Trp Ser Pro Ser Thr Ile Gln
            420                 425                 430

Ser Leu Val Gly Ser Thr Val Gln Leu Arg Tyr His Arg Arg Ser Leu
        435                 440                 445

Tyr Cys Pro Asp Asn Pro Ser Ile Arg Pro Thr Ser Glu Leu Lys Asn
    450                 455                 460

Cys Val Leu Gln Thr Asp Gly Phe Tyr Glu Cys Val Phe Gln Pro Ile
465                 470                 475                 480

Phe Leu Leu Ser Gly Tyr Thr Met Trp Ile Arg Ile Asn His Ser Leu
                485                 490                 495

Gly Ser Leu Asp Ser Pro Pro Thr Cys Val Leu Pro Asp Ser Val Val
            500                 505                 510

Lys Pro Leu Pro Pro Ser Asn Val Lys Ala Glu Ile Thr Ile Asn Thr
        515                 520                 525

Gly Leu Leu Lys Val Ser Trp Glu Lys Pro Val Phe Pro Glu Asn Asn
    530                 535                 540

Leu Gln Phe Gln Ile Arg Tyr Gly Leu Asn Gly Lys Glu Ile Gln Trp
545                 550                 555                 560

Lys Thr His Glu Val Phe Asp Ala Lys Ser Lys Ser Ala Ser Leu Pro
                565                 570                 575

Val Ser Asp Leu Cys Ala Val Tyr Val Val Gln Val Arg Cys Arg Arg
            580                 585                 590

Leu Asp Gly Leu Gly Tyr Trp Ser Asn Trp Ser Ser Pro Ala Tyr Thr
        595                 600                 605

Leu Val Met Asp Val Lys Val Pro Met Arg Gly Pro Glu Phe Trp Arg
    610                 615                 620

Ile Met Asp Gly Asp Ile Thr Lys Lys Glu Arg Asn Val Thr Leu Leu
625                 630                 635                 640

Trp Lys Pro Leu Met Lys Asn Asp Ser Leu Cys Ser Val Arg Arg Tyr
                645                 650                 655

Val Val Lys His Arg Thr Ala His Asn Gly Thr Trp Ser Gln Asp Val
            660                 665                 670

Gly Asn Gln Thr Asn Leu Thr Phe Leu Trp Ala Glu Ser Ala His Thr
        675                 680                 685

Val Thr Val Leu Ala Ile Asn Ser Ile Gly Ala Ser Leu Val Asn Phe
    690                 695                 700
```

-continued

```
Asn Leu Thr Phe Ser Trp Pro Met Ser Lys Val Asn Ala Val Gln Ser
705                 710                 715                 720

Leu Ser Ala Tyr Pro Leu Ser Ser Ser Cys Val Ile Leu Ser Trp Thr
                725                 730                 735

Leu Ser Pro Asn Asp Tyr Ser Leu Leu Tyr Leu Val Ile Glu Trp Lys
            740                 745                 750

Asn Leu Asn Asp Asp Asp Gly Met Lys Trp Leu Arg Ile Pro Ser Asn
        755                 760                 765

Val Asn Lys Tyr Tyr Ile His Asp Asn Phe Ile Pro Ile Glu Lys Tyr
    770                 775                 780

Gln Phe Ser Leu Tyr Pro Val Phe Met Glu Gly Val Gly Lys Pro Lys
785                 790                 795                 800

Ile Ile Asn Gly Phe Thr Lys Asp Asp Ile Ala Lys Gln Gln Asn Asp
                805                 810                 815

Ala Gly Glu Gln Lys Leu Ile Ser Glu Glu Asp Leu Gly Gly Glu Gln
            820                 825                 830

Lys Leu Ile Ser Glu Glu Asp Leu His His His His His His
        835                 840                 845


<210> SEQ ID NO 120
<211> LENGTH: 1045
<212> TYPE: PRT
<213> ORGANISM: Artificial Sequence
<220> FEATURE:
<223> OTHER INFORMATION: mLEPR.hFc aa 1-818: Mouse LEPR (L22-G839 of
      NP_666258.2) aa 819-1045: human IgG1 tag (D104-K330 of P01857)

<400> SEQUENCE: 120

Leu Asn Leu Ala Tyr Pro Ile Ser Pro Trp Lys Phe Lys Leu Phe Cys
1               5                   10                  15

Gly Pro Pro Asn Thr Thr Asp Asp Ser Phe Leu Ser Pro Ala Gly Ala
            20                  25                  30

Pro Asn Asn Ala Ser Ala Leu Lys Gly Ala Ser Glu Ala Ile Val Glu
        35                  40                  45

Ala Lys Phe Asn Ser Ser Gly Ile Tyr Val Pro Glu Leu Ser Lys Thr
    50                  55                  60

Val Phe His Cys Cys Phe Gly Asn Glu Gln Gly Gln Asn Cys Ser Ala
65                  70                  75                  80

Leu Thr Asp Asn Thr Glu Gly Lys Thr Leu Ala Ser Val Val Lys Ala
                85                  90                  95

Ser Val Phe Arg Gln Leu Gly Val Asn Trp Asp Ile Glu Cys Trp Met
            100                 105                 110

Lys Gly Asp Leu Thr Leu Phe Ile Cys His Met Glu Pro Leu Pro Lys
        115                 120                 125

Asn Pro Phe Lys Asn Tyr Asp Ser Lys Val His Leu Leu Tyr Asp Leu
    130                 135                 140

Pro Glu Val Ile Asp Asp Ser Pro Leu Pro Pro Leu Lys Asp Ser Phe
145                 150                 155                 160

Gln Thr Val Gln Cys Asn Cys Ser Leu Arg Gly Cys Glu Cys His Val
                165                 170                 175

Pro Val Pro Arg Ala Lys Leu Asn Tyr Ala Leu Leu Met Tyr Leu Glu
            180                 185                 190

Ile Thr Ser Ala Gly Val Ser Phe Gln Ser Pro Leu Met Ser Leu Gln
        195                 200                 205

Pro Met Leu Val Val Lys Pro Asp Pro Pro Leu Gly Leu His Met Glu
    210                 215                 220
```

```
Val Thr Asp Asp Gly Asn Leu Lys Ile Ser Trp Asp Ser Gln Thr Met
225                 230                 235                 240

Ala Pro Phe Pro Leu Gln Tyr Gln Val Lys Tyr Leu Glu Asn Ser Thr
                245                 250                 255

Ile Val Arg Glu Ala Ala Glu Ile Val Ser Ala Thr Ser Leu Leu Val
            260                 265                 270

Asp Ser Val Leu Pro Gly Ser Ser Tyr Glu Val Gln Val Arg Ser Lys
        275                 280                 285

Arg Leu Asp Gly Ser Gly Val Trp Ser Asp Trp Ser Ser Pro Gln Val
    290                 295                 300

Phe Thr Thr Gln Asp Val Val Tyr Phe Pro Pro Lys Ile Leu Thr Ser
305                 310                 315                 320

Val Gly Ser Asn Ala Ser Phe His Cys Ile Tyr Lys Asn Glu Asn Gln
                325                 330                 335

Ile Ile Ser Ser Lys Gln Ile Val Trp Trp Arg Asn Leu Ala Glu Lys
            340                 345                 350

Ile Pro Glu Ile Gln Tyr Ser Ile Val Ser Asp Arg Val Ser Lys Val
        355                 360                 365

Thr Phe Ser Asn Leu Lys Ala Thr Arg Pro Arg Gly Lys Phe Thr Tyr
    370                 375                 380

Asp Ala Val Tyr Cys Cys Asn Glu Gln Ala Cys His His Arg Tyr Ala
385                 390                 395                 400

Glu Leu Tyr Val Ile Asp Val Asn Ile Asn Ile Ser Cys Glu Thr Asp
                405                 410                 415

Gly Tyr Leu Thr Lys Met Thr Cys Arg Trp Ser Pro Ser Thr Ile Gln
            420                 425                 430

Ser Leu Val Gly Ser Thr Val Gln Leu Arg Tyr His Arg Arg Ser Leu
        435                 440                 445

Tyr Cys Pro Asp Ser Pro Ser Ile His Pro Thr Ser Glu Pro Lys Asn
    450                 455                 460

Cys Val Leu Gln Arg Asp Gly Phe Tyr Glu Cys Val Phe Gln Pro Ile
465                 470                 475                 480

Phe Leu Leu Ser Gly Tyr Thr Met Trp Ile Arg Ile Asn His Ser Leu
                485                 490                 495

Gly Ser Leu Asp Ser Pro Pro Thr Cys Val Leu Pro Asp Ser Val Val
            500                 505                 510

Lys Pro Leu Pro Pro Ser Asn Val Lys Ala Glu Ile Thr Val Asn Thr
        515                 520                 525

Gly Leu Leu Lys Val Ser Trp Glu Lys Pro Val Phe Pro Glu Asn Asn
    530                 535                 540

Leu Gln Phe Gln Ile Arg Tyr Gly Leu Ser Gly Lys Glu Ile Gln Trp
545                 550                 555                 560

Lys Thr His Glu Val Phe Asp Ala Lys Ser Lys Ser Ala Ser Leu Leu
                565                 570                 575

Val Ser Asp Leu Cys Ala Val Tyr Val Val Gln Val Arg Cys Arg Arg
            580                 585                 590

Leu Asp Gly Leu Gly Tyr Trp Ser Asn Trp Ser Ser Pro Ala Tyr Thr
        595                 600                 605

Leu Val Met Asp Val Lys Val Pro Met Arg Gly Pro Glu Phe Trp Arg
    610                 615                 620

Lys Met Asp Gly Asp Val Thr Lys Lys Glu Arg Asn Val Thr Leu Leu
625                 630                 635                 640
```

-continued

```
Trp Lys Pro Leu Thr Lys Asn Asp Ser Leu Cys Ser Val Arg Arg Tyr
                645                 650                 655

Val Val Lys His Arg Thr Ala His Asn Gly Thr Trp Ser Glu Asp Val
            660                 665                 670

Gly Asn Arg Thr Asn Leu Thr Phe Leu Trp Thr Glu Pro Ala His Thr
        675                 680                 685

Val Thr Val Leu Ala Val Asn Ser Leu Gly Ala Ser Leu Val Asn Phe
    690                 695                 700

Asn Leu Thr Phe Ser Trp Pro Met Ser Lys Val Ser Ala Val Glu Ser
705                 710                 715                 720

Leu Ser Ala Tyr Pro Leu Ser Ser Ser Cys Val Ile Leu Ser Trp Thr
                725                 730                 735

Leu Ser Pro Asp Asp Tyr Ser Leu Leu Tyr Leu Val Ile Glu Trp Lys
            740                 745                 750

Ile Leu Asn Glu Asp Asp Gly Met Lys Trp Leu Arg Ile Pro Ser Asn
        755                 760                 765

Val Lys Lys Phe Tyr Ile His Asp Asn Phe Ile Pro Ile Glu Lys Tyr
    770                 775                 780

Gln Phe Ser Leu Tyr Pro Val Phe Met Glu Gly Val Gly Lys Pro Lys
785                 790                 795                 800

Ile Ile Asn Gly Phe Thr Lys Asp Ala Ile Asp Lys Gln Gln Asn Asp
                805                 810                 815

Ala Gly Asp Lys Thr His Thr Cys Pro Pro Cys Pro Ala Pro Glu Leu
            820                 825                 830

Leu Gly Gly Pro Ser Val Phe Leu Phe Pro Pro Lys Pro Lys Asp Thr
        835                 840                 845

Leu Met Ile Ser Arg Thr Pro Glu Val Thr Cys Val Val Val Asp Val
    850                 855                 860

Ser His Glu Asp Pro Glu Val Lys Phe Asn Trp Tyr Val Asp Gly Val
865                 870                 875                 880

Glu Val His Asn Ala Lys Thr Lys Pro Arg Glu Glu Gln Tyr Asn Ser
                885                 890                 895

Thr Tyr Arg Val Val Ser Val Leu Thr Val Leu His Gln Asp Trp Leu
            900                 905                 910

Asn Gly Lys Glu Tyr Lys Cys Lys Val Ser Asn Lys Ala Leu Pro Ala
        915                 920                 925

Pro Ile Glu Lys Thr Ile Ser Lys Ala Lys Gly Gln Pro Arg Glu Pro
    930                 935                 940

Gln Val Tyr Thr Leu Pro Pro Ser Arg Asp Glu Leu Thr Lys Asn Gln
945                 950                 955                 960

Val Ser Leu Thr Cys Leu Val Lys Gly Phe Tyr Pro Ser Asp Ile Ala
                965                 970                 975

Val Glu Trp Glu Ser Asn Gly Gln Pro Glu Asn Asn Tyr Lys Thr Thr
            980                 985                 990

Pro Pro Val Leu Asp Ser Asp Gly  Ser Phe Phe Leu Tyr  Ser Lys Leu
        995                 1000                1005

Thr Val  Asp Lys Ser Arg Trp  Gln Gln Gly Asn Val  Phe Ser Cys
    1010                1015                1020

Ser Val  Met His Glu Ala Leu  His Asn His Tyr Thr  Gln Lys Ser
    1025                1030                1035

Leu Ser  Leu Ser Pro Gly Lys
    1040                1045
```

METHODS OF TREATMENT USING A LEPTIN RECEPTOR AGONIST ANTIBODY

CROSS-REFERENCE TO RELATED APPLICATIONS

This application is a divisional application of U.S. patent application Ser. No. 16/377,089, filed Apr. 5, 2019, which claims the benefit under 35 U.S.C § 119(e) of U.S. provisional application No. 62/653,731, filed Apr. 6, 2018, which is herein specifically incorporated by reference in its entirety.

TECHNICAL FIELD

The present invention is related to therapeutic methods of treating metabolic dysfunction and restoring insulin sensitivity in leptin deficiency and lipodystrophy using agonist antibodies and antigen-binding fragments of agonist antibodies that bind human leptin receptor (LEPR).

SEQUENCE LISTING

An official copy of the sequence listing is submitted concurrently with the specification electronically via EFS-Web as an ASCII formatted sequence listing with a file name of 10436US02SEQ_LIST_ST25, a creation date of, May 5, 2022, and a size of about 110,592 bytes. The sequence listing contained in this ASCII formatted document is part of the specification and is herein incorporated by reference in its entirety.

BACKGROUND

Leptin is a polypeptide hormone predominantly expressed by adipose tissue and is involved in the regulation of metabolism, neuroendocrine function, immunity, energy balance and food intake. Leptin activity is mediated by interaction with, and signaling through, the leptin receptor. Leptin receptor, (also known as “LEPR,” “WSX,” “OB receptor,” “OB-R,” and “CD295”) is a single-pass transmembrane receptor of the class I cytokine receptor family with a large (818 amino acid) extracellular domain. Leptin deficiency, leptin resistance, and certain LEPR signaling-defective/signaling impaired mutations, are associated with obesity, type 2 diabetes, dyslipidemia, lipodystrophies, hepatic steatosis, non-alcoholic and alcoholic fatty liver diseases, severe insulin resistance, Leprechaunism/Donohue syndrome, Rabson-Mendenhall syndrome, and related complications. Therapeutic approaches to address leptin resistance, leptin deficiency, and hypoleptinemia (e.g., lipodystrophy) have mostly focused on the delivery of supplemental leptin or leptin analogues to affected individuals. Such approaches, however, have generally shown limited efficacy, particularly in leptin-resistant individuals, and are frequently associated with adverse side effects. Thus, a need exists in the art for alternative approaches to treating leptin resistance and other conditions associated with leptin deficiency or hypoleptinemia.

BRIEF SUMMARY OF THE INVENTION

The present invention provides antibodies and antigen-binding fragments thereof that bind human leptin receptor (LEPR). The antibodies of the present invention are agonist antibodies; i.e., binding of the anti-LEPR antibodies of the invention to LEPR causes, inter alia, activation of leptin receptor signaling in cells. In certain embodiments, the antibodies of the present invention do not compete with leptin for binding to LEPR. The antibodies of the present invention are useful, e.g., for mimicking, substituting for, or supplementing the normal biological activity of leptin in a subject. The antibodies and antigen-binding fragments of the present invention are therefore useful in the therapeutic treatment of diseases and disorders associated with leptin resistance and leptin deficiency.

The antibodies of the invention can be full-length (for example, an IgG1 or IgG4 antibody) or may comprise only an antigen-binding portion (for example, a Fab, F(ab')2 or scFv fragment), and may be modified to affect functionality, e.g., to eliminate residual effector functions (Reddy et al., 2000, J. Immunol. 164:1925-1933).

Exemplary anti-LEPR antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-LEPR antibodies. Table 2 sets forth the nucleic acid sequence identifiers of the HCVRs, LCVRs, HCDR1, HCDR2 HCDR3, LCDR1, LCDR2 and LCDR3 of the exemplary anti-LEPR antibodies.

The present invention provides antibodies or antigen-binding fragments thereof that specifically bind LEPR, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind LEPR, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind LEPR, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-LEPR antibodies listed in Table 1. In certain embodiments, the HCVR/LCVR amino acid sequence pair is selected from the group consisting of SEQ ID NOs: 2/10, 18/10, 26/10, 34/10, 42/10, 50/10, 58/66, 74/66 and 82/66.

The present invention also provides antibodies or antigen-binding fragments thereof that specifically bind LEPR, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind LEPR, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-LEPR antibodies listed in Table 1. In certain embodiments, the HCDR3/LCDR3 amino acid sequence pair is selected from the group consisting of SEQ ID NOs: 8/16, 24/16, 32/16, 40/16, 48/16, 56/16, 64/72, 80/72 and 88/72.

The present invention also provides antibodies or antigen-binding fragments thereof that specifically bind LEPR, comprising a set of six CDRs (i.e., HCDR1, HCDR2, HCDR3, LCDR1, LCDR2, and LCDR3) contained within any of the exemplary anti-LEPR antibodies listed in Table 1. In certain embodiments, the HCDR1, HCDR2, HCDR3, LCDR1, LCDR2, and LCDR3 amino acid sequences set is selected from the group consisting of SEQ ID NOs: 4, 6, 8, 12, 14, 16; 20, 22, 24, 12, 14, 16; 28, 30, 32, 12, 14, 16; 36, 38, 40, 12, 14, 16; 44, 46, 48, 12, 14, 16; 52, 54, 56, 12, 14, 16; 60, 62, 64, 68, 70, 72; 76, 78, 80, 68, 70, 72; and 84, 86, 88, 68, 70, 72.

In a related embodiment, the present invention provides antibodies, or antigen-binding fragments thereof that specifically bind LEPR, comprising a set of six CDRs (i.e., HCDR1, HCDR2, HCDR3, LCDR1, LCDR2, and LCDR3) contained within an HCVR/LCVR amino acid sequence pair as defined by any of the exemplary anti-LEPR antibodies listed in Table 1. For example, the present invention includes antibodies or antigen-binding fragments thereof that specifically bind LEPR, comprising the HCDR1, HCDR2, HCDR3, LCDR1, LCDR2, and LCDR3 amino acid sequences set contained within an HCVR/LCVR amino acid sequence pair selected from the group consisting of SEQ ID NOs: 2/10, 18/10, 26/10, 34/10, 42/10, 50/10, 58/66, 74/66 and 82/66. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-LEPR antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1, HCDR2, HCDR3), wherein the HCDR1, HCDR2, HCDR3 amino acid sequence set is as defined by any of the exemplary anti-LEPR antibodies listed in Table 1.

The present invention also provides nucleic acid molecules encoding an LCVR, wherein the LCVR comprises a set of three CDRs (i.e., LCDR1, LCDR2, LCDR3), wherein the LCDR1, LCDR2, LCDR3 amino acid sequence set is as defined by any of the exemplary anti-LEPR antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-LEPR antibody listed in Table 1.

The present invention also provides recombinant expression vectors capable of expressing a polypeptide comprising a heavy or light chain variable region of an anti-LEPR antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In another aspect, the invention provides a pharmaceutical composition comprising a recombinant human antibody or fragment thereof which specifically binds LEPR and a pharmaceutically acceptable carrier. In a related aspect, the invention features a composition which is a combination of an anti-LEPR antibody and a second therapeutic agent. In one embodiment, the second therapeutic agent is any agent that is advantageously combined with an anti-LEPR antibody.

As used throughout this disclosure, the term “subject” is interchangeable with the term “patient”. A subject or patient may be an adult. Pediatric patients are also contemplated as benefitting from the methods and compositions provided herein.

In yet another aspect, the invention provides therapeutic methods for enhancing or stimulating LEPR signaling using an anti-LEPR antibody or antigen-binding portion of an antibody of the invention. The therapeutic methods according to this aspect of the invention comprise administering a therapeutically effective amount of a pharmaceutical composition comprising an antibody or antigen-binding fragment of an antibody of the invention to a subject in need thereof. The disorder treated is any disease or condition which is improved, ameliorated, inhibited or prevented by stimulating or activating LEPR signaling, or otherwise mimicking the natural activity of leptin in vitro or in vivo.

In some aspects, provided herein are therapeutic methods for treating or preventing metabolic dysfunction or hypoleptinemia. The methods comprise administering a pharmaceutical composition comprising an antibody or antigen-binding fragment thereof that binds human leptin receptor (LEPR) and activates LEPR signaling, and a pharmaceutically acceptable carrier or diluent, to a subject in need thereof.

In some aspects, provided herein are therapeutic methods for treating or preventing metabolic dysfunction or hypoleptinemia, or a disease or condition associated with metabolic dysfunction or hypoleptinemia, or one or more symptoms of the disease or condition. The methods comprise administering a pharmaceutical composition comprising an antibody or antigen-binding fragment thereof that binds human LEPR and activates LEPR signaling, and a pharmaceutically acceptable carrier or diluent, to a subject in need thereof.

In some embodiments, the condition is selected from the group consisting of non-alcoholic fatty liver disease, non-alcoholic steatohepatitis (NASH), female infertility, amenorrhea, abnormal hormone cycle, impaired immune function, hypothyroidism, obesity, monogenic obesity, diabetes type I, diabetes type II, lipodystrophy, congenital lipodystrophy, generalized lipodystrophy, acquired lipodystrophy, partial lipodystrophy, congenital partial lipodystrophy, congenital generalized lipodystrophy, acquired partial lipodystrophy, and acquired generalized lipodystropy.

In some embodiments, the one or more symptoms of the disease or condition associated with metabolic dysfunction or hypoleptinemia is selected from the group consisting of adiposity, obesity, hyperphagia, hyperglycemia, hypertriglyceridemia, hypercholesterolemia, insulin resistance, dyslipidemia, delay in growth, delay in pubertal growth spurt, abnormal growth hormone secretion, elevated HbA1c, low bone mineral density (or low bone mass), low bone mineral content, and low lean body mass. The symptoms of the disease or condition associated with metabolic dysfunction or hypoleptinemia can be prevented, ameliorated, or lessened in severity and/or duration, or reduced, following administration of the antibody or antigen-binding fragment thereof that binds human LEPR.

In yet other aspects, provided herein are methods for treating metabolic complications of lipodystrophy. Such methods comprise administering a pharmaceutical composition comprising an antibody or antigen-binding fragment thereof that binds human leptin receptor (LEPR) and activates LEPR signaling, and a pharmaceutically acceptable carrier or diluent, to a subject in need thereof. In some embodiments, the treatment alleviates hyperglycemia, decreases insulin resistance, decreases hypertriglyceridemia, lowers circulating cholesterol levels, and/or lowers HbA1c levels in the subject. Lipodystrophy can include acquired partial lipodystrophy, acquired generalized lipodystrophy, congenital partial lipodystrophy, and congenital generalized lipodystrophy.

Congenital leptin deficiency is a rare disease characterized by pathogenic variants of LEPR or leptin. Some subjects have circulating leptin but the protein is non-functional due to the genetic mutation, for example, p.N103K, which encodes a bioinactive form of leptin. Some subjects have very little or no circulating leptin. Other genes can be involved in impaired leptin signaling including LMNA, PPARG, PLIN1, AKT2, CIDEC, LIPE, and ADRA2A, and the anti-LEPR antibodies and antigen-binding fragments thereof provided herein are useful in mitigating the effects of such mutations on leptin signaling.

In some aspects, provided herein are methods for treating congenital leptin deficiency. Such methods comprise administering a pharmaceutical composition comprising an antibody or antigen-binding fragment thereof that binds human leptin receptor (LEPR) and activates LEPR signaling, and a pharmaceutically acceptable carrier or diluent, to a subject in need thereof. In some embodiments, the subject has lipodystrophy and failed metreleptin treatment. In some embodiments, the symptoms associated with congenital lipodystrophy are prevented, ameliorated, or lessened in severity and/or duration, or reduced, following administration of the antibody or antigen-binding fragment thereof that binds human LEPR. In some embodiments, the treatment reverses or mitigates one or more of hyperphagia, obesity, hyperinsulinemia, dyslipidemia, and hepatosteatosis in the subject. In some embodiments, the subject's blood glucose is decreased, the subject's body weight is decreased, the subject exhibits decreased food intake, the subject's fat mass is decreased, the subject's lean mass is increased, and/or the subject's bone mass is increased.

In some aspects, provided herein are therapeutic methods for treating non-alcoholic fatty liver disease or nonalcoholic steatohepatitis (NASH). In some aspects, the subject is hypoleptinemic, lipodystrophic, or leptin deficient. According to this aspect, the methods comprise administering a pharmaceutical composition comprising an antibody or antigen-binding fragment thereof that binds human LEPR and activates LEPR signaling, and a pharmaceutically acceptable carrier or diluent, to a subject in need thereof. In some embodiments, the subject's liver weight is decreased after treatment. In some embodiments, the symptoms of non-alcoholic fatty liver disease, including non-alcoholic hepatic steatosis, are diminished in the subject after treatment. In some embodiments, the plasma levels of alanine transaminase (ALT) and/or plasma levels of aspartate transaminase (AST) are decreased in the subject.

In yet other aspects, provided herein are methods for treating female infertility, amenorrhea, or restoring normal hormone cycles associated with metabolic dysfunction or hypoleptinemia. Such methods comprise administering a pharmaceutical composition comprising an antibody or antigen-binding fragment thereof that binds human LEPR and activates LEPR signaling, and a pharmaceutically acceptable carrier or diluent, to a subject in need thereof. In some aspects, administration of the antibody or antigen-binding fragment thereof that binds human LEPR can increase fertility and/or increase the opportunity for conception. In some aspects, the subject conceives. In some aspects, the treatment can restore or initiate normal menstrual cycling.

In some aspects, provided herein are methods for treating impaired immune function associated with metabolic dysfunction or hypoleptinemia. Such methods comprise administering a pharmaceutical composition comprising an antibody or antigen-binding fragment thereof that binds human LEPR and activates LEPR signaling, and a pharmaceutically acceptable carrier or diluent, to a subject in need thereof. In some embodiments, following administration of the antibody or antigen-binding fragment thereof that binds human LEPR, the CD4+ T-cell counts are increased.

In other aspects, provided herein are therapeutic methods for increasing bone mass in a subject having a metabolic dysfunction or hypoleptinemia. The methods comprise administering a pharmaceutical composition comprising an antibody or antigen-binding fragment thereof that binds human LEPR and activates LEPR signaling, and a pharmaceutically acceptable carrier or diluent, to a subject in need thereof.

In other aspects, provided herein are therapeutic methods for treating adiposity or obesity, or reducing body weight. According to this aspect, the methods comprise administering a pharmaceutical composition comprising an antibody or antigen-binding fragment thereof that binds human LEPR and activates LEPR signaling, and a pharmaceutically acceptable carrier or diluent, to a subject in need thereof. In some embodiments, the treatment reduces fat mass but not lean mass.

In some embodiments, the subject in need thereof is hypoleptinemic, lipodystrophic, or leptin deficient. In some embodiments, the subject in need thereof is not hypoleptinemic or leptin deficient. In some embodiments, the metabolic dysfunction, adiposity, or obesity is not associated with or caused by a signaling-defective or signaling-impaired LEPR mutation.

In some embodiments, administration of the antibody or antigen-binding fragment thereof that binds human LEPR and activates LEPR signaling according to a method provided herein, stimulates hypothalamic STAT3 signaling or enhances leptin-induced or leptin-independent STAT3 signaling.

In some embodiments, administration of the antibody or antigen-binding fragment thereof that binds human LEPR and activates LEPR signaling lowers circulating plasma triglycerides and/or lowers circulating plasma total cholesterol.

In other aspects, provided herein are therapeutic methods for treating hyperphagia, hyperglycemia, insulin resistance, dyslipidemia, nonalcoholic steatohepatitis (NASH), or nonalcoholic fatty liver disease by stimulating hypothalamic STAT3 signaling. Such methods comprise administering a pharmaceutical composition comprising an antibody or antigen-binding fragment thereof that binds human leptin receptor (LEPR) and activates LEPR signaling, and a pharmaceutically acceptable carrier or diluent, to a subject in need thereof. In some embodiments, the treatment lowers circulating plasma triglycerides. In some embodiments, the treatment lowers circulating plasma total cholesterol.

In yet other aspects, provided herein are methods for treating delay in growth, lack of pubertal growth spurt, and/or abnormal growth hormone secretion associated with congenital leptin deficiency. Such methods comprise administering a pharmaceutical composition comprising an antibody or antigen-binding fragment thereof that binds human LEPR and activates LEPR signaling, and a pharmaceutically acceptable carrier or diluent, to a subject in need thereof.

In yet other aspects, provided herein are methods for treating hypothyroidism associated with congenital leptin deficiency. Such methods comprise administering a pharmaceutical composition comprising an antibody or antigen-binding fragment thereof that binds human LEPR and activates LEPR signaling, and a pharmaceutically acceptable carrier or diluent, to a subject in need thereof.

In yet other aspects, provided herein are methods for treating low bone mineral density and/or bone mineral content associated with hypoleptinemia and/or leptin deficiency. Such methods comprise administering a pharmaceutical composition comprising an antibody or antigen-binding fragment thereof that binds human LEPR and activates LEPR signaling, and a pharmaceutically acceptable carrier or diluent, to a subject in need thereof.

One or more further therapeutic agents can be administered with the antibody or antigen-binding fragment thereof that binds human LEPR to the subjects described herein. The second therapeutic agent can be selected from the group consisting of a recombinant human leptin, a PCSK9 inhibitor, a statin, ezetimibe, insulin, an insulin variant, an insulin secretagogue, metformin, a sulfonylurea, a sodium glucose cotransporter 2 (SGLT2) Inhibitor, a GLP-1 agonist/analogue, a glucagon (GCG) inhibitor, a glucagon receptor (GCGR) inhibitor, an angiopoietin-like protein (ANGPTL) inhibitor, Phentermine, Orlistat, Topiramate, Bupropion, Topiramate/Phentermine, Bupropion/Naltrexone, Bupropion/Zonisamide, Pramlintide/Metreleptin, Lorcaserin, Cetilistat, Tesofensine, Velneperit, an anticonvulsant, digoxin, coumadin, Vitamin D, Thyroxine, a thyroid supplement, a vitamin supplement, a calcium supplement, carnitine, Coenzyme Q10, an anti-constipation medication, an anti-allergic medications, gabapentin, a narcotic, ketamine, lidocaine, or venlafaxine hydrochloride.

The present invention also provides a method for treating, preventing or ameliorating (i) lipodystrophy (of any type) and/or monogenic obesity; (ii) a condition associated with lipodystrophy and/or monogenic obesity; or (iii) an symptom of (i) or (ii); in a patient comprising administering, to the patient who is in need thereof, an agonist antibody or antigen-binding fragment thereof that binds specifically to LEPR (e.g., H4H17319P2). For example, in an embodiment of the invention, the condition associated with lipodystrophy and/or monogenic obesity is extreme early onset obesity; hyperphagia and impaired satiety; impaired immune function ($CD4^+$ counts); insulin resistance; non-alcoholic fatty liver disease; NASH, dyslipidemia; diabetes; reproductive dysfunction; hypogonadism; lack of pubertal growth spurt; hypothyroidism; impaired thyroid function; low bone mineral density and/or low bone mass. In an embodiment of the invention, said symptom is enlarged liver, elevated liver enzymes, elevated blood levels of alanine aminotransferase (ALT), elevated blood levels of aspartate aminotransferase (AST), high adiposity; body mass index >$85^{th}$ percentile for age and gender; abnormal food seeking behavior; abnormal food aggressive behavior; recurrent and potentially lethal infections; hyperinsulinemia; liver steatosis; progression to NASH (lipodystrophy); hypertriglyceridemia; elevated HbA1c; elevated glucose levels; impaired glucose tolerance; delayed pubertal development; reduced expression of secondary sexual characteristics; no or irregular menses; infertility; short stature; abnormal growth hormone secretion; altered T3; altered TSH; and/or altered free thyroxine levels.

In an embodiment of the invention, an agonist anti-LEPR antibody or antigen-binding fragment thereof (e.g., H4H17319P2; see WO2017/66204) is dosed as follows: (i) one or more doses of about 5 mg/kg body weight intravenously; then (ii) one or more doses of about 250-300 mg, e.g., 250 mg or about 300 mg subcutaneously once per week; then (iii) optionally, one or more doses of about 250 mg or about 300 mg subcutaneously once per month or about 28 days. For example, (i) one or more doses of about 5 mg/kg body weight intravenously; then (ii) one or more doses of about 250 mg or about 300 mg subcutaneously once per week. In an embodiment of the invention, the antibody is dosed as follows (i) 5 mg/kg body weight intravenously once (on day 1); then (ii) four doses of about 250 mg or about 300 mg subcutaneously once per week (e.g., on days 4, 11, 18 and 25); then (iii) one or more doses of about 250 mg or about 300 mg subcutaneously once per month or 28 days (e.g., on days 53, 81, 109, 137, 165 and 193, etc.). For example, in an embodiment of the invention, the first subcutaneous dose occurs on about day 4 which is about three days after the intravenous dose which occurs on day 1.

Other embodiments will become apparent from a review of the ensuing detailed description.

BRIEF DESCRIPTION OF THE FIGURES

FIG. 7A shows the fat mass of mice before dosing with anti-LEPR antibodies H4H18482P2, H4H18487P2 or H4H18492P2. FIG. 7B shows the fat mass of mice treated with 30 mg/kg of H4H18482P2, H4H18487P2 or H4H18492P2.

FIG. 9A shows body weight (left) and daily food intake (right) of $Lepr^{hu/hu}$ mice throughout the course of the study showing that induction of leptin deficiency leads to rapid body weight gain and hyperphagia. N=14 per group. FIG. 9B shows body composition analysis by micro-CT imaging performed 1 day in advance of HDD (day −1), 1 day in advance of monoclonal antibody dosing (day 6 post-HDD) and 6 days post dosing (day 13 post-HDD). Quantification of fat mass (left) and lean mass (right) are shown for control monoclonal antibody (N=14) and H4H17319P2 (N=14) dosing groups (gray and black bars, respectively). FIG. 9C. Chemistry analyses of plasma obtained 6 days post-treatment (Day 13) from induced leptin-deficient $Lepr^{hu/hu}$ mice treated with a single dose of control monoclonal antibody (gray bars, N=14)) or H4H17319P2 (black bars, N=14).

FIG. 10A. Schematic showing gene targeting for generation of leptin receptor ectodomain humanized $Lepr^{hu/hu}$ mice. FIG. 10B. Body weight (9 week old) and micro-CT quantification of body composition (9 to 12 week old) male wild-type ($Lepr^{+/+}$, gray bars) and $Lepr^{hu/hu}$ (black bars) mice. Data are mean±SEM. N=6-10 per group. FIG. 10C. Insulin tolerance test (0.75 U/kg, IP) for 8 to 11 week old male $Lepr^{+/+}$ (gray circles) and $Lepr^{hu/hu}$ (black circles) mice. Data are mean±SEM. N=8-9 per group. FIG. 10D. Serum leptin levels in 9 to 13 week old male $Lepr^{+/+}$ (gray bars) and $Lepr^{hu/hu}$ (black bars) mice. Data are mean±SEM. N=8-9 per group.

FIG. 11A. Body weight (left), percent change in body weight from baseline on day 0 (middle) and cumulative food intake (right) in 8 week old male C57BL/6N mice following hydrodynamic DNA delivery (HDD) on day 0 of mouse leptin receptor ectodomain-encoding plasmid (mLeprECD.hFc, black circles) or control plasmid (Control hFc, gray circles). Data are mean±SEM. N=6 per group. FIG. 11B. Micro-CT quantification of body composition on 7 days post-HDD of mouse leptin receptor ectodomain-encoding plasmid (mLeprECD.hFc, black bars) or control plasmid (Control hFc, gray bars). Data are mean±SEM, for fat mass, lean mass, bone mass, bone mineral content, and bone density (left to right). N=6 per group.

FIG. 12A. Body weight (left) and food intake (right) of female mice throughout the course of the study showing that induction of leptin deficiency leads to rapid body weight gain and hyperphagia. Increases in body weight continue following control monoclonal antibody administration (N=14). N=10-11 per group. FIG. 12B. Body composition analysis by micro-CT imaging for female mice was performed 1 day in advance of HDD (day −1), 1 day in advance of monoclonal antibody dosing (day 6 post-HDD) and 6 days post dosing (day 13 post-HDD). Data are mean±SEM for fat mass, lean mass, bone mass, bone mineral content, and bone density (left to right). N=10-11 per group. FIG. 12C. Body composition analysis by micro-CT imaging for male mice was performed 1 day in advance of HDD (day −1), 1 day in advance of monoclonal antibody dosing (day 6 post-HDD) and 6 days post dosing (day 13 post-HDD). Data are mean±SEM for bone mass, bone mineral content, and bone density (left to right). N=14 per group.

FIG. 13A shows change in body weight from pre-HDD for mice (left) and cumulative food intake (right). N=6-11 per group. FIG. 13B demonstrates micro-CT quantification of body composition for $Lepr^{hu/hu}$ mice prior on day 13 post-HDD (7 days after treatment). Fat mass, lean mass bone mass, bone mineral content, and bone density (left to right). N=5-10 per group. FIG. 13C shows insulin tolerance testing on day 10 post-HDD (3 days after treatment) in mice fasted for 4 h prior to insulin treatment (1.0 U/kg, IP) at 0 min. Blood glucose levels and the glucose area under the curve (AUC) for the insulin tolerance test are shown (left and right, respectively). N=6-11 per group. FIG. 13D provides chemistry analyses of plasma lipids obtained on Day 16 or Day 17. N=6-11 per group.

FIGS. 14A-14G. Male lipodystrophic aP2-$nSrebp1c^{Tg/+}$; $Lepr^{hu/hu}$ mice (Tg), 27 to 30 weeks old, were dosed once-weekly with 10 mg/kg (SC) of control monoclonal antibody (gray circles or bars) or H4H17319P2 (black circles or bars). As reference, 27 to 30 week old, male non-transgenic $Lepr^{hu/hu}$ mice (nonTg) were also dosed once-weekly with 10 mg/kg (SC) of control monoclonal antibody (open diamonds and white bars). All data are mean±SEM. *, P<0.05 of the respective group denoted by symbol color or bar versus nonTg mice dosed with control monoclonal antibody at the indicated time point. #, P<0.05 of the respective group denoted by symbol color or bar versus Tg mice dosed with control monoclonal antibody at the indicated time point. $, P<0.05 day 27 versus day −5 of the respective group. FIG. 14A, left and right, show body weight and cumulative food intake, respectively. N=8-9 per group. FIG. 14B, Left and right, show lean mass and fat mass, respectively, quantified by micro-CT imaging prior to dosing on day −5 and following treatment on day 27. N=9 per group. FIG. 14C provides blood glucose levels throughout the study (left) and percent hemoglobin A1c levels on day 28 (right). N=9 per group. FIG. 14D provides blood glucose levels and glucose area under the curve (AUC) from insulin tolerance testing (0.5 U/kg IP) on day 23. N=9 per group. FIGS. 14E and 14F shows that circulating lipids (E) and liver enzyme levels (F) are reduced in H4H17319P2-treated lipodystrophic Lepr$^{hu/hu}$ (Tg) mice. Chemistry analyses of plasma obtained on day 28 for lipid (triglyceride, cholesterol, LDL-C and HDL-C) and liver enzyme levels (alanine transaminase, ALT, and aspartate transaminase, AST). N=9 per group. FIG. 14G provides liver weights, liver triglyceride content, and representative hematoxylin and eosin stained liver sections from livers harvested on day 30 (left, middle and right respectively). N=5 per group.

FIG. 15A. Left, body weights at 12 to 24 weeks of age. Middle, fat mass quantified by micro-CT imaging at approximately 15 to 20 weeks of age. Right, plasma leptin levels measured at 19 to 21 weeks of age. N=17-28 per group. FIG. 15B. Blood glucose levels during an insulin tolerance test (0.75 U/kg insulin, IP) at 18 to 20 weeks of age. N=12-13 per group. FIG. 15C. Left to right, plasma levels of triglycerides, cholesterol, LDL-C and HDL-C at 15 to 17 weeks of age. N=20 to 28 per group.

FIG. 16A. Body composition by micro-CT imaging showing bone mass, bone mineral content, and bone density (left to right), quantified prior to dosing on day −5 and following treatment on day 27. N=9 per group.

FIG. 17A provides immunohistochemical staining for pSTAT3 Y705 in the arcuate nucleus (Arc) and ventromedial hypothalamus (Vmh) at approximately −1.52 mm from bregma showing an increased number of pSTAT3 Y705$^+$ cells in male 32 to 38 week old lipodystrophic (Tg) mice. Brain sections are from brains harvested 3 days after treatment with a single dose of control or H4H17319P2 (10 mg/kg SC) or infusion of leptin (30 μg/day SC). Representative photomicrographs and quantification of the number of pSTAT3 Y705+ cells in the Arc and Vmh (left, middle and right, respectively) are shown. N=4-5 per group. FIG. 17B, left, provides blood glucose levels during the study. Middle and right, blood glucose levels and area under the curve for glucose levels during insulin tolerance testing on day 9. N=8-9 per group. FIG. 17C provides body weight (left), change in body weight (middle) and cumulative food intake (right). N=8-9 per group of Tg mice. N=5 for nonTg mice. FIG. 17D provides chemistry analyses of plasma obtained on day 13 for triglyceride, cholesterol, LDL-C and HDL-C showing reduction in plasma triglycerides and cholesterol with H4H17319P2 treatment. N=8-9 per group of Tg mice. N=5 for nonTg mice. FIG. 17E provides liver mass (left) and liver triglyceride content (right) for livers obtained on day 14. N=6-9 per group of Tg mice. N=5 for nonTg mice.

FIG. 18A provides percent change in body weight from pre-dose on day 0 (left) and food intake (right) during the study in lean female mice. N=6-7 per group. FIG. 18B demonstrates quantitative NMR analyses showing percent change in fat mass (left) and lean mass (right) from pre-dose day 0, during the study in lean female mice. N=6-7 per group. FIG. 18C demonstrates percent change in body weight from pre-dose on day −1 during the study in lean monkeys. N=12 per group. FIG. 18D demonstrates percent change in body weight from mean pre-dose of days −14, −7 and −1 (left) and percent change in fat mass (middle) and lean mass (right) as quantified by DEXA (Dual Energy X-Ray Absorptiometry for measuring body composition) during the study in high body fat monkeys. N=4 and 8 for control and H4H17319P2 dosing groups, respectively.

FIG. 20A-20B is a table providing the assessment schedule for a patient undergoing treatment with H4H17319P2 in Treatment Period 1 (A) and Period 2 and Extended Treatment Period (B).

FIG. 21A provides blood glucose in mg/dL, FIG. 21B provides body weight in grams and FIG. 21C provides cumulative food intake in grams. Grey circles, Lepr$^{hu/hu}$ administered IgG4$^P$ Control (N=5). Black squares, Lepr$^{hu/hu}$ Lep$^{-/-}$ administered IgG4$^P$ Control (N=7). White squares, Lepr$^{hu/hu}$ Lep$^{-/-}$ administered H4H17319P2 (N=8). Data expressed as mean+SEM. *, P<0.05 for Lepr$^{hu/hu}$ Lep$^{-/-}$+H4H17319P2 group vs. $Lepr^{hu/hu}$, $Lep^{-/-}$+$IgG4^P$ Control by two-way ANOVA with Tukey post-hoc test. Two mice were excluded from the $Lepr^{hu/hu}$ $Lep^{-/-}$+$IgG4^P$ Control group and one mouse from the $Lepr^{hu/hu}$ $Lep^{-/-}$+H4H17319P2 group for food intake assessment due to excessive shredding of food in their cage.

FIG. 22A provides fat mass, FIG. 22B provides bone mass and FIG. 22C provides lean mass in grams. Mice were given a baseline scan on D-5, prior to study initiation. Post-mAb scan was conducted on Day 35 of the study. Grey bars, $Lepr^{hu/hu}$ administered $IgG4^P$ Control (N=5). Black bars, $Lepr^{hu/hu}$ $Lep^{-/-}$ administered $IgG4^P$ Control (N=7). White bars, $Lepr^{hu/hu}$ $Lep^{-/-}$ administered H4H17319P2 (N=8). Mice were given weekly subcutaneous injections of 10 mg/kg of either H4H17319P2 or isotype control antibody. Data expressed as mean+SEM. *, P<0.05 vs. baseline; #, P<0.05 vs. $Lepr^{hu/hu}$+$IgG4^P$ Control at the respective time point; +, P<0.05 vs. H4H17319P2 group at the respective time point. Statistical analyses were conducted by two-way ANOVA with Tukey post-hoc test.

FIG. 23A provides blood glucose in mg/dL, FIG. 23B provides body weight in grams and FIG. 23C provides cumulative food intake in grams. Grey circles, $Lepr^{hu/hu}$ administered $IgG4^P$ Control (N=7-8). Black squares, $Lepr^{A409E/A409E}$ administered $IgG4^P$ Control (N=9-10). White squares, $Lep^{A409E/A409E}$ administered H4H17319P2 (N=10). Data expressed as mean+SEM. *, P<0.05 for $Lepr^{A409E/A409E}$ H4H17319P2 group vs. $Lepr^{A409E/A409E}$ IgG4P Control by mixed-effects model with Sidak post-hoc test. One mouse was excluded from the $Lepr^{hu/hu}$+$IgG4^P$ Control group and one mouse from the $Lepr^{A409E/A409E}$+$IgG4^P$ Control group for food intake assessment due to death during the study. One mouse was excluded from the $Lepr^{hu/hu}$+$IgG4^P$ Control group and three mice from the $Lepr^{A409E/A409E}$+$IgG4^P$ Control group for food intake assessment due to excessive shredding of food during the study.

FIGS. 24A-24C demonstrate fat, bone and lean mass by uCT body composition analysis in a murine model of congenital leptin receptor deficiency. FIG. 24A provides fat mass, FIG. 24B provides bone mass, and FIG. 24C provides lean mass in grams. Mice were given a baseline scan on D-1, prior to study initiation. Post-mAb scan was conducted on Day 41 of the study. Grey bars, $Lepr^{hu/hu}$ administered $IgG4^P$ Control (N=7-8). Black bars, $Lepr^{A409E/A409E}$ administered $IgG4^P$ Control (N=9-10). White bars, $Lepr^{A409E/A409E}$ administered H4H17319P2 (N=10). Mice were given weekly subcutaneous injections of 10 mg/kg of either H4H17319P2 or isotype control ($IgG4^P$) antibody. Data expressed as mean+SEM. *, P<0.05 vs. baseline; #, P<0.05 vs. $Lepr^{hu/hu}$+$IgG4^P$ Control at the respective time point; +, P<0.05 vs. $Lepr^{A409E/A409E}$ H4H17319P2 at the respective time point. All statistical analyses were conducted using a mixed-effects model with Sidak post-hoc test.

FIG. 25 depicts a schedule of events for Part A cohorts of a first-in-human clinical trial and includes procedures to be carried out on each visit for screening, treatment, and follow-up visits.

FIG. 26 depicts a schedule of events for Part B cohorts of a first-in-human clinical trial and includes procedures to be carried out on each visit for prescreening, screening, and baseline determinations.

FIG. 27 depicts a second schedule of events for Part B cohorts of a first-in-human clinical trial and includes procedures to be carried out on each visit for treatment and follow-up.

DETAILED DESCRIPTION OF THE INVENTION

Figure 1:
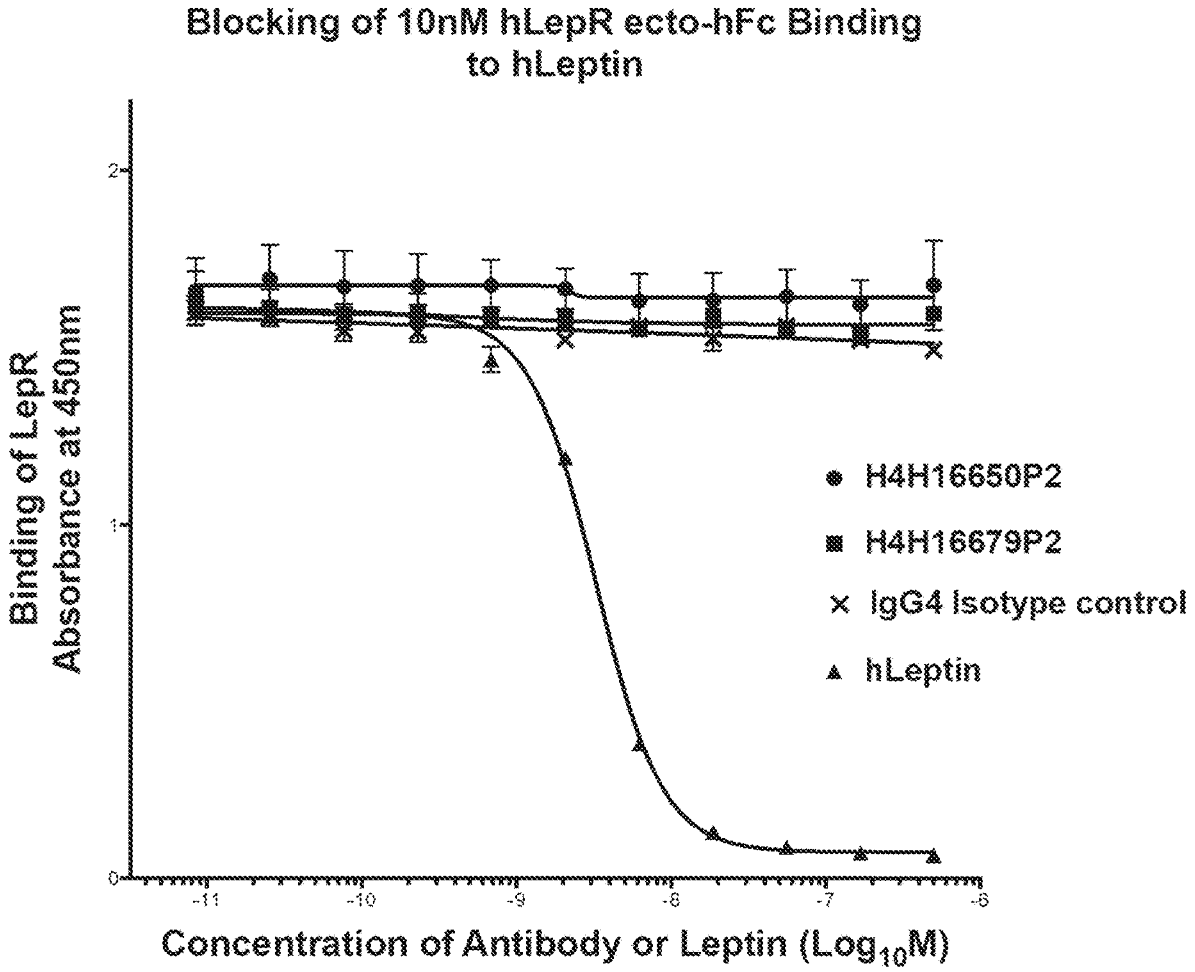
FIG. 1 depicts the binding of dimeric human LEPR to human Leptin in the presence of increasing concentrations of test anti-LEPR antibodies or control molecules, as measured by ELISA (absorbance at 450 nm).

Leptin is an adipose tissue hormone that governs energy balance as well as metabolic and neuroendocrine function (Flak and Myers, Mol Endocrinol. 2016; 30: 3-12; Zhang et al. Nature. 1994; 372: 425-432). In a state of energy deficit low circulating leptin levels drive adaptive responses, including increasing hunger and energy conservation through modulation of neuroendocrine pathways. Leptin modulates energy and metabolic balance by engaging the leptin receptor (LEPR), a member of the class I cytokine receptor family (Tartaglia et al., 1995). LEPR is encoded by a single gene and alternative splicing gives rise to multiple splice isoforms of LEPR that differ at their C-terminal sequence (Baumann et al., 1996). Of these splice isoforms, LEPR-b is the principal isoform that mediates leptin's effects and is the only isoform to stimulate JAK-STAT signaling (Baumann et al., 1996; Tartaglia et al., 1995; White and Tartaglia, 1996). LEPR-b expressing neurons in the brain are the principal targets and mediators of leptin action on energy, metabolic and neuroendocrine homeostasis. This is supported by the observations that selective neuronal expression of Lepr-b in $Lepr^{db/db}$ mice rescues the obesity, diabetic and reproductive phenotypes (de Luca et al., 2005). Additionally, genetic deletion of Lepr from neurons phenocopies the obese and hyperglycemic phenotypes of $Lepr^{db/db}$ animals (Cohen et al., 2001). Leptin deficiency due to genetic loss-of-function mutations in the Lep gene leads to hyperphagia, obesity, insulin resistance, dyslipidemia, and impaired neuroendocrine function in mice that is reversed with leptin treatment (Barash et al., 1996; Campfield et al., 1995; Chehab et al., 1996; Halaas et al., 1995; Pelleymounter et al., 1995). Clinically, the leptin analog, metreleptin, reverses obesity as well as metabolic and reproductive dysfunction in patients with monogenic obesity due to leptin deficiency (Farooqi et al., 1999; Farooqi et al., 2002). Similar to primary leptin deficiency, disease states of secondary hypoleptinemia are associated with glucose and lipid metabolic dysfunction that can be reversed with leptin treatment. Congenital and acquired generalized lipodystrophies are rare and severe diseases characterized by a near complete loss of adipose tissue depots (Brown et al., 2016; Patni and Garg, 2015). The very low circulating leptin levels in these patients results in a state of hyperphagia, hypertriglyceridemia, hypercholesterolemia, hepatic steatosis, insulin resistance and diabetes (Brown et al., 2016; Patni and Garg, 2015). A severe complication of hypertriglyceridemia, especially when TG levels exceed 500 mg/dL to 1000 mg/dL, is acute and recurrent pancreatitis (Yadav and Pitchumoni 2003), which can be life-threatening with a mortality rate over 40% when accompanied by complications like infection or organ failure (UK Guidelines 2005). Ectopic lipid deposition in the liver (hepatic steatosis) can lead to steatohepatitis, which is characterized by fat accumulation, cellular injury, and inflammation in the liver, and is one of the most common causes of cirrhosis (El-Zayadi 2008, Federico 2006, and Festi 2004).

Leptin treatment reduces hyperphagia and improves dyslipidemia, hepatic steatosis and glycemic control in Tg-aP2-nSrebp1c mice that develop a near complete loss of adipose depots characteristic of generalized lipodystrophy (Shimomura et al., 1999; Shimomura et al., 1998). Metreleptin mitigates metabolic dysfunction in patients with generalized lipodystrophy (Oral et al., 2002), but is not approved for the treatment of patients with partial lipodystrophy (Ajluni et al., 2016).

Lipodystrophy patients often experience other serious co-morbidities such as chronic renal disease, cardiovascular complications, autoimmune diseases, and peripheral T-cell lymphoma, acute lymphoblastic leukemia, and Hodgkin's lymphoma.

Patients with congenital leptin deficiency present in the first few months of life with rapid weight gain and immunologic abnormalities, with significantly increased risk of mortality within the first and second decades of life (Funcke, et al., Monogenic forms of childhood obesity due to mutations in the leptin gene. Mol Cell Pediatr. 2014; 1(1): 3); (Dubern, et al., Leptin and leptin receptor-related monogenic obesity. Biochimie. 2012; 94(10): 2111-5); (Paz-Filho, et al., Ten years of leptin replacement therapy. Obesity reviews. 2011; 12: e315-e323.). While there are no approved therapies for congenital leptin deficiency, in several small open-label studies of patients with monogenic obesity due to leptin loss of function mutations, leptin treatment markedly reduced appetite, body weight, adiposity, metabolic abnormalities, gap between bone age and chronological age, hormonal abnormalities, and immunologic abnormalities (Wabitsch, et al., Severe Early-Onset Obesity Due to Bioinactive Leptin Caused by a p.N103K Mutation in the Leptin Gene. J Clin Endocrinol Metab. 2015; 100(9): 3227-3230); (Farooqi, et al., Effects of recombinant leptin therapy in a child with congenital leptin deficiency. N Engl J Med. 1999; 341(12): 879-84); (Licinio, et al., Phenotypic effects of leptin replacement on morbid obesity, diabetes mellitus, hypogonadism, and behavior in leptin-deficient adults. Proc Natl Acad Sci USA. 2004; 101(13): 4531-6); (Gibson et al., Congenital Leptin Deficiency Due to Homozygosity for the Delta133G mutation: report of another case and evaluation of response to four years of leptin therapy. J Clin Endocrin. & Metab. 2004; 89(10): 4821-4826). Others report leptin therapy resulted in a rapid and sustained increase in plasma thyroid hormone levels and facilitated appropriately timed pubertal development, and improved numbers of circulating CD4(+) T cells and T cell proliferation and cytokine release (Farooqi et al., Beneficial effects of leptin on obesity, T cell hyporesponsiveness, and neuroendocrine/metabolic dysfunction of human congenital leptin deficiency. J Clin Invest. 2002; 110(8): 1093-1103). However, in some cases, the development of anti-metreleptin antibodies with neutralizing activity leaves patients without any targeted therapeutic options (Ozsu, et al., Early-onset severe obesity due to complete deletion of the leptin gene in a boy. J Pediatr Endocrinol Metab. 2017; 30(11): 1227-1230). Provided herein are methods of using a leptin receptor agonist, such as H4H17319P2 (See WO2017/66204), to treat patients with congenital leptin deficiency.

Provided herein are agonist monoclonal antibodies that activate human LEPR with similar potency to leptin. The monoclonal antibody-mediated activation of the LEPR is effective in reversing the severe body weight gains and metabolic dysfunction in mouse models of primary and secondary leptin deficiency disorders. Furthermore, the LEPR agonist monoclonal antibodies reduce adiposity and body weight in normal weight mice, as well as normal and high body fat non-human primates, and stimulate LEPR in the presence of circulating leptin.

It is to be understood that the present disclosure is not limited to particular methods and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described.

Definitions

The expression "leptin receptor," "LEPR," and the like, as used herein, refers to the human leptin receptor, comprising the amino acid sequence as set forth in SEQ ID NO:113 (see also UniProtKB/Swiss-Prot Accession No. P48357). Alternative names for LEPR used in the scientific literature include "OB receptor," "OB-R," and "CD295." LEPR is also referred to as "WSX" (see, e.g., U.S. Pat. No. 7,524,937). The expression "LEPR" includes both monomeric and multimeric (e.g., dimeric) LEPR molecules. As used herein, the expression "monomeric human LEPR" means a LEPR protein or portion thereof that does not contain or possess any multimerizing domains and that exists under normal conditions as a single LEPR molecule without a direct physical connection to another LEPR molecule. An exemplary monomeric LEPR molecule is the molecule referred to herein as "hLEPR.mmh" comprising the amino acid sequence of SEQ ID NO:114 (see, e.g., Example 3, herein). As used herein, the expression "dimeric human LEPR" means a construct comprising two LEPR molecules connected to one another through a linker, covalent bond, non-covalent bond, or through a multimerizing domain such as an antibody Fc domain. An exemplary dimeric LEPR molecule is the molecule referred to herein as "hLEPR.mFc" comprising the amino acid sequence of SEQ ID NO:115 (see, e.g., Example 3, herein), or the molecule referred to herein as "hLEPR.hFc" comprising the amino acid sequence of SEQ ID NO:116. As used herein, expressions such "anti-LEPR antibody," "antibody that specifically binds LEPR," "LEPR-specific binding protein," and the like, unless specifically indicated otherwise, refer to molecules that bind full length human LEPR, monomeric human LEPR, dimeric human LEPR, or other constructs that comprise or consist of the LEPR extracellular domain.

All references to proteins, polypeptides and protein fragments herein are intended to refer to the human version of the respective protein, polypeptide or protein fragment unless explicitly specified as being from a non-human species. Thus, the expression "LEPR" means human LEPR unless specified as being from a non-human species, e.g., "mouse LEPR," "monkey LEPR," etc.

As used herein, the expression "cell surface-expressed LEPR" means one or more LEPR protein(s), or the extracellular domain thereof, that is/are expressed on the surface of a cell in vitro or in vivo, such that at least a portion of a LEPR protein is exposed to the extracellular side of the cell membrane and is accessible to an antigen-binding portion of an antibody. A "cell surface-expressed LEPR" can comprise or consist of a LEPR protein expressed on the surface of a cell which normally (e.g., in the native or wild-type state) expresses LEPR protein. Alternatively, "cell surface-expressed LEPR" can comprise or consist of LEPR protein expressed on the surface of a cell that normally does not express human LEPR on its surface but has been artificially engineered to express LEPR on its surface.

As used herein, the expressions such as "anti-LEPR antibody," or "antibody that binds human leptin receptor," include both monovalent antibodies with a single specificity, as well as bispecific antibodies comprising a first arm that binds LEPR and a second arm that binds a second (target) antigen, wherein the anti-LEPR arm comprises any of the HCVR/LCVR or CDR sequences as set forth in Table 1 herein.

The term "antibody", as used herein, means any antigen-binding molecule or molecular complex comprising at least one complementarity determining region (CDR) that specifically binds to or interacts with a particular antigen (e.g., LEPR). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-LEPR antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In certain embodiments of the invention, the anti-LEPR antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The present invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention includes variants of the anti-LEPR antibodies disclosed herein comprising one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention includes anti-LEPR antibodies and antigen-binding fragments thereof that comprise amino acid sequences that are substantially similar or substantially identical to one or more variable domain or CDR amino acid sequences as found in any of the exemplary anti-LEPR antibodies disclosed herein.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains:

serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

As used herein, the term "subject" refers to an animal, preferably a mammal, more preferably a human, in need of amelioration, prevention and/or treatment of a disease or disorder associated with leptin deficiency. The subject can be adult or pediatric. The subject may have a metabolic dysfunction such as a general or partial lipodystrophy. The subject may have a congenital leptin deficiency or acquired leptin deficiency. Subjects having congenital leptin deficiencies includes subjects with gene mutations that result in little to no circulating levels of leptin or circulating but bioinactive leptin. The subject may have one or more symptoms associated with leptin deficiency. As used herein, the term "subject" is interchangeable with the term "patient". In some aspects, the subject has neutralizing antibodies against metreleptin.

As used herein, the terms "treat", "treating", or "treatment" refer to the reduction or amelioration of the severity of at least one symptom of leptin deficiency due to the administration of a therapeutic agent such as an antibody of the present invention to a subject in need thereof. The terms include inhibition of progression of the associated disease or of worsening of the condition or symptoms associated with the disease. The terms also include positive prognosis of disease, i.e., the subject may be free of symptoms upon administration of a therapeutic agent such as an antibody of the present invention. Positive prognosis can include the mitigation of any of the following conditions: hyperphagia, hyperglycemia, insulin resistance, dyslipidemia or hepatic steatosis.

The terms "prevent", "preventing" or "prevention" refer to inhibition of manifestation of any symptoms, conditions, or indications associated with leptin deficiency.

The therapeutic agent may be administered at a therapeutic dose to the subject. By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding) and is discussed in greater detail herein.

Anti-LEPR Antibodies Comprising Fc Variants

According to certain embodiments of the present invention, anti-LEPR antibodies are provided comprising an Fc domain comprising one or more mutations which enhance or diminish antibody binding to the FcRn receptor, e.g., at acidic pH as compared to neutral pH. For example, the present invention includes anti-LEPR antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-LEPR antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

The anti-LEPR antibodies of the present invention may comprise a modified Fc domain having reduced effector function. As used herein, a "modified Fc domain having reduced effector function" means any Fc portion of an immunoglobulin that has been modified, mutated, truncated, etc., relative to a wild-type, naturally occurring Fc domain such that a molecule comprising the modified Fc exhibits a reduction in the severity or extent of at least one effect selected from the group consisting of cell killing (e.g., ADCC and/or CDC), complement activation, phagocytosis and opsonization, relative to a comparator molecule comprising the wild-type, naturally occurring version of the Fc portion. In certain embodiments, a "modified Fc domain having reduced effector function" is an Fc domain with reduced or attenuated binding to an Fc receptor (e.g., FcγR).

In certain embodiments of the present invention, the modified Fc domain is a variant IgG1 Fc or a variant IgG4

Fc comprising a substitution in the hinge region. For example, a modified Fc for use in the context of the present invention may comprise a variant IgG1 Fc wherein at least one amino acid of the IgG1 Fc hinge region is replaced with the corresponding amino acid from the IgG2 Fc hinge region. Alternatively, a modified Fc for use in the context of the present invention may comprise a variant IgG4 Fc wherein at least one amino acid of the IgG4 Fc hinge region is replaced with the corresponding amino acid from the IgG2 Fc hinge region. Non-limiting, exemplary modified Fc regions that can be used in the context of the present invention are set forth in US Patent Application Publication No. 2014/0243504.

Other modified Fc domains and Fc modifications that can be used in the context of the present invention include any of the modifications as set forth in US 2014/0171623; U.S. Pat. No. 8,697,396; US 2014/0134162; WO 2014/043361. Methods of constructing antibodies or other antigen-binding fusion proteins comprising a modified Fc domain as described herein are known in the art.

Biological Characteristics of the Antibodies

The present invention includes antibodies and antigen-binding fragments thereof that bind human LEPR and activate LEPR signaling. Such antibodies may be referred to herein as "agonist antibodies." In the context of the present invention, "activation of LEPR signaling" means the stimulation of an intracellular effect that normally results from the interaction of leptin with LEPR in cells that express LEPR. In certain embodiments, "activation of LEPR signaling" means the transcriptional activation of STAT3, which can be detected using any method that can measure or identify, directly or indirectly, STAT3 activity, e.g., using a labeled version of STAT3 expressed in a reporter cell line. For example, the present invention includes antibodies and antigen-binding fragments thereof that activate LEPR signaling in a cell-based reporter assay, e.g., using a cell based assay format as defined in Example 7 herein, or a substantially similar assay. Cell-based reporter assays that detect LEPR activation, such as the assay set forth in Example 7 herein, can produce a detectable signal that may be expressed in terms of an $EC_{50}$ value (i.e., the antibody concentration required to produce half-maximal signaling) and/or a percentage of the maximal signaling observed in the presence of leptin. In certain exemplary embodiments of the present invention, anti-LEPR antibodies are provided that activate LEPR signaling with an $EC_{50}$ value of less than about 12.0 nM in a cell-based reporter assay, e.g., using an assay format as defined in Example 7 herein, or a substantially similar assay. In certain exemplary embodiments of the present invention, anti-LEPR antibodies are provided that activate LEPR signaling with maximum percent activation relative to leptin signaling of greater than about 65% in a cell-based reporter assay, e.g., using an assay format as defined in Example 7 herein, or a substantially similar assay.

The present invention includes antibodies and antigen-binding fragments thereof that bind monomeric human LEPR with high affinity. For example, the present invention includes anti-LEPR antibodies that bind monomeric human LEPR (e.g., hLEPR.mmh, SEQ ID NO:114) with a $K_D$ of less than about 150 nM as measured by surface plasmon resonance at 25° C. or 37° C., e.g., using an assay format as defined in Example 3 herein, or a substantially similar assay. According to certain embodiments, anti-LEPR antibodies are provided that bind monomeric human LEPR at 25° C. with a $K_D$ of less than about 150 nM, less than about 140 nM, less than about 130 nM, less than about 120 nM, less than about 110 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, or less than about 300 pM, as measured by surface plasmon resonance, e.g., using an assay format as defined in Example 3 herein, or a substantially similar assay.

The present invention also includes antibodies and antigen-binding fragments thereof that bind monomeric human LEPR (e.g., hLEPR.mmh, SEQ ID NO:114) with a dissociative half-life (t½) of greater than about 50 minutes as measured by surface plasmon resonance at 25° C. or 37° C., e.g., using an assay format as defined in Example 3 herein, or a substantially similar assay. According to certain embodiments, anti-LEPR antibodies are provided that bind monomeric human LEPR at 25° C. with a t½ of greater than about 50 minutes, greater than about 55 minutes, greater than about 60 minutes, greater than about 65 minutes, or longer, as measured by surface plasmon resonance, e.g., using an assay format as defined in Example 3 herein, or a substantially similar assay.

The present invention also includes antibodies and antigen-binding fragments thereof that bind dimeric human LEPR (e.g., hLEPR.mFc, SEQ ID NO:115) with high affinity. For example, the present invention includes anti-LEPR antibodies that bind dimeric human LEPR with a $K_D$ of less than about 1.5 nM as measured by surface plasmon resonance at 25° C. or 37° C., e.g., using an assay format as defined in Example 3 herein, or a substantially similar assay. According to certain embodiments, anti-LEPR antibodies are provided that bind dimeric human LEPR at 25° C. with a $K_D$ of less than about 150 nM, less than about 130 nM, less than about 110 nM, less than about 80 nM, less than about 70 nM, less than about 60 nM, less than about 50 nM, less than about 40 nM, less than about 30 nM, less than about 20 nM, or less than about 10 nM, as measured by surface plasmon resonance, e.g., using an assay format as defined in Example 3 herein, or a substantially similar assay.

The present invention also includes antibodies and antigen-binding fragments thereof that bind dimeric human LEPR (e.g., hLEPR.mFc, SEQ ID NO:115) with a dissociative half-life (t½) of greater than about 10 minutes as measured by surface plasmon resonance at 25° C. or 37° C., e.g., using an assay format as defined in Example 3 herein, or a substantially similar assay. According to certain embodiments, anti-LEPR antibodies are provided that bind dimeric human LEPR at 25° C. with a t½ of greater than about 10, greater than about 15 minutes, greater than about 20 minutes, greater than about 25 minutes, greater than about 30 minutes, greater than about 40 minutes, greater than about 50 minutes, greater than about 60 minutes, greater than about 70 minutes, or longer, as measured by surface plasmon resonance, e.g., using an assay format as defined in Example 3 herein, or a substantially similar assay.

The present invention also includes antibodies and antigen-binding fragments thereof that bind LEPR in complex with human leptin ("LEPR in complex with human leptin" may also be represented by the expression "leptin:LEPR"). For example, the present invention includes antibodies and antigen-binding fragments thereof that are capable of binding to a pre-formed complex comprising hLEPR and human leptin. That is, according to certain embodiments, the interaction between anti-LEPR antibodies and LEPR is not inhibited by the presence of leptin in complex with LEPR; likewise, the interaction between leptin and LEPR, according to this aspect of the invention, is not inhibited by the presence of an anti-LEPR antibody. An exemplary assay format for determining whether an antibody or antigen-binding fragment thereof binds to LEPR in complex with human leptin is set forth in Example 4 herein.

Similarly, the present invention also includes antibodies and antigen-binding fragments thereof that bind LEPR and do not block the LEPR:leptin interaction. For example, the present invention includes antibodies and antigen-binding fragments thereof that are capable of binding LEPR, thereby producing an antibody:LEPR complex, wherein the resulting antibody:LEPR complex is capable of interacting with leptin to produce a three-member complex comprising the antibody, LEPR and leptin. An exemplary assay format for determining whether an antibody or antigen-binding fragment thereof is capable of binding LEPR in a manner that does not block or interfere with the interaction between LEPR and leptin is set forth in Example 5 herein.

The present invention also includes antibodies and antigen-binding fragments thereof that bind cell surface-expressed LEPR in the presence and/or absence of human leptin. Cell surface-expressed LEPR means LEPR or a portion thereof (e.g., an extracellular portion of LEPR) expressed on the surface of a cell, either naturally or in an engineered cell line, such that an antibody or antigen-binding fragment thereof is capable of binding to the LEPR molecule. In certain embodiments, cell surface-expressed LEPR includes recombinant complexes comprising an extracellular domain of LEPR connected to a cell via a tag or anchor (e.g., a GPI anchor as illustrated in Example 6 herein). According to this aspect of the invention, antibodies are provided which are capable of binding cell surface-expressed LEPR in the absence of leptin, and are also capable of binding cell surface-expressed LEPR in the presence of leptin (i.e., under circumstances wherein leptin is capable of binding to cell surface-expressed leptin). That is, according to certain embodiments, the interaction between anti-LEPR antibodies and cell surface-expressed LEPR is not inhibited by the presence of leptin in complex with cell surface-expressed LEPR. Antibodies according to this aspect of the invention are capable of forming a three-member complex on the surface of a cell comprising the antibody, cell surface-expressed LEPR and leptin. An exemplary assay format for determining whether an antibody or antigen-binding fragment thereof is capable of binding cell surface-expressed LEPR in the presence and absence of human leptin is set forth in Example 6 herein.

The antibodies of the present invention may possess one or more of the aforementioned biological characteristics, or any combination thereof. The foregoing list of biological characteristics of the antibodies of the invention is not intended to be exhaustive. Other biological characteristics of the antibodies of the present invention will be evident to a person of ordinary skill in the art from a review of the present disclosure including the working Examples herein.

Epitope Mapping and Related Technologies

The present invention also includes anti-LEPR antibodies comprising variants of any of the HCVR, LCVR, and/or CDR amino acid sequences disclosed herein having one or more conservative substitutions. For example, the present invention includes anti-LEPR antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein. In certain embodiments, the present invention provides anti-LEPR antibodies comprising variant HCVR, LCVR and/or CDR amino acid sequences relative to the sequences set forth in Table 1 herein (e.g., comprising conservative amino acid substitutions), wherein such variant antibodies nonetheless exhibit one or more functions and/or properties of the exemplary anti-LEPR antibodies disclosed herein.

The extracellular domain of human LEPR contains an N-terminal cytokine receptor homology domain (CRH-1), an immunoglobulin-like (Ig) domain, and a second CRH domain (CRH-2) that is referred to as the leptin-binding domain (LBD). (Carpenter et al. (2012) Structure 20:487-97). Furthermore, LEPR shares the greatest homology and similar extracellular domain size and organization with granulocyte colony stimulating factor (GCSF) and glycoprotein 130 (gp13). (Haniu et al. (1998) J Biol Chem 273(44): 28691-699).

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The present invention includes anti-LEPR antibodies that interact with one or more epitopes found within amino acids M1-D839 of human LEPR (SEQ ID NO: 113). As set forth in Example 11, 201 peptides from human LEPR had significantly reduced deuteration uptake when bound to antibody H4H16650P2. The peptides corresponding to amino acids 162-169 (amino acids LYVLPEVL of human LEPR, SEQ ID NO: 113) and 170-191 (amino acids EDSPLVPQKGSF of human LEPR, SEQ ID NO: 113) had slower deuteration rates when bound to H4H16650P2, indicating that this antibody binds at least two human LEPR epitopes having the sequences LYVLPEVL or EDSPLVPQKGSF (amino acids 162-169 or 170-191, respectively of SEQ ID NO: 113).

The epitope to which the antibodies of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a LEPR protein. Alternatively, the epitope may consist of a plurality of non-contiguous amino acids (or amino acid sequences) of LEPR. In some embodiments, the epitope is located on or near the leptin-binding domain of LEPR. In other embodiments, the epitope is located at a region distinct from the leptin-binding domain of LEPR, e.g., at a location on the surface of LEPR at which an antibody, when bound to such an epitope, does not interfere with leptin binding to LEPR.

Various techniques known to persons of ordinary skill in the art can be used to identify the amino acids within an epitope recognized by a particular antibody. Exemplary techniques include, e.g., alanine scanning mutational analysis, peptide blot analysis, and peptide cleavage analysis. In addition, methods such as epitope excision, epitope extraction and chemical modification of antigens can be employed (Tomer, 2000, *Protein Science* 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography analysis of an antibody in complex with its antigen may also be used to identify the amino acids within a polypeptide with which an antibody interacts.

The present invention further includes anti-LEPR antibodies that bind to the same epitope as any of the specific exemplary antibodies described herein (e.g. antibodies comprising any of the amino acid sequences as set forth in Table 1 herein). Likewise, the present invention also includes anti-LEPR antibodies that compete for binding to LEPR with any of the specific exemplary antibodies described herein (e.g. antibodies comprising any of the amino acid sequences as set forth in Table 1 herein).

One can determine whether an antibody binds to the same epitope as, or competes for binding with, a reference anti-LEPR antibody by using routine methods known in the art and exemplified herein. For example, to determine if a test antibody binds to the same epitope as a reference anti-LEPR antibody of the invention, the reference antibody is allowed to bind to a LEPR protein. Next, the ability of a test antibody to bind to the LEPR molecule is assessed. If the test antibody is able to bind to LEPR following saturation binding with the reference anti-LEPR antibody, it can be concluded that the test antibody binds to a different epitope than the reference anti-LEPR antibody. On the other hand, if the test antibody is not able to bind to the LEPR molecule following saturation binding with the reference anti-LEPR antibody, then the test antibody may bind to the same epitope as the epitope bound by the reference anti-LEPR antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., *Cancer Res.* 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-LEPR antibody, the above-described binding methodology is performed in two orientations: In a first orientation, the reference antibody is allowed to bind to a LEPR protein under saturating conditions followed by assessment of binding of the test antibody to the LEPR molecule. In a second orientation, the test antibody is allowed to bind to a LEPR molecule under saturating conditions followed by assessment of binding of the reference antibody to the LEPR molecule. If, in both orientations, only the first (saturating) antibody is capable of binding to the LEPR molecule, then it is concluded that the test antibody and the reference antibody compete for binding to LEPR. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-LEPR antibodies of the present invention can be fully human antibodies. Methods for generating monoclonal antibodies, including fully human monoclonal antibodies are known in the art. Any such known methods can be used in the context of the present invention to make human antibodies that specifically bind to human LEPR.

Using VELOCIMMUNE™ technology, for example, or any other similar known method for generating fully human monoclonal antibodies, high affinity chimeric antibodies to LEPR are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-LEPR antibody. While the constant region selected may vary according to specific use, high affinity antigen-binding and target specificity characteristics reside in the variable region. In certain instances, fully human anti-LEPR antibodies are isolated directly from antigen-positive B cells.

Bioequivalents

The anti-LEPR antibodies and antibody fragments of the present invention encompass proteins having amino acid sequences that vary from those of the described antibodies but that retain the ability to bind human LEPR. Such variant antibodies and antibody fragments comprise one or more additions, deletions, or substitutions of amino acids when compared to parent sequence, but exhibit biological activity that is essentially equivalent to that of the described antibodies. Likewise, the anti-LEPR antibody-encoding DNA sequences of the present invention encompass sequences that comprise one or more additions, deletions, or substitutions of nucleotides when compared to the disclosed sequence, but that encode an anti-LEPR antibody or antibody fragment that is essentially bioequivalent to an anti-LEPR antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-LEPR antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-LEPR antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-LEPR antibodies that bind to human LEPR but not to LEPR from other species. The present invention also includes anti-LEPR antibodies that bind to human LEPR and to LEPR from one or more non-human species. For example, the anti-LEPR antibodies of the invention may bind to human LEPR and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee LEPR. According to certain exemplary embodiments of the present invention, anti-LEPR antibodies are provided which specifically bind human LEPR and cynomolgus monkey (e.g., *Macaca fascicularis*) LEPR. Other anti-LEPR antibodies of the invention bind human LEPR but do not bind, or bind only weakly, to cynomolgus monkey LEPR.

Multispecific Antibodies

The antibodies of the present invention may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, *J. Immunol.* 147:60-69; Kufer et al., 2004, *Trends Biotechnol.* 22:238-244. The anti-LEPR antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

The present invention includes bispecific antibodies wherein one arm of an immunoglobulin binds human LEPR, and the other arm of the immunoglobulin is specific for a second antigen. The LEPR-binding arm can comprise any of the HCVR/LCVR or CDR amino acid sequences as set forth in Table 1 herein.

An exemplary bispecific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The invention provides pharmaceutical compositions comprising the anti-LEPR antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-LEPR antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

In a patient, e.g., a pediatric patient, it may be advantageous to administer, e.g., intravenously, the antibody at a therapeutically effective dosage of about 5 mg/kg body weight, or about 1 mg/kg body weight to about 20 mg/kg body weight, or about 1 mg/kg body weight to about 15 mg/kg body weight, or about 5 mg/kg body weight to about 10 mg/kg body weight. For example, an intravenous (IV) loading dose of about 5 mg/kg can be chosen to achieve antibody serum concentrations at or above 100 mg/L. It may be further advantageous to administer the antibody subcutaneously at a dosage of about 250 mg, or at a dosage of about 300 mg, or at a dosage of about 100 mg to about 500 mg, or about 200 mg to about 300 mg. For example, a weekly subcutaneous (SC) maintenance dose of 250 mg H4H17319P2 or 300 mg H4H17319P2 will sustain trough concentrations in serum at or above 100 mg/L. In some aspects, a SC dosing regimen commences several days after administration of the IV loading dose to best maintain targeted trough concentrations in serum. In some aspects, the first SC dose is administered 2 to 7 days after the loading dose, for example, 2 days, 3, days, 4 days, 5 days, 6 days, or 7 days after the loading dose. In some aspects, the SC dose is administered once every 3 to 14 days, for example, once every 3 days, once every 4 days, once every 5 days, once every 6 days, once a week, once every 10 days, or once every 2 weeks, for example, for 3 weekly SC doses past the first SC dose, followed by monthly doses (about every 28 days). In an embodiment of the invention, a therapeutically effective dose of antibody (e.g., H4H17319P2) is as set forth in FIG. 19 herein, but is optionally continued past the last monthly dose shown therein.

In some aspects, it is desirable to maintain trough concentrations in serum between about 50 mg/L to about 200 mg/L, or about 100 mg/L, or about 150 mg/L, or at or above 50 mg/L, or at or above 100 mg/L, or at or above 150 mg/L.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, *CRC Crit. Ref. Biomed. Eng.* 14:201). In another embodiment, polymeric materials can be used; see, Medical Applications of Controlled Release, Langer and Wise (eds.), 1974, *CRC Pres*., Boca Raton, Fla. In yet another embodiment, a controlled release system can be placed in proximity of the composition's target, thus requiring only a fraction of the systemic dose (see, e.g., Goodson, 1984, in *Medical Applications of Controlled Release*, supra, vol. 2, pp. 115-138). Other controlled release systems are discussed in the review by Langer, 1990, *Science* 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present invention includes methods comprising administering to a subject in need thereof a therapeutic composition comprising an anti-LEPR antibody (e.g., an anti-LEPR antibody comprising any of the HCVR/LCVR or CDR sequences as set forth in Table 1 herein). The therapeutic composition can comprise any of the anti-LEPR antibodies disclosed herein, or antigen-binding fragments thereof, and a pharmaceutically acceptable carrier or diluent.

The antibodies and antigen-binding fragments provided herein are useful, inter alia, for the treatment, prevention and/or amelioration of any disease or disorder associated with or mediated by a metabolic dysfunction or hypoleptinemia, for example, non-alcoholic fatty liver disease, NASH, female infertility, amenorrhea, abnormal hormone cycle, impaired immune function, hypothyroidism, obesity, monogenic obesity, diabetes type I, diabetes type II, lipodystrophy, congenital lipodystrophy, generalized lipodystrophy, acquired lipodystrophy, partial lipodystrophy, congenital partial lipodystrophy, congenital generalized lipodystrophy, acquired partial lipodystrophy, and acquired generalized lipodystropy, or otherwise treatable by stimulating or activating LEPR signaling or mimicking the natural activity of leptin in vitro or in vivo. For example, the antibodies and antigen-binding fragments thereof are useful for treating lipodystrophy conditions. Exemplary lipodystrophy conditions that are treatable by the antibodies and antigen-binding fragments of the present invention include, e.g., congenital generalized lipodystrophy, congenital partial lipodystropy, acquired generalized lipodystrophy, familial partial lipodystrophy, acquired partial lipodystrophy, centrifugal abdominal lipodystrophy, lipoatrophia annularis, localized lipodystrophy, and HIV-associated lipodystrophy, and the symptoms associated with such conditions.

The anti-LEPR antibodies and antigen-binding fragments thereof provided herein are useful for the treatment, prevention and/or amelioration of monogenic obesity and/or lipodystrophy. Monogenic obesity and lipodystrophy can be associated with many pathologies including, for example: extreme early onset obesity with subjects having BMI greater than $85^{th}$ percentile for age and gender; hyperphagia and impaired satiety, with subjects exhibiting food seeking behavior and food aggressive behavior; impaired immune function with reduced CD4+ T-cell counts and recurrent (and possibly lethal) infections; insulin resistance and hyperinsulinemia; non-alcoholic fatty liver disease, liver steatosis, and progression to lipodystrophy; dyslipidemia leading to hypertriglyceridemia; diabetes with elevated HbA1c and/or glucose levels, and impaired glucose tolerance; reproductive dysfunction to hypogonadism, delayed pubertal development; reduced expression of secondary sexual characteristics, no or irregular menses, and infertility; lack of pubertal growth spurt resulting in short stature, abnormal growth hormone secretion; hypothyroidism or impaired thyroid function, altered T3 or TSH or free thyroxine levels; and variable bone changes, including bone density and bone mineral content. The spectrum of conditions and symptoms associated with monogenic obesity and/or lipodystrophy can differ given the underlying causative genetics, e.g. AGPAT2, LMNA, BSCL2, or others. A given mutation can result in leptin or LEPR loss of function that has variations on endocrine severity, for example, irregular menses versus complete amenorrhea.

The antibodies and antigen-binding fragments provided herein are also useful for treating, mitigating, or preventing one or more symptoms of a disease or condition associated with metabolic dysfunction or hypoleptinemia. Such symptoms include adiposity, obesity, hyperphagia, hyperglycemia, hypertriglyceridemia, hypercholesterolemia, insulin resistance, dyslipidemia, delay in growth, delay in pubertal growth spurt, abnormal growth hormone secretion, elevated HbA1c, low bone mineral density (or low bone mass), low bone mineral content, and low lean body mass.

The present invention also includes anti-LEPR antibodies and antigen-binding fragments thereof that are useful for restoring leptin signaling to cells, tissues and organs expressing one or more LEPR mutations. Such mutations can be associated with metabolic dysfunction or hypoleptinemia and diseases or conditions pertaining to metabolic dysfunction or hypoleptinemia, for example, obesity, congenital lipodystrophy, infertility, and non-alcoholic fatty liver disease. For example, certain LEPR mutants have been identified that exhibit no, or reduced signaling in the presence of leptin and are associated with obesity and related disorders. As used herein, a LEPR mutant that exhibits no signaling in the presence of leptin is referred to as a "signaling-defective LEPR mutant." An exemplary signaling-defective LEPR mutation is LEPR-A409E (Farooqi et al., 2007, *N Engl J Med* 356(3): 237-247). As used herein, a LEPR mutant that exhibits reduced signaling in the presence of leptin (as compared to wild-type LEPR) is referred to as a "signaling-impaired LEPR mutant." An exemplary signaling-impaired LEPR mutation is LEPR-P316T (Mazen et al., 2011, *Mol Genet Metab* 102:461-464). Thus, the present invention includes anti-LEPR antibodies and antigen-binding fragments thereof that are useful for the treatment, prevention and/or amelioration of diseases and disorders caused by or associated with one or more signaling-defective (e.g., A409E) and/or signaling-impaired (e.g., P316T) LEPR mutants.

The present invention also includes anti-LEPR antibodies and antigen-binding fragments thereof that are useful for restoring leptin signaling by mitigating mutations in the leptin gene. Some subjects have circulating leptin but the protein is non-functional due to the genetic mutation, for example, a p.N103K mutation in the leptin gene, which encodes a bioinactive form of leptin. Some subjects have very little or no circulating leptin. Other genes can be involved in impaired leptin signaling including LMNA, PPARG, AGPAT2, BSCL2, PLIN1, AKT2, CIDEC, LIPE, and ADRA2A, and the anti-LEPR antibodies and antigen-binding fragments thereof provided herein are useful in mitigating the effects of such mutations on leptin signaling.

The anti-LEPR antibodies and antigen-binding fragments thereof of the present invention are also useful for the treatment or prevention of one or more conditions, diseases or disorders selected from the group consisting of obesity, monogenic obesity, metabolic syndrome, diet-induced food craving, functional hypothalamic amenorrhea, type 1 diabetes, type 2 diabetes, female infertility, amenorrhea, impaired immune function, hypothyroidism, insulin resistance, severe insulin resistance including severe insulin resistance due to mutation in insulin receptor, severe insulin resistance not caused by mutation in the insulin receptor, severe insulin resistance caused by a mutation in downstream signaling pathways or induced by other causes, non-alcoholic and alcoholic fatty liver diseases, nonalcoholic steatohepatitis (NASH), Alzheimer's disease, leptin deficiency, leptin resistance, lipodystrophies, Leprechaunism/Donohue syndrome, Rabson-Mendenhall syndrome.

The LEPR agonist antibodies provided herein are useful for treating metabolic dysfunction. The methods comprise administering a pharmaceutical composition comprising an antibody or antigen-binding fragment thereof that binds human leptin receptor (LEPR) and activates LEPR signaling, and a pharmaceutically acceptable carrier or diluent, to a subject in need thereof.

The LEPR agonist antibodies provided herein are useful for treating adiposity or obesity, or reducing body weight. In some embodiments, the treatment reduces fat mass but not lean mass in the treated subject. In some aspects, the treatment causes the subject to consume fewer calories or to reduce food intake.

The LEPR agonist antibodies provided herein are useful for treating female infertility or restoring normal hormone cycles associated with leptin deficiency. In some aspects, the treatment can increase fertility and/or increase the opportunity for conception. In some aspects, the treatment can restore normal menstrual cycling. Methods for restoring normal menstrual cycling which has been disrupted due, at least in part, to leptin deficiency are also part of the present invention.

As demonstrated herein, the method is useful when subject in need thereof is hypoleptinemic or leptin deficient or not hypoleptinemic or leptin deficient. The method is useful when the metabolic dysfunction, adiposity, or obesity is or is not associated with or caused by a signaling-defective or signaling-impaired LEPR mutation.

The LEPR agonist antibodies provided herein are useful for treating non-alcoholic fatty liver disease or nonalcoholic steatohepatitis (NASH) in a hypoleptinemic, lipodystrophic, or leptin deficient patient. The treatment can diminish the symptoms of non-alcoholic fatty liver disease, such as hepatic steatosis, in the subject. In some instances, the plasma levels of alanine transaminase (ALT) and/or aspartate transaminase (AST) are decreased in the subject after receiving treatment.

The LEPR agonist antibodies provided herein are useful for treating hyperphagia, hyperglycemia, insulin resistance, dyslipidemia, nonalcoholic steatohepatitis (NASH), or non-alcoholic fatty liver disease by stimulating hypothalamic STAT3 signaling. The treatment can lower circulating plasma triglycerides and/or circulating plasma total cholesterol.

The LEPR agonist antibodies provided herein are useful for treating lipodystrophy. The treatment alleviates hyperglycemia, decreases insulin resistance, and/or lowers HbA1c levels in the subject receiving treatment.

The LEPR agonist antibodies provided herein are useful for treating infertility and/or amenorrhea associated with metabolic disease or hypoleptinemia. The treatment regulates hormonal cycles and can improve conception rates in the female subject receiving treatment. The treatment can restore normal menstrual cycling.

The LEPR agonist antibodies provided herein are useful for treating impaired immune function such as reduced CD4+ T-cell counts associated with hypoleptinemia and/or leptin deficiency. The treatment can improve immune function, for example, can increase CD4+ T-cell counts.

The LEPR agonist antibodies provided herein are useful for treating delay in growth, lack of pubertal growth spurt, and/or abnormal growth hormone secretion associated with congenital leptin deficiency. The treatment can improve growth, can facilitate pubertal growth spurt, and/or can improve growth hormone secretion.

The LEPR agonist antibodies provided herein are useful for treating hypothyroidism associated with congenital leptin deficiency. Treatment can improve the symptoms associated with hypothyroidism.

The LEPR agonist antibodies provided herein are useful for treating low bone mineral density and/or bone mineral content associated with hypoleptinemia and/or leptin deficiency. Treatment can improve bone mineral density and/or can improve bone mineral content.

In the context of the methods of treatment described herein, the anti-LEPR antibody may be administered as a monotherapy (i.e., as the only therapeutic agent) or in combination with one or more additional therapeutic agents (examples of which are described elsewhere herein).

Combination Therapies and Formulations

The present invention includes compositions and therapeutic formulations comprising any of the anti-LEPR antibodies described herein in combination with one or more additional therapeutically active components, and methods of treatment comprising administering such combinations to subjects in need thereof.

The anti-LEPR antibodies of the present invention may be co-formulated with and/or administered in combination with one or more additional therapeutically active component(s), such as. e.g., pharmaceutical products prescribed for the treatment of obesity, hypercholesterolemia, hyperlipidemia, type 2 diabetes, type 1 diabetes, appetite control, amenorrhea, infertility, etc. Examples of such additional therapeutically active components include, e.g., recombinant human leptin (e.g., metreleptin [MYALEPT]), PCSK9 inhibitors (e.g., anti-PCSK9 antibodies [alirocumab, evolocumab, bococizumab, lodelcizumab, ralpancizumab, etc.]), statins (atorvastatin, rosuvastatin, cerivastatin, pitavastatin, fluvastatin, simvastatin, lovastatin, pravastatin, etc.), ezetimibe, insulin, insulin variants, insulin secretagogues, metformin, sulfonylureas, sodium glucose cotransporter 2 (SGLT2) inhibitors (e.g., dapaglifozin, canaglifozin, empagliflozin, etc.), GLP-1 agonists/analogues (e.g., extendin-4, exenatide, liraglutide, lixisenatide, albiglutide, dulaglutide, etc.), glucagon (GCG) inhibitors (e.g., anti-GCG antibodies), glucagon receptor (GCGR) inhibitors (e.g., anti-GCGR antibodies, small molecule GCGR antagonists, GCGR-specific antisense oligonucleotides, anti-GCGR aptamers [e.g., Spiegelmers], etc.), angiopoietin-like protein (ANGPTL) inhibitors (e.g., anti-ANGPTL3 antibodies, anti-ANGPTL4 antibodies, anti-ANGPTL8 antibodies, etc.), Phentermine, Orlistat, Topiramate, Bupropion, Topiramate/Phentermine, Bupropion/Naltrexone, Bupropion/Zonisamide, Pramlintide/Metreleptin, Lorcaserin, Cetilistat, Tesofensine, Velneperit, etc. Further examples include, e.g., fish oil, pioglitazone, setmelanotide, fibrates (e.g. fenofibrate), prednisone, niacin, anticonvulsants, digoxin, Coumadin, Vitamin D, thyroxine, a thyroid supplement, a vitamin supplement, a calcium supplement, carnitine, Coenzyme Q10, anti-constipation medication, anti-allergic medications, gabapentin, a narcotic, ketamine, lidocaine, and venlafaxine hydrochloride. In an embodiment of the invention, the anti-LEPR antibodies of the present invention are not formulated or administered with an anorectic agent.

The additional therapeutically active component(s), e.g., any of the agents listed above or derivatives thereof, may be administered just prior to, concurrent with, or shortly after the administration of an anti-LEPR antibody of the present invention; (for purposes of the present disclosure, such administration regimens are considered the administration of an anti-LEPR antibody "in combination with" an additional therapeutically active component). The present invention includes pharmaceutical compositions in which an anti-LEPR antibody of the present invention is co-formulated with one or more of the additional therapeutically active component(s) as described elsewhere herein.

The present invention also includes methods of using the compositions and therapeutic formulations comprising any of the anti-LEPR antibodies described herein in combination with therapeutic procedures such as plasmapheresis.

Administration Regimens

According to certain embodiments of the present invention, multiple doses of an anti-LEPR antibody (or a pharmaceutical composition comprising a combination of an anti-LEPR antibody and any of the additional therapeutically active agents mentioned herein) may be administered to a subject over a defined time course. The methods according to this aspect of the invention comprise sequentially administering to a subject multiple doses of an anti-LEPR antibody of the invention. As used herein, "sequentially administering" means that each dose of anti-LEPR antibody is administered to the subject at a different point in time, e.g., on different days separated by a predetermined interval (e.g., hours, days, weeks or months). The present invention includes methods which comprise sequentially administering to the patient a single initial dose of an anti-LEPR antibody, followed by one or more secondary doses of the anti-LEPR antibody, and optionally followed by one or more tertiary doses of the anti-LEPR antibody.

The terms "initial dose," "secondary doses," and "tertiary doses," refer to the temporal sequence of administration of the anti-LEPR antibody of the invention. Thus, the "initial dose" is the dose which is administered at the beginning of the treatment regimen (also referred to as the "baseline dose," "loading dose," "starting dose," and the like); the "secondary doses" are the doses which are administered after the initial dose; and the "tertiary doses" are the doses which are administered after the secondary doses. The initial, secondary, and tertiary doses may all contain the same amount of anti-LEPR antibody, but generally may differ from one another in terms of frequency of administration. In certain embodiments, however, the amount of anti-LEPR antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

Diagnostic and Analytic Uses of the Antibodies

The anti-LEPR antibodies of the present invention may also be used to detect and/or measure LEPR, or LEPR-expressing cells in a sample, e.g., for diagnostic purposes. For example, an anti-LEPR antibody, or fragment thereof, may be used to diagnose a condition or disease characterized by aberrant expression (e.g., over-expression, under-expression, lack of expression, etc.) of LEPR. Exemplary diagnostic assays for LEPR may comprise, e.g., contacting a sample, obtained from a patient, with an anti-LEPR antibody of the invention, wherein the anti-LEPR antibody is labeled with a detectable label or reporter molecule. Alternatively, an unlabeled anti-LEPR antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure LEPR in a sample include enzyme-linked immunosorbent assay (ELISA), radioimmunoassay (RIA), fluorescence-activated cell sorting (FACS), and positron emission tomography (PET) scanning.

Samples that can be used in LEPR diagnostic assays according to the present invention include any tissue or fluid sample obtainable from a patient which contains detectable quantities of LEPR protein, or fragments thereof, under normal or pathological conditions. Generally, levels of LEPR in a particular sample obtained from a healthy patient (e.g., a patient not afflicted with a disease or condition associated with abnormal LEPR levels or activity) will be measured to initially establish a baseline, or standard, level of LEPR. This baseline level of LEPR can then be compared against the levels of LEPR measured in samples obtained from individuals suspected of having a LEPR related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Antigen-Binding Proteins that Specifically Bind the Leptin Receptor (LEPR)

Anti-LEPR antibodies were obtained by immunizing a VELOCIMMUNE® mouse (i.e., an engineered mouse comprising DNA encoding human immunoglobulin heavy and kappa light chain variable regions) with an immunogen comprising the extracellular domain of LEPR. The antibody immune response was monitored by a LEPR-specific immunoassay. Using previously described techniques, fully human anti-LEPR antibodies were isolated and purified.

Certain biological properties of the exemplary anti-LEPR antibodies generated in accordance with the methods of this Example are described in detail in the Examples set forth below.

Example 2. Heavy and Light Chain Variable Region Amino Acid and Nucleic Acid Sequences Table 1 sets forth the amino acid sequence identifiers of the heavy and light chain variable regions and CDRs of selected anti-LEPR antibodies of the invention. The corresponding nucleic acid sequence identifiers are set forth in Table 2.

TABLE 1

| Amino Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H4H16650P2 | 2 | 4 | 6 | 8 | 10 | 12 | 14 | 16 |
| H4H16679P2 | 18 | 20 | 22 | 24 | 10 | 12 | 14 | 16 |
| H4H17319P2 | 26 | 28 | 30 | 32 | 10 | 12 | 14 | 16 |
| H4H17321P2 | 34 | 36 | 38 | 40 | 10 | 12 | 14 | 16 |
| H4H18417P2 | 42 | 44 | 46 | 48 | 10 | 12 | 14 | 16 |
| H4H18438P2 | 50 | 52 | 54 | 56 | 10 | 12 | 14 | 16 |
| H4H18445P2 | 58 | 60 | 62 | 64 | 10 | 12 | 14 | 16 |
| H4H18446P2 | 66 | 68 | 70 | 72 | 10 | 12 | 14 | 16 |
| H4H18449P2 | 74 | 76 | 78 | 80 | 10 | 12 | 14 | 16 |
| H4H18482P2 | 82 | 84 | 86 | 88 | 90 | 92 | 94 | 96 |
| H4H18487P2 | 98 | 100 | 102 | 104 | 90 | 92 | 94 | 96 |
| H4H18492P2 | 106 | 108 | 110 | 112 | 90 | 92 | 94 | 96 |

TABLE 2

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H4H16650P2 | 1 | 3 | 5 | 7 | 9 | 11 | 13 | 15 |
| H4H16679P2 | 17 | 19 | 21 | 23 | 9 | 11 | 13 | 15 |
| H4H17319P2 | 25 | 27 | 29 | 31 | 9 | 11 | 13 | 15 |
| H4H17321P2 | 33 | 35 | 37 | 39 | 9 | 11 | 13 | 15 |
| H4H18417P2 | 41 | 43 | 45 | 47 | 9 | 11 | 13 | 15 |
| H4H18438P2 | 49 | 51 | 53 | 55 | 9 | 11 | 13 | 15 |
| H4H18445P2 | 57 | 59 | 61 | 63 | 9 | 11 | 13 | 15 |
| H4H18446P2 | 65 | 67 | 69 | 71 | 9 | 11 | 13 | 15 |
| H4H18449P2 | 73 | 75 | 77 | 79 | 9 | 11 | 13 | 15 |
| H4H18482P2 | 81 | 83 | 85 | 87 | 89 | 91 | 93 | 95 |
| H4H18487P2 | 97 | 99 | 101 | 103 | 89 | 91 | 93 | 95 |
| H4H18492P2 | 105 | 107 | 109 | 111 | 89 | 91 | 93 | 95 |

Antibodies are typically referred to herein according to the following nomenclature: Fc prefix (e.g. "H4H," "H1M," "H2M," etc.), followed by a numerical identifier (e.g. "16650," "16679," etc.), followed by a "P" or "N" suffix. Thus, according to this nomenclature, an antibody may be referred to herein as, e.g., "H4H16650P2," "H4H16679P2," etc. The Fc prefixes on the antibody designations used herein (H4H, H1M and H2M) indicate the particular Fc region isotype of the antibody. For example, an "H4H" antibody has a human IgG4 Fc, whereas an "H1M" antibody has a mouse IgG1 Fc, (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

"Comparator mAb" as used in Examples herein refers to Fab9F8 described in Fazeli et al. (2006) J Immunol Methods 312:190-200 and Carpenter et al. (2012) Structure 20(3): 487-97.

See International patent application publication no. WO2017/66204.

Example 3: Surface Plasmon Resonance Derived Binding Affinities and Kinetic Constants of Human Monoclonal Anti-LEPR Antibodies Equilibrium dissociation constants ($K_D$ values) for LEPR binding to purified anti-LEPR monoclonal antibodies were determined using a real-time surface plasmon resonance biosensor using a Biacore 4000 instrument. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore sensor surface was first derivatized by amine coupling with a monoclonal mouse anti-human Fc antibody (GE, #BR- 1008-39) to capture anti-LEPR monoclonal antibodies. Binding studies were performed on following LEPR reagents: human LEPR extracellular domain expressed with a C-terminal myc-myc-hexahistidine tag (hLEPR.mmh; SEQ ID NO: 114), *Macaca fascicularis* LEPR extracellular domain expressed with a C-terminal myc-myc-hexahistidine tag (mfLEPR.mmh; SEQ ID NO: 117), human LEPR extracellular domain expressed with a C-terminal mouse IgG2a Fc tag (hLEPR.mFc; SEQ ID NO: 115), mouse LEPR extracellular domain expressed with a C-terminal myc-myc-hexahistidine tag (mLEPR.mmh; SEQ ID NO: 118) and rat LEPR extracellular domain expressed with a C-terminal myc-myc-hexahistidine tag (rLEPR.mmh; SEQ ID NO: 119). Different concentrations of LEPR reagents were first prepared in HBS-ET running buffer (100 nM-3.7 nM; 3-fold serial dilution) and were injected over anti-human Fc captured anti-LEPR monoclonal antibody surface for 4 minutes at a flow rate of 304/minute, while the dissociation of monoclonal antibody bound LEPR reagent was monitored for 10 minutes in HBS-ET running buffer. Kinetic association ($k_a$) and dissociation ($k_d$) rate constants were determined by fitting the real-time binding sensorgrams to a 1:1 binding model with mass transport limitation using Scrubber 2.0c curve-fitting software. Binding dissociation equilibrium constants ($K_D$) and dissociative half-lives (t½) were calculated from the kinetic rate constants as:

$$K_D(M) = \frac{kd}{ka}, \text{ and } t\frac{1}{2}\ (\text{min}) = \frac{\ln(2)}{60 * kd} \quad (2)$$

Binding kinetics parameters for hLEPR.mmh, mfLEPR.MMH or hLEPR.mFc, binding to different anti-LEPR monoclonal antibodies of the invention at 25° C. and 37° C. are shown in Tables 3 through 8.

TABLE 3

Binding kinetics parameters of hLEPR-MMH binding to LEPR monoclonal antibodies at 25° C.

| monoclonal antibody Captured | mAb Capture Level (RU) | 100 nM hLEPR-MMH Bound (RU) | $k_a$ (1/Ms) | $k_d$ (1/s) | $K_D$ (M) | t½ (min) |
|---|---|---|---|---|---|---|
| H4H16650P2 | 167 ± 0.3 | 51 | 2.81E+04 | 2.23E−04 | 7.93E−09 | 52 |
| H4H16679P2 | 192 ± 0.7 | 39 | 2.34E+04 | 2.46E−04 | 1.05E−08 | 47 |
| H4H18417P2 | 163 ± 0.4 | 28 | 6.14E+04 | 7.90E−03 | 1.29E−07 | 1.5 |
| H4H18438P2 | 166 ± 0.4 | 22 | 3.00E+04 | 2.26E−03 | 7.54E−08 | 5.1 |
| H4H18445P2 | 194 ± 1.1 | 45 | 4.42E+04 | 4.78E−03 | 1.08E−07 | 2.4 |
| H4H18446P2 | 163 ± 2.4 | 16 | 1.81E+04 | 9.51E−04 | 5.25E−08 | 12 |
| H4H18449P2 | 176 ± 1.3 | 54 | 2.91E+04 | 2.35E−04 | 8.08E−09 | 49 |
| H4H18482P2 | 163 ± 0.4 | 47 | 6.31E+04 | 6.77E−03 | 1.07E−07 | 1.7 |
| H4H18487P2 | 190 ± 1.2 | 42 | 4.73E+04 | 7.03E−03 | 1.48E−07 | 1.6 |
| H4H18492P2 | 167 ± 3.1 | 87 | 8.10E+04 | 8.98E−04 | 1.11E−08 | 13 |
| H4H17319P2 | 200 ± 0.4 | 36 | 2.61E+04 | 5.29E−04 | 2.03E−08 | 22 |
| H4H17321P2 | 221 ± 0.5 | 32 | 2.36E+04 | 1.96E−04 | 8.31E−09 | 59 |
| Isotype Control monoclonal antibody | 171 ± 0.4 | 4 | NB* | NB* | NB* | NB* |

*NB indicates that no binding was observed under the current experimental conditions.

TABLE 4

Binding kinetics parameters of hLEPR-MMH binding to LEPR monoclonal antibodies at 37° C.

| monoclonal antibody Captured | mAb Capture Level (RU) | 100 nM hLEPR-MMH Bound (RU) | $k_a$ (1/Ms) | $k_d$ (1/s) | $K_D$ (M) | t½ (min) |
|---|---|---|---|---|---|---|
| H4H16650P2 | 210 ± 2.5 | 77 | 4.85E+04 | 9.58E−04 | 1.98E−08 | 12 |
| H4H16679P2 | 239 ± 2 | 61 | 3.84E+04 | 8.42E−04 | 2.19E−08 | 14 |
| H4H18417P2 | 206 ± 3.2 | 22 | 7.70E+04 | 1.80E−02 | 2.33E−07 | 0.6 |
| H4H18438P2 | 206 ± 2.4 | 32 | 3.38E+04 | 5.76E−03 | 1.70E−07 | 2.0 |
| H4H18445P2 | 234 ± 2 | 38 | 5.13E+04 | 1.68E−02 | 3.26E−07 | 0.7 |
| H4H18446P2 | 188 ± 3.4 | 21 | 2.12E+04 | 2.56E−03 | 1.21E−07 | 4.5 |
| H4H18449P2 | 206 ± 2.1 | 73 | 3.94E+04 | 8.15E−04 | 2.07E−08 | 14 |
| H4H18482P2 | 188 ± 0.8 | 38 | 9.53E+04 | 1.93E−02 | 2.03E−07 | 0.6 |
| H4H18487P2 | 219 ± 1.7 | 30 | 6.51E+04 | 1.86E−02 | 2.86E−07 | 0.6 |
| H4H18492P2 | 192 ± 2.2 | 93 | 1.17E+05 | 4.18E−03 | 3.59E−08 | 2.8 |
| H4H17319P2 | 264 ± 0.3 | 44 | 3.54E+04 | 3.41E−03 | 9.63E−08 | 3.4 |
| H4H17321P2 | 290 ± 0.4 | 61 | 2.95E+04 | 4.38E−04 | 1.48E−08 | 26 |
| Isotype Control monoclonal antibody | 193 ± 1.5 | 6 | NB* | NB* | NB* | NB* |

*NB indicates that no binding was observed under the current experimental conditions.

TABLE 5

Binding kinetics parameters of mfLEPR.MMH binding to LEPR monoclonal antibodies at 25° C.

| monoclonal antibody Captured | mAb Capture Level (RU) | 100 nM mfLEP.MMH Bound (RU) | $k_a$ (1/Ms) | $k_d$ (1/s) | $K_D$ (M) | t½ (min) |
|---|---|---|---|---|---|---|
| H4H16650P2 | 166 ± 0.6 | 93 | 6.02E+04 | 1.37E−04 | 2.27E−09 | 84 |
| H4H16679P2 | 191 ± 0.7 | 66 | 4.37E+04 | 1.41E−04 | 3.22E−09 | 82 |
| H4H18417P2 | 162 ± 0.3 | 33 | 8.83E+04 | 1.23E−02 | 1.39E−07 | 0.9 |
| H4H18438P2 | 166 ± 0.6 | 5 | IC* | IC* | IC* | IC* |
| H4H18445P2 | 193 ± 0.6 | 58 | 5.90E+04 | 4.86E−03 | 8.24E−08 | 2.4 |
| H4H18446P2 | 163 ± 2.8 | 23 | 1.93E+04 | 1.12E−03 | 5.83E−08 | 10 |
| H4H18449P2 | 175 ± 0.5 | 6 | IC* | IC* | IC* | IC* |
| H4H18482P2 | 163 ± 0.8 | 63 | 1.01E+05 | 6.74E−03 | 6.66E−08 | 1.7 |
| H4H18487P2 | 189 ± 0.5 | 59 | 7.37E+04 | 6.79E−03 | 9.21E−08 | 1.7 |
| H4H18492P2 | 165 ± 2.4 | 52 | 1.10E+05 | 1.20E−02 | 1.10E−07 | 1.0 |
| H4H17319P2 | 213 ± 0.5 | 83 | 4.00E+04 | 4.63E−04 | 1.16E−08 | 25 |
| H4H17321P2 | 236 ± 0.4 | 75 | 3.26E+04 | 1.33E−04 | 4.07E−09 | 87 |
| Isotype Control monoclonal antibody | 171 ± 0.4 | 0 | NB* | NB* | NB* | NB* |

*NB indicates that no binding was observed under the current experimental conditions.

*IC indicates that observed binding was inclusive and was unable to fit the real time binding data under the current experimental conditions.

TABLE 6

Binding kinetics parameters of mfLEPR.MMH binding to LEPR monoclonal antibodies at 37° C.

| monoclonal antibody Captured | mAb Capture Level (RU) | 100 nM mfLEPR.MMH Bound (RU) | $k_a$ (1/Ms) | $k_d$ (1/s) | $K_D$ (M) | t½ (min) |
|---|---|---|---|---|---|---|
| H4H16650P2 | 204 ± 1.7 | 134 | 1.22E+05 | 7.00E−04 | 5.76E−09 | 16 |
| H4H16679P2 | 232 ± 1.1 | 104 | 6.49E+04 | 6.77E−04 | 1.04E−08 | 17 |
| H4H18417P2 | 202 ± 1.3 | 28 | 1.22E+05 | 2.63E−02 | 2.17E−07 | 0.4 |
| H4H18438P2 | 203 ± 1.3 | 7 | IC* | IC* | IC* | IC* |
| H4H18445P2 | 232 ± 0.9 | 48 | 7.17E+04 | 1.90E−02 | 2.64E−07 | 0.6 |
| H4H18446P2 | 188 ± 2.9 | 30 | 2.53E+04 | 3.54E−03 | 1.40E−07 | 3.3 |
| H4H18449P2 | 202 ± 1 | 6 | IC* | IC* | IC* | IC* |
| H4H18482P2 | 187 ± 1.2 | 52 | 1.52E+05 | 2.04E−02 | 1.34E−07 | 0.6 |
| H4H18487P2 | 216 ± 0.7 | 44 | 1.10E+05 | 1.95E−02 | 1.78E−07 | 0.6 |
| H4H18492P2 | 191 ± 1.4 | 34 | 2.34E+05 | 3.94E−02 | 1.69E−07 | 0.3 |
| H4H17319P2 | 274 ± 0.5 | 113 | 5.39E+04 | 3.24E−03 | 6.01E−08 | 3.6 |
| H4H17321P2 | 304 ± 0.7 | 143 | 4.97E+04 | 2.57E−04 | 5.18E−09 | 45 |
| Isotype Control monoclonal antibody | 190 ± 1 | 1 | NB* | NB* | NB* | NB* |

*NB indicates that no binding was observed under the current experimental conditions.

*IC indicates that observed binding was inclusive and was unable to fit the real time binding data under the current experimental conditions.

TABLE 7

Binding kinetics parameters of hLEPR.mFc binding to LEPR monoclonal antibodies at 25° C.

| monoclonal antibody Captured | mAb Capture Level (RU) | 100 nM hLEPR-mFc Bound (RU) | $k_a$ (1/Ms) | $k_d$ (1/s) | $K_D$ (M) | t½ (min) |
|---|---|---|---|---|---|---|
| H4H16650P2 | 165 ± 0.2 | 102 | 1.06E+05 | 8.32E−05 | 7.85E−10 | 139 |
| H4H16679P2 | 190 ± 1.2 | 78 | 5.84E+04 | 9.68E−05 | 1.66E−09 | 119 |
| H4H18417P2 | 162 ± 0.6 | 90 | 1.40E+05 | 5.63E−04 | 4.04E−09 | 21 |
| H4H18438P2 | 165 ± 1.2 | 51 | 5.19E+04 | 2.44E−04 | 4.70E−09 | 47 |
| H4H18445P2 | 192 ± 0.4 | 76 | 1.22E+05 | 4.92E−04 | 4.03E−09 | 23 |
| H4H18446P2 | 162 ± 2.8 | 20 | 3.20E+04 | 2.08E−04 | 6.48E−09 | 56 |
| H4H18449P2 | 174 ± 0.6 | 116 | 7.05E+04 | 6.82E−05 | 9.64E−10 | 169 |
| H4H18482P2 | 162 ± 0.5 | 88 | 1.44E+05 | 4.91E−04 | 3.42E−09 | 24 |
| H4H18487P2 | 188 ± 0.6 | 85 | 1.06E+05 | 6.03E−04 | 5.70E−09 | 19 |

TABLE 7-continued

Binding kinetics parameters of hLEPR.mFc binding to LEPR monoclonal antibodies at 25° C.

| monoclonal antibody Captured | mAb Capture Level (RU) | 100 nM hLEPR-mFc Bound (RU) | $k_a$ (1/Ms) | $k_d$ (1/s) | $K_D$ (M) | t½ (min) |
|---|---|---|---|---|---|---|
| H4H18492P2 | 166 ± 3.2 | 129 | 2.27E+05 | 1.39E−04 | 6.13E−10 | 83 |
| H4H17319P2 | 200 ± 0.5 | 69 | 4.77E+04 | 1.64E−04 | 3.45E−09 | 70 |
| H4H17321P2 | 221 ± 0.4 | 65 | 4.10E+04 | 8.93E−05 | 2.18E−09 | 129 |
| Isotype Control monoclonal antibody | 170 ± 0.7 | −2 | NB* | NB* | NB* | NB* |

*NB indicates that no binding was observed under the current experimental conditions.

TABLE 8

Binding kinetics parameters of hLEPR.mFc binding to LEPR monoclonal antibodies at 37° C.

| monoclonal antibody Captured | mAb Capture Level (RU) | 100 nM hLEPR-mFc Bound (RU) | $k_a$ (1/Ms) | $k_d$ (1/s) | $K_D$ (M) | t½ (min) |
|---|---|---|---|---|---|---|
| H4H16650P2 | 199 ± 1.9 | 145 | 1.57E+05 | 2.80E−04 | 1.79E−09 | 41 |
| H4H16679P2 | 229 ± 2.3 | 116 | 1.21E+05 | 3.10E−04 | 2.56E−09 | 37 |
| H4H18417P2 | 199 ± 1.1 | 111 | 1.85E+05 | 1.05E−03 | 5.64E−09 | 11 |
| H4H18438P2 | 199 ± 0.6 | 82 | 7.02E+04 | 5.98E−04 | 8.53E−09 | 19 |
| H4H18445P2 | 229 ± 2 | 104 | 1.56E+05 | 6.08E−04 | 3.89E−09 | 19 |
| H4H18446P2 | 186 ± 2.5 | 34 | 4.27E+04 | 5.48E−04 | 1.28E−08 | 21 |
| H4H18449P2 | 198 ± 1.6 | 148 | 1.33E+05 | 1.68E−04 | 1.26E−09 | 69 |
| H4H18482P2 | 185 ± 1.3 | 109 | 1.89E+05 | 7.26E−04 | 3.84E−09 | 16 |
| H4H18487P2 | 215 ± 1.5 | 99 | 1.23E+05 | 6.06E−04 | 4.93E−09 | 19 |
| H4H18492P2 | 189 ± 1.8 | 160 | 4.33E+05 | 5.00E−04 | 1.16E−09 | 23 |
| H4H17319P2 | 262 ± 0.5 | 100 | 8.51E+04 | 6.52E−04 | 7.66E−09 | 18 |
| H4H17321P2 | 289 ± 0.4 | 110 | 5.53E+04 | 1.74E−04 | 3.15E−09 | 66 |
| Isotype Control monoclonal antibody | 188 ± 0.8 | 1 | NB* | NB* | NB* | NB* |

*NB indicates that no binding was observed under the current experimental conditions.

At 25° C., anti-LEPR monoclonal antibodies bound to hLEPR-MMH with $K_D$ values ranging from 7.93 nM to 148 nM, as shown in Table 5. At 37° C., anti-LEPR monoclonal antibodies bound to hLEPR-MMH with $K_D$ values ranging from 14.8 nM to 326 nM, as shown in Table 4.

Ten out of 12 anti-LEPR monoclonal antibodies of the invention bound to mfLEPR.MMH. At 25° C., anti-LEPR monoclonal antibodies bound to mfLEPR.MMH with $K_D$ values ranging from 2.27 nM to 139 nM, as shown in Table 7. At 37° C., anti-LEPR monoclonal antibodies bound to mfLEPR.MMH with $K_D$ values ranging from 5.18 nM to 264 nM, as shown in Table 8.

At 25° C., anti-LEPR monoclonal antibodies bound to hLEPR-mFc with $K_D$ values ranging from 613 pM to 5.7 nM, as shown in Table 7. At 37° C., anti-LEPR monoclonal antibodies bound to hLEPR-mFc with $K_D$ values ranging from 1.16 nM to 12.8 nM, as shown in Table 8.

None of the anti-LEPR monoclonal antibodies of the invention bound to mLEPR.MMH or rLEPR.MMH at 25° C. or at 37° C. (data not shown).

Example 4. Anti-LEPR Antibodies of the Invention Bind LEPR in the Presence of Leptin:LEPR Binding Blocking of anti-LEPR antibodies from binding to LEPR by human Leptin was evaluated using a real-time surface plasmon resonance biosensor on a Biacore T200 instrument. The entire study was performed in 10 mM HEPES pH 7.4, 150 mM NaCl, 3 mM EDTA, and 0.05% v/v Surfactant Tween-20 (HBS-ET running buffer) at 25° C. The Biacore CM5 sensor surface was first derivatized by amine coupling human Leptin (R&D Systems, #398-LP) using standard EDC/NHS surface chemistry. A complex of human LEPR and human Leptin, was formed by injecting 20 nM of human LEPR extracellular domain expressed with a C-terminal myc-myc-hexahistidine tag (hLEPR-MMH; SEQ ID NO: xx), over the human Leptin immobilized Biacore sensor surface at a flow rate of 10 µL/minute or 25 µL/minute for 4 minutes, to achieve a binding response of approximately 200 RU. To evaluate whether antibody binding to hLEPR-MMH is blocked by human Leptin, 200 nM of anti-LEPR monoclonal antibodies were injected over the preformed hLEPR-MMH:human Leptin complex, at a flow rate of 504/minute or 254/minute for 4-5 minutes. All the anti-LEPR antibodies of this invention bound to the complex of hLEPR-MMH and human Leptin ("Leptin:LEPR") with nearly similar signal strength and the observed binding, expressed in RUs, are reported in Table 9. This result indicates that human Leptin does not block the binding of hLEPR-MMH to the anti-LEPR antibodies tested.

TABLE 9

| Binding of anti-LEPR monoclonal antibodies to the pre-complex of hLEPR-MMH and human Leptin. | | |
|---|---|---|
| Antibody | hLEPR-MMH Bound (RU) | 200 nM mAb Bound (RU) |
| H4H16650P2 | 196 | 81 |
| H4H16679P2 | 195 | 90 |
| H4H17319P2 | 196 | 92 |

Example 5. Human Leptin Receptor Blocking ELISA

For the ELISA, human Leptin (hLeptin; R&D Systems, #398-LP-01M) was coated at a concentration of 5 μg/mL in PBS on a 96-well microtiter plate overnight at 4° C. Non-specific binding sites were subsequently blocked using a 0.5% (w/v) solution of BSA in PBS. A constant amount of 10 nM of extracellular domain portion of LEPR protein that was expressed with a C-terminal human Fc tag (hLEPR.hFc; SEQ ID NO: 116) was titrated with anti-LEPR antibodies, hLeptin protein, or an isotype control antibody ranging from 8.5 pM to 500 nM in serial dilution. These antibody-protein or protein-protein complexes were then incubated for 1.5 hour at room temperature (RT). Complexes were subsequently transferred to microtiter plates coated with hLeptin and incubated for 2 hours at RT, the wells were washed, and plate-bound hLEPR.hFc was detected with an anti-human IgG polyclonal antibody conjugated with horseradish peroxidase (Jackson ImmunoResearch Inc, #109-035-098). Samples were developed with a TMB solution (BD Biosciences, #555214; substrate A and B mixed at 1:1 ratio as per manufacturer's instructions) to produce a colorimetric reaction and then neutralized with 1M sulfuric acid before measuring absorbance at 450 nm on a Victor X5 plate reader.

Data analysis was performed using a sigmoidal dose-response model within Prism™ software (Graph Pad). Percent blockade at maximum concentration of the antibody tested was calculated as an indicator of the ability of the antibodies to block the binding of 10 nM of hLEPR.hFc to human Leptin on the plate. In the calculation, binding signal of 10 nM of hLEPR.hFc without the presence of the antibody was referenced as 100% binding or 0% blocking; and the baseline signal of buffer alone without the presence of hLEPR.hFc was referenced as 0% binding or 100% blocking. The blocking data at 500 nM antibody concentration is summarized in Table 10.

As shown in Table 10, none of the anti-LEPR antibodies of the invention demonstrated >28% blocking of the binding of hLEPR.hFc to the hLeptin coated surface. However, the Comparator Antibody and the hLeptin, as the positive control, were able to block 99% of the hLEPR.hFc binding to the hLeptin coated surface. The isotype control antibody demonstrated no measurable blocking at concentrations up to 500 nM.

TABLE 10

| ELISA blocking of hLEPR.hFc binding to hLeptin by anti-LEPR antibodies | |
|---|---|
| Antibody | 500 nM Ab Blocking of 10 nM hLEPR.hFc Binding to hLeptin (% blockade) |
| H4H18487P2 | 5 |
| H4H18417P2 | 16 |
| H4H18482P2 | 25 |
| H4H18492P2 | −3 |
| H4H18445P2 | 28 |
| H4H18446P2 | −5 |
| H4H18449P2 | 8 |
| H4H18438P2 | 15 |
| H4H16650P2 | −7 |
| H4H16679P2 | 7 |
| H4H173319P2 | 9 |
| H4H173321P2 | 6 |
| Controls | |
| Isotype control antibody | −3 |
| Human Leptin | 99 |
| Comparator Antibody | 99 |
| Mouse IgG2a Isotype control | 32 |

Example 6. Cell Binding by FACS Analysis with HEK293/Mycx2-hLepR(Ecto)-GPI Anchored Cells Leptin receptor, LEPR, is a single-pass transmembrane receptor of the class I cytokine receptor family (Tartaglia et al. (1997) *J Biol Chem* 7:272(10):6093-6). LEPR can bind to Leptin, a protein predominantly expressed by adipose tissue that is involved in regulation of food intake and metabolism (Friedman et al. (2014) *J Endocrinol* 223(1):T1-8).

In order to assess cell binding by anti-LEPR antibodies HEK293 stable cell lines were generated. One cell line, known hereafter as HEK293/hLEPR-GPI, stably expressed the extracellular domain of human LEPR (amino acids 22-839 of accession #P48357 (SEQ ID NO:113), Isoform B) with an N-terminal myc-myc tag and C-terminal peptide sequence from human carboxypeptidase M that guides the addition of GPI (Glycosylphosphatidylinositol) (Deddish et al. (1990) *J. Biological Chemistry* 265:25:15083-89) such that the protein can be GPI-anchored to the membrane. Another HEK293 cell line was generated to stably express the full length human LEPR (amino acids 1-1165 of accession #P48357 (SEQ ID NO:113), Isoform B) along with a luciferase reporter (Stat3-luciferase, Stat3-luc, SA Bioscience, #CLS-6028L), and is known hereafter as HEK293/Stat3-luc/hLEPR-FL. HEK293 cells with the Stat3-luciferase reporter only (HEK293/Stat3-luc) were also generated as a control cell line.

For the FACS analysis, HEK293 parental cells and HEK293/hLEPR-GPI cells were dissociated and plated onto 96-well v-bottom plates at $5\times10^5$ cells/well in PBS containing 2% FBS (FACS buffer). In order to test whether the ability of anti-hLEPR antibodies to bind to cells is affected by the presence of Leptin, FACS buffer with or without 1 μM human Leptin (R&D Systems, #398-LP) was incubated with the cells for 30 minutes at 4° C., followed by the addition of anti-LEPR antibodies or control antibodies at 10 nM in FACS buffer. The cells were subsequently incubated for 30 minutes at 4° C., followed by washing and then incubation with 16 μg/mL of Alexa Fluor®-647 conjugated secondary antibody (Jackson ImmunoResearch Laboratories Inc., #109-547-003) for 30 minutes at 4° C. Cells were subsequently fixed using BD CytoFix™ (Becton Dickinson,

#554655), filtered, and analyzed on a HyperCyt Flow Cytometer (Beckman Coulter). Unstained and secondary antibody alone controls were also tested for all cell lines. The results were analyzed using ForeCyt (IntelliCyt) and FlowJo version 10 software to determine the geometric means of fluorescence for viable cells. The geometric mean of fluorescence for each sample was then normalized to the geometric mean of unstained cells to obtain relative binding per condition referred to as "binding ratios", and these binding ratios were recorded for each antibody tested.

As shown in Table 11, 9 anti-LEPR antibodies of the invention tested at 10 nM demonstrated binding to HEK293/hLEPR-GPI cells with binding ratios ranging from 824 to 3374 fold without Leptin. The anti-LEPR antibodies also bound in the presence of 1 μM Leptin with binding ratios of 398 and 4184 fold. As shown in Table 11, the Comparator Antibody tested at 10 nM demonstrated binding to HEK293/hLEPR-GPI cells with a binding ratio of 2349-fold without Leptin but showed significantly less binding to cells in the presence of 1 μM Leptin with binding ratio of 112. The anti-LEPR antibodies did not demonstrate any significant binding to the HEK293 parental cells with binding ratios with and without 1 μM Leptin ranging from 1 to 9 fold. The isotype control antibodies and secondary antibodies alone samples also did not demonstrate significant binding to either cell line with or without Leptin, with binding ratios ranging from 1 to 6 fold.

As shown in Table 12, four antibodies of the invention tested at 70 nM without Leptin, demonstrated binding to HEK293/hLEPR-GPI cells with binding ratios ranging from 707 to 1131 fold and to HEK293/Stat3-luc/hLEPR-FL cells with binding ratios ranging from 42 to 51. The anti-LEPR antibodies did not demonstrate any significant binding to the HEK293/Stat3-luc cells with binding ratios ranging from 1 to 8 fold. The isotype control antibodies and secondary antibodies alone samples also did not demonstrate significant binding to any of the cell lines tested, with binding ratios ranging from 1 to 2 fold.

TABLE 11

Binding of 10 nM anti-LEPR antibodies to HEK293/hLEPR-GPI and HEK293 parental cells +/− 1 μM Human Leptin

| | Binding Ratio: Normalized to Unstained Sample of Each Cell Line | | | | |
|---|---|---|---|---|---|
| | No added Leptin | | 1 μM Leptin | | |
| Antibody | HEK293 parental | HEK293/ hLEPR-GPI | HEK293 parental | HEK293/ hLEPR-GPI | Antibody Type |
| H4H16650P2 | 5 | 2420 | 4 | 3124 | Agonist |
| H4H16679P2 | 5 | 2058 | 8 | 2223 | Agonist |
| H4H18417P2 | 1 | 1835 | 2 | 2604 | Potentiator |
| H4H18438P2 | 2 | 1486 | 3 | 2414 | Potentiator |
| H4H18445P2 | 2 | 2016 | 3 | 2488 | Potentiator |
| H4H18449P2 | 5 | 3374 | 9 | 3113 | Potentiator |
| H4H18482P2 | 1 | 1966 | 3 | 2704 | Potentiator |
| H4H18487P2 | 1 | 2422 | 3 | 2670 | Potentiator |
| H4H18492P2 | 3 | 2603 | 7 | 4184 | Potentiator |

TABLE 11

Binding of 10 nM anti-LEPR antibodies to HEK293/hLEPR-GPI and HEK293 parental cells +/− 1 μM Human Leptin

| | Binding Ratio: Normalized to Unstained Sample of Each Cell Line | | | | |
|---|---|---|---|---|---|
| | No added Leptin | | 1 μM Leptin | | |
| Antibody | HEK293 parental | HEK293/ hLEPR-GPI | HEK293 parental | HEK293/ hLEPR-GPI | Antibody Type |
| Comparator | 6 | 2349 | 3 | 112 | N/A |
| Isotype control antibody | 1 | 6 | 2 | 4 | N/A |
| Secondary antibody alone | 1 | 3 | 2 | 3 | N/A |
| Unstained | 1 | 1 | 1 | 1 | N/A |

*Classification of antibodies as "Agonist" or "Potentiator" is based in part on the results observed in Examples 7 and 8 herein.

TABLE 12

| Binding of 70 nM anti-LEPR antibodies to HEK293/hLEPR-GPI, HEK293/Stat3-hLEPR-FL, and HEK293/Stat3-luc parental cells | | | | |
|---|---|---|---|---|
| | Binding Ratio: Normalized to Unstained Sample of Each Cell Line | | | |
| Antibody | HEK293/ Stat3-luc | HEK293/ hLEPR-GPI | HEK293/ Stat3-luc hLEPR-FL | Antibody Type |
| H4H16650P2 | 6 | 707 | 42 | Agonist |
| H4H16679P2 | 8 | 1078 | 51 | Agonist |
| H4H17319P2 | 7 | 1131 | 47 | Agonist |
| H4H17321P2 | 7 | 1126 | 46 | Agonist |
| Isotype control antibody | 2 | 2 | 2 | |
| Secondary antibody alone | 1 | 1 | 1 | |
| Unstained | 1 | 1 | 1 | |

Example 7. Anti-LEPR Antibodies of the Invention Activate LEPR Signaling in the Presence or Absence of Leptin A bioassay was developed to detect the transcriptional activation of STAT3 via LEPR activation using a reporter cell line that stably expresses full-length human LEPR (hLEPR; amino acids 1 through 1165 of accession number NP_002294.2) along with a luciferase reporter (STAT3-Luc; Qiagen, #CLS-6028L) in an IMR-32 cell line, a human neuroblastoma cell line. The resulting stable cell line, referred to as IMR-32/STAT3-Luc/hLEPR, was isolated and maintained in MEM-Earl medium supplemented with 10% FBS, NEAA, 1 ug/mL Puromycin, 100 ug/mL of Hygromycin B and Penicillin/Streptomycin/L-Glutamine (Complete Medium).

The resulting bioassay was used to measure the effect of anti-LEPR antibodies of the invention on LEPR signaling in the presence or absence of Leptin. For the bioassay, IMR-32/STAT3-Luc/hLEPR cells were plated at the density of 20,000 cells/100 ul/well for 96 well format in the complete medium, and the following day replaced with the appropriate volume of Opti-MEM medium supplemented with 1% BSA and 0.1% FBS (Assay Buffer) for 30 minutes. To measure the effect of the antibodies of the invention in the absence of Leptin, the anti-LEPR antibodies or an isotype control antibody and human Leptin (hLeptin; R&D Systems, #398-LP) were half-log serially diluted to final concentrations ranging from 100 nM to 300 fM in Assay Buffer, which were added to the cells and subsequently incubated overnight at 37° C. in 5% CO2.

To measure the effect of the antibodies of the invention in the presence of Leptin, a fixed concentration of human Leptin at 200 μM in Assay Buffer was added to the cells, immediately followed by the addition of anti-LEPR antibodies or isotype control antibody that were half-log serially diluted to final concentrations ranging from 100 nM to 300 fM. The samples were then incubated overnight at 37° C. in 5% CO2. OneGlo reagent (Promega, #E6051) was then added to the samples and luciferase activity was measured on an Envision Multilabel Plate Reader (Perkin Elmer) in Luminescent mode. The relative light unit (RLU) values were obtained and the results were analyzed using nonlinear regression with Graph Pad Prism software (Graph Pad). The maximum RLU value obtained from the hLeptin dose response was defined as 100% activation in the IMR-32/STAT3-Luc/hLEPR assay.

As shown in Table 13, in Study 1, in the absence of hLeptin, all of the anti-LEPR antibodies tested demonstrated weak stimulation of the IMR-32/STAT3-Luc/hLEPR cells with $EC_{50}$ values ranging from 134 pM to 11.9 nM and maximal activation ranging from 5% to 13% respectively that of maximum activation obtained from the hLeptin dose response. In Study 2, in the absence of hLeptin, the 4 anti-LEPR antibodies tested demonstrated stimulation of the IMR-32/STAT3-Luc/hLEPR cells with $EC_{50}$ values ranging from 61.9 pM to 206.9 pM and maximal activation ranging from 65% to 68% respective to the maximum activation obtained from the hLeptin dose response. In Study 1, in the presence of 200 pM of hLeptin, all of the anti-LEPR antibodies tested demonstrated stimulation of the IMR-32/STAT3-Luc/hLEPR cells with $EC_{50}$ values ranging from 20.2 pM to 523 pM and maximal activation ranging from 66% to 107% respectively that of maximum activation obtained from the hLeptin dose response. Because these antibodies enhanced leptin-induced LEPR signaling, these antibodies were classified as "potentiators", as defined herein. In Study 2, in the presence of 200 pM of hLeptin, the 4 anti-LEPR antibodies tested demonstrated stimulation of the IMR-32/STAT3-Luc/hLEPR cells with $EC_{50}$ values ranging from 51.9 pM to 257.3 pM with maximal activation ranging from 76% to 88% that of maximum activation obtained from the hLeptin dose response. LEPR signaling was not appreciably enhanced by these antibodies in the presence of leptin. The isotype control antibody did not demonstrate any measurable stimulation of the IMR-32/STAT3-Luc/hLEPR cells in any of the assays.

TABLE 13

| Activation of hLEPR by anti-LEPR Antibodies | | | | |
|---|---|---|---|---|
| | IMR-32/LEPR without human Leptin | | IMR-32/LEPR with 200 pM human Leptin | |
| Antibody | $EC_{50}$ (M) | % activation | $EC_{50}$ (M) | % activation |
| Study 1 | | | | |
| H4H18445P2 | 1.19E−08 | 5 | 4.10E−10 | 97 |
| H4H18446P2 | 3.73E−10 | 6 | 3.42E−11 | 68 |
| H4H18449P2 | 2.12E−10 | 13 | 5.23E−11 | 66 |
| H4H18438P2 | 1.49E−09 | 5 | 2.02E−11 | 76 |
| H4H18482P2 | 2.69E−10 | 7 | 1.69E−10 | 94 |
| H4H18487P2 | 8.01E−10 | 6 | 4.10E−10 | 107 |
| H4H18492P2 | 1.34E−10 | 5 | 2.74E−11 | 94 |
| H4H18417P2 | 1.53E−10 | 5 | 5.23E−10 | 87 |

TABLE 13-continued

| Activation of hLEPR by anti-LEPR Antibodies | | | | |
|---|---|---|---|---|
| | IMR-32/LEPR without human Leptin | | IMR-32/LEPR with 200 pM human Leptin | |
| Antibody | $EC_{50}$ (M) | % activation | $EC_{50}$ (M) | % activation |
| Study 2 | | | | |
| H4H16650P2 | 6.19E−11 | 68 | 5.19E−11 | 88 |
| H4H16679P2 | 8.62E−11 | 65 | 7.37E−11 | 88 |
| H4H17319P2 | 1.867E−10 | 68 | 1.914E−10 | 76 |
| H4H17321P2 | 2.069E−10 | 66 | 2.573E−10 | 76 |

Example 8. Anti-LEPR Antibodies of the Invention Activate Signaling in Cells Expressing Signaling-Defective or Signaling-Impaired LEPR Mutants LEPR mutants have been identified that exhibit defective or impaired leptin-mediated signaling and are associated with early-onset obesity. For example, LEPR-A409E is a signaling-defective mutant LEPR protein that does not transduce leptin signals to STAT3; the A409E mutant was originally identified as a monogenic cause of early onset obesity. (Farooqi et al., 2007, *N Engl J Med* 356(3): 237-247). LEPR-P316T is a signaling-impaired mutant LEPR protein that has also been shown to be associated with early-onset obesity. (Mazen et al., 2011, *Mol Genet Metab* 102:461-464).

In this Example, the ability of anti-LEPR antibodies of the invention to stimulate LEPR signaling in cell lines expressing signaling-defective or signaling-impaired LEPR mutants was assessed. In particular, reporter cell lines (HEK293) were constructed expressing either wild-type LEPR, LEPR-A409E (signaling-defective) or LEPR-P316T (signaling-impaired). Cells were treated with either vehicle only, recombinant human leptin, control IgG, or agonist anti-LEPR antibodies of the present invention (H4H16650 or H4H16679), and the extent of LEPR signaling (as measured by Western blot detection of pSTAT3-Y705 expression relative to STAT3 expression) was determined.

Figure 2A:
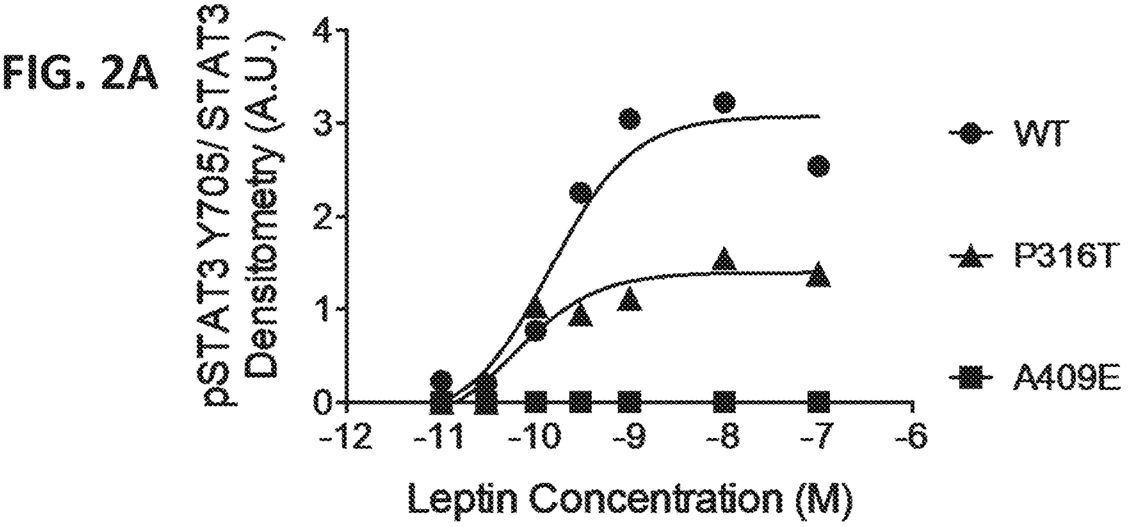
FIGS. 2A-2C illustrates the extent of LEPR signaling in HEK293 cells expressing either wild-type LEPR (circles), a signaling-defective LEPR mutant (A409E, squares), or a signaling-impaired LEPR mutant (P316T, triangles). LEPR signaling is expressed as ratio of pSTAT3-Y705/STAT3, measured by densitometry from Western blots prepared from cells treated with increasing concentrations of leptin (FIG. 2A), H4H16650 (FIG. 2B), or H4H16679 (FIG. 2C).
Figure 2B:
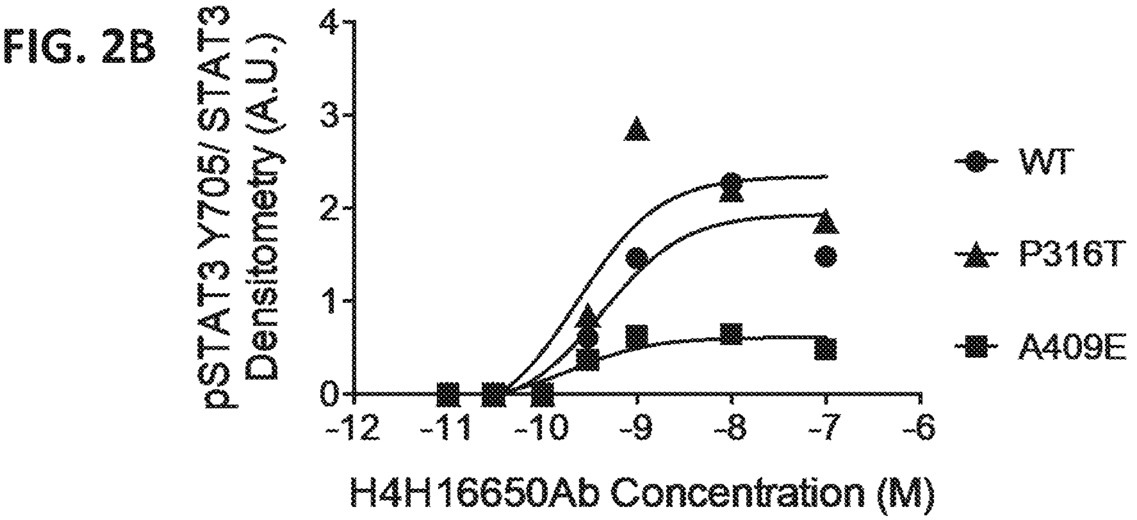
Figure 2C:
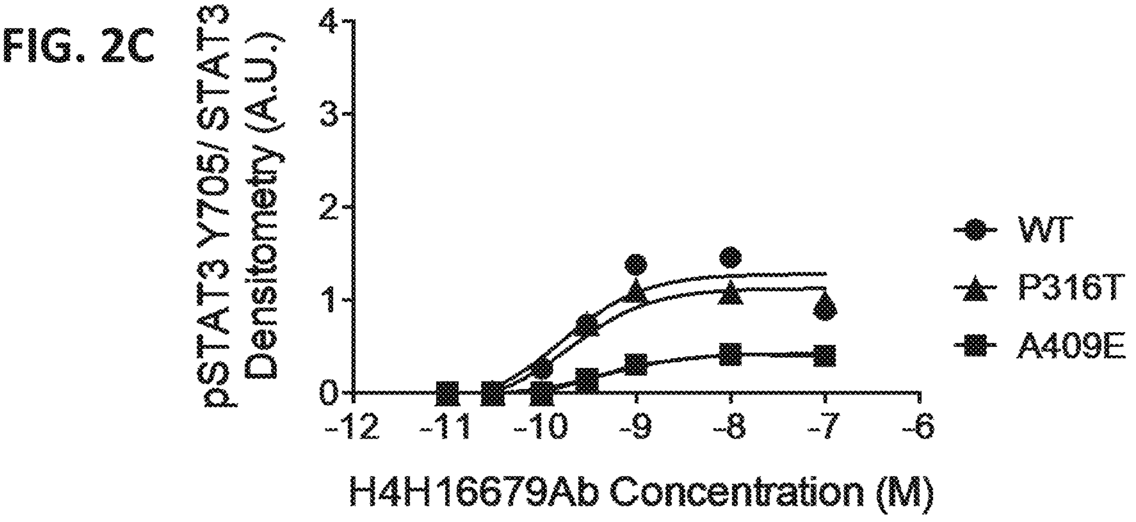

The agonist anti-LEPR antibodies of the present invention (H4H16650 and H4H16679) were shown in these experiments to stimulate LEPR signaling in cells expressing the LEPR-A409E mutant or the LEPR-P316T mutant (as measured by STAT3 expression) in a dose-dependent manner (FIG. 2, panels B and C). By contrast, leptin treatment induced only modest signaling in cells expressing the LEPR-P316T mutant, and no signaling in cells expressing the LEPR-A409E mutant. (FIG. 2, panel A). Moreover, no LEPR signaling was detected in any of the cell lines treated with vehicle or IgG control antibody (data not shown). Other signaling-defective or signaling-impaired LEPR mutants were tested in this assay but were not activated by anti-LEPR mutants (data not shown), suggesting that this rescue effect may be mutant-dependent.

The results of this Example indicate that the agonist anti-LEPR antibodies of the present invention may be useful in the treatment of diseases and disorders (e.g., early-onset obesity) that are caused by or associated with certain signaling-defective or signaling-impaired LEPR mutants (e.g., LEPR-P316T or LEPR-A409E).

Example 9: Octet Cross-Competition Between Different Anti-LEPR Monoclonal Antibodies Binding competition between a panel of different anti-LEPR monoclonal antibodies was determined using a real time, label-free bio-layer interferometry assay on the Octet HTX biosensor platform (Pall ForteBio Corp.). The entire experiment was performed at 25° C. in buffer containing 10 mM HEPES, 150 mM NaCl, 3 mM EDTA, and 0.05% v/v Surfactant Tween-20, 1 mg/mL BSA, pH7.4 (HBS-EBT) with the plate shaking at the speed of 1000 rpm. To assess whether two antibodies were able to compete with one another for binding to their respective epitopes on recombinant human LEPR expressed with a C-terminal myc-myc-hexahistidine tag (hLEPR.mmh; SEQ ID NO: 114), around 0.25 nm or 0.34 nm of hLEPR-MMH was first captured onto anti-penta-His antibody coated Octet biosensor tips (Fortebio Inc, #18-5122) by submerging the biosensor tips for 5 minutes in wells containing 20 μg/mL of hLEPR-MMH. The antigen captured biosensor tips were then saturated with a first anti-LEPR monoclonal antibody (subsequently referred to as mAb-1) by dipping into wells containing 50 μg/mL solution of mAb-1 for 210 seconds. The biosensor tips were then subsequently dipped into wells containing a 50 μg/mL solution of a second anti-LEPR monoclonal antibody (subsequently referred to as mAb-2) for 150 seconds. The biosensor tips were washed in HBS-EBT buffer in between every step of the experiment. The real-time binding response was monitored during the entire course of the experiment and the binding response at the end of every step was recorded. The response of mAb-2 binding to hLEPR-MMH pre-complexed with mAb-1 was compared and competitive/non-competitive behavior of different anti-LEPR monoclonal antibodies was determined as shown in Table 14 and Table 15.

TABLE 14

| Cross-competition between anti-LEPR monoclonal antibodies | |
|---|---|
| First antibody (mAb-1) binding to captured hLEPR-MMH | Second antibody (mAb-2) shown to compete with mAb-1 |
| H4H18492P2 | H4H18417P2 |
| | H4H18438P2 |
| H4H18417P2 | H4H18492P2 |
| | H4H18438P2 |
| H4H18438P2 | H4H18492P2 |
| | H4H18417P2 |
| H4H16650P2 | H4H16679P2 |
| H4H16679P2 | H4H16650P2 |
| H4H18445P2 | H4H18482P2 |
| | H4H18487P2 |
| | H4H18446P2 |
| H4H18446P2 | H4H18482P2 |
| | H4H18487P2 |
| | H4H18445P2 |
| H4H18482P2 | H4H18445P2 |
| | H4H18487P2 |
| H4H18487P2 | H4H18445P2 |
| | H4H18482P2 |
| H4H18449P2 | None |
| Comparator Antibody | None |

TABLE 15

| Cross-competition between anti-LEPR monoclonal antibodies | |
|---|---|
| mAb-1 | mAb-2 that competes with mAb-1 |
| H4H17319P2 | H4H17321P2 |
| | H4H16650P2 |
| | H4H16679P2 |

TABLE 15-continued

| Cross-competition between anti-LEPR monoclonal antibodies | |
|---|---|
| mAb-1 | mAb-2 that competes with mAb-1 |
| H4H17321P2 | H4H17319P2 |
| | H4H16650P2 |
| | H4H16679P2 |
| H4H16650P2 | H4H17319P2 |
| | H4H17321P2 |
| | H4H16679P2 |
| H4H16679P2 | H4H17319P2 |
| | H4H17321P2 |
| | H4H16650P2 |

Example 10: In Vivo Efficacy of LEPR Agonist Antibodies H4H16650P2, H4H16679P2, H4H17319P2 and H4H17321P2 in an Inducible Mouse Model of Leptin Deficiency The effects of four specific agonist anti-LEPR antibodies of the invention, H4H16650P2, H4H16679P2, H4H17319P2, and H4H17321P2 on food intake, body weight and adiposity were determined in an inducible model of leptin deficiency in genetically engineered LEPR$^{Hu/Hu}$ mice, that express a leptin receptor which is composed of the human LEPR ectodomain sequence in place of the murine LEPR ectodomain sequence. The model of leptin deficiency was induced by hydrodynamic DNA delivery (HDD) of a plasmid encoding an hFc-tagged mouse LEPR ectodomain (referred to herein as mLEPR.hFc or "Leptin trap"; SEQ ID NO: 120). The Leptin trap when expressed is secreted and binds circulating Leptin. After HDD of 50 μg of the DNA construct encoding the Leptin trap, mice exhibited increased food consumption and increased adiposity and body weight.

Figure 3:
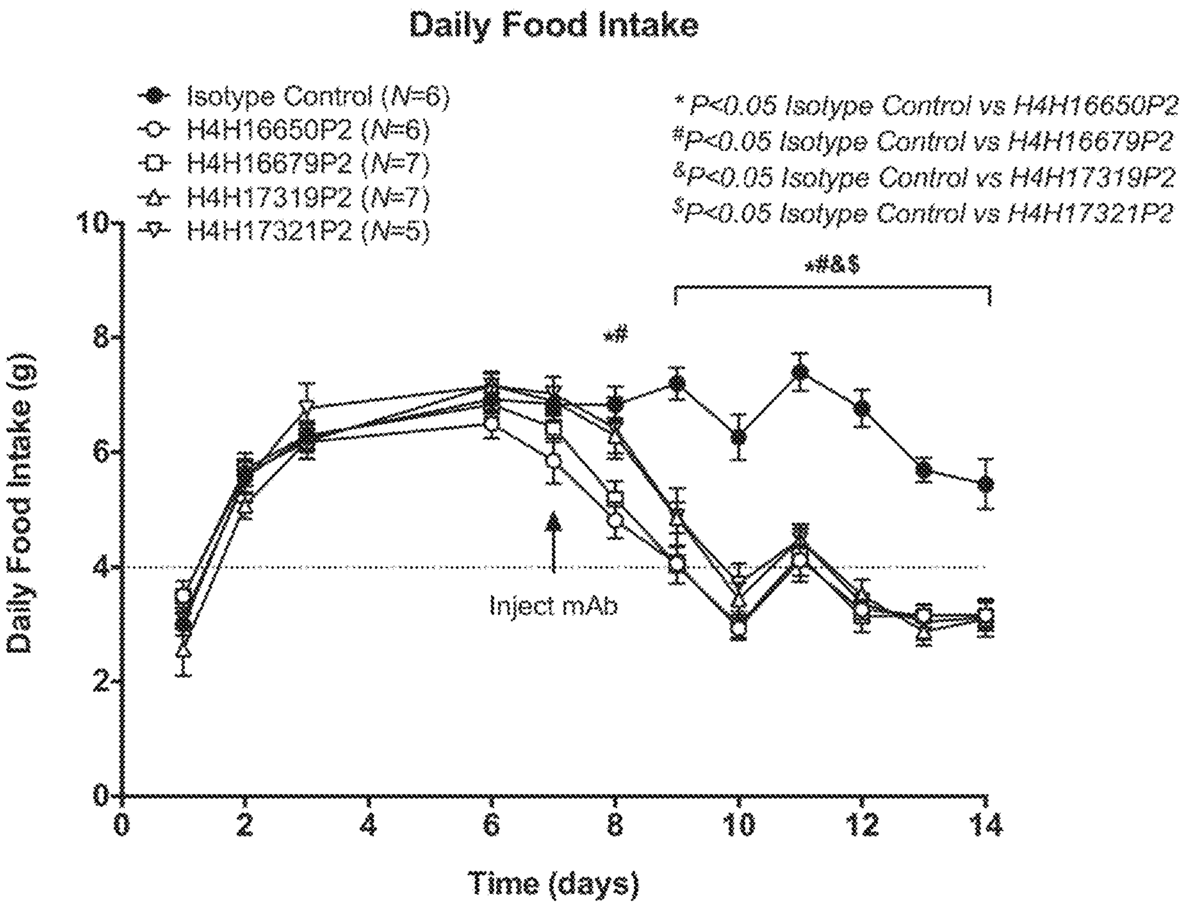
FIG. 3 shows the average daily food intake of leptin-deficient mice dosed with either an isotype control antibody at 3 mg/kg, or a LEPR antibody selected from H4H16650P2, H4H16679P2, H4H17319P2 or H4H17321P2 at 3 mg/kg.
Figure 4:
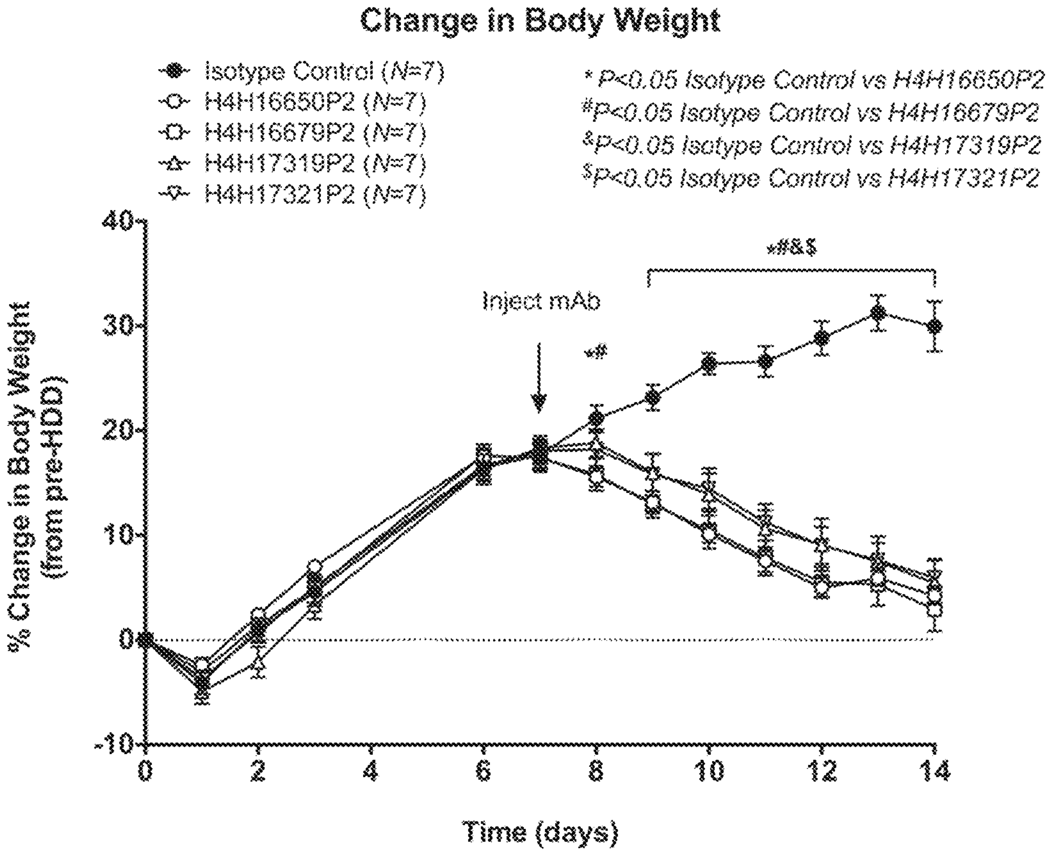
FIG. 4 shows the average percent change in body weight of mice dosed with either an isotype control antibody at 3 mg/kg, or a LEPR antibody selected from H4H16650P2, H4H16679P2, H4H17319P2 or H4H17321P2 at 3 mg/kg.
Figure 5:
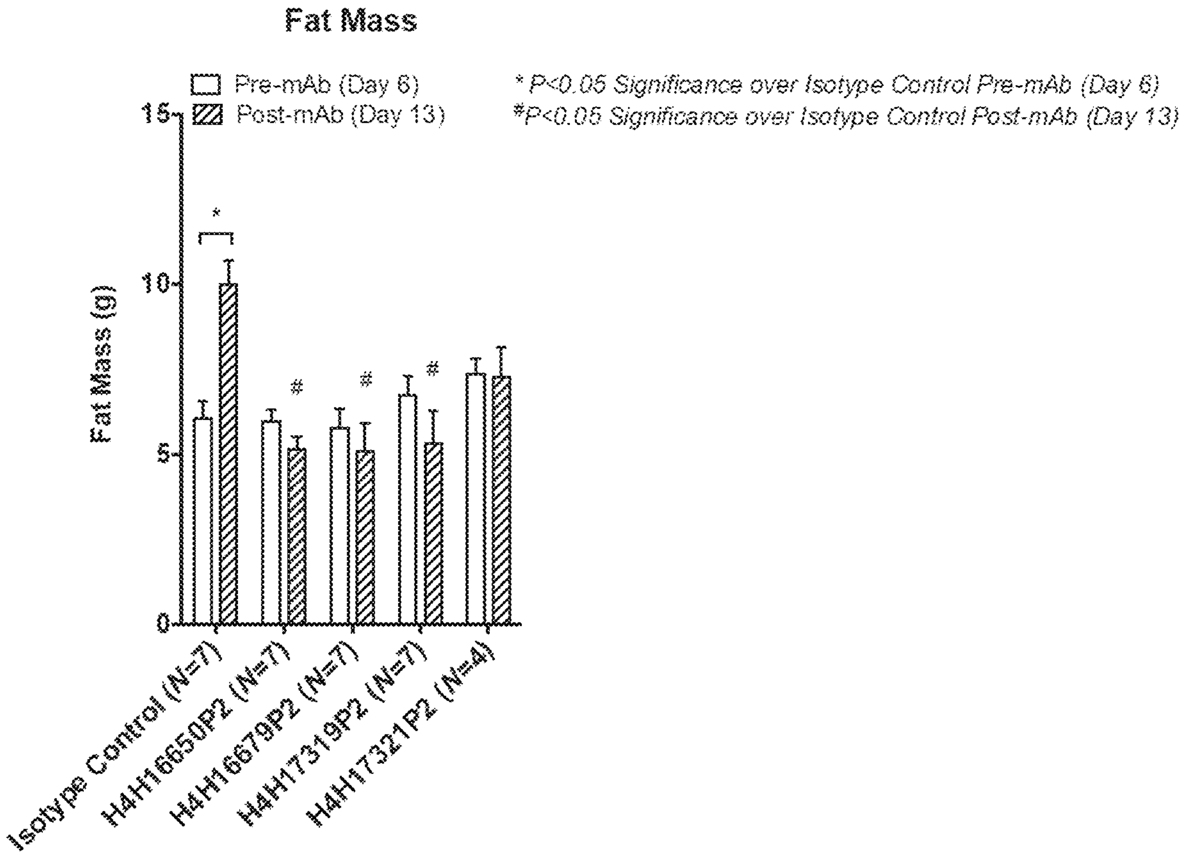
FIG. 5 shows the average fat mass for animals in each antibody treatment group quantified by µCT 1 day prior to (bars not shaded) and 6 days following antibody treatment (shaded bars) expressed as mean±SEM.

Baseline daily food intake was measured between 7 and 4 days prior to administration of the Leptin trap (days −7 and −4). On day 0, thirty-five 13- to 17-week old male LEPR$^{Hu/Hu}$ mice were successfully subjected to HDD with the Leptin trap. On days 6 and 13 post HDD, retro-orbital bleeds were collected and body composition including adiposity was quantified by μCT. On day 7 post HDD, mice were randomized into five groups of 7 mice based on percent body weight change from day 0. Each group received via subcutaneous injection either a single dose of isotype control antibody at 3 mg/kg, H4H16650P2 at 3 mg/kg, H4H16679P2 at 3 mg/kg, H4H17319P2 at 3 mg/kg, or H4H17321 at 3 mg/kg. The isotype control antibody did not bind any known mouse protein. Food intake and body weight were measured for each animal for the duration of the study. FIG. 3 summarizes the average daily food intake for each treatment group. In FIG. 3, the dotted line represents the average baseline food intake prior to HDD injection. The percent change in body weight from day 0 was calculated for each animal at each time point. FIG. 4 summarizes the average percent change in body weight for animals in each antibody treatment group. FIG. 5 summarizes the average fat mass for animals in each antibody treatment group quantified by μCT 1 day prior to and 6 days following antibody treatment. All results are expressed as mean±SEM.

As shown in FIGS. 3 and 4, following HDD with the Leptin trap, similar increases in food intake and percent change in body weight were observed among the groups of mice before antibody treatment. As shown in FIG. 3, mice treated with antibodies H4H16650P2 or H4H16679P2 at 3 mg/kg exhibited significant reductions in food intake starting at one day after antibody treatment (day 8 post HDD) and at subsequent time points measured as compared to mice injected with the isotype control antibody. Mice treated with antibodies H4H17319P2 or H4H17321P2 at 3 mg/kg exhibited a significant reduction in food intake at two days post antibody treatment (day 9 post HDD) and at the other subsequent time points measured as compared to mice injected with isotype control antibody. As shown in FIG. 4, mice treated with antibody H4H16650P2 at 3 mg/kg exhibited a significant reduction in percent body weight change one day after antibody treatment (day 8 post HDD) and at other subsequent time points measured as compared to mice injected with isotype control antibody. One day after antibody treatment, on day 8, mice treated with the isotype control showed a 21.16±1.27% increase in body weight from day 0, whereas mice treated with H4H16650P2 had a 15.57±0.9% increase in body weight from day 0. Mice treated with antibodies H4H16679P2, H4H17319P2 or H4H17321P2 at 3 mg/kg exhibited a significant reduction in percent body weight change two days after antibody treatment (day 9 post HDD) and at other subsequent time points measured as compared to mice injected with isotype control antibody. On day 9, the % body weight changes from day 0 were 23.18±1.22, 13.17±1.05, 12.95±1.26, 15.98±1.78 and 15.83±2.01 for mice treated with isotype control, H4H16650P2, H4H16679P2, H4H17319P2, or H4H17321P2, respectively. As shown in FIG. 5, mice treated with isotype control antibody at 3 mg/kg demonstrated a significant increase in fat mass 6 days after antibody treatment (day 13 post HDD) as compared to 1 day prior to antibody treatment (day 6 post HDD). Mice treated with antibodies H4H16650P2, H4H16679P2, H4H17319P2, or H4H17321P2 at 3 mg/kg did not gain adipose mass after antibody treatment as compared to pre-antibody treatment. After 6 days of treatment (day 13 post HDD), mice treated with antibodies H4H16650P2, H4H16679P2 or H4H17319P2 at 3 mg/kg demonstrated significant decreases in fat mass as compared to mice treated with isotype control antibody at 3 mg/kg.

Example 11: Epitope Mapping of H4H16650P2 Binding to Human Leptin Receptor (hLEPR.Mmh) by Hydrogen Deuterium Exchange Experiments were conducted to determine the amino acid residues of hLEPR.mmh (amino acids M1-D839 of SEQ ID NO: 114) with which H4H16650P2 interacts. For this purpose, H/D exchange epitope mapping with mass spectrometry was carried out. A general description of the H/D exchange method is set forth in, e.g., Ehring (1999) Analytical Biochemistry 267(2):252-259; and Engen and Smith (2001) Anal. Chem. 73:256A-265A.

Experimental procedure. HDX-MS experiments were performed on an integrated Waters HDX/MS platform, consisting of a Leaptec HDX PAL system for the deuterium labeling, a Waters Acquity M-Class (Auxiliary solvent manager) for the sample digestion and loading, a Waters Acquity M-Class (μBinary solvent manager) for the analytical column gradient, and Synapt G2-Si mass spectrometer for peptic peptide mass measurement.

The labeling solution was prepared in 10 mM PBS buffer in D20 at pD 7.0 (equivalent to pH 6.6). For deuterium labeling, 3.8 μL of hLEPR.mmh (8 pmol/μL) or hLEPR.mmh premixed with the antibody in 2:1 molar ratio was incubated with 56.2 μL D20 labeling solution for various time-points (e.g., undeuterated control=0 sec, labeled for 1 min and 20 min). The deuteration was quenched by transferring 50 μL sample to 50 μL pre-chilled quench buffer (0.2 M TCEP, 6 M guanidine chloride in 100 mM phosphate buffer, pH 2.5) and the mixed sample was incubated at 1.0° C. for two minutes. The quenched sample was then injected into a Waters HDX Manager for online pepsin/protease XIII digestion. The digested peptides were trapped onto an ACQUITY UPLC BEH C18 1.7-μm, 2.1×5 mm VanGuard pre-column at 0° C. and eluted to an analytical column ACQUITY UPLC BEH C18 1.7-μm, 1.0×50 mm for a 9-minute gradient separation of 5%-40% B (mobile phase A: 0.1% formic acid in water, mobile phase B: 0.1% formic acid in acetonitrile). The mass spectrometer was set at cone voltage of 37 V, scan time of 0.5 s, and mass/charge range of 50-1700 Th.

For the identification of the peptides from human LEPR, LC-MSE data from undeuterated sample were processed and searched against the database including human LEPR, pepsin, and their randomized sequences via Waters ProteinLynx Global Server (PLGS) software. The identified peptides were imported to DynamX software and filtered by two criteria: 1) minimum products per amino acid: 0.2, and 2) replication file threshold: 3. DynamX software then automatically determined deuterium uptake of each peptide based on retention time and high mass accuracy (<10 ppm) across multiple time points with 3 replicates at each time.

Results. Using the online pepsin/protease XIII column coupled with $MS^E$ data acquisition, total 201 peptides from human LEPR were reproducibly identified in the absence or presence of the antibody, representing 70% sequence coverage. Five peptides had significantly reduced deuteration uptake (centroid delta values >0.4 daltons with p-values <0.05) when bound to H4H16650P2 as shown in the Table 16. The recorded peptide mass corresponds to the average value of the centroid MH+ mass from three replicates. These peptides, corresponding to amino acids 162-169 (amino acids LYVLPEVL of human LEPR; SEQ ID NO: 113), and to amino acids 170-181 (amino acids EDSPLVPQKGSF of human LEPR; SEQ ID NO: 113), had a slower deuteration rate when bound to H4H16650P2. These identified residues also correspond to residues acids 162-169 and 170-181 of human LEPR as defined by Uniprot entry P48357 (SEQ ID NO. 113; Human leptin receptor)

TABLE 16

Human Leptin receptor peptides with significant protection upon binding to antibody H4H16650P2

| Residues | 1 min Deuteration: hLEPR.mmh | 1 min Deuteration: hLEPR.mmh + H4H16650P2 | 1 min Deuteration: Δ | 20 min Deuteration: hLEPR.mmh | 20 min Deuteration: hLEPR.mmh + H4H16650P2 | 20 min Deuteration: Δ |
|---|---|---|---|---|---|---|
| 162-169 | 949.03 ± 0.03 | 947.99 ± 0.02 | −1.04 | 949.23 ± 0.02 | 948.16 ± 0.02 | −1.03 |
| 163-169 | 835.82 ± 0.03 | 834.79 ± 0.02 | −1.03 | 836.03 ± 0.02 | 834.94 ± 0.02 | −1.08 |
| 170-181 | 1310.02 ± 0.05 | 1309.12 ± 0.03 | −0.89 | 1309.77 ± 0.02 | 1309.38 ± 0.02 | −0.39 |

Example 12: In Vivo Efficacy Testing of LEPR Potentiator Antibodies in Humanized LEPR Mice The effects of three specific potentiator anti-LEPR antibodies of the invention, H4H18482P2, H4H18487P2 and H4H18492P2, on body weight and adiposity were determined in singly-housed genetically engineered $LEPR^{Hu/Hu}$ mice, that express a leptin receptor which is composed of the human LEPR ectodomain sequence in place of the murine LEPR ectodomain sequence (mLEPR.hFc, SEQ ID NO: 120).

Figure 6:
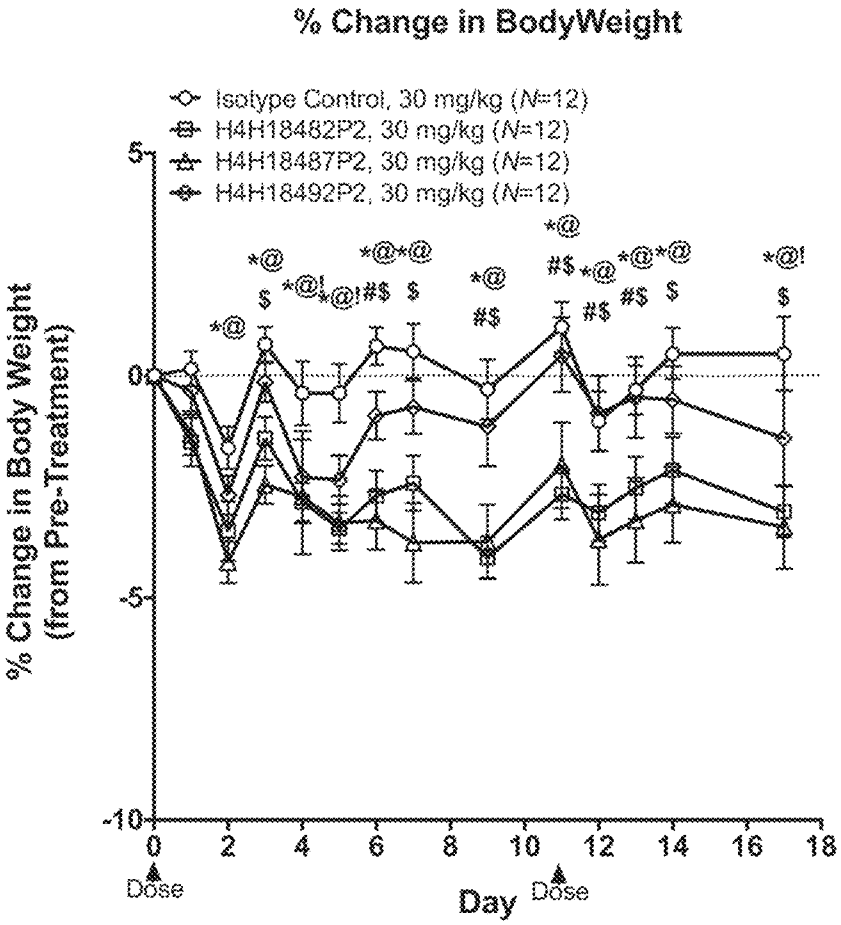
FIG. 6 shows the percent change in body weight of mice fed 30 mg/kg of an antibody selected from H4H18482P2, H4H18487P2, H4H18492P2 or an isotype control.

On days −19 body composition including adiposity was quantified by μCT. On days 0, forty-eight 14 to 16-week old female $LEPR^{Hu/Hu}$ mice were randomized to four groups of 12 mice based on body weight. On days 0 and 11, mice from each group received via subcutaneous injection a single dose of isotype control antibody at 30 mg/kg, H4H18482P2 at 30 mg/kg, H4H18487P2 at 30 mg/kg or H4H18492P2 at 30 mg/kg. The isotype control antibody does not bind any known mouse protein. Body weight was measured for the duration of the study for each animal. The percent change in body weight from day 0 was calculated for each animal at each time point. FIG. 6 summarizes the average percent change in body weight for animals in each treatment group. FIG. 6 summarizes the average fat mass for animals in each antibody treatment group quantified by μCT 19 days prior to and 11 days following antibody treatment. All results are expressed as mean±SEM.

As shown in FIG. 6, decreases in percent change in body weight were observed following dosing with the LEPR potentiator antibodies, but not the isotype control antibody. As shown in FIG. 6, mice treated with H4H18482P2 at 30 mg/kg exhibited significant decreases in percent body weight change starting two days after treatment (day 2), and at the other time points compared to mice injected with an isotype control antibody. Mice treated with H4H18487P2 at 30 mg/kg exhibited significant decreases in percent body weight change starting at day 2 and at the other time points compared to mice injected with isotype control antibody. Mice treated with H4H18492P2 at 30 mg/kg exhibited a significant reduction in percent body weight change on days 4, 5 and 17 but not at other time points compared to mice injected with isotype control antibody. Mice treated with H4H18482P2 at 30 mg/kg exhibited a significant decrease in percent body weight change starting at day 6 and on subsequent days but not days 7, 14 and 17, compared to mice injected with H4H18492P2. Mice treated with H4H18487P2 at 30 mg/kg exhibited a significant decrease in percent body weight change starting at day 3 and at the other time points, but not days 4 and 5, compared to mice injected with H4H18492P2.

Figure 7A:
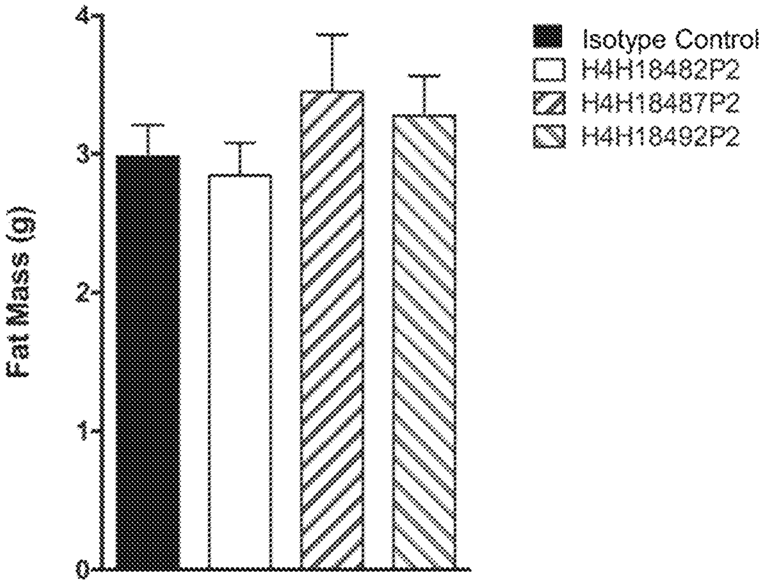
FIGS. 7A-7B.
Figure 7B:
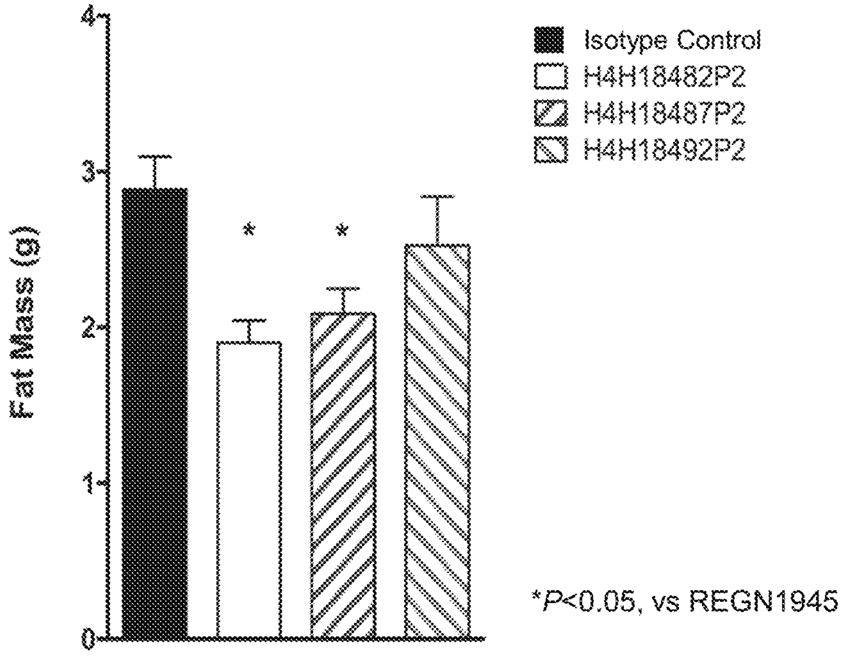
Figure 8:
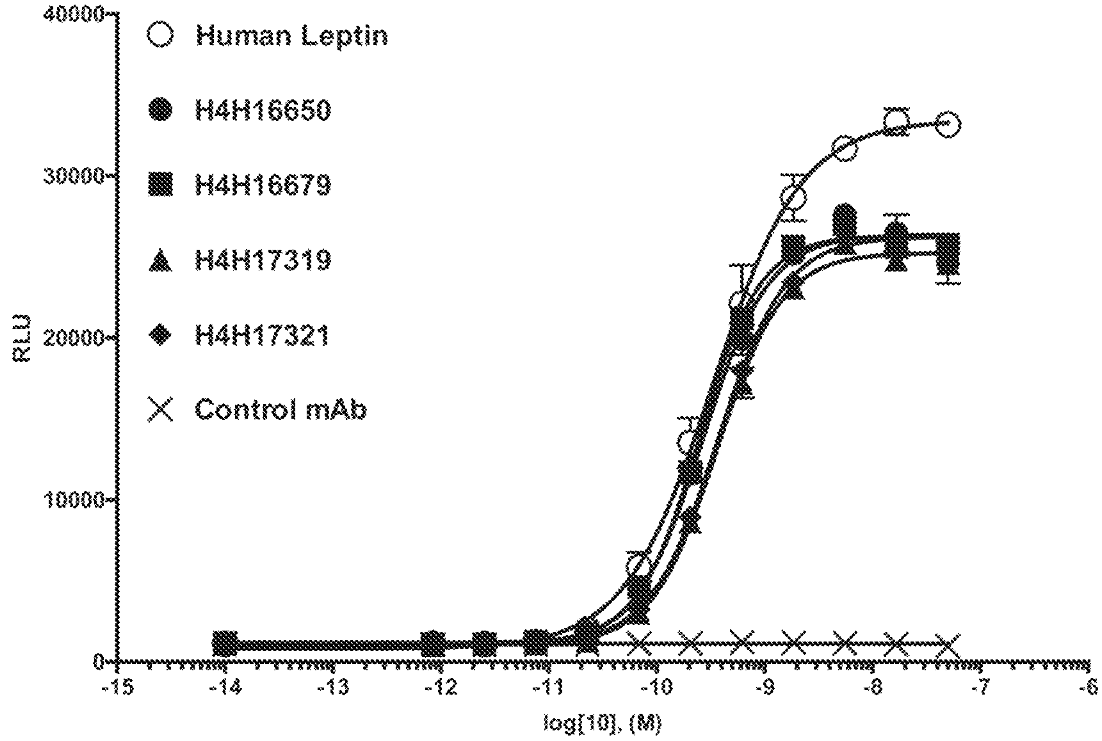
FIG. 8 shows that anti-LEPR antibodies tested activated monkey (Mf) LEPR in an IMR-32/STAT3-luc/Mf LEPR cell line.

As shown in FIG. 7A, there were no differences in fat mass between the groups prior to treatment (day −19). As shown in FIG. 7B, mice treated with antibodies H4H18482 and H4H18487, but not H4H18492, at 30 mg/kg showed a statistically significant decrease in fat mass 17 days after treatment (day 12) as compared to the isotype control antibody.

Example 13: Effect of Anti-LEPR Antibodies of the Invention on Monkey LEPR Signaling In order to assess transcriptional activation of monkey Leptin receptor, a stable cell line was developed. IMR-32 cells (human Neuroblastoma ATCC) were generated to stably express the extracellular domain of *Macaca fascicularis* LEPR (MfLEPR; amino acids 22 through 837 of accession number XP_005543194.1 with threonine at 827 changed to alanine) fused with the transmembrane and cytosolic domains of human LEPR (hLEPR; amino acids 840 through 1165 of accession number NP_002294.2) along with a luciferase reporter (STAT3-Luc; SABiosciences, #CLS-6028L). The resulting cell line, referred to hereafter as IMR-32/STAT3-Luc/MfLEPR was isolated and maintained in MEM-Earl medium supplemented with 10% FBS, NEAA, 1 ug/mL Puromycin, 100 ug/mL of Hygromycin B and Penicillin/Streptomycin/L-Glutamine.

The bioassay was performed to measure the effect of anti-LEPR antibodies of the invention on monkey LEPR signaling in the absence of Leptin. For the bioassay, IMR-32/STAT3-Luc/MfLEPR cells were plated at 10,000 cells/well in a 96-well plate in 0.1% FBS in Optimem with penicillin/streptomycin (assay buffer) and incubated overnight at 37° C. in 5% $CO_2$. The following day human leptin (hLeptin), anti-LEPR antibodies or an isotype control antibody were serially diluted from 50 nM to 0.8 μM in the assay buffer (plus a sample containing buffer alone without test molecule) and added to the cells. After 5.5 hours at 37° C. in 5% $CO_2$, luciferase activity was measured with OneGlo™ reagent (Promega, #E6031) and Victor™ X multilabel plate reader (Perkin Elmer). The results were analyzed using nonlinear regression (4-parameter logistics) with Prism™6 software (Graph Pad) to obtain $EC_{50}$ values. Percentage of activation of antibodies was calculated as the maximum range of RLU achieved by the antibody relative to that of maximum range of RLU achieved by hLeptin.

As shown in Table 17, in the absence of hLeptin, all of the anti-LEPR antibodies tested showed activation of monkey LEPR signaling in IMR-32/STAT3-Luc/mfLEPR cells with $EC_{50}$ values ranging from 266 pM to 368 pM and maximal activation ranging from 76% to 82% where 100% activation was obtained with hLeptin. hLeptin activated with an $EC_{50}$ value of 333 pM. The isotype control antibody did not demonstrate any measurable stimulation of the IMR-32/STAT3-Luc/mfLEPR cells.

TABLE 17

Activation of *Macaca fascicularis* LEPR by anti-LEPR antibodies

| Leptin or Antibody | $EC_{50}$ (M) | % Activation |
|---|---|---|
| Human Leptin | 3.33E−11 | 100 |
| H4H16650P2 | 2.66E−10 | 82 |
| H4H16679P2 | 2.49E−10 | 80 |
| H4H17319P2 | 3.65E−10 | 76 |
| H4H17321P2 | 3.68E−10 | 78 |
| Isotype control antibody | No Activation | No Activation |

Example 14: Epitope Binding to the Full-Length Extracellular Domain of Human LEPR Using Luminex MFI Signal To determine the epitope of human LEPR on which anti-LEPR antibodies of the invention bind, a Luminex FLEXMAP (FM3DD, LuminexCorp) flow cytometry based analysis was utilized to characterize the interaction of anti-LEPR antibodies with recombinant human LEPR protein domains. For the assay, approximately 3 million carboxylated Microplex® microspheres (Luminex, Cat #LC1000A), were washed, vortexed and sonicated in 0.1 M $NaPO_4$, pH 6.2 (activation buffer) and then centrifuged to remove the supernatant. The microspheres were resuspended in 120 μL of activation buffer and the carboxylate groups (—COOH) were activated by addition of 15 μL of 50 mg/mL of N-hydroxysuccinimide (NHS, Thermo Scientific, Cat #24500) followed by addition of 15 μL of 50 mg/mL of 1-ethyl-3-[3-dimethylaminopropyl]carbodiimide (EDC, ThermoScientific, Cat #22980) at 25° C. After 10 minutes, the pH of the reaction was reduced to 5.0 with the addition of 600 μL of 50 mM MES, pH 5 (coupling buffer), and the microspheres were vortexed, and centrifuged to remove supernatant. The activated beads were immediately mixed with 500 μL of 20 μg/mL monoclonal anti-myc antibodies with either a mouse IgG or a human IgG, in coupling buffer and incubated for two hours at 25° C. The coupling reaction was quenched by addition of 50 μL of 1M Tris-HCl, pH 8.0 and the microspheres were rapidly vortexed, centrifuged, and washed four times with 1 mL of DPBS, to remove uncoupled proteins and other reaction components.

The transiently expressed LEPR proteins, including human LEPR extracellular domain expressed with a C-terminal myc-myc hexahistidine tag (human LEPR-MMH, SEQ ID NO: 113), human LEPR CRH1 (D1) expressed with a C-terminal myc-myc hexahistidine tag (human LEPR CRH1 (D1)-MMH, amino acids 1-208 of SEQ ID NO: 113 with a myc-myc hexahistidine tag, amino acids 209-236), human LEPR CRH1 (D1,D2) domain expressed with a C-terminal myc-myc hexahistidine tag (human LEPR CRH1 (D1,D2)-MMH, amino acids 1-318 of SEQ ID NO: 113 with a myc-myc hexahistidine tag, amino acids 319-346), human LEPR CRH1-Ig (D1,D2,D3) domain expressed with a C-terminal myc-myc hexahistidine tag (human LEPR CRH1 (D1,D2,D3)-MMH, amino acids 1-278 of SEQ ID NO: 113 with a myc-myc hexahistidine tag, amino acids 279-306), human LEPR CRH1-Ig (D2,D3) domain expressed with a C-terminal myc-myc hexahistidine tag (human LEPR CRH1-Ig (D2,D3)-MMH, amino acids 1-198 of SEQ ID NO: 113 with a myc-myc hexahistidine tag, amino acids 199-226), human LEPR Ig (D3) domain expressed with a C-terminal myc-myc hexahistidine tag (human LEPR Ig (D3)-MMH, amino acids 1-88 of SEQ ID NO: 113 with a myc-myc hexahistidine tag, amino acids 89-116), human LEPR CRH2 domain expressed with a C-terminal myc-myc hexahistidine tag (human LEPR CRH2-MMH, amino acids 1-207 of SEQ ID NO: 113 with a myc-myc-hexahistidine tag, amino acids 208-235), human LEPR FNIII domain expressed with a C-terminal myc-myc hexahistidine tag (human LEPR FNIII-MMH, amino acids 1-204 of SEQ ID NO: 113 with a myc-myc hexahistidine tag, amino acids 205-232), and human LEPR Ig-CRH2-FNIII domain expressed with a C-terminal myc-myc hexahistidine tag (human LEPR Ig-CRH2-FNIII-MMH, amino acids 1-510 of SEQ ID NO: 113 with a myc-myc-hexahistidine tag, amino acids 511-538), were suspended in serum free CHO—S-SFM II Medium (Thermo Fisher, Cat #31033020) and were then clarified by centrifugation. Aliquots of microspheres with immobilized anti-myc monoclonal antibodies, prepared as described above, were added individually to 1 mL of the each of these protein supernatants. The microspheres were gently mixed, incubated for two hours at 25° C., washed twice with 1 mL of DBPS, centrifuged to remove the supernatant and finally resuspended in 1 mL of DPBS buffer. Forty-eight μL of anti-myc IgG coupled microspheres from individual reactions with full length human LEPR and with each of the human LEPR domain proteins were withdrawn and mixed together in 3.6 mL of PBS+20 mg/mL BSA+0.05% sodium azide (blocking buffer).

From this mixed pool, 75 μl of microspheres were plated per well on a 96 well filter plate (Millipore, Cat. No: MSBVN1250) and mixed with 25 μl of individual anti-human LEPR monoclonal antibodies (0.5 or 5 μg/mL), incubated for two hours at 25° C. and then washed twice with 200 μl of DPBS with 0.05% Tween 20 (washing buffer). To detect and quantify the amounts of bound anti-LEPR antibody levels to individual microspheres, either 100 μL of 2.5 μg/mL R-Phycoerythrin conjugated goat F(ab')2 anti-human kappa (Southern Biotech, Cat #2063-09) in blocking buffer or 100 μL of 1.25 μg/mL R-Phycoerythrin AffiniPure F(ab')2 Fragment Goat Anti-Mouse IgG, F(ab')2 Fragment Specific (Jackson Immunoresearch, Cat. No: 115-116-072) in blocking buffer, was added and incubated for 30 minutes at 25° C. After 30 minutes, the samples were washed twice with 200 μL of washing buffer and resuspended in 150 μL of wash buffer. The Median Fluorescence intensity (MFI) of the microspheres was measured in a Luminex Analyzer.

Mouse Studies

Hydrodynamic DNA Delivery

Hydrodynamic DNA delivery (HDD)-based in vivo transfection is a protocol involving rapid injection of a large volume of solution with naked plasmid DNA to express foreign proteins in live animals (Suda, 2007). Mice were weighed and expression vector was freshly prepared by suspending in a final volume of saline equal to 1/10 body weight (V/W), which was delivered by injection through the lateral tail vein. For the leptin sink model validation study (FIG. 11), 8 week old male C57BL/6N mice (Taconic) received 50 μg DNA per mouse of mLeprECD expression vector (pRG977.mROR.mLepR.ecto.hFc) or control vector (pRG977.hFc). For the H4H17319P2 evaluation study (FIG. 9), 17 to 20 week old male and female $Lepr^{hu/hu}$ mice received 50 μg DNA per mouse of mLeprECD expression vector (pRG977.mROR.mLepR.ecto.hFc).

TABLE 18

Luminex MFI signal of anti-LEPR antibodies binding to myc tag captured full-length extracellular domain of human LEPR and isonalted human LEPR domains

| Antibody | CRH1 (D1) | CRH1 (D1, D2) | CRH1-Ig (D1, D2, D3) | CRH1-Ig (D2, D3) | Ig (D3) | CRH2 | FNIII | Ig-CRH2-FNIII | Full Length extracellular domain | Probable Binding site |
|---|---|---|---|---|---|---|---|---|---|---|
| H4H18445P2 | 12 | 30 | 22 | 40 | 19 | 17 | 230 | 14544 | 6573 | FNIII |
| H4H18446P2 | 17 | 682 | 205 | 645 | 25 | 65 | 32 | 16852 | 10536 | Ig-CRH2-FNIII |
| H4H18482P2 | 13 | 40 | 21 | 52 | 27 | 23 | 167 | 15316 | 7311 | Ig-CRH2-FNIII |
| H4H18487P2 | 12 | 51 | 29 | 62 | 22 | 27 | 174 | 16320 | 7329 | Ig-CRH2-FNIII |
| H4H18417P2 | 10 | 16048 | 3334 | 5502 | 17 | 39 | 14 | 37 | 4887 | CRH1 D2 |
| H4H18438P2 | 13 | 18931 | 6572 | 8884 | 30 | 165 | 25 | 468 | 6251 | CRH1 D2 |
| H4H18492P2 | 11 | 19371 | 6354 | 8685 | 19 | 18 | 16 | 186 | 6382 | CRH1 D2 |
| H4H18449P2 | 20 | 2934 | 2056 | 42 | 24 | 15 | 13 | 43 | 7976 | CRH1(D1-2) |
| H4H16650P2 | 8 | 4722 | 2562 | 74 | 10 | 16 | 6 | 110 | 7603 | CRH1(D1-2) |
| H4H16679P2 | 12 | 4388 | 2797 | 34 | 14 | 33 | 10 | 42 | 7507 | CRH1(D1-2) |
| H4H17319P2 | 8 | 1246 | 938 | 14 | 8 | 91 | 20 | 8 | 3305 | CRH1(D1-2) |
| H4H17321P2 | 9 | 2649 | 1752 | 15 | 7 | 116 | 40 | 14 | 4696 | CRH1(D1-2) |
| Comparator mAb | −14 | 19 | −57 | 27 | 10 | 9404 | 73 | 7112 | 3908 | CRH2 |

The results of the Luminex based analysis are tabulated in Table 18. Luminex MFI signal intensities indicate that the twelve anti-LEPR antibodies of the invention bound to the complete human LEPR extracellular domain. Anti-LEPR antibodies H4H18417P2, H4H18438P2, and H4H18492P2, bound to epitopes within the CRH1 D2 domain of human LEPR. Anti-LEPR antibodies H4H18449P2, H4H16650P and H4H16679P, bound to epitopes within the CRH1(D1-2) domain of human LEPR. Anti-LEPR antibody Comparator monoclonal antibody, bound to epitopes within the CRH2 domain of human LEPR. Anti-LEPR antibody H4H18445P2 bound to epitopes within the FNIII domain of human LEPR. Anti-LEPR antibodies H4H18446P2, H4H18482P2 and H4H18487P2, bound to epitopes within the Ig-CRH2-FNIII domain of human LEPR.

Examples 15-19: Protocols for Animal Studies

All animal studies were conducted in accordance with the guidelines and approval by the Institutional Animal Care and Use Committee (IACUC) at Regeneron Pharmaceuticals. The monkey studies were also conducted in accordance with the guidelines and approval by the IACUC at Covance Laboratories.

Body Weight and Food Intake Measurement

Body weight was measured by placing the mouse in a container on a tared digital laboratory balance. The average body weight over a 3 sec dynamic weighing was used. Food intake was determined by measuring the mass of food within the food hopper using a digital laboratory scale. Food intake was calculated as the difference in weight of food remaining in the hopper from the weight of food provided in the hopper.

Body Composition

Micro-computed tomography (micro-CT) imaging was conducted with a Quantum Micro-CT imaging system (Perkin Elmer), according to the manufacturer's instructions, on live mice anesthetized with gaseous isoflurane. Body composition (fat mass, lean mass, bone mass, bone mineral content, and density) was measured using a Quantum Micro-CT imaging system (Perkin Elmer), according to the manufacturer's instructions. Scans were subsequently analyzed using AnalyzeDirect imaging software. Fat mass, lean mass, and bone mass were calculated by multiplication of the recorded tissue volumes by the respective mass densities: 0.92, 1.05, and 1.7 g/$cm^3$. Quantitative nuclear magnetic resonance (qNMR) with an EchoMRI 100 instrument (EchoMRI) was performed on live conscious mice to measure fat, lean, free water, and total water masses.

Blood Glucose Measurement

Fed blood glucose levels were measured from a tail vein nick on conscious mice using a blood glucose meter (AlphaTrak2, Zoetis) and glucose test strips (Zoetis).

Insulin Tolerance Testing

After a 4-hr fast, animals were intraperitoneally (IP) injected with 0.5, 0.75 or 1.0 U/kg dose of insulin (Humulin R, Eli Lilly and Company), as indicated. Glucose measurements were taken using an AlphaTRAK2 blood glucose meter and test strips (Zoetis) at 0, 15, 30, 60 and 120 min post-insulin injection. In the $Lepr^{hu/hu}$ characterization study, Accu-Chek® Compact Plus glucose meter and test strips (Roche Diabetes Care, Inc.) were used.

Chemistry Analyses and Hormone Assays

Unless otherwise indicated, mice were fasted for 4 h, then blood was collected via retro-orbital bleed. For serum isolations, blood was transferred to serum separator tubes (Sarstedt AG & Co.) and allowed to clot for at least 30 min on wet ice prior to centrifugation at 10,000 g for 5 min. Serum was removed and stored at −80° C. until processing for leptin quantification. For plasma measurements, blood was transferred to K3EDTA-coated tubes (Sarstedt AG & Co.). Dipeptidyl peptidase 4 (DPP4) inhibitor and protease inhibitor cocktail was added to the blood sample, which was kept on ice until processed to obtain plasma through centrifugation at 2000×g for 10 min. Plasma was aliquoted and stored at −80° C. until used for quantification of plasma lipids, liver enzymes, and leptin levels. HbA1c were measured in fresh whole blood collected in K3EDTA-coated tubes. HbA1c, plasma lipids and liver enzymes were quantified using a chemistry analyzer (Advia Chemistry XPT, Siemens). Serum or plasma leptin levels were measured using an immunoassay kit (Milliplex MAP, Millipore) and by following the manufacturer's recommended protocol.

Liver Triglyceride Quantification

Liver triglyceride content was quantified from 100 to 200 mg of liver and pulverized to powder by liquid nitrogen-cooled mortar and pestle. Powdered liver tissue was weighed and homogenized in PBS by bead homogenization (FastPrep 24-5G, MP Biomedical). The homogenate was transferred to a glass tube containing 5 mL of Folch solution (2:1 chloroform:methanol), vortexed, and centrifuged for 20 min and 1500×g. The lower phase was collected, brought up to a 5 mL volume, and vortexed. Specific volumes (25 to 50 μL) of sample and triolein standards (Verichem) were transferred to a 96-well polypropylene plate, mixed with 10 μL of a 1:1 mixture of chloroform:Triton X-100, and allowed to air-dry. To the dried samples and standards, 300 μL of triglyceride reagent (Thermo Scientific) was added, the plate was shaken for 5 min and then incubated for 20 min at 37° C. 200 μL of each reaction was transferred to a new clear polypropylene 96-well plate and absorbance at 500 nm was measured using a plate reader (Molecular Devices).

Fix Perfusion and Immunohistochemistry

Mice were anesthetized with sodium pentobarbital (110 mg/kg, IP) and transcardially perfused with 2 mL of saline followed by 150 mL of 4% paraformaldehyde in 0.1 M borate buffer, pH 9.5. Livers were post-fixed for 2 h, transferred to 70% ethanol, and processed for paraffin embedding, sectioned for hematoxylin and eosin staining at Histoserv. Brains were post-fixed for 2 h at 4° C. and then submerged in 15% sucrose in potassium phosphate buffered saline overnight at 4° C. Whole brains were mounted onto a freezing sliding microtome (Leica), sectioned at 30 μm thickness, collected in equally-spaced series and stored in cryoprotectant (20% glycerol and 30% ethylene glycol in 0.1 M phosphate buffer) and stored at −20° C. in cryoprotectant (20% glycerol and 30% ethylene glycol in 0.1 M phosphate buffer).

A series of brain sections spaced 150 μm apart from each experimental group were processed concurrently to ensure comparable staining between animals and treatments. For all immunostaining, brain sections were blocked and primary/secondary antibodies were diluted in a solution containing 1% donkey serum (Equitech), 0.03% Triton X-100, and 0.05 M potassium phosphate-buffered saline. Avidin and biotin blocking was performed according to the manufacturer's protocol (Vector Labs). Immunohistochemical staining for pStat3(Y705) (#9145, Cell Signaling Technologies; 1:1000, 16 h at 4° C.) was performed on equally spaced series of brain sections using the avidin-biotin-complex method with the chromogen, diamino-benzidine (Vector Labs). For P-STAT3 (Y705) immunohistochemistry (IHC), sections were pre-treated with 1% $H_2O_2$ in 1% NaOH for 10 min, 0.3% glycine in K-PBS for 10 min, and 0.03% SDS in K-PBS for 10 min.

Bright field images were obtained by whole slide scanning with a 40× objective on a Scanscope XT (Aperio). Sections were matched by tissue comparison with the Franklin and Paxinos mouse brain atlas. Neuroanatomical areas and distance from bregma were approximated based on this atlas. The number of pSTAT3 (Y705) immunoreactive cells was quantified bilaterally for a given area at the rostrocaudal level indicated using Halo software (Indica Labs).

Monkey Studies

All studies in *Cynomolgus* monkeys were conducted at Covance Laboratories, Inc. Monkeys were fed twice daily with Certified Primate Diet #5048 (PMI, Inc.) and were provided free access to fresh water.

Body Weights

Monkeys were weighed prior to dosing on the day of dose administration, and at least once weekly throughout the remainder of the study, as applicable.

Dual Energy X-Ray Absorptiometry (DEXA)

Whole body scans were performed using a Discovery A densitometer (Hologic) on fasted monkeys anesthetized with ketamine and dexmedetomidine and at the discretion of the veterinary staff.

Figure 10A:
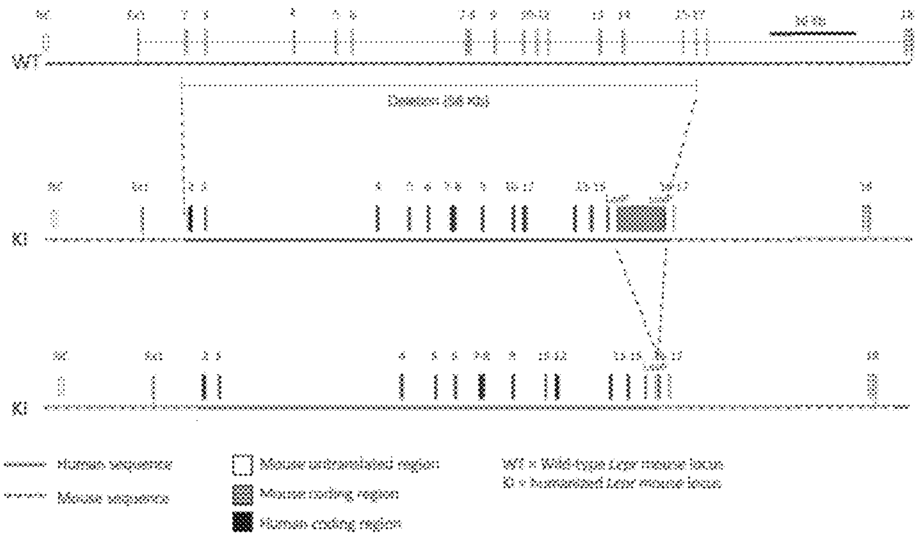
FIGS. 10A-10D.
Figure 10B:
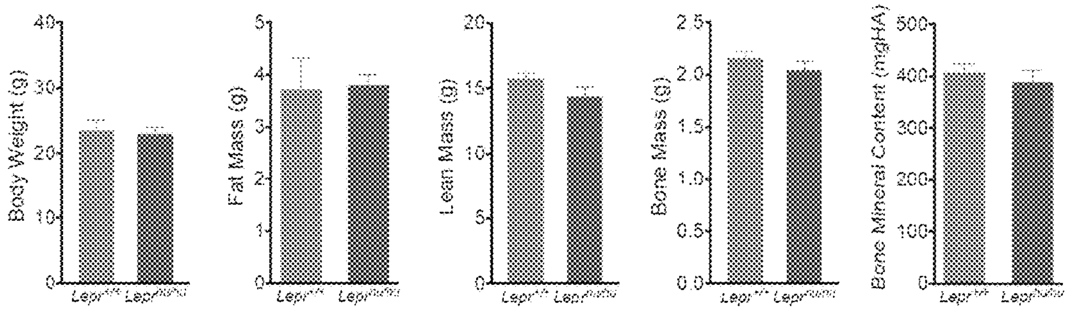
Figure 10C:
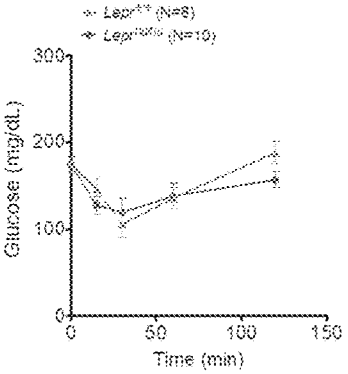
Figure 10D:
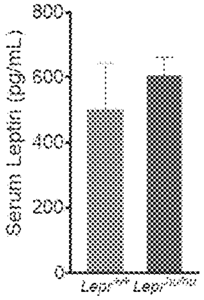

Example 15: Anti-LEPR Antibodies Reverse Obesity Induced by Leptin Deficiency Studies were performed to determine if H4H17319P2 is efficacious in vivo. Since the H4H17319P2 does not bind mouse LEPR, genetically modified mice were generated using VelociGene® technology (Valenzuela et al., 2003) in which the portion of the mouse Lepr gene encoding the LEPR extracellular domain was replaced with the corresponding human LEPR genomic sequence ($Lepr^{hu/hu}$; FIG. 10A). $Lepr^{hu/hu}$ mice do not show differences from Lepr mice with respect to body weight, body composition, insulin sensitivity and serum leptin levels (FIGS. 10B, C and D).

Figure 11A:
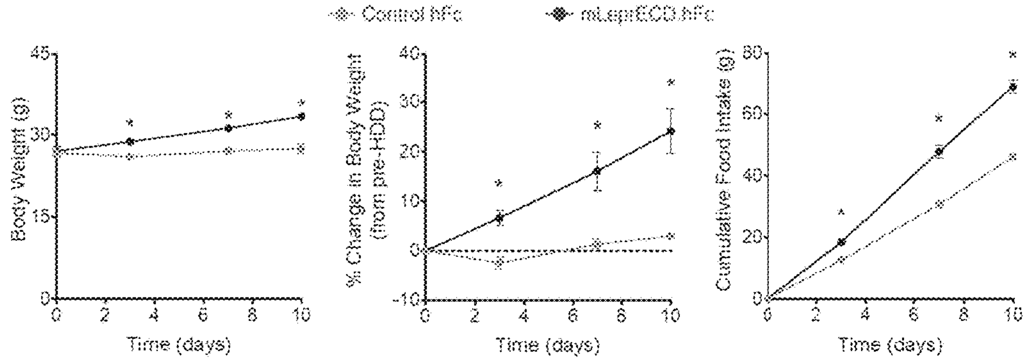
FIGS. 11A-11B.
Figure 11B:
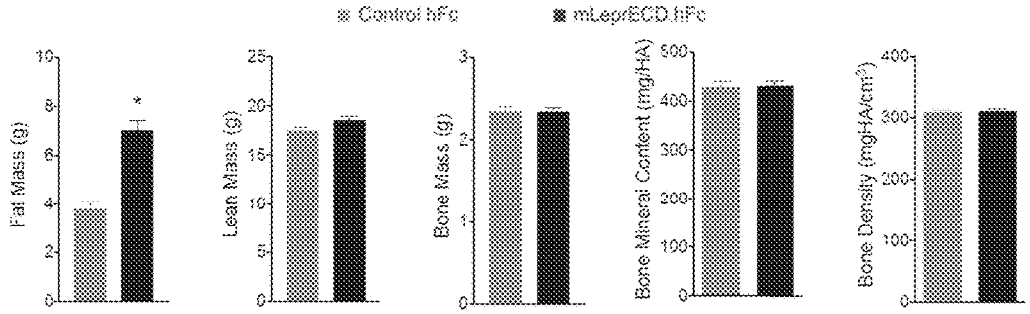

A mouse model of leptin deficiency was developed by hydrodynamic DNA delivery (HDD) of a plasmid that encodes hFc-tagged mouse Lepr ectodomain (mLeprECD) to sequester endogenous circulating mouse leptin, thus acting as a leptin sink and thereby preventing leptin signaling. Following HDD of mLeprECD, chow fed C57BL/6N mice rapidly gained body weight, with significant increases starting at day 3 post-HDD compared with mice that received HDD of control hFc (FIG. 11A). At the end of the study (day 10 post HDD), body weights were increased by 24% following HDD of mLeprECD, while only a minor increase of 3% was observed in the control group (FIG. 11A). In alignment with the body weight data, cumulative food intake following HDD of mLeprECD was significantly increased compared with the control group beginning on day 3 post HDD (FIG. 11A). To confirm that the body weight gain reflected increases in adiposity, micro-CT imaging was conducted on day 7 post HDD and showed a significant 2-fold increase in fat mass following HDD of mLeprECD compared with the control group (FIG. 11B). All other body composition parameters were similar between the groups (FIG. 11B).

Figure 9A:
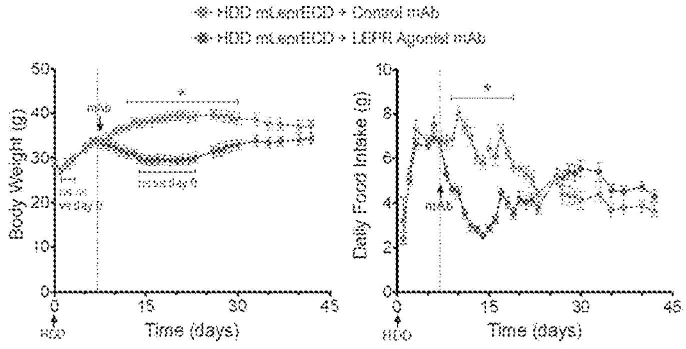
FIGS. 9A-9C. Leptin deficiency was induced by HDD of mLepr.ECD in 18 week old male $Lepr^{hu/hu}$ mice on day 0. Seven days post-HDD, mice were stratified into 2 groups based on relative percent change in body weight, and administered a single 10 mg/kg SC dose of control monoclonal antibody (gray-filled circles or bars) or H4H17319P2 (filled circles or bars). Data are mean±SEM. *, P<0.05 for H4H17319P2 vs control monoclonal antibody at the indicated time points. $, P<0.05 between pre-HDD (day −1) and either day post-HDD (day 6 or 13) within the same respective dosing group. &, P<0.05 between pre-monoclonal antibody (day 6) and post-monoclonal antibody (day 13) within the same respective dosing group. No significant difference (ns) from baseline on day 0 for the group denoted by the respective text color on the indicated days.
Figure 9:
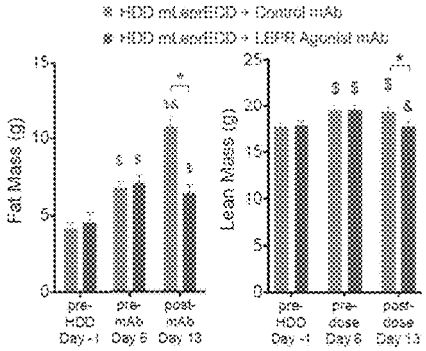
Figure 12A:
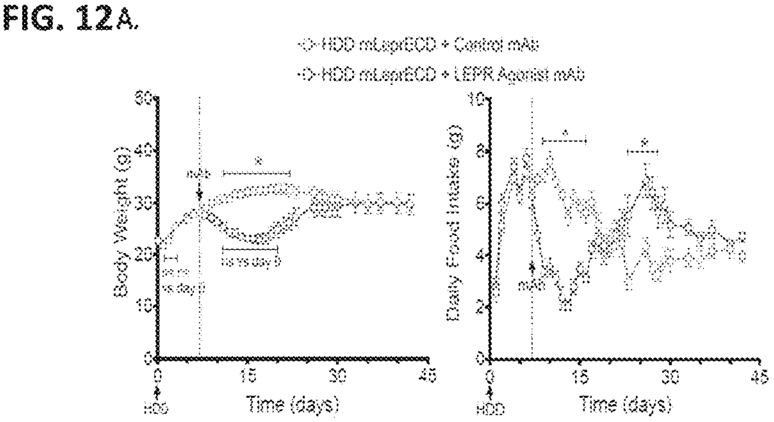
FIGS. 12A-12C. Leptin deficiency was induced by HDD of mLepr.ECD in 17 to 20 week old female or 18 week old male $Lepr^{hu/hu}$ mice on day 0. Seven days post-HDD, mice were stratified into 2 groups of animals each based on relative percent change in body weight, then administered a single 10 mg/kg SC dose of control monoclonal antibody (gray open circles or bars) or H4H17319P2 (black open circles or bars). Data are mean±SEM. *, P<0.05 for H4H17319P2 vs control monoclonal antibody at the indicated time points. $, P<0.05 between pre-HDD (day −1) and either day post-HDD (day 6 or 13) within the same respective dosing group. &, P<0.05 between pre-monoclonal antibody (day 6) and post-monoclonal antibody (day 13) within the same respective dosing group. No significant difference (ns) from baseline on day 0 for the group denoted by the respective text color on the indicated days.

To evaluate the efficacy of H4H17319P2 in vivo, leptin deficiency was induced in chow-fed male and female $Lepr^{hu/hu}$ mice by HDD of mLeprECD. As anticipated, expression of the mLeprECD promoted rapid body weight gain in both genders of $Lepr^{hu/hu}$ mice (FIGS. 9A and 12A). Seven days post-HDD, $Lepr^{hu/hu}$ mice were stratified based on relative percent change in body weight and administered a single 10 mg/kg SC dose of control or H4H17319P2. Both male and female mice administered control monoclonal antibody (hereinafter, control mAb), continued to gain body weight with a 40.5±2.7% and 44.1±4.7% increase in body weight, respectively, 14 days after HDD (FIGS. 9A and 11A). In contrast, mice treated with a single dose of the LEPR agonist monoclonal antibody lost body weight and returned to their initial body weights prior to HDD (FIGS. 9A and 11A). Since H4H17319P2 binds human but not mouse LEPR, the possibility that the improvements in body weight are secondary to the LEPR mAb interfering with the ability of mLeprECD to sequester leptin can be excluded. The loss of body weight was associated with reduced food intake (FIGS. 9A and 11A). While daily food intake did not differ between the two groups prior to dosing, mice treated with H4H17319P2 showed a significant drop in food intake when compared to the control monoclonal antibody group (FIGS. 9A and 11A). The body weight and food intake lowering effects observed with the single dose of H4H17319P2 eventually waned. Food intake remained significantly lower in male and female mice treated with H4H17319P2 than control monoclonal antibody-administered mice until 12 and 9 days post-treatment (days 19 and 16), respectively (FIGS. 9A and 11A). Body weights of male and female mice treated with H4H17319P2 remained similar to their baseline body weights till 16 and 13 days post-treatment (days 23 and 20), after which a weight gain occurred (FIGS. 9A and 11A).

Figure 12B:
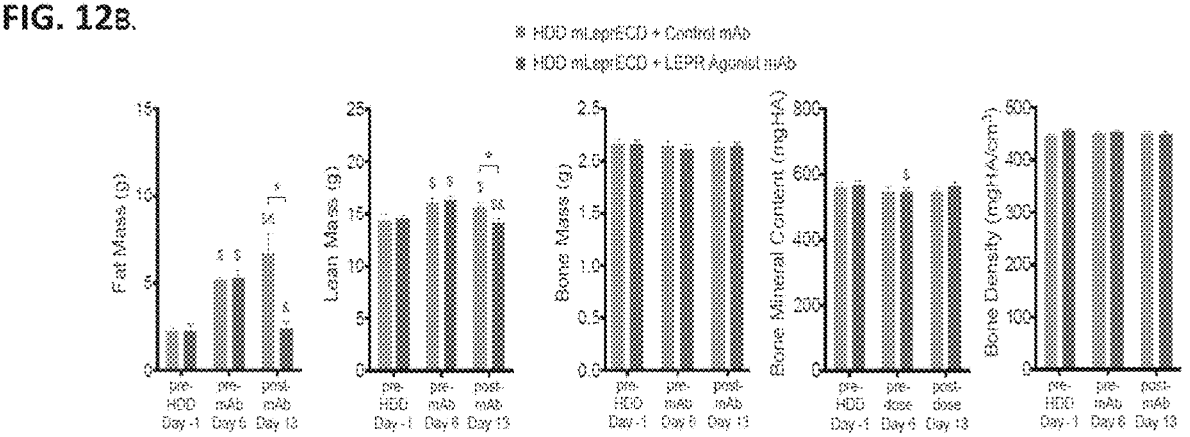
Figure 12C:
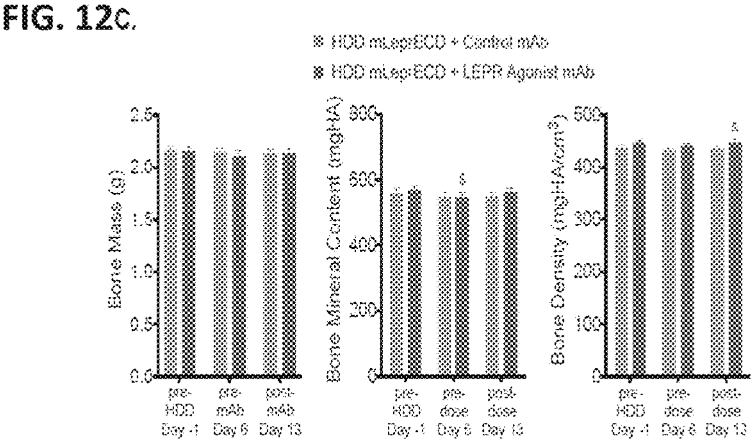

The body weight lowering induced by H4H17319P2 treatment reflected a reduction in adiposity and lean mass. Micro-CT analyses revealed that prior to HDD on day −1 and prior to treatment on day 6, both treatment groups of male or female mice showed similar body composition (FIGS. 9B, 12B and 12C). Consistent with the induced leptin deficiency, on day 6 both groups showed significant increases in fat and lean mass but not bone mass compared to pre-HDD on day −1 (FIGS. 9B, 12B and 12C). Six days after treatment (day 13), control monoclonal antibody-dosed mice showed further increases in fat mass compared to day 6, whereas no additional increases in adiposity were detected following H4H17319P2 treatment. Consistent with the changes in body weight, both fat and lean mass were reduced in H4H17319P2-treated mice relative to control monoclonal antibody-administered mice after 7 days of treatment. No treatment related effects on bone mass, bone mineral content or bone density were observed (FIGS. 12B and 123C).

Figure 9C:
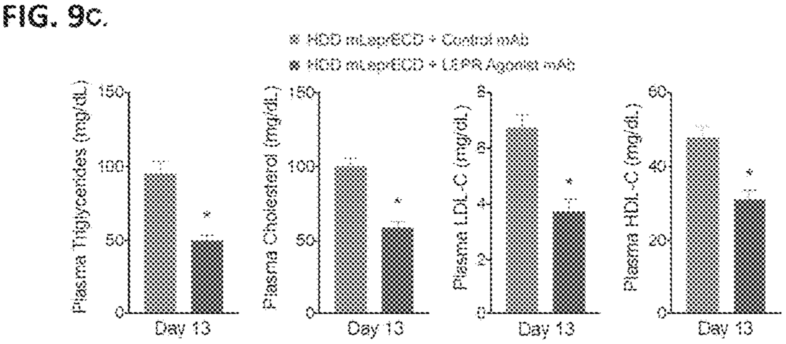

Next, H4H17319P2 was assessed for its ability to alter circulating lipids in induced leptin deficient mice. Plasma chemistry analyses revealed that H4H17319P2 lowers circulating plasma triglycerides and total cholesterol, including HDL-cholesterol (HDL-C) and LDL-cholesterol (LDL-C) as compared to control monoclonal antibody-dosed male mice after 6 days of treatment (FIG. 9C).

Figure 13A:
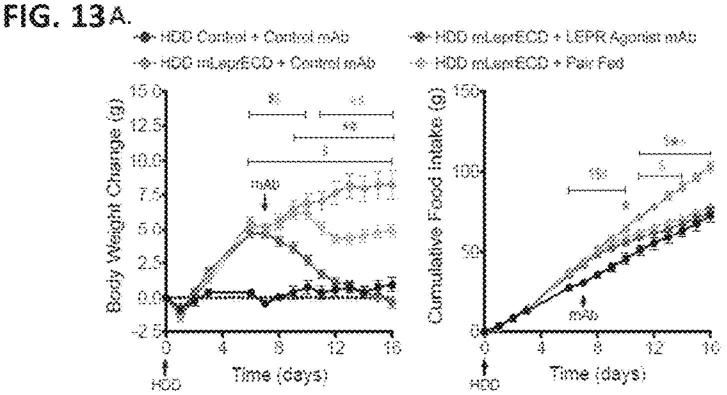
FIGS. 13A-13D. Leptin deficiency was induced by HDD of mLepr.ECD in 17 to 20 week old female $Lepr^{hu/hu}$ mice on day 0. For comparison, a group of mice were subjected to HDD with a control vector. Seven days post-HDD, mice that received mLepr.ECD were stratified into 3 groups based on body weight, and administered two (day 7 and 13) 3 mg/kg SC doses of control monoclonal antibody (gray-filled circles or bars) or H4H17319P2 (dark gray-filled circles or bars) or were pair-fed (light gray-filled circles or bars) with the amount of food consumed by induced leptin deficient mice treated with H4H17319P2. Data are mean±SEM. *, P<0.05 for the respective group denoted by symbol color or bar vs HDD mLeprECD administered control monoclonal antibody at the indicated time point. #, denotes statistical significance of HDD mLepr ECD treated with H4H17319P2 versus HDD mLeprECD pair fed animals. $, P<0.05 for the respective group denoted by symbol color or bar vs HDD control mice administered control monoclonal antibody at the indicated time points.
Figure 13B:
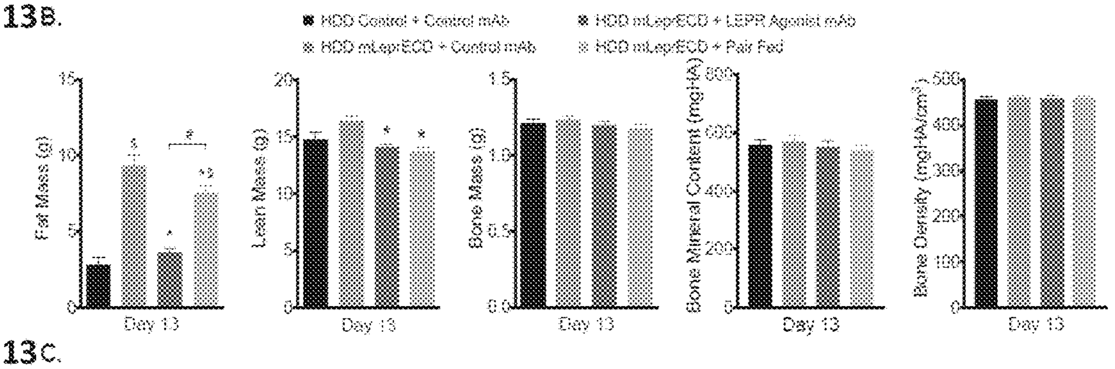

Given that leptin promotes energy expenditure in leptin deficient ob/ob mice (Halaas et al., 1995; Pelleymounter et al., 1995), the effects of pair-feeding was assessed to delineate whether reduced food intake fully accounts for the body weight lowering effects of H4H17319P2 in induced leptin deficiency. Induced leptin deficient $Lepr^{hu/hu}$ mice rapidly gained weight and were hyperphagic when compared to $Lepr^{hu/hu}$ mice that received control vector by HDD (FIG. 13A). After dosing on days 7 and 13, mice administered control monoclonal antibody continued to consume more food and gain weight, while H4H17319P2-treated mice reduced their food intake and lost body weight (FIG. 13A). Pair-feeding also promoted weight loss in $Lepr^{hu/hu}$ mice expressing mLeprECD. Of note, pair-fed mice consumed the same amount of food as H4H17319P2-treated mice but did not show the same degree of body weight loss (FIG. 13A). Consistent with these data, adiposity was decreased in pair-fed mice when compared to mice administered control monoclonal antibody but was significantly greater than the adiposity in mice treated with H4H17319P2 (FIG. 13B). By contrast, similar effects were observed between pair-feeding and H4H17319P2 treatment on decreasing lean mass relative to control monoclonal antibody-administered leptin deficient mice (FIG. 13B). No effects were observed for bone mass, bone density or bone mineral content (FIG. 13B).

Figure 13C:
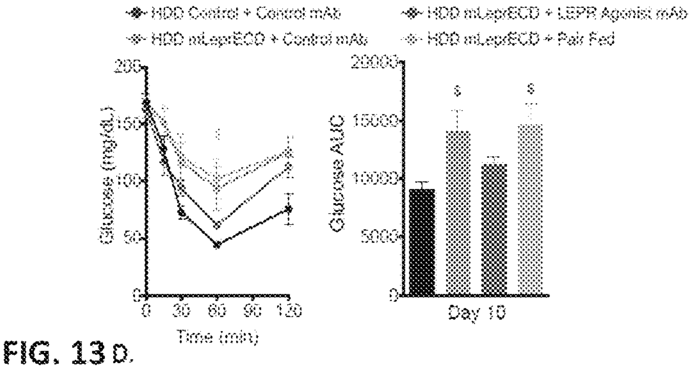

Leptin also improves insulin sensitivity in leptin deficient ob/ob mice (Muzzin et al., 1996; Pelleymounter et al., 1995). Thus, the relative effects of H4H17319P2 treatment and pair-feeding on insulin sensitivity was determined following induced leptin deficiency. Insulin tolerance tests were conducted three days after monoclonal antibody dosing or pair-feeding. As shown in FIG. 13C, control monoclonal antibody administered $Lepr^{hu/hu}$ mice expressing mLeprECD show reduced insulin sensitivity as compared to $Lepr^{hu/hu}$ mice subjected to HDD with a control vector. Notably, treatment with H4H17319P2 restored insulin sensitivity while pair-feeding had no effect in induced leptin deficient $Lepr^{hu/hu}$ mice (FIG. 13C).

Figure 13D:
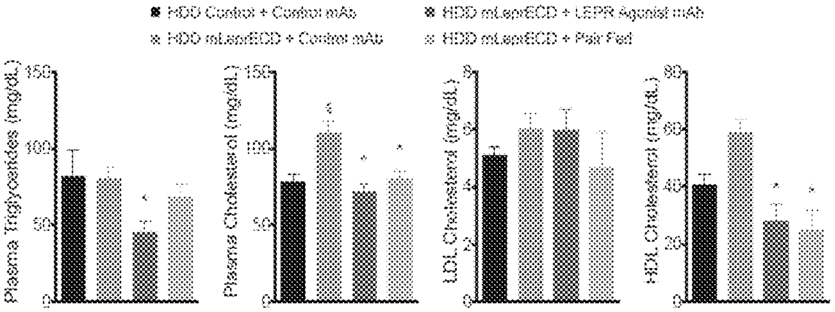

Lastly, the effect of H4H17319P2 in lowering circulating lipids primarily by decreasing food intake was ascertained. While H4H17319P2 but not pair-feeding significantly lowered plasma triglycerides in leptin deficiency, both H4H17319P2 and pair feeding reduced total plasma cholesterol and HDL-C (FIG. 13D).

In summary, the data demonstrate that in a model of induced leptin deficiency, H4H17319P2 not only reverses hyperphagia and obesity but also ameliorates insulin resistance. Of note, while reductions in food intake contribute to the body weight and adiposity lowering observed with H4H17319P2, decreased food intake is not sufficient to improve insulin sensitivity or lower plasma triglyceride levels.

Figure 15A:
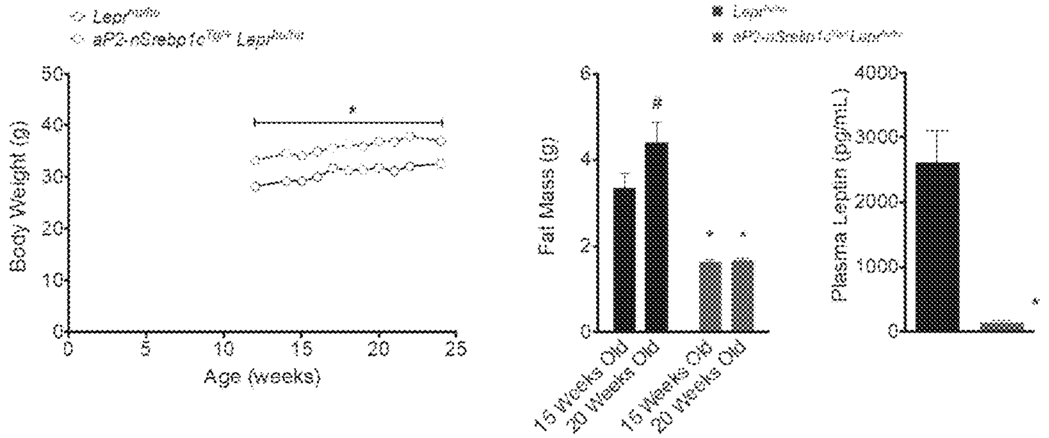
FIGS. 15A-15C. Phenotypic characterization of male nonTg Lepr$^{hu/hu}$ (black open circles or black bars) and aP2-nSrebp1c$^{Tg/+}$ Lepr$^{hu/hu}$ mice (black open circles or black bars) at the indicated ages. Data are mean±SEM. * p<0.05 versus Lepr$^{hu/hu}$ mice at respective time points.
Figure 15B:
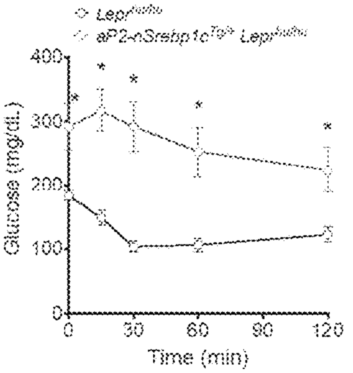
Figure 15C:
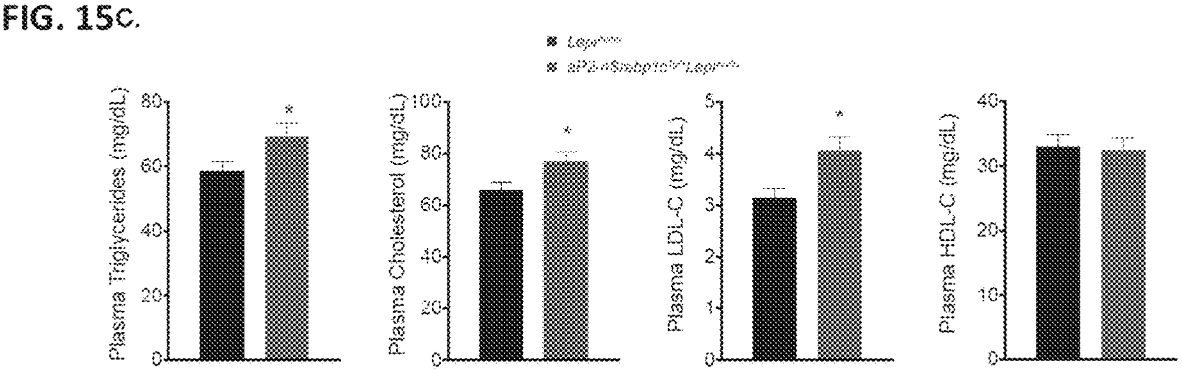

Example 16: H4H17319P2 Reverses Hyperglycemia, Insulin Resistance, Dyslipidemia and Hepatic Steatosis in Lipodystrophic Mice Next, H4H17319P2 was tested to determine if it would mitigate hyperphagia, metabolic dysfunction and liver steatosis in mice with secondary hypoleptinemia due to generalized lipodystrophy. To test this hypothesis, aP2-$nSrebp1c^{Tg/+}$ mice, which develop phenotypic features characteristic of generalized lipodystrophy (Shimomura et al., 1998), were crossed with $Lepr^{hu/hu}$ mice. aP2-$nSrebp1c^{Tg/+}$ mice express nuclear Srebp1c in adipose tissue through the aP2 promoter and were used in the classic experiment that provided the first evidence that leptin resolves the metabolic complications due to low leptin levels in generalized lipodystrophy (Shimomura et al., 1999). Male aP2-$nSrebp1c^{Tg/+}$; $Lepr^{hu/hu}$ mice (Tg) mice were heavier than aP2-nSrebp1c$+^{+/+}$; $Lepr^{hu/hu}$ (nonTg) animals (FIG. 15A). However, in line with previous reports, Tg mice display reduced adiposity and lower leptin levels as compared to nonTg mice (FIG. 15A). aP2-$nSrebp1c^{Tg/+}$; $Lepr^{hu/hu}$ mice also exhibit marked insulin resistance and mild dyslipidemia with increased plasma levels of triglycerides, total cholesterol and LDL-C relative to nonTg mice (FIGS. 15B and 15C).

Male lipodystrophic Tg mice received once weekly dose of control monoclonal antibody or H4H17319P2 at 10 mg/kg (SC). In addition, male nonTg mice also received once weekly dose of control monoclonal antibody at 10 mg/kg (SC) to serve as a reference for wildtype metabolic parameters. Prior to treatment on day 0, Tg mice showed significantly elevated body weights relative to nonTg mice (FIG. 14A). Three days after initiation of treatment, the body weights of lipodystrophic mice receiving H4H17319P2 were significantly lower than lipodystrophic mice dosed with control monoclonal antibody (FIG. 14A). Accordingly, Tg mice given control monoclonal antibody were hyperphagic and consumed more food than non-lipodystrophic nonTg mice administered control monoclonal antibody (FIG. 14A). However, Tg mice treated with H4H17319P2 consumed less food than Tg mice given control monoclonal antibody (FIG. 14A).

Figures 16, 16A:
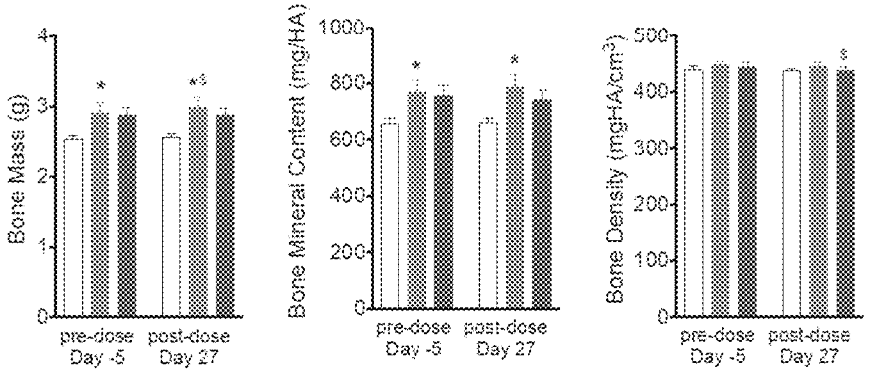
FIG. 16A. Male lipodystrophic aP2-nSrebp1c$^{Tg/+}$; Lepr$^{hu/hu}$ mice (Tg), 27 to 30 weeks old, were dosed once-weekly with 10 mg/kg (SC) of control monoclonal antibody (gray bars) or H4H17319P2 (black bars). As reference, 27 to 30 week old, male non-transgenic Lepr$^{hu/hu}$ mice (nonTg) were also dosed once-weekly with 10 mg/kg (SC) of control monoclonal antibody (white bars). All data are mean±SEM. *, P<0.05 of the respective group versus nonTg mice dosed with control monoclonal antibody at the indicated time point. #, P<0.05 of the respective group versus Tg mice dosed with control monoclonal antibody at the indicated time point. $, P<0.05 day 27 versus day −5 of the respective group.

To determine the basis for the observed body weight changes, body composition was quantified by micro-CT. These analyses revealed that lean mass differences predominantly account for the body weight changes between genotypes and treatment. Prior to treatment (day −5), lean mass was significantly elevated in lipodystrophic Tg mice as compared to nonTg mice (FIG. 14B). Conversely, Tg mice had reduced fat mass when compared to nonTg mice prior to dosing (day −5) (FIG. 14B). After 4 weeks of once per week administration, H4H17319P2 significantly lowered fat mass and lean mass in Tg mice, as compared to the fat mass and lean mass of control monoclonal antibody-dosed Tg mice (FIG. 14B). Bone mass and bone mineral content were elevated in Tg mice relative to wildtype mice but was not significantly elevated across the treatment groups prior to dosing (FIG. 16A). Moreover, no differences in bone mass or bone mineral content were observed between lipodystrophic mice administered control monoclonal antibody or H4H17319P2 (FIG. 16A). Similarly, no significant genotype- or treatment-related effects on bone density were detected (FIG. 16A). These data show that H4H17319P2 decreases lean mass and fat mass in lipodystrophic mice, but does not affect bone mass, bone mineral content or bone density.

In accordance with previous findings, lipodystrophic Tg mice displayed prominent hyperglycemia, as compared to nonTg mice prior to treatment on day 0 (FIG. 14C). Three days after treatment with H4H17319P2, ad-libitum fed blood glucose levels were normalized in Tg mice and did not differ from blood glucose levels of nonTg mice. Of note, with once weekly H4H17319P2 treatment Tg mice maintained normoglycemia to the end of the study, whereas Tg mice receiving control monoclonal antibody remained hyperglycemic throughout the study (FIG. 14C). Correspondingly, on day 28, the percent hemoglobin A1c (HbA1c) levels were reduced in lipodystrophic mice when compared to pre-treatment or to control monoclonal antibody administration (FIG. 14C). Additionally, the lowering of blood glucose levels by H4H17319P2 treatment was associated with improved insulin sensitivity. On day 23, insulin tolerance testing showed that control monoclonal antibody-administered lipodystrophic mice were insulin resistant whereas H4H17319P2-treated lipodystrophic mice were as insulin sensitive as control monoclonal antibody-administered nonTg mice (FIG. 14D). Overall, these results demonstrate that H4H17319P2 alleviates hyperglycemia, insulin resistance and lowers HbA1c levels in a mouse model of generalized lipodystrophy.

Plasma chemistry analyses conducted at the end of the study (day 28), further unveiled that H4H17319P2 reduced hypertriglyceridemia and hypercholesterolemia in mice with generalized lipodystrophy. At the end of the study, plasma levels of triglycerides, total cholesterol and LDL-C levels were significantly elevated in Tg mice that received control monoclonal antibody compared to nonTg mice that also received control monoclonal antibody (FIG. 1E). Notably, plasma triglyceride and cholesterol levels were significantly lower in Tg mice treated with H4H17319P2. Hence, H4H17319P2 improves dyslipidemia in mice with generalized lipodystrophy.

In addition to diabetes, insulin resistance and dyslipidemia, non-alcoholic fatty liver disease (including hepatic steatosis) may develop in patients with generalized and partial lipodystrophies. Hence, the effects of H4H17319P2 on liver enzyme levels, liver weight and liver steatosis in lipodystrophic mice was examined. On day 28, Tg mice that received control monoclonal antibody showed a significant increase in circulating levels of ALT and AST compared to H4H17319P2-treated Tg mice or to nonTg mice administered control monoclonal antibody (FIG. 14F). Importantly, the improved liver enzyme profile was associated with beneficial effects on liver weight and liver steatosis (FIG. 14G). Specifically, livers from lipodystrophic mice receiving control monoclonal antibody were significantly heavier than livers from nonTg mice receiving control monoclonal antibody, weighing 3.6±0.7 g (FIG. 14G). Livers from control monoclonal antibody-administered Tg mice also had higher triglyceride content, as compared to both nonTg mice that received control monoclonal antibody, and to H4H17319P2-treated lipodystrophic mice (FIG. 14G). Notably, livers from H4H17319P2-treated Tg mice were only 0.6±0.1 g heavier and exhibited no increase in liver triglyceride content when compared to livers from nonTg mice receiving control monoclonal antibody (FIG. 14G). The improvements in hepatic steatosis with H4H17319P2 were also evident from hematoxylin and eosin stained liver sections (FIG. 14G).

Example 17: H4H17319P2 Activates Hypothalamic STAT3 Signaling

Figure 17A:
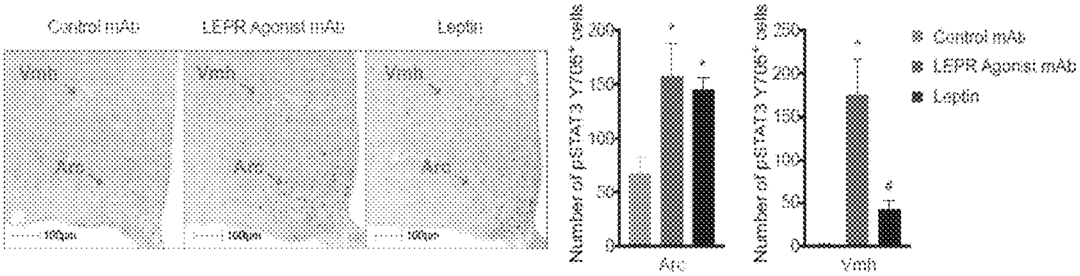
FIGS. 17A-17E: Data in FIG. 17A are for male lipodystrophic aP2-nSrebp1c$^{Tg/+}$; Lepr$^{hu/hu}$ mice (Tg), 32 to 38 week old lipodystrophic (Tg) mice that received a single dose (10 mg/kg SC) of control (gray bars) or H4H17319P2 (dark gray bars) or infusion of leptin (30 μg/day SC; black bars). For data in FIGS. 17B-17E, 27 to 30 week old male Tg mice were dosed once-weekly with 10 mg/kg (SC) of control monoclonal antibody (gray circles or bars) or H4H17319P2 (dark gray circles or bars) or infused with leptin (30 μg/day SC; black bars). Where shown, 27 to 30 week old, male non-transgenic Lepr$^{hu/hu}$ mice (nonTg) were also dosed once-weekly with 10 mg/kg (SC) of control monoclonal antibody (open diamonds and white bars). All data are mean±SEM. *, P<0.05 for the respective group denoted by symbol color or bar versus Tg mice dosed with control monoclonal antibody. #, P<0.05 for the respective group denoted by symbol color or bar versus Tg mice dosed with H4H17319P2.

LEPR activation in the Arc of the hypothalamus plays a pivotal role in governing energy and metabolic balance (Coppari et al., 2005; Cowley et al., 2001). Since H4H17319P2 alleviates hyperphagia and metabolic complications in lipodystrophic $Lepr^{hu/hu}$ mice, it was further probed whether H4H17319P2 induces STAT3 activation in the Arc akin to leptin. Immunostaining for pSTAT3 Y705 was conducted on matched brain sections obtained from male lipodystrophic Tg mice that received a single dose of control or H4H17319P2 at 10 mg/kg (SC), or a continuous infusion of human leptin at 30 μg/d (SC) for 3 days. The leptin dose was selected, since previous work showed that 5 μg/d (SC) is efficacious in lipodystrophic mice (Shimomura et al., 1999) and maximal efficacy has been observed between 10 and 42 μg/d (SC) in mice (Denroche et al., 2013; Halaas et al., 1997; Harris et al., 1998). These analyses revealed that few cells in the Arc show pSTAT3 Y705 staining in lipodystrophic mice that received control monoclonal antibody. By contrast, both leptin and H4H17319P2 induce pSTAT3 Y705 in the Arc, with a similar number of pSTAT3 Y705$^{+}$ cells being detected (FIG. 17A). Although initial focus was on the Arc due to its established role in mediating the actions of leptin and its proximal location to the median eminence, a circumventricular organ which lacks a blood brain barrier, it was noted that both leptin and H4H17319P2 induce pSTAT3 Y705 in the Vmh. However, H4H17319P2 induced pSTAT3 staining in a greater number of Vmh cells than detected with leptin treatment (FIG. 17A). In summary, these data show that leptin and H4H17319P2 induce pSTAT3 Y705 in a similar number of cells in the Arc, while the H4H17319P2 had a more pronounced effect in the Vmh.

A shortcoming of monoclonal antibodies as CNS therapeutics is their limited ability to cross the blood brain barrier, with ~0.1% of circulating concentrations being detected in the CSF (Zuchero et al., 2016). Despite this limitation, it is determined herein that H4H17319P2 not only induces STAT3 phosphorylation in the hypothalamic Arc, but also stimulates STAT3 signaling in the Vmh. The Arc is reported to be irrigated by fenestrated blood vessels, but to a lesser degree than the adjacent median eminence (Ciofi et al., 2009; Norsted et al., 2008). At present, there lacks literature evidence that the Vmh is privileged to direct exposure to blood borne molecules. While not wishing to be held by theory, a possible explanation is that monoclonal antibodies reach the Vmh by diffusion from the Arc. Alternatively, the H4H17319P2 antibody may exhibit differential signaling properties than leptin. Although functional LEPR-b are expressed in the Vmh, another possibility is that the H4H17319P2 monoclonal antibody may indirectly stimulate Vmh STAT3 signaling. Nevertheless, it is unexpected that H4H17319P2 induces STAT3 signaling in more neurons in the Vmh than leptin.

Figure 17B:
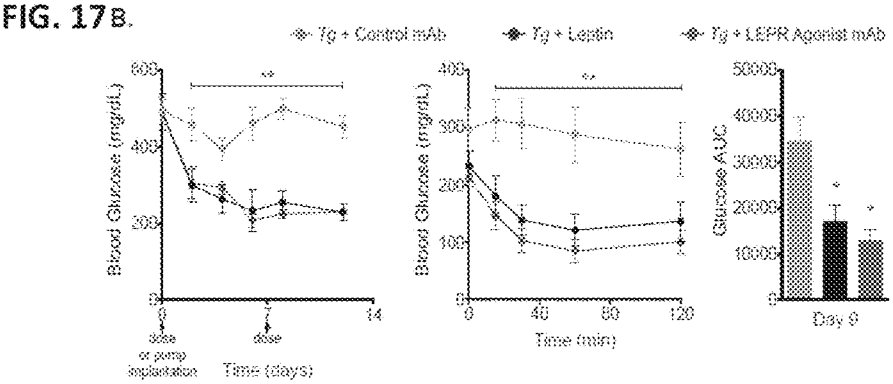

Example 18: H4H17319P2 is at Least as Efficacious as Leptin in Alleviating Metabolic and Liver Dysfunction in Lipodystrophic Mice Since H4H17319P2 engages STAT3 signaling similarly or better than leptin in the Arc and Vmh cells, the efficacy of H4H17319P2 and leptin treatment was compared in lipodystrophic mice. Male Tg mice received once weekly dose of control monoclonal antibody or LEPR agonist at 10 mg/kg (SC), or a continuous infusion of leptin at 30 μg/d (SC) for 14 days. For reference, male nonTg mice received once weekly dose of control monoclonal antibody at 10 mg/kg (SC). Prior to treatment on day 0, Tg mice were markedly hyperglycemic (FIG. 17B). Blood glucose levels were lowered to the same degree by H4H17319P2 or leptin infusion when compared with control monoclonal antibody administration (FIG. 17B). Blood glucose levels were reduced 2 days after initiating H4H17319P2 or leptin treatment and remained lowered till the end of the study (FIG. 17B). To test whether improved insulin sensitivity contributes to the glucose lowering effect, insulin tolerance tests were conducted on day 9. Indeed, insulin tolerance testing revealed that control monoclonal antibody-administered Tg mice were insulin resistant, while H4H17319P2 and leptin treated Tg mice were insulin sensitive (FIG. 17B). No differences were observed between H4H17319P2 and leptin treatment on blood glucose lowering or insulin sensitivity.

Figure 17C:
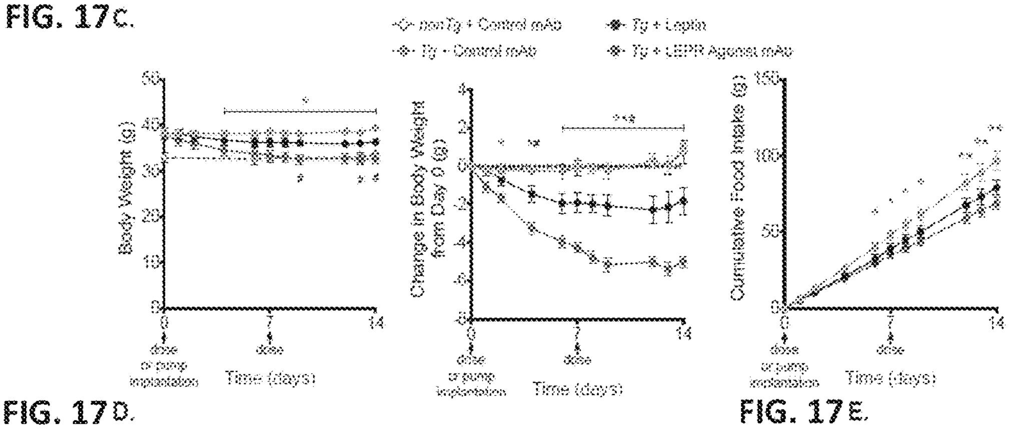

In line with previous data, H4H17319P2 promoted significant body weight loss relative to control monoclonal antibody administration in lipodystrophic mice starting 4 days after treatment (FIG. 17C). In Tg mice, H4H17319P2 decreased cumulative food intake when compared to control monoclonal antibody (FIG. 17C). Interestingly, while leptin lowered body weight and food intake in Tg mice, it resulted in a smaller body weight loss than observed with H4H17319P2 treatment (FIG. 17C).

Figure 17D:
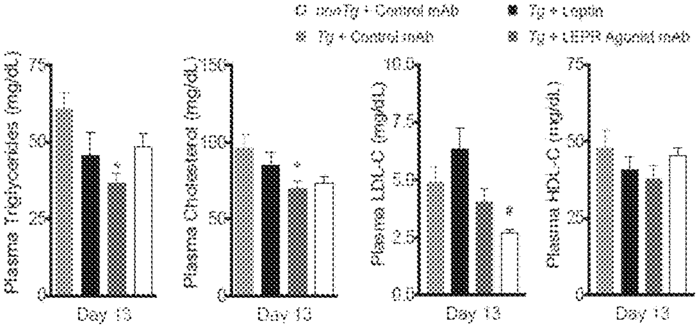
Figure 17E:
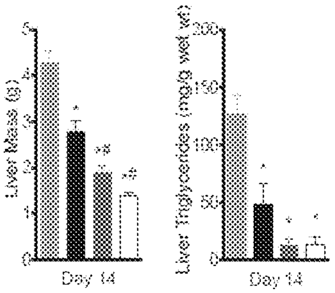

H4H17319P2 provided better benefit compared to leptin in reducing plasma lipids and resolving hepatomegaly in lipodystrophic mice. Plasma chemistry analyses on day 13 showed that in Tg mice, H4H17319P2, but not leptin lowers plasma triglyceride and cholesterol levels compared to control monoclonal antibody (FIG. 17D). No significant changes in other lipids were evident for H4H17319P2 treatment compared to control monoclonal antibody administration in Tg mice. H4H17319P2 also lowered liver mass and resolved hepatic steatosis compared to control antibody treatment in Tg mice (FIG. 17E). While these effects were similar in leptin-treated mice, a greater reduction of liver mass was observed with H4H17319P2 (FIG. 17E). Liver mass was normalized by H4H17319P2, but not leptin treatment, and was similar to the liver mass in nonTg mice that received control monoclonal antibody (FIG. 17E).

Figure 18A:
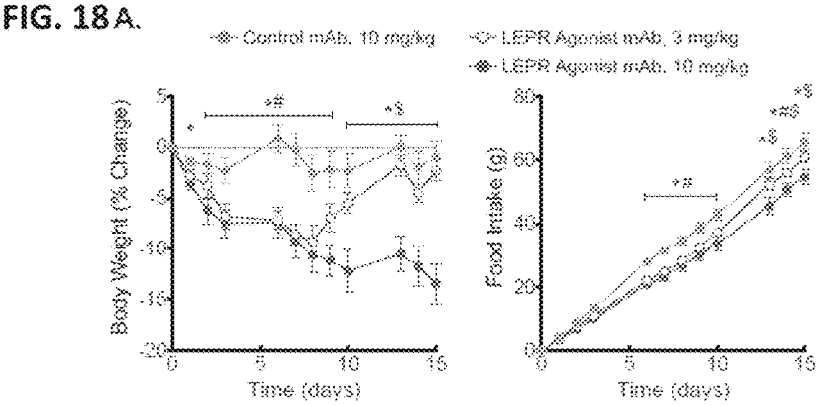
FIGS. 18A-18D: Data shown in FIGS. 18A and 18B are for 32 week old female Lepr$^{hu/hu}$ mice administered a single dose of control monoclonal antibody (10 mg/kg, SC; gray-filled circles), H4H17319P2 (3 mg/kg, SC; open circles) or H4H17319P2 (10 mg/kg; black-filled circles). Data shown in FIG. 18C are for lean male and female *Cynomolgus* monkeys administered a single dose of control (SC; gray-filled circles), H4H17319P2 (3 mg/kg, SC; open circles) or H4H17319P2 (10 mg/kg; black-filled circles). Data shown in FIG. 18D are for high body fat (~6.0 kg) male and female *Cynomolgus* monkeys administered two doses of control (IV; gray-filled circles) or H4H17319P2 (30 mg/kg, IV; black-filled circles). Data are mean±SEM. *, P<0.05 for H4H17319P2 (10 mg/kg) vs respective control vs at the indicated time points. #, P<0.05 for H4H17319P2 (3 mg/kg) vs respective control vs at the indicated time points. $, P<0.05 for H4H17319P2 (3 mg/kg) vs H4H17319P2 (10 mg/kg) at the indicated time points. &, P<0.05 for H4H17319P2 (30 mg/kg, IV) vs respective control.
Figure 18B:
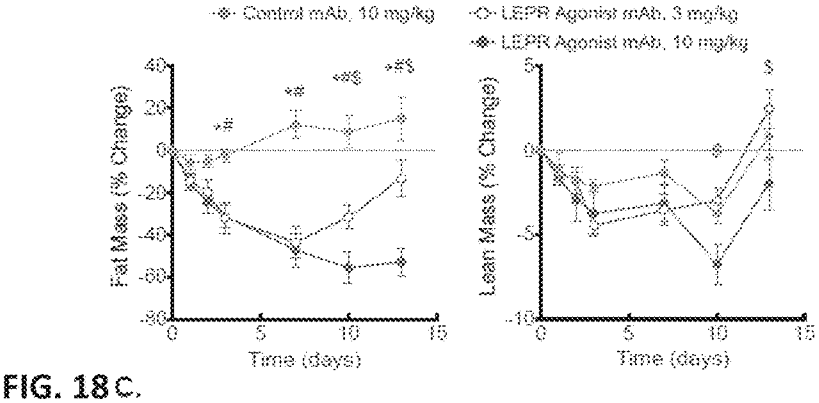

Example 19: H4H17319P2 Reduces Body Weight and Adiposity in Lean Mice and Normal and High Body Fat Monkeys In vitro binding and functional assay experiments demonstrate that H4H17319P2 does not compete for leptin binding and in the presence of leptin induces greater activation of LEPR than leptin alone. Thus, it was determined whether H4H17319P2 can elicit body weight lowering in the setting of normal body weight homeostasis. Chow-fed male Lepr$^{hu/hu}$ mice were administered a single dose of control monoclonal antibody (10 mg/kg, SC) or H4H17319P2 at 3 or 10 mg/kg on day 0. A significant decrease in body weight compared to control monoclonal antibody was observed after 1 and 2 days, following treatment with H4H17319P2 at both dose levels (FIG. 18A). Accordingly, both dose levels of H4H17319P2 reduced food intake relative to control monoclonal antibody administration (FIG. 18A). The body weight changes were associated with lowering of fat mass, but not lean mass (FIG. 18B). At both dose levels, H4H17319P2 treatment induced a −32% reduction in fat mass, while control monoclonal antibody administration resulted in a minimal −2% change in fat mass (FIG. 18B). Of note, no significant differences were observed for lean mass between control monoclonal antibody and H4H17319P2 treatment (FIG. 18B). Although both dose levels of H4H17319P2 resulted in similar magnitudes of body weight and fat mass change, the duration of the effects differed, likely reflecting differences in pharmacokinetics (FIGS. 18A and 18B).

Figure 18C:
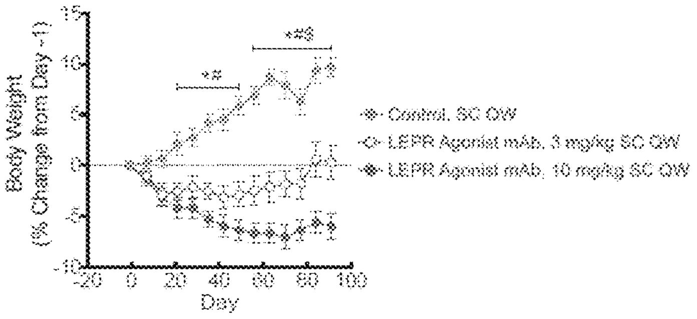

Next, the effect of H4H17319P2 treatment on promoting body weight lowering in non-human primates was assessed. First, the effects of H4H17319P2 on body weight in lean *Cynomolgus* monkeys was determined. Monkeys received either control solution, H4H17319P2 at 3 mg/kg or 10 mg/kg once weekly for 13 weeks. H4H17319P2 treatment resulted in a dose-dependent decrease in body weight relative to monkeys that received control solution (FIG. 18C). After 13 weeks of study, monkeys administered control solution gained 9.7±0.9% of their initial body weight, while H4H17319P2 treatment at 3 and 10 mg/kg resulted in a minimal 0.3±1.6% body weight change and a −6.0±1.6% body weight loss, respectively (FIG. 18C).

Figure 18D:
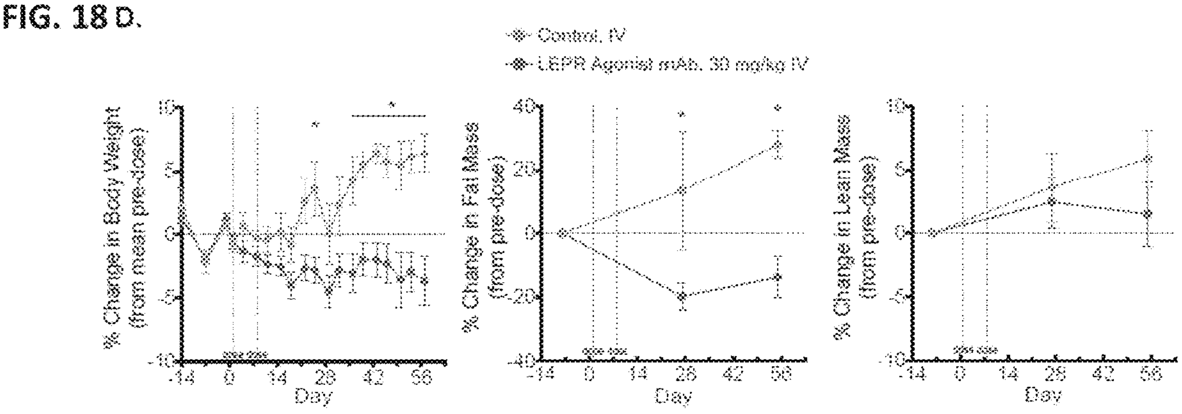

Since H4H17319P2 dose-dependently lowered body weight in lean monkeys, the effects of H4H17319P2 treatment on body weight and body composition were tested in high body fat *Cynomolgus* monkeys. Animals received control solution or LEPR agonist antibody at 30 mg/kg once weekly for 2 weeks. H4H17319P2 lowered body weight compared to control solution injection. At the end of the study (Day 56), monkeys that received two doses of H4H17319P2 showed a 3.6±1.9% decrease in body weight from baseline, whereas monkeys that received control solution gained 6.4±1.5% body weight. In parallel, H4H17319P2 treatment decreased fat mass, but not lean mass compared to control solution administration, as quantified by Dual-Energy X-ray Absorptiometry (DEXA) (FIG. 18D). Monkeys that received control solution exhibited a 28.0±1.5% gain in adiposity by the end of the study. In contrast, monkeys treated with LEPR agonist H4H17319P2, showed a marked 13.7±6.4% decrease in adiposity (FIG. 18D). Taken together, these data show that the H4H17319P2 antibody promotes body weight lowering through a selective loss in adiposity in normal weight $Lepr^{hu/hu}$ mice and both lean to high body fat non-human primates.

Example 20: Double-Blind Study Using Anti-LEPR Antibody in Humans

Obesity affects 13% people worldwide and is a risk factor for the development of type 2 diabetes, cardiovascular disease, various types of cancer and orthopedic disorders. In Western European countries, greater than 20% of individuals are obese (Ng et al., Lancet. 2014; 384: 766-781), and in the United States, the prevalence of obesity is now over 35% (Flegal et al., JAMA. American Medical Association. 2016; 315(21): 2284-2291). Diet and exercise modifications are effective in some individuals, but often result in a modest reduction in body weight with most people remaining obese (defined as a body mass index [BMI]≥30 kg/$m^2$) or overweight (defined as a BMI of 25 to <30 kg/$m^2$).

Current weight loss medications also have modest effects on body weight and/or have poor safety/tolerability, which has led to limited uptake of these interventions by payers, physicians, and patients (Zhang et al., Obes Sci Pract. 2016; 2(2): 104-114). Current standard of care pharmacotherapies, such as liraglutide, orlistat, naltrexone HCl/bupropion HCl, phentermine/topiramate, and lorcaserin HCl reduce body weight by an average of approximately 3 to 10% from baseline. Typically, body weight loss plateaus and therapy is discontinued within a year (Sjostrom et al., Lancet. 1998; 352(9123):167-72) (Smith et al., N. Engl. J. Med. 2010; 363(3):245-56). Bariatric surgery is reserved for only the most severely obese patients (BMI kg/$m^2$ or BMI≥35 kg/$m^2$ with comorbidities) with <200,000 cases per year in the US (American Society for Metabolic and Bariatric Surgery) and fewer than 150,000 cases per year in all of Europe (Angrisani et al., Obes Surg. 2017, 27:2279-2289). There is a significant unmet medical need for safe and effective therapies for the treatment and prevention of obesity and obesity related metabolic complications.

Leptin is a circulating adipose-derived hormone that binds to leptin receptors (LEPR) in the hypothalamus and modulates the control of food intake, energy expenditure, and glucose/lipid metabolism (Allison et al., J Endocrinol 2014, 223(1):T25-35). Individuals with primary leptin deficiency, due to ultra-rare homozygous loss of function mutations in the leptin (LEP) gene or with defective leptin signaling due to homozygous mutations in the LEPR, develop severe obesity, diabetes, susceptibility to infection, and infertility (Montague et al., Nature 1997, 387(6636):903-908) (Clement et al., Nature 1998, 392(6674):398-401). Recombinant human leptin administration to pediatric and adult patients with monogenic obesity due to leptin loss of function mutations resulted in robust decreases in body weight and improvement in metabolic complications (Farooqi et al., N Engl Jo Med 1999, 341(12):879-884) (Licinio et al., Proc Nat Acad Sci 2004, 101(13):4531-4536).

Secondary leptin deficiency also occurs in rare disorders of lipodystrophy, which are caused by genetic or acquired loss of leptin-producing adipose tissue from various regions of the body.

Patients with generalized and partial lipodystrophy develop varying degrees of diabetes, severe insulin resistance, hypertriglyceridemia, and fatty liver (Brown et al., J Clin Endocrinol Metab. 2016; 101(12):4500-4511). Recombinant human leptin delivered subcutaneously once daily has been shown to reduce hemoglobin A1c (HbA1c), glucose, triglycerides and liver steatosis in patients with generalized lipodystrophy (Oral et al., N Engl J Med. 2002; 346(8):570-578) (Ebihara et al., J Clin Endocrinol Metab 2007, 92(2): 532-541). The majority of the patients with generalized lipodystrophy had serum leptin levels of <4 ng/mL and subgroup analyses suggested that reductions in HbA1c and triglycerides (TG) with leptin treatment were greater in patients with generalized and partial lipodystrophy when leptin levels were <4 ng/mL (Brown et al., J Clin Endocrinol Metab. 2016; 101(12):4500-4511) (FDA Advisory Committee Meeting 2013).

Metreleptin (recombinant methionyl leptin; Novelion®) is currently approved in the US under a Risk Evaluation and Mitigation Strategies (REMS) program for the treatment of complications of leptin deficiency in patients with generalized congenital and acquired lipodystrophy, and is also approved in Japan for all subtypes of lipodystrophy. Daily dosing of metreleptin is required and adverse effects include risk for immunogenicity with ~85% of patients developing binding antibodies and ~9% developing neutralizing antibodies that cross react with endogenous leptin (Chan, Clin Endocrinol. 2016; 85(1):137-149).

In contrast to low leptin or leptin deficiency disorders, individuals who are overweight or obese typically have high levels of leptin with a median level of 10 ng/mL in males and 24 ng/mL in females in subjects with BMIs in the 30-35 kg/$m^2$ range (Ruhl and Everhart, Am J Clin Nutr. 2001; 74(3): 295-301). Circulating leptin levels for male and female adults with normal BMI of 20-25 kg/$m^2$ have median levels of 3 and 9 ng/mL, respectively (Ruhl et al., Am J Clin Nutr 2001; 74(3): 295-301), with normal ranges cited as 1.2 to 9.5 ng/mL in males and 4.1 to 25 ng/mL in females (Quest Lab Reference Range). Numerous studies have demonstrated a correlation between circulating leptin levels and BMI and body fat percentage (Ruhl et al., Am J Clin Nutr. 2001, 74(3):295-301) (Considine et al., N Engl J Med. 1996, 334(5):292-295), although there is a high degree of variability in leptin levels among individuals with similar BMIs (Buettner et al., J Endocrinol. 2002; 175(3): 745-756). Leptin levels have a diurnal variation (Gavrila et al., J Clin Endocrinol Metab. 2003, 88(6):2838-43) (Schoeller et al., J Clin Invest. 1997, 100(7):1882-87) and fluctuate based on nutritional status. Leptin levels rapidly decrease by 35-60% following a 24-hour fast in normal weight and obese individuals and continue to drop after prolonged fasting (Chan et al., J Clin Invest. 2003; 111(9): 1409-1421) (Schurgin et al., 2004, J Clin Endocrinol Metab, 89(11): 5402-5409) (Boden et al., J Clin Endocrinol Metab. 1996; 81(9): 3419-3423). Leptin levels also decrease during weight loss (Considine et al., N. Engl J Med, 1996; 334(5): 292-295) (Herrick et al., J Obes. Hindawi. 2016; 2016(2): 8375828-5) (van Dielen et al., J Clin Endocrinol Metab. 2002; 87(4): 1708-1716) and increase during weight gain (Ravussin et al., Cell Metab. 2014; 20(4): 565-572), coinciding with changes in fat mass. Recombinant human leptin administration to obese subjects resulted in minimal weight loss (3% PBO subtracted reduction in body weight) (Heymsfield et al., JAMA. 1999; 282(16): 1568-1575) (Hukshorn et al., J Clin Endocrinol Metab. 2000; 11(12): 1163-1172) (Ravussin et al., Obesity. 2009; 17(9): 1736-1743), likely due to saturation of leptin receptor signaling by high endogenous leptin levels. Several population studies suggest that there may be subsets of obese patients where leptin levels are relatively low (Ruhl and Everhart, Am J Clin Nutr. 2001; 74(3): 295-301) (Buettner et al., J Endocrinol. 2002; 175(3): 745-756) and leptin receptors may not be saturated. A key question to address is whether restoration of leptin signaling will reduce appetite, food intake and body weight in obese subjects with relatively low baseline leptin levels.

H4H17319P2 is a human anti-LEPR antibody that acts as a LEPR agonist and binds to human LEPR with nanomolar affinity. In preclinical studies, H4H17319P2 activates LEPR signaling in the presence or absence of leptin. Once weekly administration of H4H17319P2 (10 mg/kg subcutaneous [SC]) improved glycemic control, insulin sensitivity, dyslipidemia, food intake, body weight, liver mass and hepatic steatosis in lipodystrophic humanized LEPR mice. H4H17319P2 also reduced body weight and adiposity in humanized LEPR mice with inducible leptin deficiency but did not reduce body weight in diet-induced obese humanized LEPR mice. In a good laboratory practice (GLP) toxicology study in which lean cynomolgus monkeys were treated with H4H17319P2 by subcutaneous injections (3, 10, 30 mg/kg) or intravenous (100 mg/kg) once weekly for 13 weeks, H4H17319P2 exposure resulted in suppression of weight gain or induction of weight loss. Monkeys administered H4H17319P2 lost up to 8.7% body weight (group mean compared to pre-dose weights) while concurrent control animals administered placebo gained an average of 8.3% body weight over the same time period. The magnitude of the observed body weight reduction did not appear to have a clear dose or exposure response in H4H17319P2 treated animals. Body weight changes were observed to reverse upon cessation of exposure during a dose free recovery period.

As described above, administration of H4H17319P2 was well tolerated at all dose levels and by both routes of administration, without any adverse clinical effects. Transient decreases in insulin and circulating absolute lymphocyte counts (decreased T-cell numbers) were observed at approximately 30 days during the treatment period but these findings were not observed at the end of the dosing period and the effect was not dose-responsive. Lower thymus weights and decreased thymus cortical cellularity were observed in the H4H17319P2 treated groups during the treatment period and was completely or partially reversible during the recovery period. The changes in thymus and the transient reduction in T-cell numbers are likely related to decreased nutritional intake and reductions in body weight in monkeys who are in the growth phase and would likely not be observed in adult humans with normal nutritional status.

This study is a first-in-human (FIH), randomized, double-blind, placebo-controlled two-part study designed to assess the safety, tolerability, pharmacokinetics (PK), and pharmacodynamics (PD) of intravenous (IV) and SC administered doses of H4H17319P2 in healthy participants. The aims of Part A are to evaluate the safety, tolerability, PK, and PD of single ascending IV and SC doses in healthy male and female subjects. Interim analysis of PK/PD, safety, and tolerability in Part A will be used to select a dose regimen for evaluation in Part B. Subjects enrolled in Part A are not eligible to enroll in Part B. For Part B, new subjects, who are overweight or obese, will be enrolled to evaluate safety, tolerability, PK, and PD of repeated doses of H4H17319P2 (at a single dose level) or placebo for 12 weeks. The effects of H4H17319P2 on biomarkers such as food intake, appetite, body composition, and body weight will be assessed in 4 different cohorts defined by baseline leptin levels.

Objectives

The primary objective of the study is to evaluate the safety and tolerability of H4H17319P2 in healthy subjects. The secondary objectives of the study were to:

- Characterize the Pharmacokinetic (PK) profile of single and repeated doses of H4H17319P2;
- Estimate the effects of repeated doses of H4H17319P2 on body weight;
- Assess the effects of repeated doses of H4H17319P2 on ad lib energy intake in overweight and obese subjects;
- Evaluate the effects of single and repeated doses of H4H17319P2 on soluble forms of lipid-regulating proteins (sLEPR and ANGPTL3) levels over time;
- Assess the immunogenicity of single and repeated doses of H4H17319P2.

Other exploratory objectives of the study are to:

1. Estimate the effects of single doses of H4H17319P2 on body weight and serum/plasma glycemic and lipid parameters
2. Estimate the effects of repeated doses of H4H17319P2 over 12 weeks on:
   - Serum/plasma glycemic and lipid parameters
   - Patient reported appetite assessments that can impact feeding behavior (e.g., hunger, fullness, and satiety)
   - Total and the distribution of fat and lean body mass by dual X-ray absorptiometry (DXA) imaging
   - Quantification of SC and visceral fat (including liver fat) by magnetic resonance imaging (MRI) imaging
   - Other exploratory biomarkers including leptin, thyroid hormone (T3, T4, thyroid-stimulating hormone [TSH]), luteinizing hormone (LH), testosterone, estradiol, cortisol, and adiponectin.

Rationale

Part A is a single ascending dose FIH design where up to 88 healthy subjects will be randomized 3:1 to H4H17319P2 vs. placebo in up to 7 ascending single dose cohorts (up to 5 IV and 2 SC) to assess the safety, tolerability and pharmacokinetics of a single ascending dose of H4H17319P2 with a follow-up period of 112 days. Seven ascending single dose cohorts will have 8 subjects randomized to receive H4H17319P2 or placebo (6 active: 2 placebo) in each dose level. The study design also includes 2 additional optional cohorts (16 subjects randomized to receive H4H17319P2 or placebo (12 active: 4 placebo in each cohort). If interim analyses from the ascending dose cohorts suggest that there may be effects of covariates (e.g., age, body weight or gender) on the PK profiles, the optional cohorts may be enrolled to collect additional data on one or more doses (up to the maximum dose in this study of 30 mg/kg IV) to obtain a better estimate of the effects of covariates on PK.

Part A of the study consists of a screening period (days −21 to −2), a pre-baseline visit (day −1) where subjects will be admitted for an in-clinic 2-day stay (for subjects receiving IV and for SC doses that are in the safety-sentinel block) or a 1-day clinic stay (for subjects who receive SC dosing), a follow up period (day 3 to day 113) with an end of study visit (day 113).

Evaluation of safety and tolerability is the primary objective of Part A and safety will be carefully assessed throughout the study. The starting and maximum doses administered in this study are expected to be ~10 000 and ~20-fold lower, respectively than the exposures observed in the toxicology studies. Throughout the clinical study, safety assessments include vital signs, physical examination, electrocardiograms (ECGs), laboratory tests including hematology/differentials, and monitoring of adverse events (AEs). Body weight will also be assessed. Pharmacodynamic measures will also be collected in this study but meaningful changes in PD markers are not expected to be observed in this population of lean/overweight subjects, based on upon the minimal effects in body weight (<1 kg) observed with metreleptin in lean individuals (Heymsfield, 1999).

Pharmacodynamic measures include body weight, metabolic parameters (glucose, lipids), and ANGPTL3, a potential marker that may be regulated by leptin and/or insulin (Muniyappa, 2017) (Nidhina Haridas, 2015). Body weight will be carefully assessed at each visit. In the event that single doses of H4H17319P2 treatment have a clinically meaningful effect on body weight in lean/overweight subjects, the timing of safety/dose escalation decisions may be modified and additional safety data collected (e.g., waiting for day 15 safety assessments) before dose escalation decisions are made.

Part B is a repeated dose study at a single dose level with a 12-week treatment period to evaluate the safety, PK and effects of H4H17319P2 on body weight in overweight/obese subjects. Several population studies suggest that there are obese patient subsets in whom leptin levels are relatively low (Ruhl, 2001) (Buettner, 2002) and leptin receptors might not be saturated. A key question that is being addressed in Part B is whether restoration of leptin signaling will reduce appetite, food intake and body weight in overweight or obese subjects with relatively low baseline leptin levels.

Therefore, Part B will evaluate the effects of H4H17319P2 on body weight, food intake, metabolic parameters and body composition in subjects with varying body weights and relatively low baseline leptin levels. Healthy subjects who are overweight or obese (BMI range 25-40 kg/$m^2$) will be enrolled into 4 distinct cohorts defined by prescreening leptin level. Enrollment into 4 distinct cohorts will be performed to ensure an adequate number of subjects are studied across a range of relatively low baseline leptin levels and BMI ranges. Stratification by cohort will occur at randomization to H4H17319P2 vs placebo. Up to approximately 20 subjects will be enrolled in each of 4 cohorts for a total sample size of up to 81 subjects for Part B as defined below. Leptin levels and BMI will be measured at the prescreening visit to initially assess eligibility for the study and for 1 of the 4 cohorts. Enrollment into the study will occur at screening for subjects meeting eligibility. If enrollment into a specific cohort has reached the maximum number allowed, the subject will not be eligible for enrollment. Some cohorts may be difficult to enroll given the low prevalence of obesity with low leptin levels; the sponsor may elect to stop enrollment within a specific cohort.

The 4 cohorts in Part B are defined as follows:

Cohort 1: Male and female subjects with a prescreening BMI between 28.0 and 40.0 kg/$m^2$, inclusive with a prescreening fasting leptin level of <5 ng/mL Cohort 2: Male and female subjects with a prescreening BMI from 25.0 to <28 kg/$m^2$ with a prescreening fasting leptin level of <5 ng/mL Cohort 3: Male subjects with a prescreening BMI between 28.0 and 40.0 kg/$m^2$, inclusive and a prescreening fasting leptin level between 5.0 and 8.0 ng/mL inclusive Cohort 4: Female subjects with a prescreening BMI between 28.0 and 40.0 kg/$m^2$, inclusive and a prescreening fasting leptin level between 5.0 and 24.0 ng/mL, inclusive Note: Eligibility for one of the cohorts above is based upon BMI and leptin levels at the prescreening visit. If the BMI and/or leptin levels do not fall in the ranges defined by the cohorts, the subject will not be eligible for enrollment. If prescreening BMI or leptin levels are borderline for inclusion into 1 or more than 1 cohort, BMI and leptin measurements may be repeated once during the prescreening window. For repeated measures, the lowest leptin level will be used for inclusion into one of the cohorts. If enrollment into a specific cohort has reached the maximum number allowed, the subject will not be eligible for enrollment.

The initiation of Part B will be triggered by an interim analysis of available safety, PK, and PD data from Part A to select an appropriate dose, dosing frequency, and mode of administration (IV or SC) for Part B. Subjects enrolled in Part A will not be eligible to participate in Part B. The Part B study design consists of a prescreening period (days −60 to −14) to assess BMI and fasting leptin levels and eligibility for 1 of the 4 cohorts, a screening period (days −32 to −14), a baseline period consisting of (days −29 to −1), a treatment period (days 1 to 85), and an off-treatment follow-up period (days 107 to 191). Subjects will be admitted for a 2-day in-clinic stay for accurate appetite and ad lib food intake assessments during the baseline period (scheduled between days −14 to −1) and at 2 time points during the treatment period (days 29 to 30 and days 84 to 85). The in-clinic stays are necessary to assess precise caloric intake in an ad lib food assessment in a controlled setting in which there are standardized meals and minimization of cues that can affect food intake besides appetite (e.g., time of day, eating behaviors of others, portion size, etc). Subjects will also be admitted for a 2-day in-clinic stay on day −1. On day 1 during the treatment period, subjects will receive the first dose of study drug or placebo, have blood sampling for serial PK and other laboratory measurements, and stay overnight to complete a 24-hour PK assessment on day 2.

Visits during the treatment period for blood sampling will occur once weekly. The study drug dose and frequency will be determined by the interim analysis of the PK data from Part A and may be every 4 weeks or every 2 weeks (with a maximum frequency of no more than once every week).

Body composition by DXA and quantification of liver, abdominal, and thigh fat by MRI will be performed at baseline, near end-of-treatment and during the follow-up period. After the treatment period, subjects will be followed for a 16-week off drug period to assess safety and PD effects. Assessment of safety and tolerability of repeated doses at a single dose level (based on safety and tolerability from Part A) will be the primary objective of Part B of the study. Throughout the study, safety assessments will include vital signs, physical examination, ECGs, laboratory tests, monitoring of AEs. Anti-drug antibodies will also be assessed. In addition, secondary objectives to evaluate body weight, ad lib food intake and metabolic parameters such as glucose and lipids will be carefully assessed throughout the study.

Pharmacodynamic measures in Part B include baseline and on-treatment assessments of parameters that may be impacted by increases in leptin receptor signaling. These PD assessments include patient reported measures of appetite, quantitative measures of food intake in a controlled inpatient setting, precise measurements of body composition and fat mass by DXA, and precise measurement of body weight using calibrated scales. In addition, metabolic parameters such as leptin, glucose, insulin, homeostasis model assessment-estimated insulin resistance (HOMA-IR), HbA1c, lipids will be measured at baseline, during and at the end of the treatment period to assess the effects of H4H17319P2 on insulin sensitivity and lipid metabolism. MRI of the liver will also be performed at baseline and after treatment to determine whether H4H17319P2 has an impact on liver steatosis.

Rationale for Pharmacodynamic and Biomarker Variables

Ad Libitum Food Intake Assessment (Part B Only)

It is hypothesized that treatment with H4H17319P2 will increase hypothalamic leptin receptor signaling and have downstream effects in neurons that affect feeding behaviors. H4H17319P2 treatment resulted in a significant reduction in food intake and body weight in inducible leptin deficient mice. Although quantitative food intake assessments were not performed in studies of cynomolgus monkeys, H4H17319P2 treatment resulted in a significant effect on body weight and fat mass. In the current study, the effects of H4H17319P2 on food intake in overweight/obese subjects with relatively low leptin levels will be assessed at baseline and at 2 time points during treatment using a rigorous quantitative inpatient ad lib food intake assessment as described previously (Krishna, 2009) (Addy, 2008). Briefly, subjects will be admitted after fasting to the clinical trial unit and will be provided a standardized breakfast, lunch and dinner in order to establish a standardized baseline energy intake. After an overnight fast, subjects will be presented with an ad lib breakfast, lunch and dinner to quantify food/energy intake. Subjects will consume all test meals in specialized rooms that mask the perception of time/time of day and social cues.

Meals of known caloric density will be provided in 4-5 times excess portions and will be presented in a way to mask total number of calories consumed. Subjects will be asked to eat as much or as little as they like. Meals will be weighed prior to and after the food intake assessment in order to quantify food intake, and calories ingested will be calculated.

Appetite Assessments (Part B Only)

Appetite Effects of Leptin are Central to its Mechanism of Action, and Thus are a Proximate assessment of the predicted mechanism of action of H4H17319P2. Individuals with hypoleptinemia, either from mutations in LEP or from generalized lipodystrophy, manifest insatiable appetites, which drive food intake and obesity. Metreleptin treatment of these individuals increases satiety and decreases food intake (Farooqi, 1999) (Farooqi, 2007) (McDuffie, 2004). The effect of H4H17319P2 on appetite using questionnaires (Flint, 2000) (Dalton, 2015) that measure various components of appetite (e.g., hunger, satiety) will be performed at baseline and during follow-up.

Appetite will be assessed prior to and after a standard caloric load during the in-clinic visits, and an additional appetite questionnaire will be completed daily during the baseline, treatment, and follow-up periods.

ANGPTL3

Angiopoietin like protein 3 (ANGPTL3) regulates lipoprotein levels such as TG, low density lipoprotein C (LDL-C) through inhibition of lipoprotein lipase (reviewed by Tikka, 2016). Levels of ANGPTL3 may be regulated by feeding, leptin and/or insulin (Minicocci, 2012) (Nidhina, 2015). Levels of ANGPTL3 are elevated in patients with lipodystrophy, and reduced after treatment with metreleptin (Muniyappa, 2017), and the reduction of ANGPTL3 may mediate enhanced lipase clearance of TG rich lipoproteins. ANGPTL3 and TG levels are also increased in a mouse model of lipodystrophy and are normalized after treatment with H4H17319P2. Therefore, ANGPTL3 may be a pharmacodynamic marker that may decrease in the setting of increased leptin receptor signaling. ANGPTL3 will be measured at baseline and after treatment at several time points in Part A and B.

Soluble LEPR

Leptin circulates in the blood stream both as a free entity and also can be bound to a sLEPR, which is generated via shedding of the LEPR ectodomain (Sinha, 1996) (Lammert, 2001). Soluble LEPR may regulate bioavailability and/or clearance of leptin (Lou, 2010). It is possible that target saturation may be dependent upon saturation of sLEPR and therefore variability in linear and nonlinear target mediated kinetics may be influenced by sLEPR levels. Therefore, in Part A and B, sLEPR will be measured at baseline and at various time points (corresponding to sampling for antibody pharmacokinetics) during the treatment period.

Imaging (Part B Only)

DXA and MRI imaging will be performed at baseline, near the end of treatment, and at the end of the study to estimate the change from baseline in total and regional fat distribution, SC and visceral fat in the thigh/abdominal regions, and in liver fat content. In a pilot study in cynomolgus monkeys, preclinical data demonstrated that H4H17319P2 reduced body weight by reducing total fat mass, without effects on lean mass (assessed by DXA). DXA has shown to be a useful quantitative biomarker of total fat mass and regional fat distribution in clinical studies. For example, significant differences in regional fat distribution using DXA (% fat trunks to % fat legs (fat mass ratio [FMR]) of 1.78±0.53) were observed in patients with partial lipodystrophy compared to normal subjects (Aijluni, 2017). DXA has also been used to quantify changes in total and regional fat mass in trials of weight loss agents such as GLP-1 agonists (Jendle, 2009) and cognitive therapy (Ponti, 2018).

Magnetic resonance imaging (MRI) has shown to be an effective means to measure fat content in a variety of tissues, including liver (Aijluni, 2017) and muscle (Burakiewicz, 2017) by imaging of whole organs using dedicated pulse sequences, or by spectroscopy in a limited volume of tissue. MRI has also shown high-contrast images for the measurement of abdominal fat volume and distribution (Klopfenstein, 2012), where patients with familial lipodystrophy type 2 have shown a 2.5-fold greater percent of visceral fat than control patients (Al-Attar, 2007). The fat fraction in muscle can also be evaluated by quantitative MRI, as shown by multiple muscular dystrophy studies, where spectroscopy and pulse sequences allowing anatomical imaging and fat fraction estimations have shown promise in evaluating disease progression (Burakiewicz, 2017).

In the current study, MRI of the abdomen and thigh will be performed to quantify regional changes in SC, visceral and liver fat at baseline and after treatment with H4H17319P2

Rationale for Dose Selection

Intravenous and SC doses were selected for Part A based upon efficacy, safety, and pharmacokinetic data from preclinical studies in mouse models of lipodystrophy and monogenic obesity and from monkey toxicology studies. The highest dose in this FIH study will be no more than 30 mg/kg and the starting dose will be approximately 0.3 mg/kg. In the GLP toxicology study in cynomolgus monkeys, H4H17319P2 was well tolerated up to 100 mg/kg IV weekly for 12 weeks with a no-observed-adverse-event level (NOAEL) of 100 mg/kg. Based on predicted serum exposure of H4H17319P2 in humans, the planned maximum dose of 30 mg/kg in this FIH study has an exposure multiple of twenty-fold below the NOAEL. The initial starting dose of 0.3 mg/kg has a safety margin of over 10,000 below the highest dose tested in the GLP toxicology study and is predicted to provide H4H17319P2 concentrations in human above the limit of quantitation and therefore to provide useful PK information.

Goals for dose selection for Part B include ensuring a wide range of exposures to assess tolerability and to facilitate the characterization of exposure-response relationships, as well as the elucidation of pharmacokinetic profiles that enable the characterization of both linear and non-linear pharmacokinetics. Additionally, dose selection should ensure exposures above and below putative PD marker thresholds that may be of interest (e.g., sLEPR saturation). The dose for Part B will be based upon interim safety, PK and PK/PD data from Part A. The selection of dose levels, the dosing interval, and the route of administration (IV or SC) will be based upon the safety, pharmacokinetics and, if available, PK/PD, data from Part A, as well as from preclinical studies in animals. The dose in Part B will not exceed those evaluated in Part A and administration will likely be every 4 weeks or every 2 weeks but will not be administered more frequently than once weekly.

The dose regimen will not exceed exposures observed in the toxicology studies.

Criteria

Up to 169 subjects (up to 88 for Part A and up to 81 for Part B) will be the Enrolled Target Population: The target population will be healthy lean or overweight males and females for Part A and healthy overweight or obese males and females with varying baseline leptin levels for Part B.

Key Inclusion Criteria

A subject must meet the following criteria at screening to be eligible for inclusion in Part A of the study:

1. Males and females 18 to 50 years of age, inclusive
2. Body mass index (BMI) from 18.5 to <30.0 kg/m$^2$
3. Subject is judged by the investigator to be in good health and free from major comorbidities based on medical history, physical examination, laboratory safety tests performed at screening and/or prior to administration of initial dose of study drug
4. Willing and able to comply with clinic visits, study-related procedures, and comply with dietary instructions
5. Willing to maintain usual diet and exercise regimen throughout the study
6. Able and willing to provide signed informed consent A subject must meet all of the following criteria at screening (except for BMI and leptin eligibility, which are determined at prescreening) to be eligible for inclusion in Part B of the study:

1. Males and females 18 to 65 years of age, inclusive
2. Have a body mass index (BMI) and a fasting leptin level at the prescreening visit as defined below by one of the cohorts. If enrollment into a specific cohort has reached the maximum number allowed, the subject will not be eligible for enrollment.
3. Subject is judged by the investigator to be free from major comorbidities based upon medical history, physical examination, laboratory safety tests performed at screening and/or prior to administration of initial dose of study drug. Subjects can have a history of mild hyperlipidemia and/or mild hypertension but should be on stable doses of lipid lowering or blood pressure lowering medicines for at least 2 months prior to screening
4. Willing and able to comply with clinic visits, study-related procedures, and comply with dietary instructions
5. Willing to maintain usual diet and exercise regimen throughout the study
6. Able and willing to provide signed informed consent Exclusion Criteria A subject who meets any of the following criteria at screening will be excluded from Part A of the study:

1. History of clinically significant cardiovascular (e.g., history of hypertension, myocardial infarction, stroke, peripheral vascular disease, heart failure, arrhythmias), respiratory, hepatic, renal, gastrointestinal, endocrine (e.g., hyperlipidemia), hematological, or neurological disease.
2. History of type 1 or 2 diabetes or prediabetes or with fasting blood glucose (FBG) at screening>100 mg/dL or with HbA1c at screening of >5.7%.
3. Fasting LDL-C≥130 mg/dL, TG>250 mg/dL
4. Clinically significant abnormal complete blood count, clinical chemistry, urine analysis or urine drug screening test at screening. Trivial deviations in laboratory results are allowed. NOTE: Any abnormal laboratory results (e.g., creatine phosphokinase (CPK) within 3× upper limit of normal (ULN) with suspected cause due to rigorous physical activities) may be repeated once during the screening period.

A subject who meets any of the following criteria at screening will be excluded from Part B of the study:

1. History of clinically significant cardiovascular (e.g., history of moderate-severe hypertension, myocardial infarction, stroke, peripheral vascular disease, heart failure, arrhythmias), respiratory, hepatic, renal, gastrointestinal, endocrine, hematological, or neurological disease.
2. History of type 1 or 2 diabetes or with FBG at screening>126 mg/dL or with HbA1c at screening of >6.5%. A diagnosis of "pre-diabetes" is allowed.
3. Fasting LDL-C>160 or TG>500 mg/dL
4. Clinically significant abnormal complete blood count, clinical chemistry, urine analysis or urine drug screening test at screening except for mild lipid or glycemic abnormalities as described above. Trivial deviations in laboratory results are allowed. NOTE: Any abnormal laboratory results (e.g., CPK within 3×ULN with suspected cause due to rigorous physical activities) may be repeated once during the screening period.

5. Restricted eating habits (e.g., vegetarian or vegan), aversion to specific food categories used in the food intake assessment, or eating behaviors that would interfere or confound the interpretation of the food intake, appetite, or food control assessments A subject who meets any of the following criteria at screening will be excluded from Part A and Part B of the study:

1. Hospitalization (i.e., >24 hours) for any reason within 60 days of the screening visit
2. Subject has any physical examination findings and/or history of any illness that, in the opinion of the study investigator, might confound the results of the study or poses an additional risk to the subject by their participation in the study.
3. History of hypothalamic amenorrhea or lipodystrophy.
4. Change in body weight of more than 5% over the past 3 months prior to screening.
5. Previous history of bariatric procedures for obesity (e.g., sleeve gastrectomy, gastric bypass, banding, etc).
6. Procedures for weight reduction (e.g., liposuction) or body contouring in the past 6 months.
7. Treatment with medications for (over-the-counter [OTC] or prescribed) weight loss (e.g., lorcaserin, phentermine/topiramate, naltrexone HCl/bupropion HCl, liraglutide) in the past 3 months.
8. History of major psychiatric disorders, eating disorders (e.g., bulimia, anorexia).
9. Current cigarette smoker or former smoker (cigarettes or e-cigarettes) who stopped smoking within 3 months prior to screening.
10. History of recreational drug (including marijuana) or alcohol abuse (>2 drinks per day) within a year prior to the screening visit.
11. History of hepatitis B infection or a positive hepatitis B surface antigen (HbsAg+) at screening.
12. History of HIV infection or HIV seropositive at the screening visit.
13. History of hepatitis C infection or positive hepatitis C antibody test result at screening.
14. Any malignancy within the past 10 years, except for basal cell or squamous epithelial carcinomas of the skin or carcinoma in situ of the cervix or anus, that have been resected, with no evidence of metastatic disease for 3 years.
15. History of active or latent tuberculosis (TB). NOTE: History of latent TB is defined as either a positive tuberculin skin test (TST; defined as a skin induration>5 mm, regardless of *Bacillus* Calmette-Guerin (BCG) or other vaccination history) or a positive (not indeterminate) QuantiFERON® TB Gold test).
16. For Part A: sitting or supine blood pressure readings on at least 2 determinations (>140/90 or <90/60) and resting pulse (<45 or >125) or with orthostatic changes (drop of >20 mm Hg systolic and/or >10 mm Hg diastolic, position) at screening and baseline visits. For Part B: sitting or supine blood pressure readings on at least 2 determinations (>150/90 or <90/50) and resting pulse (<45 or >125) or with orthostatic changes (drop of >20 mm Hg systolic and/or >10 mm Hg diastolic, position) at screening visit. If blood pressure readings are elevated, blood pressure readings may be repeated or subjects may be rescreened once.
17. Subject has an estimated glomerular filtration rate (using MDRD equation) of <60 mL/min/1.73 $m^2$ at screening.
18. Clinical significant abnormal ECG or with abnormal intervals confirmed on at least 2 determinations (QTcF>450 msec for males >470 msec for females; PR<120 msec or >220 msec; QRS>100 msec).
19. Hypersensitivity to doxycycline (or tetracycline class drugs) or other components of the formulation.
20. History of acute hypersensitivity and/or anaphylaxis to protein therapeutics.
21. History of severe allergies (including latex or anaphylactic reactions or allergies), that in the opinion of the investigator could represent a substantial risk to the subject.
22. Participation in any clinical research study evaluating another investigational drug (including biologics) or therapy within 90 days or at least 5 half-lives (whichever is longer) of an investigational biologic drug, or at least 4 weeks for other investigational products, or 6 months for immunotherapy prior to the screening visit.
23. Pregnant or breastfeeding women.
24. Women of childbearing potential* who are unwilling to practice highly effective contraception prior to the initial dose/start of the first treatment, during the study, and for at least 4 months after the last dose. Highly effective contraceptive measures include:
    a. stable use of combined (estrogen and progestogen containing) hormonal contraception (oral, intravaginal, transdermal) or progestogen-only hormonal contraception (oral, injectable, implantable) associated with inhibition of ovulation initiated 2 or more menstrual cycles prior to screening
    b. intrauterine device (IUD); intrauterine hormone-releasing system (IUS)
    c. bilateral tubal ligation
    d. vasectomized partner
    e. and or sexual abstinence†, ‡.

*Postmenopausal women must be amenorrheic for at least 12 months in order not to be considered of childbearing potential. Pregnancy testing and contraception are not required for women with documented hysterectomy or tubal ligation.

†Sexual abstinence is considered a highly effective method only if defined as refraining from heterosexual intercourse during the entire period of risk associated with the study treatments.

‡Periodic abstinence (calendar, symptothermal, post-ovulation methods), withdrawal (coitus interruptus), spermicides only, and lactational amenorrhea method (LAM) are not acceptable methods of contraception. Female condom and male condom should not be used together.
25. Sexually active men who are unwilling to use the following forms of medically acceptable birth control during the study drug treatment period and for 4 months after the last dose of study drug: vasectomy with medical assessment of surgical success OR consistent use of a condom. Sperm donation is prohibited during the study and for 4 months after the last dose of study drug.
26. Use of concomitant medications, except those listed under permitted medications or nutritional supplements.

Description of Study Cohorts and Dose Escalation

Seven sequential ascending dose cohorts are planned to include doses of 0.3 mg/kg up to a maximum dose of 30 mg/kg. Each dose cohort will consist of 8 subjects: 6 randomized to receive H4H17319P2 and 2 randomized to receive placebo. In order to optimize safety, 8 subjects (6 active: 2 placebo) each in cohorts 1 (0.3 mg/kg IV), cohort 2 (1 mg/kg IV), cohort 3 (3 mg/kg IV), cohort 4 (300 mg SC), and cohort 5 (10 mg/kg IV) will be divided into 2 blocks. Two subjects (1 active: 1 placebo) will be enrolled in block 1 as a safety-sentinel group and the remaining 6 subjects (5 active: 1 placebo) will be enrolled in block 2. Subjects in block 1 will be enrolled first and will be dosed on the same day. Enrollment of subjects in block 2 will begin only after both subjects in block 1 have safely completed at least 24-hours safety assessments, the safety data has been reviewed by the investigator and by the sponsor medical monitor, and agreement by the investigator and by the sponsor medical monitor that enrollment of subjects in block 2 can begin. All subjects in block 2 may be dosed on the same day.

The 8 subjects (6 active: 2 placebo) each in cohorts 6 (600 mg SC) and cohort 7 (30 mg/kg IV) will be divided into 2 blocks of 4 subjects (3 active: 1 placebo). Dosing of each block will be performed on different days. Ascending dose cohorts will be enrolled as follows:

Cohort 1: H4H17319P2 at 0.3 mg/kg IV, single dose

Cohort 2: H4H17319P2 at 1 mg/kg IV, single dose

Cohort 3: H4H17319P2 at 3 mg/kg IV, single dose

Cohort 4: H4H17319P2 at 300 mg SC, single dose

Cohort 5: H4H17319P2 at 10 mg/kg IV, single dose

Cohort 6: H4H17319P2 at 600 mg SC, single dose

Cohort 7: H4H17319P2 at a nominal dose of 30 mg/kg IV, single dose

The optional cohorts will enroll if PK variability is larger than expected and additional subjects are required to examine the role of specific covariates such as age, weight, gender:

Cohort 8: H4H17319P2 at a nominal dose of 30 mg/kg IV, single dose

Cohort 9: H4H17319P2 at a nominal dose of 30 mg/kg IV, single dose A maximal dose of up to 30 mg/kg IV has been assigned to cohorts 8 and 9 but a lower dose may be administered, depending upon emerging PK data.

Dose Escalation: The Safety/Dose Escalation Team will include the investigator, medical/study director, study biostatistician, and risk management lead. Investigator(s), and other study site personnel, the sponsor study team including medical monitor, will also be blinded to the treatment administered. There may be unblinded individuals with the sponsor but these unblinded individuals will not be part of the sponsor's study team.

Dose escalation to cohort 2 (1 mg/kg) may proceed once all subjects in the previous cohort have completed day 8 safety assessments and the blinded safety data have been reviewed at a Safety/Dose Escalation Team meeting.

Dose escalation to cohort 3 (3 mg/kg IV) and cohort 4 (300 mg SC) may proceed once all subjects in the previous cohort have completed day 8 safety assessments and the blinded safety data have been reviewed at a Safety/Dose Escalation Team meeting. Dosing in cohort 4 can occur in parallel with dosing in cohort 3.

Dose escalation to cohort 5 (10 mg/kg IV) may proceed once all subjects in the cohort 3 have completed day 8 safety assessments and the blinded safety data have been reviewed at a Safety/Dose Escalation Team meeting.

Dose escalation to cohort 6 (600 mg SC) may proceed in parallel with cohort 5 but only once all subjects in the cohort 4 have completed day 8 safety assessments and the blinded safety data have been reviewed at a Safety/Dose Escalation Team meeting.

A nominal dose of 30 mg/kg IV has been assigned to cohort 7 but a lower dose may be administered, depending upon emerging PK data. Prior to dose escalation to 30 mg/kg IV, all subjects in cohort 5 will have completed day 8 safety assessments and the blinded safety data reviewed at a Safety/Dose Escalation Team meeting. Timing of safety/dose escalation decisions may be modified and additional safety data collected if pharmacodynamic effects on body weight are greater than expected. For example, if body weight is reduced by >3% in at least 3 out of the 6 subjects at 8 days, the observation period will be extended to day 15 before any dose escalation decisions will be made; if body weight is further reduced to >5% over 2 weeks in at least 3 out of the 6 subjects, the observation period will be extended to 4 weeks before deciding on dose escalation.

TABLE 19

| Dosing Cohorts in Parts A and B of Study | |
|---|---|
| Experimental: Part A: Single dose cohort 1<br>Cohort 1 will receive a single IV dose of H4H17319P2 or matching placebo | Drug: H4H17319P2<br>Drug: Placebo |
| Experimental: Part A: Single dose cohort 2<br>Cohort 2 will receive a sequential ascending single IV dose of H4H17319P2 or matching placebo | Drug: H4H17319P2<br>Drug: Placebo |
| Experimental: Part A: Single dose cohort 3<br>Cohort 3 will receive a sequential ascending single IV dose of H4H17319P2 or matching placebo | Drug: H4H17319P2<br>Drug: Placebo |
| Experimental: Part A: Single dose cohort 4<br>Cohort 4 will receive a sequential ascending single SC dose of H4H17319P2 or matching placebo | Drug: H4H17319P2<br>Drug: Placebo |
| Experimental: Part A: Single dose cohort 5<br>Cohort 5 will receive a sequential ascending single IV dose of H4H17319P2 or matching placebo | Drug: H4H17319P2<br>Drug: Placebo |
| Experimental: Part A: Single dose cohort 6<br>Cohort 6 will receive a sequential ascending single SC dose of H4H17319P2 or matching placebo | Drug: H4H17319P2<br>Drug: Placebo |
| Experimental: Part A: Single dose cohort 7<br>Cohort 7 will receive a sequential ascending single IV dose of H4H17319P2 or matching placebo | Drug: H4H17319P2<br>Drug: Placebo |
| Experimental: Part A: Single dose cohort 8<br>Cohort 8 will receive a single IV dose of H4H17319P2 or matching placebo | Drug: H4H17319P2<br>Drug: Placebo |
| Experimental: Part A: Single dose cohort 9<br>Cohort 9 will receive a single IV dose of H4H17319P2 or matching placebo | Drug: H4H17319P2<br>Drug: Placebo |
| Experimental: Part B: Repeated dose cohort 10<br>Cohort 10 will receive repeated IV or SC doses of H4H17319P2 or matching placebo | Drug: H4H17319P2<br>Drug: Placebo |

Study Design

This is a phase I randomized, double-blind, placebo-controlled 2-part study of the safety, tolerability, PK and pharmacodynamics (PD) of single and repeated doses of H4H17319P2 in healthy participants. In Part A, healthy lean or overweight subjects will be enrolled to evaluate the safety, tolerability, PK, and PD of single ascending intravenous (IV) and subcutaneous (SC) doses. Interim PK and safety information from Part A will be used to select the dose level, frequency, and mode of administration (IV or SC) for Part B. In Part B, overweight/obese subjects with body mass index (BMI) 25-40 kg/$m^2$ will be enrolled to evaluate the safety, tolerability, PK, and PD of repeated doses of H4H17319P2 in 4 distinct cohorts defined by baseline leptin levels.

In Part A, up to 88 subjects will be randomized to up to 7 sequential ascending single dose (up to 5 IV and 2 SC) cohorts (cohorts 1, 2, 3, 4, 5, 6, 7) and 2 optional single dose cohorts (cohorts 8 and 9). The 7 sequential single dose cohorts will have 8 subjects randomized to receive H4H17319P2 or placebo (6 active: 2 placebo) in each dose level. The 2 additional optional single dose cohorts will have up to 16 subjects randomized to receive H4H17319P2 or placebo (12 active: 4 placebo). Up to 5 single IV dose levels (0.3, 1.0, 3, 10, and 30 mg/kg) and 2 SC doses (300 and 600 mg) will be evaluated in a single ascending fashion. Decisions on whether to escalate doses will be based upon analysis of safety parameters and AEs. Interim analyses of antibody concentrations over time, exploratory PD measures and if applicable, PK/PD relationships among dose cohorts may also inform dose escalation decisions. Decision on enrollment of the 2 optional cohorts at dose levels up to a maximum of 30 mg/kg will be based upon interim analyses of PK profile variability.

Optional cohorts: Cohorts 8 and 9 will be enrolled if larger than expected PK variability is observed among subjects and additional subjects are needed to understand the effects of specific co-variates on PK profiles. Subjects in specific subgroups within the population defined by the inclusion/exclusion criteria, such as pre-specified number of males, females, age ranges, body weight or specific BMI cut points may be enrolled. A nominal dose of 30 mg/kg IV has been assigned to cohorts 8 and 9 but a lower dose may be administered, depending upon emerging PK data. Each of cohort 8 and 9 will enroll 16 subjects (4 assigned to receive placebo and 12 to receive H4H17319P2). Prior to dose escalation to 30 mg/kg IV, all subjects in cohort 5 will have completed day 8 safety assessments and the blinded safety data reviewed at a Safety/Dose Escalation Team meeting. The Part A study design consists of a screening period (days −21 to −2), a pre-baseline visit (day −1) where subjects will be admitted for an in-clinic stay with 2 overnight stays (for subjects receiving IV and for subjects receiving SC doses who are in the safety-sentinel block) or a 1-day clinic stay (for other subjects who receive SC dosing), a follow-up period (day 3 to day 113) and an end-of study visit (day 113). Throughout the study, safety assessments include vital signs, body weight, physical examination, ECGs, laboratory tests, and monitoring of AE, PK measures, and various PD assessments.

In Part B, up to 81 subjects with BMI 25-40 kg/$m^2$ will be enrolled into 4 cohorts (up to approximately 20 per cohort) defined by baseline leptin levels and randomized (3:1 or 6:1 H4H17319P2 vs placebo depending upon cohort assignment) into a placebo-controlled, double-blind, 12-week repeated dose study. The selection of dose, the dosing interval, and mode of administration (IV vs SC) will be based upon the safety, PK and if available, PK/PD, data from Part A. The PK profiles of H4H17319P2 from Part A will be used to predict concentrations in serum following repeated administration.

The study consists of a prescreening period (days −60 to −14), a screening period (days −32 to −14), a baseline period (day −29 to −1) to obtain baseline measurements of body weight, body composition by DXA and MRI, and an in-clinic stay to collect baseline measurements of fasting leptin, body weight, appetite assessments, and ad lib food intake assessment. Subjects will be admitted for a 2-day in-clinic stay on day −1. On day 1, subjects will receive the first dose of study drug or placebo, have serial blood sampling for pharmacokinetic measurements, and stay overnight for 24-hour PK sampling on day 2 when they will be discharged. Study drug may be administered every 4 weeks or every 2 weeks, but will be administered no more frequently than once every week during the treatment period (dose frequency will be determined by the interim analysis of the PK data from Part A).

Visits during the treatment period will occur up to every week to collect precise and repeated measurements of body weight, and serum metabolic parameters (glucose, insulin, HOMA-IR, lipids). Follow-up assessments of appetite and ad lib food intake will be conducted during in-clinic stays at week 4 and at the end of the treatment period (12 weeks). Subjects will also complete a daily appetite questionnaire during the baseline, treatment, and follow-up periods. Follow-up assessments of DXA and MRI imaging will also be performed. After the treatment period, subjects will be followed for a 16-week off drug period. Throughout the study, safety assessments will include vital signs, physical examination, ECGs, laboratory tests, and monitoring of AEs. Drug concentration, target engagement markers (sLEPR), and exploratory biomarkers will also be measured throughout study.

Study Duration

The duration of Part A of the study for a subject is approximately 19 weeks, including the screening period. The duration of Part B of the study for a subject is approximately 35 weeks including the prescreening/screening/baseline period. The end of study is defined as the last visit of the last subject in Part B.

Treatments(s) Dose/Route/Schedule

H4H17319P2 will be supplied as a lyophilized powder in a sterile, single-use 20 mL glass vial for either IV or SC administration. Placebo matching H4H17319P2 is prepared in the same formulation without the addition of protein. For Part A, single doses will be administered IV and SC. For Part B, the selection of dose, the dosing interval, and mode of administration (IV vs SC) will be based upon the safety, PK and if available, PK/PD, data from Part A.

Procedures and Assessments

Safety will be assessed by monitoring/evaluation of TEAEs, vital signs, physical examinations, electrocardiograms (ECGs), and laboratory tests. To assess pharmacokinetics, dense and sparse samples will be collected for measurement of H4H17319P2 concentration in serum at pre-specified time points. Pharmacodynamics will be assessed by measuring body weight and waist circumference, food intake and appetite assessments, and body composition using DXA and MRI.

Primary Outcome Measures:

1. Number of treatment-emergent adverse events (TEAEs) [Time Frame: Week 12 (End of treatment period)]

Secondary Outcome Measures:

1. Concentrations of H4H17319P2 in serum over time [Time Frame: Up to week 27 (End of study)]
2. Percent change in body weight in overweight or obese subjects [Time Frame: Baseline to week 12]
3. Absolute change in body weight in overweight or obese subjects [Time Frame: Baseline to week 12]
4. Change from baseline in caloric intake in response to standardized meals in overweight or obese subjects [Time Frame: Baseline to week 12]
5. Change in lipid-regulating protein levels over time after single doses of H4H17319P2 [Time Frame: Up to week 16]
6. Change in lipid-regulating protein levels over time after repeated doses of H4H17319P2 [Time Frame: Up to week 27]
7. Incidence of anti-drug antibodies to H4H17319P2 over time after single doses of H4H17319P2 [Time Frame: Up to week 16]
8. Incidence of anti-drug antibodies to H4H17319P2 over time after repeated doses of H4H17319P2 [Time Frame: Up to week 27]

Pharmacokinetic Variables

Concentrations of total H4H17319P2 will be measured in addition to time. Pharmacokinetic parameters may include, but are not limited to, the following:

$AUC_{last}$—area under curve (AUC) computed from time zero to the time of the last positive concentration $AUC_{0-\tau}$—AUC computed across a dosing interval with length T $C_{max}$—peak concentration $t_{max}$—time to $C_{max}$ CL—clearance $C_{trough}$—trough concentration Note that for Part B, the choice of these (and other) parameters depends on the final sampling schedule chosen as well as the resulting data obtained.

Anti-Drug Antibody Variables

Anti-drug antibody (ADA) variables include ADA response and titer as follows:

- Treatment-emergent response, defined as any post-dose positive ADA assay response when the baseline results are negative
- Treatment boosted ADA response, defined as any post-dose positive ADA assay response that is 9-fold or greater over baseline titer levels when baseline is positive in the ADA assay
- Titer values
- Titer category
  - Low (titer<1,000)
  - Moderate (1,000≤titer≤0,000)
  - High (titer>10,000)

Pharmacodynamic and Other Biomarker Variables

Pharmacodynamic and biomarker variables are: Body weight, ad lib food intake assessments, Appetite assessments, Serum/plasma glycemic (e.g., fasting glucose, insulin, HbA1c) and lipid parameters (e.g., total cholesterol, TG, LDL-C, HDL-C), DXA measurements of fat and lean mass overall and by body location, MRI quantification of regional SC and visceral fat, ANGPTL3, Leptin, and sLEPR. Additional exploratory biomarkers will include effects of H4H17319P2 on thyroid hormone (T3, T4, TSH), luteinizing hormone (LH), testosterone, estradiol, cortisol, and adiponectin.

Efficacy Procedures

Body weight will be assessed during screening and throughout the study at designated study visits. Body weight will be assessed in triplicate using high precision calibrated digital scales before other study assessments are performed. Subjects should void (empty bladder) prior to weight assessment. Subjects should only be wearing undergarments and no shoes during weight assessments. Body weights will be recorded to the nearest 0.1 kg.

All anthropometric measurements should be done in triplicate, with the final reported value being the average. Triceps, subscapular, suprailiac, and thigh skinfold thickness should be taken from the right side of the body in areas of dry, intact skin, excepting if a deformity or missing limb requires otherwise. To measure waist circumference, the subject is instructed to stand straight and relaxed with arms at their side and feet together pointing forward. The iliac crest and lowest rib margins are identified by palpation, and skin overlying these areas is marked with a pen. The midpoint between these skin markings is then identified using a tape measure and marked with a pen. The waist circumference at the midpoint mark is then measured using a tape measure at the end of a gentle expiration. Height is measured in the fully erect standing position at end-inhalation using a calibrated stadiometer, and recorded to the nearest 0.1 cm. For Part B and optional cohorts in Part A, height will be measured as a single measurement at the prescreening or screening visit, respectively. Body mass index will be calculated using the average of the weight (kilograms) divided by the square of the height (meters). In Part A (except for the optional cohorts), the average height is to be used for the calculation. In Part B and optional cohorts in Part A, the values for height (single measurement at prescreening or screening, respectively) and weight (average of 3 determinations) at each visit are used for the calculation of BMI.

Ad libitum food intake will be assessed. Subjects will be excluded at screening if they have abnormal eating behaviors or aversions to foods used in the food intake assessment. Energy intake (breakfast+lunch+dinner) using an ad lib food intake assessment will be quantified in Part B at baseline, after 4-weeks of treatment, and at the end of treatment period (12-weeks). Subjects will be asked to avoid strenuous activity and alcohol consumption 1 day prior to the in-clinic visits when food assessments will be assessed.

Subjects will be admitted to the clinic in a fasting state, arriving to the clinic in the morning. In the 4-week on-treatment inpatient food intake assessments, subjects will receive their assigned treatment (study drug or placebo). They will then be provided a standardized breakfast, lunch and dinner of fixed caloric and macronutrient content, and then fasted overnight. The following day, they will be provided an ad lib breakfast, an ad lib lunch and an ad lib dinner. During the ad lib test meals, subjects will be provided a quantity of food that is in great excess (4-5 times) of a typical portion. Meals will be designed by a nutritionist to be of standardized macronutrient content and known caloric density. All meals and serving items will be covertly weighed using a dedicated calibrated scale prior to test meals and after test meals to accurately assess the amount of food consumed to within 0.1 g. Subjects will consume all meals in private, specialized rooms free of clocks, radios, cell phones, and televisions, so as to eliminate time or social cues that might influence food intake. Meals will be presented in a way to mask the quantity of food consumed, so that food intake will not be affected by visual/social cues of overeating such as the amount of food available. Subjects will be asked to eat as much or as little as they like, and for the duration of the test meal they will be undisturbed and be forbidden from engaging in leisure activities such as reading, listening to music, talking on the phone, or watching videos. Subjects will be permitted to leave the test meal room when they have been adequately satiated, and if they have not done so after 1 hour the meal will be terminated by study personnel.

In-Clinic Appetite Assessment and Daily Appetite Questionnaire (Part B Only)

In-clinic appetite will be assessed by survey questions (Flint, 2000), with subjects instructed to record their answer on a visual analog scale. Subjects will complete an in-clinic appetite assessment within approximately 30 minutes before and after the standardized dinner during the first day of in-clinic stays as well as a daily appetite questionnaire during the baseline, treatment, and follow-up periods. Care will be taken to ensure that research subjects do not share results of the survey with other study participants. Details of the questions used in the in-clinic appetite assessment and daily appetite questionnaire for Part B of the study will be described in a study manual and the questions (when finalized) will be submitted to the ethics committee for review before the start of Part B.

Body Composition by DXA (Part B Only)

DXA is extensively used in clinical whole-body skeletal densitometry. Total examination times are brief (~6 to 7 minutes) and ionizing radiation doses are minimal at ~0.1 mGy. Dual X-ray absorptiometry has the capability to provide estimates of lean body mass (LBM) and body composition, and it has been used for LBM measurements in a clinical research setting. Clinical validity of DXA for LBM measurements is supported by longitudinal studies demonstrating a significant association between changes in LBM and decline in physical function (Goodpaster, 2006). Dual X-ray absorptiometry will be performed twice during the baseline period, at the end of treatment visit, and at the end of study. Regarding individual subject preparation for DXA scans, efforts should be made to maintain consistent hydration, consistent intake of meals, consistent intake of caffeine, consistent activity (no strenuous activities 24 hours before scans), consistent clothing, and consistent subject positioning on the D×A table for scans throughout the study. Also, the DXA scans should be obtained at the same general time of day for any given subject throughout the study.

Body Composition by MRI (Part B Only)

Magnetic resonance imaging is used in the measurement of hepatic fat fraction. A multi-echo gradient-recalled echo sequence acquiring axial images to cover the entire liver is recommended. The echo times shall be such that at successive echo times (TEs), fat and water alternate between out-of-phase and in-phase. To minimize motion artifacts, these should be acquired under brief breath hold periods. The full acquisition should take 3 to 5 minutes. Scanning of the thighs for fat fraction requires careful positioning of the subject and immobilization using shaped foam supports and localizers. The complete thigh MRI acquisition may take up to 10 minutes. Subjects may be required to fast 10 to 12 hours prior to a morning scan.

Study Schedule of Events and Footnotes

Study assessments and procedures are presented by period and visit in FIGS. 25, 26, and 27 with the following footnotes:

1. Clinic discharge for non-sentinel SC dosing groups, but site has the option for subject to stay overnight with discharge the following day.
2. Clinical discharge for IV dosing and safety-sentinel SC dosing
3. On day 1 for the IV cohorts in Part A, vital signs should also be measured and AEs monitored pre-dose, at 30 minutes, at the end of study drug infusion, and at 1 hour, 2 hours, 4 hours, and 8 hours post infusion. On day 1 for the SC cohorts in Part A, vital signs should also be measured and AEs monitored pre-dose, at 30 minutes after injection, and at 1 hour, 2 hours, 4 hours, and 8 hours post injection. For dose administration in Part B on day 1, vital signs should also be measured and AEs monitored pre-dose, at 30 minutes, at the end of study drug infusion for IV doses, and at 1 hour, 2 hours, 4 hours, and 8 hours after infusion or injection for IV or SC doses, respectively. On subsequent days of dosing, vital signs should also be measured and AEs monitored pre-dose, at 30 minutes, at the end of study drug infusion for IV doses, and at 1 hour, 2 hours, and 4 hours after infusion or injection for IV and SC doses, respectively. Vital signs also include orthostatic blood pressure assessments at the screening visit (Part A and B) and on day 1 (Part A only). For orthostatic assessments, blood pressure and pulse rate are measured with the subject lying supine for approximately 10 minutes, after standing for approximately 1 minute, and after standing for approximately 3 minutes.
4. Blood draws collected after fasting for at least 8 hours. On days of dosing, only the pre-dose sample needs to be under fasted conditions.
5. Body weight must be measured in triplicate while in a fasted state, after voiding (empty bladder) without shoes and wearing only undergarments using a dedicated, calibrated scale.
6. Skin fold thickness should be taken in triplicate from the following regions: triceps, subscapular, suprailiac and thigh in order to provide an adequate description of the body fat distribution.
7. Collection of samples for drug concentration, sLEPR concentration, and ANGPTL3 concentration on day 1 will be pre-infusion/injection, post-infusion/injection ±15 mins, and at 1 hour±15 mins, 2 hours±15 mins, 4 hours±15 mins, 8 hours±15 mins, 12 hours±15 mins, and 24 hours±15 mins post-infusion/injection. sLEPR and ANGPTL3 may only be analyzed at a subset of the timepoints that drug concentration is measured.
8. DNA can be collected at any visit
9. Option to stay overnight with discharge the following day. For Part B, subjects will also be admitted to the clinic one day prior to day 1 (day −1) and stay overnight. Day 1 procedures (except for assessments that must be performed after an overnight fast, ECG, PK measurements, and study drug administration) such as drug screen, urinalysis, and urine pregnancy tests may be performed on day −1.
10. Visit at day 30 must occur exactly 1 day after visit at day 29.
11. Visit at day 85 must occur 1 day after visit at day 84.
12. Frequency of study drug dosing in Part B will depend on the results obtained in Part A.
13. Two baseline images (DXA and MRI) will be obtained from day −29 to day −14. Both DXA and MRI can be conducted on the same day or different days; however, the 1st and 2nd DXA and the 1st and 2nd MRI must be performed on separate days
14. DXA and MRI procedures for visit 18 may be performed up to 5 days prior to the visit, or up to 5 days after visit 18, but DXA and MRI should not be performed <24 hours after dosing of study drug. DXA and MRI procedures for visit 24 may be performed up to 7 days prior to visit 24.
15. For Part B, actual sample collection schedule will depend on interim review of PK data from Part A. However, since it is repeat-dosing, dense sampling will be performed after the first dose and trough samples at other time points.
16. In-clinic appetite assessment will be performed before and after standardized dinner
17. Site will check subject's adherence to completion of daily appetite questionnaire at each designated visit.
18. ECG will be performed pre-dose.

Safety

Vital signs, including temperature, blood pressure, pulse, and respiration rate will be collected after the subject has been in resting sitting or supine position for at least 10 minutes predose at time points according to FIGS. 25-27.

A thorough physical examination will be performed at time points according to FIGS. 25-27. Care should be taken to examine and assess any abnormalities that may be present, as indicated by the subject's medical history.

Electrocardiograms should be performed before blood is drawn during visits requiring blood draws. A standard 12-lead ECG will be performed at time points according to FIGS. 25-27. A 12-lead ECG should be performed in the supine position after the subject is resting for at least 10 minutes. The ECG will be interpreted locally by the investigator. Heart rate will be recorded from the ventricular rate, and the PR, QRS, RR, QTcB and QTcF intervals will be recorded. Any clinically significant abnormality should be documented as an AE/SAE as applicable. Each ECG tracing will be analyzed in comparison with the screening record trace. The ECG strips or reports will be retained with the source.

Hematology, chemistry, urinalysis, drug screening, and pregnancy testing samples (serum or urine) will be analyzed. Detailed instructions for blood sample collection are in the laboratory manual provided to study sites. Samples for laboratory testing will be collected at visits according to FIGS. 25-27. Tests will include: Blood Chemistry: Sodium, Potassium, Chloride, Bicarbonate, Calcium, Glucose, Albumin, Total serum protein, Creatinine, Blood urea nitrogen (BUN), Aspartate aminotransferase (AST), Alanine aminotransferase (ALT), Alkaline phosphatase, Lactate dehydrogenase (LDH), Gamma-glutamyl Transferase (GGT), Total bilirubin, Total cholesterol (low-density lipoprotein [LDL] and high-density lipoprotein [HDL]), Triglycerides, Uric acid, Creatine phosphokinase (CPK), LDL-C, HDL-C; Hematology: Hemoglobin, Hematocrit, Red blood cells (RBCs), White blood cells (WBCs), Red cell indices (mean corpuscular volume, [MCV], mean corpuscular hemoglobin, [MCH], mean corpuscular hemoglobin concentration [MCHC], red blood cell distribution width [RDW]), Platelet count, Differential (*Additional testing by flow cytometry may be performed to assess cell subpopulations if clinically significant, abnormalities are observed) including Neutrophils, Lymphocytes, Monocytes, Basophils, and Eosinophils; Urinalysis: Color, Glucose, RBC, Clarity, Blood Hyaline and other casts, pH, Bilirubin, Bacteria, Specific gravity, Leukocyte esterase, Epithelial cells, Ketones, Nitrite, Crystals, Protein, WBC, Yeast; Other Laboratory Tests: Leptin, insulin and endocrine hormones such as thyroid hormone (T3, T4, TSH), luteinizing, hormone (LH), testosterone, estradiol, as well as HbA1c will be evaluated in Parts A and B. For Part B serum leptin will be measured at the prescreening visit to determine subject eligibility for, 1 of 4 cohorts. Leptin will also be measured throughout the study as noted in FIGS. 25-27. Other proteins that will be measured include adiponectin and cortisol.

Abnormal Laboratory Values and Laboratory Adverse Events

All laboratory values must be reviewed by the investigator or authorized designee. Significantly abnormal test results that occur after start of treatment must be repeated to confirm the nature and degree of the abnormality. When necessary, appropriate ancillary investigations should be initiated. If the abnormality fails to resolve or cannot be explained by events or conditions unrelated to the study medication or its administration, the Medical/Study Director must be consulted.

The clinical significance of an abnormal test value, within the context of the disease under study, must be determined by the investigator.

Drug Concentration Measurements and Samples

Samples for measurement of H4H17319P2 concentration in serum during Part A will be collected at the time points listed in FIG. 25. Nominally, samples for measurement of H4H17319P2 concentration in serum during Part B will be collected at the time points listed in FIG. 27. However, once the schedule of events for Part B has been confirmed based upon interim analysis of data from Part A, samples for measurement of H4H17319P2 in serum during Part B will be collected at a set of (possibly) revised time points. Any unused samples may be used for exploratory biomarker research.

Anti-Drug Antibody Measurements and Samples

Samples for anti-drug antibody assessment for Parts A and B will be collected at time points listed in FIGS. 25 and 27. Any unused samples may be used for exploratory biomarker research.

Pharmacodynamic and Exploratory Biomarker Procedures

In this study, research assessments will be performed to explore how H4H17319P2 may modify appetite, food intake, body weight, and circulating markers such as soluble LEPR and ANGPTL3, as well as exploratory biomarkers.

Soluble LEPR is present in circulation of healthy and disease subjects. It is a non-signaling form of the leptin receptor that is able to bind to leptin and may regulate its bioavailability. H4H17319P2 may bind to sLEPR in circulation in a dose dependent and time dependent manner. Soluble LEPR will be measured pre-dose on visit at day 1 and subsequent visits noted in FIGS. 25 and 27. The change in sLEPR may reflect target engagement and saturation after H4H17319P2 administration.

ANGPTL3 is an endogenous inhibitor of lipoprotein lipase, which regulates circulating triglycerides. It is possible that H4H17319P2 regulates triglycerides via ANGPTL3; therefore, circulating concentrations of ANGPTL3 will be measured in serum pre-dose and post treatment at various time points following dosing to capture the post-prandial changes. The dose dependent effect of H4H17319P2 on ANGPTL3 will be explored in both Parts A and B as outlined in FIGS. 25-27.

Other exploratory biomarkers that may be measured in serum or plasma include leptin, adiponectin and endocrine hormones, which are thought to be modulated during weight loss. The markers will be measured according to the biomarker assessment collections in FIGS. 25-27.

Adverse Reactions and Adverse Events

Emergency equipment and medication for the treatment of infusion reactions must be available for immediate use. All infusion reactions must be reported as AEs and graded using appropriate grading scales. The infusion should be interrupted if any of the following AEs are observed: cough, rigors/chills, rash, pruritus (itching), urticaria (hives, welts, wheals), diaphoresis (sweating), hypotension, dyspnea (shortness of breath), vomiting, and flushing.

The reaction(s) should be treated symptomatically, and the infusion should not be restarted. If investigators feel there is a medical need for treatment or discontinuation of the infusion other than described above, they should use clinical judgment to provide the appropriate response according to typical clinical practice.

The infusion should be terminated and NOT restarted if any of the following AEs occur: Anaphylaxis, laryngeal/pharyngeal edema, severe bronchospasm, chest pain, seizure, severe hypotension, other neurological symptoms (confusion, loss of consciousness, paresthesia, paralysis, etc), any other symptom or sign that, in the opinion of the investigator, warrants termination of the IV infusion. Consider anaphylaxis if the following is observed (Sampson, 2006): acute onset of an illness (minutes to several hours) with involvement of the skin, mucosal tissue, or both (e.g., generalized hives, pruritus or flushing, swollen lips-tongue-uvula) and at least one of the following: Respiratory compromise (e.g., dyspnea, wheeze-bronchospasm, stridor, reduced peak expiratory flow, hypoxemia) and reduced blood pressure or associated symptoms of end-organ dysfunction (e.g., hypotonia [collapse], syncope, incontinence).

Emergency equipment and medication for the treatment of systemic reactions must be available for immediate use. All infusion reactions must be reported as AEs and graded using the grading scales as instructed. Acute systemic reactions following injection of study drug (SC) should be treated using clinical judgment to determine the appropriate response according to typical clinical practice.

Local injection site reactions must be reported as AEs and graded according to the Food and Drug Administration (FDA) September 2007 Guidance for Industry, Toxicity Grading Scale for Healthy Adult and Adolescent Volunteers Enrolled in Preventive Vaccine Clinical Trials (provided in the study Regulatory Binder).

An AE is any untoward medical occurrence in a subject administered a study drug, which may or may not have a causal relationship with the study drug. Therefore, an AE is any unfavorable and unintended sign (including abnormal laboratory finding), symptom, or disease, which is temporally associated with the use of a study drug, whether or not considered related to the study drug. An AE also includes any worsening (i.e., any clinically significant change in frequency and/or intensity) of a pre-existing condition that is temporally associated with the use of the study drug.

A serious adverse event (SAE) is any untoward medical occurrence that at any dose:

- Results in death—includes all deaths, even those that appear to be completely unrelated to study drug (e.g., a car accident in which a subject is a passenger).
- Is life-threatening—in the view of the investigator, the subject is at immediate risk of death at the time of the event. This does not include an AE that had it occurred in a more severe form, might have caused death.
- Requires inpatient hospitalization or prolongation of existing hospitalization. Inpatient hospitalization is defined as admission to a hospital or an emergency room for longer than 24 hours. Prolongation of existing hospitalization is defined as a hospital stay that is longer than was originally anticipated for the event, or is prolonged due to the development of a new AE as determined by the investigator or treating physician.
- Results in persistent or significant disability/incapacity (substantial disruption of one's ability to conduct normal life functions).
- Is a congenital anomaly/birth defect.
- Is an important medical event—Important medical events may not be immediately life-threatening or result in death or hospitalization, but may jeopardize the subject or may require intervention to prevent one of the other serious outcomes listed above (e.g., intensive treatment in an emergency room or at home for allergic bronchospasm; blood dyscrasias or convulsions that do not result in hospitalization; or development of drug dependency or drug abuse).

Criteria for reporting SAEs must be followed for these events.

An adverse event of special interest (AESI; serious or non-serious) is one of scientific and medical concern specific to the sponsor's product or program, for which ongoing monitoring and rapid communication by the investigator to the sponsor can be appropriate. Such an event might warrant further investigation in order to characterize and understand it. Depending on the nature of the event, rapid communication by the trial sponsor to other parties (e.g., regulators) might also be warranted.

Infusion reactions are defined as any relevant AE that occurs during the infusion or within 2 hours after the infusion is completed. All infusion reactions must be reported as AEs and graded.

The investigator (or designee) will record all AEs that occur from the time the informed consent is signed until the end of study. Laboratory, vital signs, or ECG abnormalities are to be recorded as AEs. All SAEs, regardless of assessment of causal relationship to study drug, must be reported to the sponsor (or designee) within 24 hours.

Information not available at the time of the initial report must be documented in a follow-up report. Substantiating data such as relevant hospital or medical records and diagnostic test reports may also be requested. In the event the investigator is informed of an SAE after the subject completes the study, the following will apply:

Part A: SAE with an onset within 30 days of the end of study or within 112 days of last study drug administration if the subject early terminated from the study—the SAE will be reported to the sponsor. The investigator should make every effort to obtain follow-up information on the outcome until the event is considered chronic and/or stable.

Part B: SAE with an onset within 30 days of the end of study or within 112 days of last study drug administration if the subject early terminated from the study—the SAE will be reported to the sponsor. The investigator should make every effort to obtain follow-up information on the outcome until the event is considered chronic and/or stable.

Part A and B: SAE with an onset day greater than 30 days from the end of study/early termination visit—only fatal SAEs and those deemed by the investigator to be drug-related SAEs will be reported to the sponsor. The investigator should make every effort to obtain follow-up information on the outcome of a drug-related SAE until the event is considered chronic and/or stable.

Results

In the initial (Part A) single ascending dose portion of the study, patients were randomized 3:1 to H4H17319P2 vs. placebo in one of 7 cohorts to receive doses from 0.3 mg/kg intravenously (IV) up to 30 mg/kg IV, and 300 mg subcutaneously (SC) to 600 mg SC. Fifty-six patients have been dosed with H4H17319P2 or placebo, and pharmacokinetic (PK) and safety data are available for a minimum of 85 days after dose administration. Review of the blinded data has not revealed any serious or severe adverse events with any of the doses administered, and no death was reported. Treatment with H4H17319P2 or placebo was generally well tolerated when administered via the IV or SC route. There were no treatment interruptions or discontinuations. Headache was the most commonly reported treatment-emergent adverse event (TEAE). There were no clinically significant abnormalities or dose dependent shifts from baseline in safety laboratory parameters, vital signs or ECGs.

Example 21: Clinical Use of Anti-LEPR Antibody for Treatment of Congenital Leptin Deficiency in a Pediatric Patient Briefly, a patient presented at 6 months of age with extreme obesity, hyperphagia, hyperinsulinemia, dyslipidemia, grade 2 hepatosteatosis, and low leptin levels (0.55 ng/mL). The patient was diagnosed with leptin gene deletion ($LEP^{-/-}$) by polymerase chain reaction and the diagnosis was confirmed by multiplex ligation-dependent probe amplification under European Medical Genetics Quality Network standards. The patient was started on metreleptin therapy at 24 months of age and responded with a 10 kg weight loss (from 37 kg to 27 kg) over the ensuing 6 months. The patient then began quickly gaining weight. Recently, the patient has had respiratory compromise requiring hospitalization, presumably as a result of extreme obesity and frequent infections. The physician tested for neutralizing antibodies by measuring leptin levels 1 hour after metreleptin administration. Laboratory tests demonstrated leptin levels <0.1 ng/mL, confirming that the patient had developed neutralizing antibodies to metreleptin. These findings explain the patient's weight gain and demonstrate that metreleptin is no longer an effective therapy for the treatment of this patient's condition.

H4H17319P2 treatment will be used to restore LEPR signaling in congenital leptin deficiency and improve hyperphagia, weight gain, and metabolic complications of this condition.

Inclusion/Exclusion Criteria for Additional Pediatric Patients

A patient must meet the following criteria to be eligible for inclusion in this compassionate use program:

1. Congenital leptin deficiency, with confirmed genetic diagnosis of LEP loss-of-function variant and/or gene deletion
2. Severe obesity, defined for adults as BMI kg/$m^2$ and for children as weight >$97^{th}$ percentile for age and gender
3. Leptin levels <1.0 ng/mL
4. Evidence of neutralizing antibodies to metreleptin, defined as:
   loss of metreleptin effectiveness, in the judgement of the treating physician, with documented evidence of weight gain on leptin therapy AND
   leptin levels <1.0 ng/mL, 1 hour after injection of leptin OR positive neutralizing antibody activity assay performed by Aegerion, the manufacturer of metreleptin.

Patients eligible for an ongoing clinical trial for treatment of congenital leptin deficiency will be excluded.

Dose Selection

The dose regimen described herein is anticipated to be generally well tolerated. H4H17319P2 was well-tolerated in healthy adult volunteers when administered as single doses of 0.3 to 30 mg/kg IV and 300 and 600 mg SC. A maximal concentration in serum of 1035 mg/L was observed at a 30 mg/kg IV dose, which is almost twice the maximum value predicted to be observed in pediatric patients over the course of treatment. In addition, predicted area under the concentration-time curve (AUC) over a 1-week dosing interval at steady-state is expected to be at least 8 times lower than the AUC at steady state over the same dosing interval (at the no observed adverse effect level [NOAEL]) estimated from a pharmacokinetic model derived from 3 preclinical toxicology studies in cynomolgus monkeys.

A 5 mg/kg intravenous (IV) loading dose was chosen in order to rapidly achieve concentrations of H4H17319P2 in serum at or above 100 mg/L. Inclusion of this IV loading dose will allow immediate assessment of maximal concentration ($C_{max}$) of H4H17319P2 in serum. A weekly subcutaneous (SC) maintenance dose of 250 mg H4H17319P2 will sustain trough concentrations in serum at or above 100 mg/L. This SC dosing regimen is to commence 3 days after administration of the IV loading dose to best maintain targeted trough concentrations in serum.

Treatment and Evaluation Schedule

The initial treatment and evaluation plan for pediatric patients is outlined in Table 20. Treatment and evaluation recommendations will be updated and communicated to the physician(s) as PK and PD data are available. The plan should be followed as closely as possible, and any deviations should be noted. Prior to administering H4H17319P2 or performing any of the below assessments, written informed consent must be obtained. After a single IV loading dose of 5 mg/kg on day 1, H4H17319P2 will be administered as a Q7 day (weekly) SC dose of 250 mg. The first SC dose will be administered on day 4.

H4H17319P2 will be administered once via IV on day 1 over a 1-hour infusion. Intravenous administration of H4H17319P2 should be via the specified types of IV infusion pumps (Alaris, Gemini, PC-1, or similar; Baxter, Flo-Gard 6201 or similar; Hospira, Lifecare 5000 or similar) and IV infusion sets (Baxter, Product Code 2C6571 or similar; Alaris, Product No. 2430-0500 or similar; Alaris, Product No. 11532269 or similar; Hospira Product No. 14255-28 or similar; Baxter, Product Code 2H6480 or similar; Hospira Product No. 12336-05 or similar). The in-line filter and the IV infusion pump must be able to deliver as little as 1 mL/minute accurately.

The timing of serum sampling for H4H17319P2 drug concentration and anti-H4H17319P2 antibody measurements, body weight assessments, metabolic parameter assessments and the shipment of samples to the trial sponsor is also provided in Table 20. A patient's H4H17319P2 levels and body weight measurements may be used to update dose level and dosing frequency recommendations after day 25 and to establish whether H4H17319P2 administration is showing signs of benefit in this patient. Measuring antibody concentrations will allow assessment of whether the dose and dose regimen selected was optimal or whether adjustments are required. Any unused serum samples collected for drug concentration and anti-drug antibody (ADA) assessments may be used to investigate unexpected adverse events and for research purposes and may be stored for up to 15 years.

Any other disease-related clinical parameters obtained by a physician as part of routine and standard care of the patient should be communicated to the trial sponsor for safety monitoring purposes. This includes but is not limited to vital signs and laboratory values (i.e., blood chemistry with liver enzymes, hematology, metabolic parameters). Such information could inform further dosing for the patient and may also help determine whether H4H17319P2 administration is showing signs of benefit or harm.

In the event of anaphylaxis or hypersensitivity, additional serum samples should be collected as close to the event as possible. Additional labels will be provided in the event of unscheduled sample collections.

Emergency equipment and medication for the treatment of infusion reactions after IV infusion of H4H17319P2 or systemic reactions after the injection of H4H17319P2 must be available at the site. Acute IV infusion or systemic injection reactions following administration of H4H17319P2 should be treated using clinical judgment to determine the appropriate response according to typical clinical practice. All safety-related findings and adverse events that the treating physician becomes aware of should be reported to the trial sponsor as soon as possible and strictly in accordance with any local requirements pertaining to the use of investigational products on a compassionate use basis. Such adverse events include any untoward medical occurrence that results in death, is life threatening, requires in-patient hospitalization or prolongation of existing hospitalization, results in persistent or significant disability/incapacity, is a congenital anomaly/birth defect, or is an important medical event (such as intensive treatment in an emergency room or at home for allergic bronchospasm; blood dyscrasias or convulsions that do not result in hospitalization; or development of drug dependency or drug abuse).

TABLE 20

Schedule of Treatments, Assessments, and Sample Collections

| Day | REGN4461 Administration | Serum Sample Collection for PK Analysis | Serum Sample Collection for ADA Analysis | Body Weight | Sample Collection for Metabolic Parameters† | Shipments of Serum Samples to Sponsor |
|---|---|---|---|---|---|---|
| 1 | 5 mg/kg IV | X (pre-dose) and X (1-hour post-dose) | X (pre-dose) | X | X | |
| 2 | | | | | | |
| 3 | | | | | | |
| 4 | 250 mg SC | X (pre-dose) | | X | X | |
| 5 | | X | | | | |
| 6 | | | | | | |
| 7 | | X | | | | |
| 8 | | | | | | |
| 9 | | X | | | | |
| 10 | | | | | | |
| 11 | 250 mg SC | X (pre-dose) | | X | X | X |
| 12 | | | | | | |
| 13 | | X | | | | |
| 14 | | X | | | | |
| 15 | | | | | | |
| 16 | | X | | | | |
| 17 | | | | | | |
| 18 | 250 mg SC | X (pre-dose) | | X | X | |
| 19 | | | | | | |
| 20 | | | | | | |
| 21 | | | | | | |
| 22 | | | | | | |
| 23 | | | | | | |
| 24 | | | | | | |
| 25 | 250 mg SC | X (pre-dose) | | X | X | X |
| 53 | 250 mg SC | X (pre-dose) | | X | X | |
| 81 | 250 mg SC | X (pre-dose) | | X | X | |
| 109 | 250 mg SC | X (pre-dose) | X (pre-dose) | X | X | X |
| 137 | 250 mg SC | X (pre-dose) | | X | X | |
| 165 | 250 mg SC | X (pre-dose) | | X | X | |
| 193 | 250 mg SC | X (pre-dose) | X (pre-dose) | X | X | X |

†Administration of H4H17319P2 and pre-dose serum collections will continue weekly unless modifications are recommended based on the sponsor's review of PK and body weight data.

Preparation of H4H17319P2 for 5 mg/kg Dose Administered Via IV Infusion Bag

The volume of reconstituted H4H17319P2 to be added to the IV bag for a dose of 5 mg/kg is listed below in Table 21.

TABLE 21

Amounts of 50 mg/mL H4H17319P2 to be Added to a 100 mL Saline-Containing IV Bag for a Dose of 5 mg/kg

| Patient Weight (kg) | Volume of IP (ml) | Volume of Saline to Remove from IV Bag (mL) | Number of IP Vials |
|---|---|---|---|
| 40 | 4.0 | 4.0 | 1 |
| 41 | 4.1 | 4.1 | 1 |
| 42 | 4.2 | 4.2 | 1 |
| 43 | 4.3 | 4.3 | 1 |
| 44 | 4.4 | 4.4 | 1 |
| 45 | 4.5 | 4.5 | 1 |
| 46 | 4.6 | 4.6 | 1 |
| 47 | 4.7 | 4.7 | 1 |
| 48 | 4.8 | 4.8 | 1 |
| 49 | 4.9 | 4.9 | 2 |
| 50 | 5.0 | 5.0 | 2 |
| 51 | 5.1 | 5.1 | 2 |
| 52 | 5.2 | 5.2 | 2 |
| 53 | 5.3 | 5.3 | 2 |
| 54 | 5.4 | 5.4 | 2 |
| 55 | 5.5 | 5.5 | 2 |
| 56 | 5.6 | 5.6 | 2 |
| 57 | 5.7 | 5.7 | 2 |
| 58 | 5.8 | 5.8 | 2 |

TABLE 21-continued

Amounts of 50 mg/mL H4H17319P2 to be Added to a 100 mL Saline-Containing IV Bag for a Dose of 5 mg/kg

| Patient Weight (kg) | Volume of IP (ml) | Volume of Saline to Remove from IV Bag (mL) | Number of IP Vials |
|---|---|---|---|
| 59 | 5.9 | 5.9 | 2 |
| 60 | 6.0 | 6.0 | 2 |
| 61 | 6.1 | 6.1 | 2 |
| 62 | 6.2 | 6.2 | 2 |
| 63 | 6.3 | 6.3 | 2 |
| 64 | 6.4 | 6.4 | 2 |
| 65 | 6.5 | 6.5 | 2 |
| 66 | 6.6 | 6.6 | 2 |
| 67 | 6.7 | 6.7 | 2 |
| 68 | 6.8 | 6.8 | 2 |
| 69 | 6.9 | 6.9 | 2 |
| 70 | 7.0 | 7.0 | 2 |
| 71 | 7.1 | 7.1 | 2 |
| 72 | 7.2 | 7.2 | 2 |
| 73 | 7.3 | 7.3 | 2 |
| 74 | 7.4 | 7.4 | 2 |
| 75 | 7.5 | 7.5 | 2 |

IP = investigational product

Each vial of H4H17319P2 will be reconstituted with 4.9 mL of sterile water for injection.

Once reconstituted, each vial of H4H17319P2 will contain 4.8 mL withdrawal volume. When reconstituted for IV administration, the concentration in a vial of H4H17319P2 will be 50 mg/mL. The steps for reconstitution are as follows:

1. Obtain the required number of vials of lyophilized H4H17319P2 along with a 100 mL infusion bag of 0.9% sodium chloride
2. Prepare H4H17319P2 while working on a hard, clean surface
3. Remove the cap(s) from the vial(s) and wipe the top surface of the vial with an alcohol swab.
4. For each vial to be used for dosing, obtain one 21-gauge needle and one 10.0 mL polypropylene syringe. Without removing the cap from the needles, attach the 21-gauge needles to the 10.0 mL polypropylene syringe. With the cover on, pull back the plunger on the 10.0 mL syringe to the 5.5 mL mark. This is to draw air into the syringes.
5. Remove the caps from the 21-gauge needles. Insert the needles into the rubber top of the vial containing the sterile water for injection. Push the plungers down to inject all the air into the vial. Turn the vial upside down in one hand, and make sure that the tip of the needle is in the water. Pull at least 5.5 mL of sterile water for injection into the syringe. Do not set the needles down on a dirty surface, touch the needles with fingers or breathe directly on the needles.
6. Prime the syringes by inverting the syringes (needle up) and depressing the plunger until air has been expelled from the syringes. Continue to depress the plungers until a small amount of liquid comes out and the plungers reach 4.9 mL.
7. Place the H4H17319P2 vial on a hard surface and insert the needle in the top. Add the 4.9 mL of sterile water for injection into the drug vial, directing the stream of water onto the side of the vial and into the powdered drug.
8. Remove the needles from the vial after pushing all the water out of the syringes and into the vial. Discard the needles and syringes into a Sharps container.
9. Gently swirl the vial in an upright position until all the powder is dissolved.
10. Do not shake the vial. Shaking may result in foaming.

IV Administration of H4H17319P2

The steps for administering the antibody are as follows:

1. Use standard aseptic technique to withdraw the appropriate amount of H4H17319P2 according to Table 21 using an appropriate size polypropylene syringe and 21-gauge needle. Do not set the needle down on a dirty surface, touch the needle with fingers, or breathe directly onto the needle.
2. Before adding the H4H17319P2 solutions to the 100 mL IV bag, withdraw a volume of 0.9% sodium chloride from the IV bag equal to the volume of H4H17319P2 to be added to the IV bag.
3. Add the appropriate volume of H4H17319P2 to the IV bag, then invert the IV bag 10 times to ensure that the drug and 0.9% sodium chloride are well mixed.
4. The prepared IV bag will be labelled according to the approved labelling requirements by the site. The label should include: patient initials, preparation date/time, H4H17319P2 mg in 0.9% sodium chloride bag 1×1, directions to infuse intravenously the entire contents of the infusion bag and flush over 1 hour per protocol, use by date/time, and the treating physician's name.
5. H4H17319P2 should be infused within 4 hours of reconstitution.

Subcutaneous Preparation and Administration of H4H17319P2

Each vial of H4H17319P2 will be reconstituted with 1.4 mL of sterile water for injection. Once reconstituted, each vial will contain 1.2 mL withdrawable volume. When reconstituted for SC administration, the H4H17319P2 concentration is 150 mg/mL. Two vials of H4H17319P2 will be required for dosing.

1. Prepare H4H17319P2 while working on a hard, clean surface.
2. Remove the cap(s) from the vial(s) and wipe the vial(s) top surface with an alcohol swab.
3. Without removing the cap from the needle, attach a 21-gauge needle to a 3.0 mL polypropylene syringe. With the cover on, pull back the plunger on the syringe to the 2.0 mL mark to draw air into the syringe. Remove the cap from the 21-gauge needle. Insert the needle into the rubber top of the vial containing the sterile water for injection. Push the plunger down to inject all the air into the vial. Turn the vial upside down in one hand, and make sure that the tip of the needle is in the water. Pull a minimum of 2.0 mL of sterile water for injection into the syringe. Do not set the needle down on a dirty surface, touch the needle with fingers, or breathe directly on the needle.
4. Prime the syringe by inverting the syringe (needle up) and depressing the plunger until air has been expelled from the syringe. Continue to depress the plunger until a small amount of liquid comes out and the plunger reaches the 1.4 mL mark.
5. Place the H4H17319P2 vial on a hard surface and insert the needle in the top. Add the 1.4 mL of sterile water for injection into the H4H17319P2 vial, directing the stream of water onto the side of the vial and into the powdered drug.
6. Remove the needle from the vial after pushing all the water out of the syringe and into the vial. Discard the needle and syringe into a Sharps container.
7. Gently swirl the vial in an upright position until all the powder is dissolved.
8. Do not shake the vial. Shaking may result in foaming.

SC Administration of 250 mg Dose of H4H17319P2

This dose requires 2 injections of H4H17319P2. One injection is 0.67 mL SC injection and the other is 1.0 mL SC injection.

1. Obtain a 1.0 mL polypropylene plastic syringe and a 3.0 mL polypropylene syringe and attach a 21-gauge needle to each syringe.
2. Obtain 2 vials of lyophilized H4H17319P2.
3. Reconstitute each vial of lyophilized H4H17319P2 with 1.4 mL sterile water for injection as indicated above.
4. With the needle cover on, pull back the plunger on the 1.0 mL polypropylene syringe to the 1.0 mL mark to draw air into the syringe.
5. Remove the needle cap and insert the needle into the rubber top of the vial.
6. Push the plunger down and inject all the air into the vial.
7. Keeping the needle in the vial, turn the vial upside down in one hand, and make sure that the tip of the needle is in the liquid. Use other hand to pull back on the plunger to draw a minimum of 1.0 mL of drug into the syringe. Replace the cap on the needle. Remove the capped needle and put in a Sharps container.

8. Without removing the cover of the needle, attach a 27-gauge 0.5-inch needle on to the 1.0 mL polypropylene syringe containing a minimum of 1.0 mL of drug.
9. Remove the needle cap and prime the 27-gauge 0.5-inch needle with the drug. Replace the cap on the needle.
10. The prepared SC syringe is 0.67 mL=100 mg/0.67 mL.
11. The prepared SC syringe will be labelled according to the requirements by the site's standard operating procedure.
12. With the needle cover on, pull back the plunger on the 3.0 mL polypropylene syringe to the 1.5 mL mark to draw air into the syringe.
13. Remove the needle cap and insert the needle into the rubber top of the vial.
14. Push the plunger down and inject all the air into the vial.
15. Keeping the needle in the vial, turn the vial upside down in one hand, and make sure that the tip of the needle is in the liquid. Use other hand to pull back on the plunger to draw a minimum of 1.2 mL of drug into the syringe. Replace the cap on the needle. Remove the capped needle and put in a Sharps container.
16. Without removing the cover of the needle, attach a 27-gauge 0.5-inch needle on to the 1.0 mL polypropylene syringe containing a minimum of 1.2 mL of drug.
17. Remove the needle cap and prime the 27-gauge 0.5-inch needle with the drug. Replace the cap on the needle.
18. The prepared SC syringe is 1.0 mL=150 mg/1.0 mL.
19. The prepared SC syringe will be labelled according to the requirements by the site's standard operating procedure.
20. H4H17319P2 should be delivered within 4 hours of reconstitution.

Permanent Discontinuation of H4H17319P2

Administration of H4H17319P2 is recommended to be permanently stopped in the event of:

- Serious or severe allergic reactions considered related to H4H17319P2
- Specific types of liver dysfunction (eg, Hy's law is met ([Guidance for Industry Drug Induced Liver Injury: Premarketing Clinical Evaluation FDA 2009])
- Evidence of pregnancy
- Patient/legal representative withdraws consent
- Patient does not show clinical benefit (i.e., loss of body weight) after a period of time (to be discussed by the treating physician and Sponsor) of what is considered an optimal dose and dose regimen of H4H17319P2 by Sponsor Temporary Discontinuation of H4H17319P2

Administration of H4H17319P2 is recommended to be temporarily discontinued in the event of:

- Neutrophil count $\leq 1.0 \times 10^3/\mu L$
- Sustained ALT/AST values greater than 3× the upper limit of normal (ULN) plus total bilirubin >2×ULN or isolated AST/ALT>5×ULN
- Surgical procedure
- Hospitalization After the condition leading to temporary discontinuation of H4H17319P2 resolves, H4H17319P2 dosing may resume. A decision to temporarily discontinue H4H17319P2 and/or resume H4H17319P2 dosing should be discussed with the Sponsor representative.

The treating physician may temporarily discontinue H4H17319P2 dosing at any time, even without consultation with the Sponsor representative if the urgency of the situation requires immediate action and if this is determined to be in the patient's best interest. However, the Sponsor representative should be contacted as soon as possible. Resumption of H4H17319P2 dosing should be discussed and agreed upon between the treating physician and the Sponsor representative.

In summary, H4H17319P2 will restore LEPR signaling in the patient having congenital leptin deficiency and improve or reverse hyperphagia, weight gain, and/or metabolic complications of this condition in the patient.

Example 22: Clinical Use of Anti-LEPR Antibody for Treatment of Partial Lipodystrophy in Pediatric Patients At age 11 a female patient presented with hepatosplenomegaly and high triglycerides (>500 mg/dL) as well as a lack of fat at the extremities. She was found to have anti-GAD (glutamic acid decarboxylase) antibodies, and a commercial LMNA gene analysis was negative. Further features identified at the time of evaluation for a study evaluating the efficacy of metreleptin in the treatment of liver disease associated with lipodystrophy included atypical features of hand contractures, scoliosis, and lack of adrenarche. Her leptin level at baseline was 3.2 ng/dL.

Metreleptin therapy was started at age 13 as a part of a clinical research protocol (ClinicalTrials.gov Identifier: NCT01679197) to treat high triglycerides and severe hepatic steatosis and she continued metreleptin for 12 months without any serious adverse events. Her metabolic parameters showed marginal improvement after metreleptin, however, her liver biopsy showed improvement. She continued metreleptin as a part of another study protocol (ClinicalTrials.gov Identifier: NCT02654977). However, during the $17^{th}$ month of treatment, the patient reported fatigue, being thirsty, blurred vision and polydipsia, and had lost 5 pounds in a month. Laboratory results showed significant hyperglycemia and hyperlipidemia with a positive anion gap and positive ketones. The anti-GAD65 (65 kDa isoform of glutamic acid decarboxylase) level was 5.39 nmol/L (repeat Anti-GAD65: 8.38 nmol/L, two months later), and leptin level, drawn one-hour post injection, was undetectable. The presence of metreleptin antibody with neutralizing activity was ultimately confirmed. This low value for leptin was likely a consequence of immunogenic cross reactivity to ongoing metreleptin therapy with anti-metreleptin antibody formation, possible continuing loss of adipose tissue, or a mechanism suppressing leptin production.

Neutralizing activity to metreleptin as well as endogenous leptin was confirmed positive about 6 months later. During this time, glucose and lipid control was substantially worse, with the triglycerides consistently >2,000 mg/dL. She was maintained on high dose insulin therapy with basal+bolus regimen and transitioned to an insulin pump. She was also started on metformin. Multiple hospitalizations were required for diabetic ketoacidosis, pancreatitis, or pancreatitis prevention.

The patient was then started on fenofibrate and sequentially on pioglitazone due to worsening lipid control (triglycerides >2,000 mg/dL). One month following metreleptin withdrawal, LFTs rose substantially to 10-fold elevated above normal. Liver biopsy showed patchy portal and periportal inflammation that included plasma cells and interface injury, consistent with autoimmune hepatitis. To control the autoimmune hepatitis, she was treated with prednisone for a period of three months, which helped resolve the liver function abnormalities. Both during and subsequent to the discontinuation of the prednisone, the patient suffered multiple episodes of acute pancreatitis due to hypertriglyceridemia (as high as 8,000 mg/dL) coupled with diabetic ketoacidosis. Due to metabolic complications stated above or pancreatitis the patient was admitted regularly to the hospital.

The patient started setmelanotide (ClinicalTrials.gov Identifier: NCT03262610) at 1 mg/day and the dose was titrated upwards until triglycerides dropped below 500 mg/dl. Setmelanotide did not cause weight loss in this patient. Although there was a slight decrease in hunger scales, the effect was not robust. The treatment failed to improve glycemic control and hypertriglyceridemia. A slight decrease in total daily insulin dose was not considered clinically significant as HbA1c levels remained high. Setmelanotide showed no effect on liver fat content though visceral fat slightly decreased.

The patient's elevated triglyceride levels (>500 mg/dL and as high as >2,000 mg/dL) requires plasma exchange therapy to prevent recurrent pancreatitis. She is also being treated with empagliflozin 10 mg daily in addition to insulin aspart, insulin glargine and metformin.

Rationale

The purpose of this clinical study protocol is to provide the investigational product (IP), H4H17319P2, to a patient who meets required eligibility criteria and meets the following criteria outlined below:

- The patient has the serious or life-threatening disease for which the expanded access protocol is authorized.
- Sufficient evidence of efficacy that a clinically meaningful benefit may be expected based on proposed mechanism of action of the drug.
- There are no comparable or satisfactory alternative therapies to treat the disease or condition.
- There is nothing unique about this particular patient that suggests that that there would be an unreasonable risk posed by administering H4H17319P2 to this patient.

Anti-metreleptin antibodies with neutralizing activity have been identified in patients with generalized lipodystrophy treated with metreleptin. The consequences of these neutralizing antibodies are not well characterized but could include inhibition of endogenous leptin action and/or loss of metreleptin efficacy (Chan, et al. Immunogenicity associated with Metreleptin treatment in patients with obesity or lipodystrophy. Clin Endocrinol. 2016; 85(1):137-149). Severe infection and/or worsening metabolic control have been reported. Progressive metabolic worsening as well as the emergence of Type 1 diabetes was noted in this patient concurrent with the emergence of anti-metreleptin neutralizing antibodies, which have been persistent. It is unclear if the disease has progressed naturally or if the emergence of the antibody has played a role. Regardless, the patient's lipodystrophy cannot be adequately treated.

The objective of this individual patient expanded access protocol is to provide H4H17319P2 as a potential treatment of the severe metabolic complications resulting from lipodystrophy in this patient with refractory hypertriglyceridemia leading to recurrent bouts of pancreatitis. Additionally, the safety and efficacy of H4H17319P2 in this patient will be assessed. The treatment period will depend on the extent of the response in this single patient, who is a seriously ill lipodystrophy patient with hypertriglyceridemia and recurrent pancreatitis, with the intention of evaluating whether H4H17319P2 may offer therapeutic benefit to improve the severe metabolic abnormalities.

Primary Endpoints:

- Percent change from baseline to week 24 in fasting triglycerides
- Achievement of fasting triglycerides <500 mg/dL without the need for ongoing plasmapheresis at week 24
- Treatment-emergent adverse events Secondary Endpoints:

- Percent change from baseline to week 12 in fasting triglycerides
- Achievement of fasting triglycerides <500 mg/dL without the need for ongoing plasmapeheresis at week 12
- Change from baseline in hunger score over time
- Change from baseline in fasting glucose and glycated hemoglobin (HbA1c) over time
- Incidence of hospital admissions for pancreatitis over time
- Change from baseline in mean insulin dose requirement over time
- Change from baseline in other fasting lipid parameters, including total fasting cholesterol, HDL-C, LDL-C and VLDL-C over time
- Percent change from baseline in DEXA and liver fat parameters, if feasible, in this patient, over time
- Concentrations of total H4H17319P2 in serum over time
- Presence of anti-drug antibodies (ADAs) to H4H17319P2 over time Protocol Design The protocol comprises a 2-week screening period and 3 open-label treatment periods: Treatment Period 1 (weeks 1-12), Treatment Period 2 (weeks 13-24) and a Treatment Extension Period (weeks 25-52). During the Screening Period, the patient will be assessed for eligibility and instructed to complete a hunger questionnaire on at least 3 separate days in order to enhance the understanding of hunger symptoms associated with lipodystrophy and absence or deficiency of endogenous leptin resulting from the absence or lack of adipose tissue prior to treatment with H4H17319P2. As this condition is rare, obtaining hunger scores during Screening will allow for the collection of important patient specific details that will allow for a better understanding of hunger symptoms in this disorder.

During Treatment Period 1, the patient will receive the initial dosing regimen of H4H17319P2. At the end of Treatment Period 1 (week 12), an assessment of efficacy (TG lowering) and H4H17319P2 drug levels (PK) will be performed to determine the H4H17319P2 dosing regimen for Treatment Period 2. The dose level and dosing frequency in Treatment Period 2 will not exceed that of Treatment Period 1. At week 24, an assessment of efficacy (TG lowering) and H4H17319P2 drug levels (PK) will be performed to determine the patient's eligibility to continue to the Treatment Extension Period.

Figure 19:
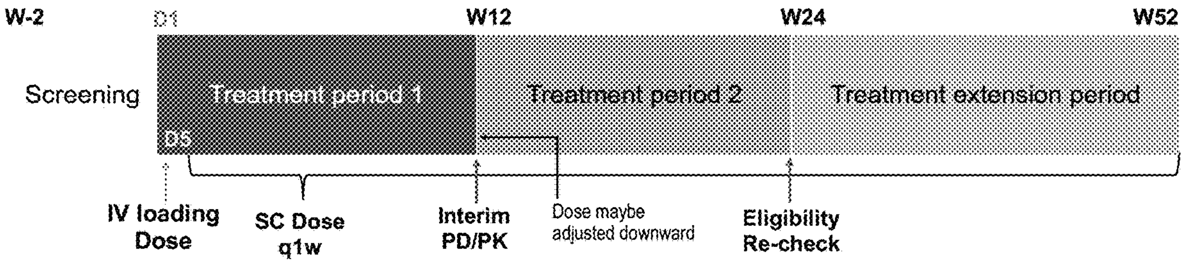
FIG. 19 depicts the single patient protocol utilized in a compassionate use clinical trial.

Thus, this patient will progress sequentially through the protocol as depicted in FIG. 19.

Fasting triglyceride (TG) levels and requirement for plasmapheresis will be the primary criteria used to assess whether a therapeutic effect has been achieved. If this patient does not exhibit the required therapeutic target response to a fasting TG level <500 mg/dL through week 24, she will be withdrawn from the protocol.

For concurrent management of hypertriglyceridemia, this patient will be eligible to continue plasmapheresis treatment as necessary in the judgement of the treating physician. Fasting TG levels to determine if a therapeutic response to H4H17319P2 treatment has been achieved should be measured at a time at least 1 week after the most recent plasmapheresis treatment.

Dose Selection

In preclinical studies described above in Examples 15-19, PD effects were associated with a wide range of exposures to H4H17319P2, while the sustainability of the effects was observed under dosing conditions where target-mediated clearance (TMC) of H4H17319P2 was saturated. In the mouse model of lipodystrophy (described above), single doses of H4H17319P2 resulted in normalization of glucose concentrations and loss of body weight. These effects were evident at concentrations of H4H17319P2 in serum above 4 mg/L but were notably more sustained at concentrations that saturated the TMC pathway. In the monkey studies described above, sustained body weight effects (either body weight loss or reduced body weight gain compared to control animals) were observed at steady-state concentrations above 30 mg/L. However, greater overall effects were seen when concentrations of H4H17319P2 exceeded 100 mg/L, the concentration required to saturate TMC in monkeys. Given that leptin-binding receptors are widely expressed, but that target (signaling) receptors are limited to the central nervous system, it is presumed that the preclinical PK/PD data reflect the need to saturate TMC associated with binding to peripheral LEPR to achieve adequate exposures in the brain. In addition, the interspecies differences in concentration required to saturate TMC and deliver sustained PD effects may be a consequence of differences in peripheral target burden.

In the human clinical study described in Example 20, saturation of the TMC pathway was evident at serum concentrations exceeding 100 mg/L based on the concentration versus time profiles. A population PK model was built utilizing data from this FIH study, which captured the relevant pharmacokinetic characteristics of H4H17319P2, when administered as a single dose in healthy volunteers. This model was employed to simulate expected concentration profiles under different dosing regimens, with the assumption that the PK characteristics of H4H17319P2 observed in healthy volunteers pertain to this patient.

H4H17319P2 will be supplied as a lyophilized powder in a sterile, single-use 20 mL glass vial for either IV or SC administration. Each vial contains 265 mg H4H17319P2, which will be reconstituted with sterile water for injection for IV administration and SC administration.

A 5 mg/kg intravenous (IV) loading dose was chosen in order to rapidly achieve concentrations of H4H17319P2 in serum at or above 100 mg/L. Inclusion of this IV loading dose will also allow immediate assessment of maximal concentration ($C_{max}$) of H4H17319P2 in serum. A weekly subcutaneous (SC) maintenance dose of 300 mg H4H17319P2 is predicted to sustain trough concentrations in serum at or above 100 mg/L. This SC dosing regimen is to commence 4 days after administration of the IV loading dose and is predicted to best maintain targeted trough concentrations in serum. On days when the patient undergoes clinically-indicated plasmapheresis, administration of H4H17319P2 must occur after plasmapheresis is completed.

Based on data from the first part of an ongoing 2-part study in 56 healthy subjects (Example 20), the dose regimen described is anticipated to be generally well tolerated. H4H17319P2 was well-tolerated in healthy adult volunteers in Example 20 when administered as single doses of 0.3 to 30 mg/kg IV and 300 and 600 mg SC. A maximal concentration in serum of 1035 mg/L was observed at a 30 mg/kg IV dose, which is greater than six times the maximum exposure predicted to be attained in this patient over the course of the study. In addition, predicted area under the concentration-time curve (AUC) over a 1-week dosing interval at steady-state is expected to be almost twenty-seven times less than the AUC at steady state over the same dosing interval (at the no observed adverse effect level [NOAEL]) estimated from a pharmacokinetic model derived from 3 preclinical toxicology studies in cynomolgus monkeys.

The initial dose of 5 mg/kg IV load plus 300 mg weekly SC maintenance is expected to be tolerable, and has been chosen to quickly achieve a serum concentration of H4H17319P2 that saturates peripheral receptors and thereby provides sustained pharmacological effects. It is possible that a lower dose level or less frequent dosing might be equally efficacious. Therefore, the dose level and dosing frequency may be adjusted downward after planned interim efficacy and drug level assessments. Additionally, as plasmapheresis can remove antibodies including H4H17319P2 from the circulation, it may be necessary to adjust dosing after plasmapheresis to ensure efficacious H4H17319P2 levels. On days the patient undergoes plasmapheresis an additional 300 mg dose of H4H17319P2 may be needed to achieve target drug concentrations. Routine maximal doses (not considering possible changes due to plasmapheresis) should not exceed 300 mg SC weekly.

Efficacy and Drug Level Assessments

Interim efficacy and drug level assessments will be performed after 12 weeks and 24 weeks of the protocol to assess whether the dosing regimen selected achieved the expected drug levels and PK profiles and effects on lipid parameters. The dose level and dosing frequency may be adjusted as needed after the efficacy and drug level assessments.

The data review committee will comprise (1) an experienced lipodystrophy specialist (2) the patient's pediatric intensive unit physician (3) one of the subspecialists involved in her care (either pediatric GI or hepatology), and (4) representative(s) from the Sponsor familiar with H4H17319P2 exposure-response relationships in preclinical and clinical studies.

Duration of Patient Participation

The total protocol duration is anticipated to be approximately 54 weeks, including the screening period. The patient's participation in this protocol will consist of the following periods: screening period, treatment period 1 [expected to be 12 weeks in duration], treatment period 2 [expected to be 12 weeks in duration], and then if the patient is eligible, a long term, treatment extension period [28 weeks]. It is anticipated that if substantial metabolic improvement, with good safety and tolerability, is demonstrated over the treatment extension period, the patient may be offered the opportunity to enroll in a future, separate extension protocol, to allow for continued treatment. This future extension protocol will be submitted and approved by applicable regulatory authorities prior to dosing the patient beyond this protocol's duration.

The end of the trial will be defined as the last patient last visit. A patient has the right to withdraw from the protocol at any time, for any reason, and without repercussion. The investigator can also withdraw the patient at any time due to clinical safety concerns or lack of efficacy.

Protocol Discontinuation

The execution of this protocol may be prematurely terminated, if in the opinion of the Principal Investigator or the Sponsor, there is sufficiently reasonable cause. The terminating party will provide written notification documenting the reason for protocol termination to either the Investigator or the Sponsor.

Circumstances that warrant termination include, but are not limited to:

- Determination of unexpected, significant, or unacceptable risk to patient
- Insufficient adherence to protocol requirements
- Insufficient complete and/or evaluable data
- Evidence of pregnancy
- Serious or severe allergic reactions considered related to the drug
- Severe liver injury or dysfunction for which no other reason can be found to explain, such as viral hepatitis A, B, or C; preexisting or acute liver disease; or another drug capable of causing the observed injury. Liver injury for this patient is defined as ALT or AST>3× over average baseline AND total bilirubin >2× over baseline (or international normalized ratio (INR)>1.5)
- Patient withdraws consent
- Plans to modify, suspend, or discontinue the development of the drug
- At the week 12 data review, it is the opinion of the data review committee that there has not been sufficient benefit observed
- At the week 24 data review, it is the opinion of the data review committee that the patient is not able to maintain a fasting TG value consistently <500 mg/dL without concomitant plasmapheresis management.

If the unanimous opinion of the data review committee is that the patient is experiencing significant clinical benefit despite being unable to maintain TG value consistently <500 mg/dL without concomitant plasmapheresis management, dosing may continue through the week 52 end of treatment visit.

Assessment of Treatment Compliance

In order to evaluate the safety, tolerability, and pharmacokinetics of the drug, it is critical that the patient receive H4H17319P2 as directed. All used H4H17319P2 will be collected to assess compliance with the protocol.

During the first 2 protocol periods (initial dose period and open label active treatment period), H4H17319P2 will be administered to the patient by an experienced health care provider. During the open label extension period, H4H17319P2 may be administered at the clinical site or self-administered/administered by the patient or designated person, respectively. If the patient chooses to self-administer H4H17319P2 or have a designated person administer H4H17319P2, training on H4H17319P2 administration must be performed by qualified clinical site personnel, and the first occurrence of self-administration must be observed by same. In addition, a medication administration diary will be provided to the patient/designee prior to initiation of self-administration or administration by a designated person such as a parent or caregiver. The diary must be completed upon each drug administration. The patient and/or her caretakers will be required to maintain a diary to monitor compliance. In addition, the time of dosing will be recorded in the patient diary. If a patient does not receive the entire dose of drug, the amount administered will be recorded. The reason(s) for the adjusted dose should be recorded in source documents and the CRF.

Additionally, blood samples will be collected according to the SOA to measure trough concentrations of H4H17319P2 and anti-H4H17319P2 antibodies in serum.

Prior and Concomitant Treatment and Procedures/Permitted Medication

Unless concomitant medications are likely to present a strong potential safety concern, the general goal of this protocol is to allow the patient with this ultra-rare condition to participate in the protocol. Therefore, the patient will be allowed chronic concomitant medications (e.g., as described below) while participating in the protocol. These may include:

- Insulin preparations to treat type 1 diabetes;
- Metformin to treat insulin resistance;
- Vitamin D to treat deficiency;
- Thyroxine or other thyroid supplements;
- Other medications commonly used in LD patients including: endocrine therapies (e.g., vitamin and calcium supplements); and other medications (e.g., carnitine, Coenzyme Q10, vitamins, anti-constipation medications, anti-allergic medications);
- Neurontin, along with required narcotic or ketamine/lidocaine infusions, patches or tablets for pain control;
- Effexor for mood;
- With the exception of low threshold drugs (i.e, anticonvulsants, digoxin, Coumadin, etc.), other medications may be permitted if on a stable dose and deemed essential by the treating physician
- Plasmapheresis may continue, at the discretion of the patient's treating physicians There are presently no data regarding H4H17319P2 interaction with the above treatments. The patient and her caretakers should be warned of possible side effects of drug interactions that could occur with any medications that the patient will be receiving.

This patient will be reminded at each visit that if it becomes necessary for her to take any other medication during the protocol duration, from Screening until the Final Protocol Visit, she must inform the protocol staff immediately, and the specific medication(s) and indication(s) must be discussed with the Investigator. All concomitant medications taken during the course of the protocol must be recorded in the source documents.

Prohibited Medications and Substances and Concomitant Procedures

Medications that could impact the efficacy assessments during the protocol duration are prohibited, such as the addition of new lipid lowering therapies or any addition of new diabetes medicines, unless deemed essential by her treating physician.

Anorectic agents or drugs with anorexia as a non-rare side effect are prohibited for the duration of the protocol.

Concomitant procedures conducted during the protocol duration, including plasmapheresis and others used to treat adverse events, are to be reported on the CRF.

Assessments and Schedule

The Schedule of Assessments (SOA) to be conducted during the protocol are depicted in FIG. 20 (A-B).

Although the procedures and assessments required in this single patient protocol are classified as "No or Minimal Risk" (with the exception of DEXA which may be classified as "Minor Increase over Minimal Risk") according to the 2008 Guidance Document "Ethical Considerations for Clinical Trials on Medicinal Products Conducted with the Paediatric Population", considerations for reducing pain and distress in the participant who is younger than 18 years of age are included.

Upon providing informed consent, the patient will enter the Screening Period. During the Screening Period, the patient will be assessed for eligibility and instructed to complete a hunger questionnaire on 3 separate days in order to enhance the understanding of hunger associated with lipodystrophy prior to treatment with H4H17319P2. During Screening, it is also critical that any additional medical history be obtained, including recent medical chart review, as necessary.

Additional medical history along with demographic data for this patient will be obtained during the Screening Period. Data to be recorded in the source document and CRF include the patient's gender, race, date of birth, and concomitant medication use.

Recent medical history will be obtained on Day 1 prior to first dose of drug to assess continued protocol eligibility and adherence to final inclusion/exclusion criteria. This recent medical history includes a review for changes from screening as well as a review of the patient's recent medication use and to assess whether or not any changes have occurred since the previous visit.

A complete physical examination will be performed to include review of peripheral lymph nodes, head, eyes (including conjunctiva), ears, nose, mouth and oropharynx, neck, heart, lungs, abdomen, musculoskeletal including back, extremities and neurologic. This patient will also be assessed with Tanner Staging; as she has not reached Tanner Stage V. This will be done according to the SOA.

Changes from baseline in any physical examination findings identified by the Investigator as clinically significant must be recorded as an AE on the appropriate CRF.

Height (cm) will be measured, without shoes, according to the SOA using a wall-mounted stadiometer.

A review of concomitant medications will be conducted during the Screening Period and at every protocol visit. Any medications taken by the patient will be recorded in source documents.

The investigator is aware that the doses of concomitant antidiabetic and lipid medications may require adjustment upon initiation of treatment as insulin resistance and hypertriglyceridemia improve. The patient will be carefully monitored during the period of adjustments to her concomitant medication(s). A patient on insulin therapy and should be monitored closely during the first several weeks of treatment as insulin doses may need to be adjusted downward as frequently as weekly (especially for those patients on high doses of insulin) to avoid hypoglycemia. Similarly, the Investigator should evaluate the need to adjust the dosages of lipid medications at each follow-up visit during treatment for patients who are on lipid medications for hypertriglyceridemia and will consider the need for plasmapheresis. If the drug treatment is discontinued for any reason, further adjustment of concomitant medications may be warranted, e.g., lipid lowering medication to mitigate the potential risk of pancreatitis.

Vital signs will be obtained in the sitting position following at least 5 minutes of rest each time they are measured according to the SOA. Blood pressure (BP; mmHg) and heart rate (HR; bpm) will be performed using the same methodology throughout the protocol (manual or automated). All BP and HR measurements are to be obtained in the sitting position following at least 5 minutes of rest. All measurements will be taken in triplicate, approximately 2 minutes apart. When possible, BP should be taken in the non-dominant arm throughout the protocol, using the same methodology (automated or manual). Repeat measures and more frequent monitoring can be implemented for significant increases in BP or HR.

To allow for a trough blood pressure reading, the patient should be instructed not to take protocol medication on protocol days when vital signs are to be measured in the clinic, but will take the medication at the clinic. This is particularly important during treatment period 1 visits, where blood pressure is monitored more intensively over the course of the post-dose period in the clinic, as according to the SOA.

Body temperature (° C.) and respiration rate (breaths/minute) will be obtained in the sitting position following at least 5 minutes of rest.

Single 12-lead electrocardiograms will be performed following a period of at least 10 minutes of rest in the supine position.

Clinical safety laboratory tests are to be performed by the local laboratory and patients are to be fasting for 8 hours. Safety laboratory tests are to be drawn prior to dosing.

All clinically significant laboratory abnormalities will be followed-up by repeat testing and further investigated according to the judgment of the Investigator.

Liver function test abnormalities will be evaluated in accordance with FDA Guidance (2009). Hematology and clinical chemistry samples will be collected in the fasted state. Complete blood count with platelet count and standard indices will be obtained.

Chemistry: Sodium, potassium, chloride, $CO_2$, albumin, total protein, glucose, blood urea nitrogen (BUN), creatinine, uric acid, aspartate aminotransferase (AST), alanine aminotransferase (ALT), gamma-glutamyl-transpeptidase (GGT), creatine phosphokinase (CPK), alkaline phosphatase, total bilirubin, direct bilirubin, lactate dehydrogenase (LDH), calcium and phosphorus.

Urinalysis: pH, glucose, protein, ketones, bilirubin, blood, urobilinogen, specific gravity, nitrite, and leukocytes by dipstick analysis or machine urinalysis. Urine microscopic examination will be performed if positive findings on dipsticks warrant further examination.

Coagulation profile: Prothrombin time (PT) or international normalized ratio (INR), and partial thromboplastin time (PTT), also referred to as activated partial thromboplastin time (aPTT).

Injection sites will be carefully inspected, evaluated and scored during the protocol period. The injection site evaluation will include identification and measurement of areas of erythema, edema and induration, as well as the presence of localized pain, tenderness and itching.

Unscheduled evaluations may also be recorded as warranted by clinical conditions.

Anti-Drug Antibody (ADA) Measurements

Blood samples for measurement of anti-drug antibodies will be collected prior to dosing, and then at the time-points identified in the SOA. If this patient demonstrates a positive ADA, she will be followed until resolution.

Patient Questionnaires

The patient questionnaires will be answered by the patient and/or her caretaker after careful training.

Hunger Scores

Hunger will be assessed using a 3-part questionnaire as well as a set of 2 global questions asked at particular protocol visits according to the SOA. Hunger will be assessed using a numeric rating score ranging from 0-10; with 0=not hungry at all and 10=hungriest possible. All daily Hunger Questionnaire scores will be assessed by asking the patient to score their hunger based on a Likert-like scale, where 0 is not hungry at all and 10 is hungriest possible. Hunger Questionnaire scores will be recorded on a daily basis, prior to the patient's morning meal. The Hunger Questionnaire should be completed on three separate days during screening and at clinic visits prior to dosing in the morning. Patients will record their hunger scores prior to the morning meal (fasted). Global Hunger Questions: Two global questions will be asked at certain protocol visits according to the Schedule of Assessments.

SF-36 Health Questionnaire

The SF-36 is a multi-purpose, short-form health survey with only 36 questions. It yields an 8-scale profile of functional health and well-being scores as well as psychometrically-based physical and mental health summary measures and a preference-based health utility index. It is a generic measure, as opposed to one that targets a specific age, disease, or treatment group. Accordingly, the SF-36 has proven useful in surveys of general and specific populations, comparing the relative burden of diseases, and in differentiating the health benefits produced by a wide range of different treatments.

Patient Health Questionnaire-9 (PHQ-9)

The PHQ-9 is a nine-item depression scale of the Patient Health Questionnaire. The PHQ-9 is a tool for assisting clinicians in diagnosing depression as well as selecting and monitoring treatment. After the patient has completed the PHQ-9 questionnaire, it is scored by the protocol staff.

If at any time during the protocol an individual patient's PHQ-9 score is 0, the patient should be referred to a MHP. The PHQ-9 will be implemented according to the SOA.

Columbia-Suicide Severity Rating Scale (C-SSRS)

The C-SSRS is a tool used not only to predict suicide attempts but also assesses the full range of evidence-based ideation and behavior items, with criteria for next steps (e.g., referral to mental health professionals (MHPs)). There are two versions of the C-SSRS that will be utilized in this protocol according to the SOA: (1) The Baseline/Screening version of the scale combines the Baseline and Screening forms to assess suicidality in a patient's lifetime and during a predefined time period. This version can assess a patient's lifetime suicidality for data collection purposes as well as eligibility based on inclusion/exclusion criteria. (2) The Since Last Visit version of the scale assesses suicidality since the patient's last visit. This version is meant to assess patients who have completed at least one initial C-SSRS assessment, and should be used in every subsequent visit. The 'Since Last Visit' version of the C-SSRS is asking about any suicidal thoughts or behaviors the patient/participant may have had since the last time you have administered the C-SSRS.

If at any time during the protocol a patient has a suicidal ideation of type 4 or 5, or any suicidal behavior, the patient should be referred to a MHP.

After the Screening Period in which confirmation of patient eligibility is determined, the patient will enter the Treatment Period 1. In this phase, the first dose of H4H17319P2 will be administered IV on Protocol Day 1. The first subcutaneous (SC) dose administration will occur on protocol day 5. The patient will return to the clinic every week for her dose administration. Laboratory and testing assessments are as described in FIG. 20.

Detailed descriptions of the safety, laboratory, PK and ADA assessment to be conducted during this protocol are provided in the following sections.

The patient will be required to fast overnight on the day preceding all visits, beginning with the screening Visit. She will be allowed to take her usual medications with a sip of water on the morning of each clinic visit.

Assessments may occur over multiple days during the Screening Period. In order to obtain sufficient baseline data on symptoms of hunger collected on 3 separate days, the screening period should be a minimum of 3 days and up to 2 weeks.

In order to provide flexibility to this patient and the protocol staff for the number of clinic visits, the actual scheduling of clinic visits can allow flexibility in timing of visits. During the treatment period 1 and treatment period 2, the goal will be for visits to occur within +/−3 days. All data collected, even if outside of visit windows, will be included in analyses of endpoints.

Monitoring of adverse events will be conducted throughout the protocol. Adverse events will be recorded in the CRFs from Screening through the Final Protocol Visit. Adverse events that occur after the start of drug administration will be considered treatment emergent adverse events (TEAEs). SAEs will be recorded through the Final Protocol Visit. All adverse events should be monitored until they are resolved or are clearly determined to be due to a patient's stable or chronic condition or intercurrent illness(es).

Adverse Events: Definitions, Documentation, and Reporting

An adverse event (AE) is any untoward medical occurrence associated with the use of a drug in humans, whether or not considered drug related. An adverse event (also referred to as an adverse experience) can be any unfavorable and unintended sign (e.g., an abnormal laboratory finding), symptom, or disease temporally associated with the use of a drug, without any judgment about causality. An AE can arise from any use of the drug (e.g., off-label use, use in combination with another drug) and from any route of administration, formulation, or dose, including an overdose.

H4H17319P2 was well-tolerated in the first in human study. Drug-Related TEAEs (for which the adverse event was assessed as possibly or probably related to drug by the investigator) were reported. Because of the very limited clinical experience to date with H4H17319P2, there may be other unknown side effects. The PIs (or a covering clinician) will be available at all times to protocol participants in the event of a clinical emergency; both this availability and how to reach the investigators in an emergency will be clearly communicated orally and in writing to protocol participants. All protocol interventions will be provided free of cost.

An AE or suspected adverse reaction is considered serious (SAE) if, in the view of either the investigator or sponsor, it results in any of the following outcomes:

Death.

Life-threatening. Life-threatening means that the patient was at immediate risk of death from the reaction as it occurred, i.e., it does not include a reaction which hypothetically might have caused death had it occurred in a more severe form.

In-patient hospitalization or prolongation of existing hospitalization. Hospitalization admissions and/or surgical operations scheduled to occur during the protocol period, but planned prior to protocol entry are not considered AEs if the illness or disease existed before the patient was enrolled in the protocol, provided that it did not deteriorate in an unexpected manner during the protocol (e.g., surgery performed earlier than planned).

A persistent or significant incapacity or substantial disruption of the ability to conduct normal life functions.

Important medical event. An important medical event is an event that may not result in death, be life-threatening, or require hospitalization but may be considered an SAE when, based upon appropriate medical judgment, it may jeopardize the patient or patient and may require medical or surgical intervention to prevent one of the outcomes listed in the definitions for SAEs. Examples of such medical events include allergic bronchospasm requiring intensive treatment in an emergency room or at home, blood dyscrasias or convulsions that do not result in in-patient hospitalization, or the development of drug dependency or drug abuse.

Monitoring of Adverse Events and Period of Observation

Each patient must be carefully monitored for the development of any AEs. This information should be obtained in the form of non-leading questions (e.g., "How are you feeling?") and from signs and symptoms detected during each examination, observations of protocol personnel, and spontaneous reports from patients.

AEs will be recorded in the source documents starting from Screening up to and including the Final Protocol Visit. SAEs and deaths will be recorded on the SAE CRFs starting from the time the ICF is signed and continuing through the Final Protocol Visit. All AEs should be monitored until they are resolved or are clearly determined to be due to a patient's stable or chronic condition or intercurrent illness(es).

All AEs (serious and non-serious) spontaneously reported by the patient and/or in response to an open question from protocol personnel or revealed by observation, physical examination or other diagnostic procedures will be recorded on the appropriate CRF. Any clinically relevant deterioration in laboratory assessments or other clinical findings is considered an AE and must be recorded on the appropriate CRF. When possible, signs and symptoms indicating a common underlying pathology should be noted as one comprehensive event.

Any SAE that occurs at any time after completion of the protocol, which the investigator considers to be related to the drug, must be reported to the sponsor.

All SAEs that occur during the course of the protocol must be reported by the investigator to the Medical Monitor within 24 hours from the point in time when the investigator becomes aware of the SAE. All SAEs must be reported whether or not considered causally related to the drug. SAE forms will be completed and the information collected will include patient number, a narrative description (which may include relevant history, concomitant medications, and relevant laboratory and diagnostic test results) of the event and an assessment by the investigator as to the severity of the event and relatedness to drug. Follow-up information on the SAE may be requested by the sponsor or its designee.

All SAE correspondence should be communication to sponsor.

Patients will be monitored carefully during the treatment period during on site clinic visits as well as periodic telephone calls made to the patients by the protocol staff. In the event a patient is withdrawn from treatment due to an AE, the patient should be encouraged to complete the final protocol/early termination visit in order to monitor the event to resolution and obtain additional protocol defined safety assessments.

As mentioned above, the patient should be referred to a MHP if he/she has a PHQ-9 score greater than 10, any suicidal behavior, or any suicidal ideation of type 4 or 5 on the C-SSRS. A referral to a MHP should also be made if in the opinion of the Investigator it is necessary for the safety of the patient. If a patient's psychiatric disorder can be adequately treated with psycho- and/or pharmacotherapy, then the patient, at the discretion of the MHP, should be continued in the trial.

If there are serious, unexpected adverse drug reactions associated with the use of the drug, the appropriate regulatory agency(ies), Ethics Committees (EC) and all participating investigators will be notified on an expedited basis. It is the responsibility of the investigator to promptly notify the Institutional Review Board (IRB)/Independent Ethics Committee (IEC) where required of the IRB/IEC of all unexpected serious adverse drug reactions involving risk to human patients. An unexpected event is one that is not reported in the IB.

For both serious and non-serious AEs, the Investigator must determine both the intensity of the event and the relationship of the event to H4H17319P2 administration. Only those injection site reactions considered clinically significant by the Investigator will be recorded as AEs.

Intensity of all AEs including clinically significant treatment-emergent laboratory abnormalities, injection site reactions and potential systemic reactions will be graded according to the CTCAE Version 4.03. The CTCAE grade refers to the severity of the AE and ranges from Grade 1 (mild AE), Grade 2 (moderate AE), Grade 3 (severe AE) and Grade 4 (life-threatening or disabling AE) to Grade 5 (death related to AE).

Adverse events not listed by the CTCAE will be graded as follows:

Mild: discomfort noticed but no disruption of normal daily activity.

Moderate: discomfort sufficient to reduce or affect daily activity.

Severe: inability to work or perform normal daily activity.

Life threatening: represents an immediate threat to life.

Relationship to H4H17319P2 administration will be determined by the investigator according to the following criteria:

None: No relationship between the event and the administration of drug. The event is related to other etiologies, such as concomitant medications or patient's clinical state.

Unlikely: The current state of knowledge indicates that a relationship to H4H17319P2 is unlikely or the temporal relationship is such that H4H17319P2 would not have had any reasonable association with the observed event.

Possible: A reaction that follows a plausible temporal sequence from administration of the H4H17319P2 and follows a known response pattern to the suspected drug. The reaction might have been produced by the patient's clinical state or other modes of therapy administered to the patient.

Probable: A reaction that follows a plausible temporal sequence from administration of the H4H17319P2 and follows a known response pattern to the drug. The reaction cannot be reasonably explained by the known characteristics of the patient's clinical state or other modes of therapy administered to the patient.

For the purpose of safety analyses, all AEs that are classified as possible or probable will be considered treatment-related events.

Administrative Requirements

Good Clinical Practice

The protocol will be conducted in accordance with the International Council on Harmonization (ICH) for Good Clinical Practice (GCP) and the appropriate regulatory requirement(s). The Investigator will be thoroughly familiar with the appropriate use of the drug as described in the protocol and IB. Essential clinical documents will be maintained to demonstrate the validity of the protocol and the integrity of the data collected. Master files should be established at the beginning of the protocol, maintained for the duration of the protocol and retained according to the appropriate regulations.

Ethical Considerations

The protocol will be conducted in accordance with ethical principles founded in the Declaration of Helsinki. The IRB/IEC will review all appropriate protocol documentation in order to safeguard the rights, safety, and well-being of the patients. The protocol will only be conducted at sites where IRB/IEC approval has been obtained. The protocol, IB, informed consent, advertisements (if applicable), written information given to the patients (including diary cards), safety updates, annual progress reports, and any revisions to these documents will be provided to the IRB/IEC by the Investigator.

H4H17319P2 will treat partial lipodystrophy (PLD) in the patient as well as ameliorate hepatosplenomegaly, high triglycerides and lack of fat at the extremities in the patient, which are associated with the PLD.

Examples 23 and 24: Effects of Agonist Anti-LEPR Antibody in Mouse Models of Congenital Leptin Deficiency and Congenital LEPR Deficiency The effects of a specific agonist anti-LEPR antibody of the invention, H4H17319P2 on blood glucose levels, body weight, food intake, and body composition (fat mass, lean mass and bone mass) were determined in murine models of congenital leptin deficiency and congenital leptin receptor deficiency due to loss of function mutation. Genetically engineered $Lepr^{hu/hu}$ $Lep^{-/-}$ mice that express a leptin receptor, which is composed of the human LEPR ectodomain sequence in place of the murine LEPR ectodomain sequence, and do not express leptin were utilized as a murine model of congenital leptin deficiency. The model of congenital LEPR deficiency is genetically engineered $Lepr^{huA409E/huA409E}$ mice that express a leptin receptor, which is composed of the human LEPR ectodomain sequence with the missense A409E mutation in place of the murine LEPR ectodomain sequence.

Example 23: Effects of H4H174319P2 in a Murine Model of Congenital Leptin Deficiency On day 0, sixteen 27 to 32 week old female $Lepr^{hu/hu}$ $Lep^{-/-}$ mice were stratified to two groups based on body weight. Each group received via subcutaneous injection a once-weekly administration of isotype control ($IgG4^P$) antibody at 10 mg/kg or H4H17319P2 at 10 mg/kg on days 0, 7, 14, 21, 28 and 35. Seven of 27 to 32 week old female $Lepr^{hu/hu}$ control mice received via subcutaneous injection a once-weekly administration of isotype control ($IgG4^P$) antibody at 10 mg/kg on days 0, 7, 14, 21, 28 and 35. On days −5 and 35, body composition was quantified by μCT. Food intake, body weight and blood glucose levels were measured for the duration of the study for each animal. FIG. 21 summarizes the blood glucose levels, body weight and cumulative food intake for each treatment group. FIG. 22 summarizes the fat mass, lean mass, and bone mass for animals in each antibody treatment group quantified by μCT 5 days prior to and 35 days following antibody treatment. All results are expressed as mean±SEM.

Figures 21A, 21B, 21C:
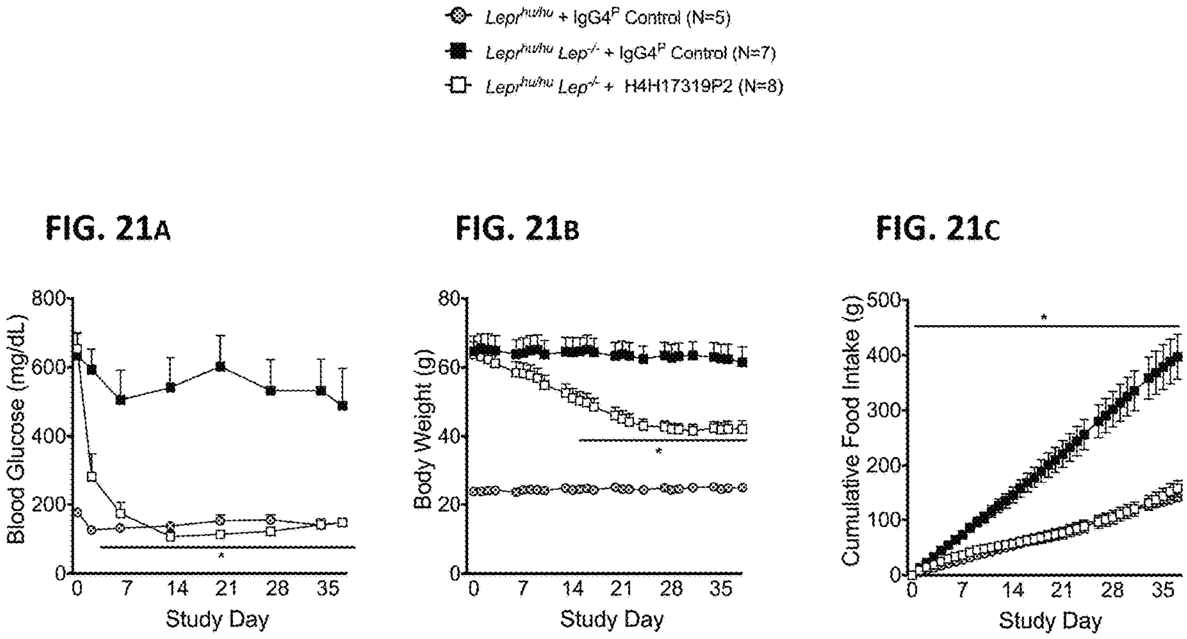
FIGS. 21A-21C demonstrate the effects of H4H17319P2 on blood glucose, body weight and food intake in a murine model of congenital leptin deficiency.
Figure 22A:
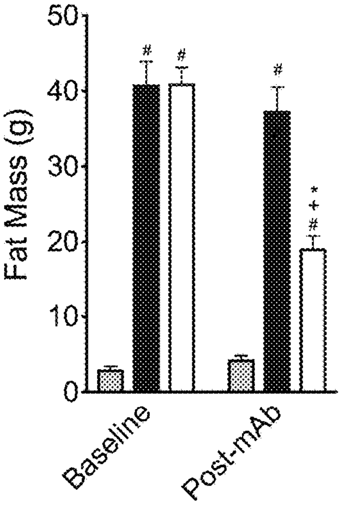
FIGS. 22A-22C demonstrate fat, bone and lean mass by uCT body composition analysis in a murine model of congenital leptin deficiency.
Figure 22B:
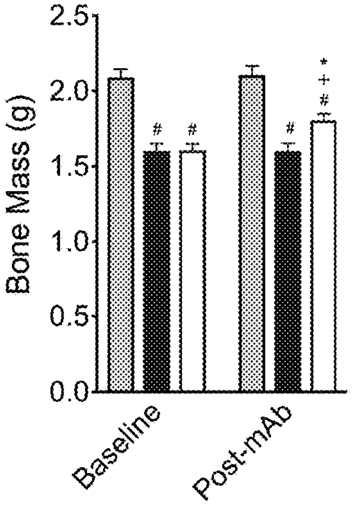
Figure 22C:
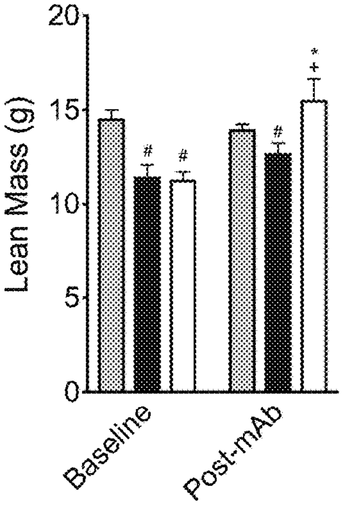

As shown in FIG. 21A, on day 0 prior to administration of antibody, leptin-deficient $Lepr^{hu/hu}$ $Lep^{-/-}$ mice were hyperglycemic when compared to control $Lepr^{hu/hu}$ mice. Leptin-deficient mice treated with H4H17319P2 at 10 mg/kg exhibited significant reductions in blood glucose levels starting 2 days after antibody treatment and at the other subsequent time points measured compared to leptin-deficient mice injected with isotype control ($IgG4^P$) antibody. Leptin-deficient mice $Lepr^{hu/hu}$ $Lep^{-/-}$ that received Isotype control ($IgG4^P$) antibody at 10 mg/kg remained hyperglycemic at all time points measured.

As shown in FIG. 21B, on day 0 prior to administration of antibody, leptin-deficient $Lepr^{hu/hu}$ $Lep^{-/-}$ mice were significantly heavier when compared to control $Lepr^{hu/hu}$ mice. Leptin-deficient mice treated with H4H17319P2 at 10 mg/kg exhibited significant reductions in body weight starting 15 days after antibody treatment and at the other subsequent time points measured compared to leptin-deficient mice injected with isotype control ($IgG4^P$) antibody. Leptin-deficient mice $Lepr^{hu/hu}$ $Lep^{-/-}$ that received isotype control ($IgG4^P$) antibody at 10 mg/kg did not show reductions in body weight from baseline at all time points measured.

As shown in FIG. 21C, leptin-deficient $Lepr^{hu/hu}$ $Lep^{-/-}$ mice exhibited a significant reduction in cumulative food intake at two days post-H4H17319P2 treatment and at the other subsequent time points measured compared to leptin deficient mice injected with isotype control ($IgG4^P$) antibody.

As shown in FIG. 22, prior to antibody administration on day −5, leptin-deficient $Lepr^{hu/hu}$ $Lep^{-/-}$ mice showed significantly increased amounts of fat mass, reduced lean mass and reduced bone mass when compared to $Lepr^{hu/hu}$ mice. On day 35, leptin-deficient $Lepr^{hu/hu}$ $Lep^{-/-}$ mice treated with H4H17319P2 at 10 mg/kg exhibited a significant reduction in fat mass, and a gain in lean and bone mass compared to leptin deficient mice injected with isotype control ($IgG4^P$) antibody.

Example 24

On day 0, twenty 24 to 28 week old male $Lepr^{huA409E/huA409E}$ mice were stratified to two groups based on body weight. Each group received via subcutaneous injection a once-weekly administration of isotype control ($IgG4^P$) antibody at 5 mg/kg or H4H17319P2 at 5 mg/kg on days 0, 7, 14, 21, 28, 35, and 42. Eight 24 to 28 week old male $Lepr^{hu/hu}$ control mice received via subcutaneous injection a once-weekly administration of isotype control ($IgG4^P$) antibody at 5 mg/kg on days 0, 7, 14, 21, 28, 35, and 42. On days −1 and 41, body composition was quantified by μCT. Food intake, body weight and blood glucose levels were measured for the duration of the study for each animal. FIG. 23 summarizes the blood glucose levels, body weight and cumulative food intake for each treatment group. FIG. 24 summarizes the fat mass, lean mass, and bone mass for animals in each antibody treatment group quantified by μCT−1 day prior to and 41 days following antibody treatment. All results are expressed as mean±SEM.

Figures 23A, 23B, 23C:
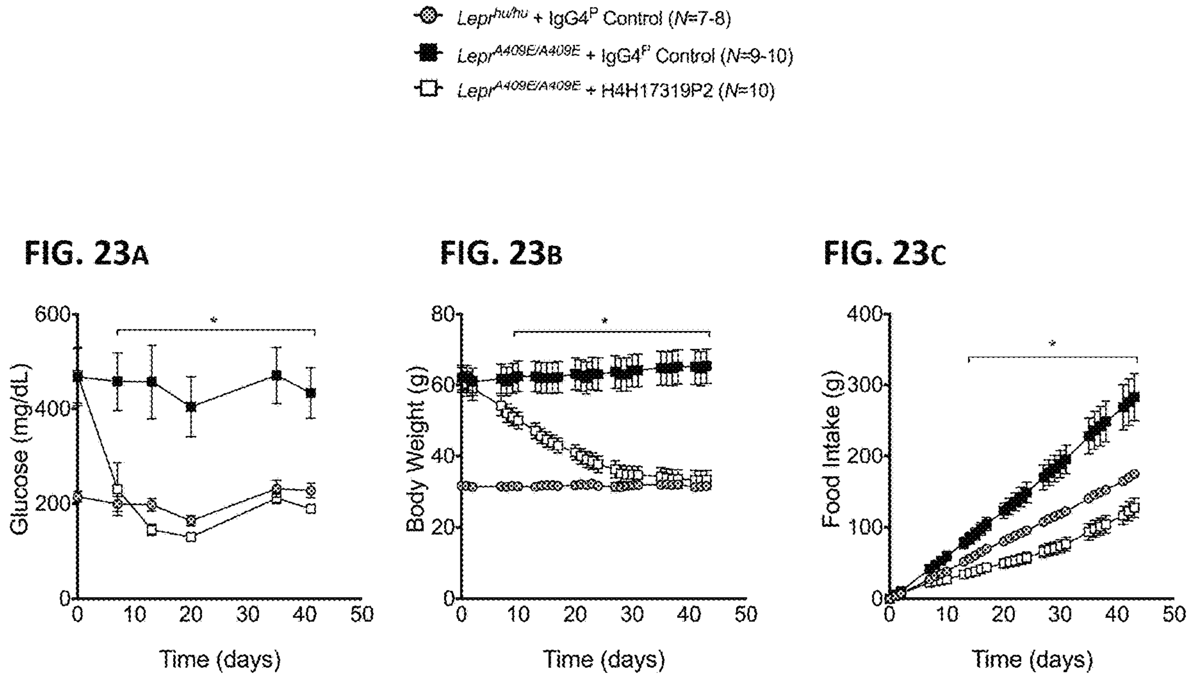
FIGS. 23A-23C demonstrate effects of H4H17319P2 on blood glucose, body weight and food intake in a murine model of congenital leptin receptor deficiency.

As shown in FIG. 23A, on day 0 prior to administration of antibody, leptin receptor deficient $Lepr^{huA409E/huA409E}$ mice were hyperglycemic when compared to control $Lepr^{hu/hu}$ mice. $Lepr^{huA409E/huA409E}$ mice treated with H4H17319P2 at 5 mg/kg exhibited significant reductions in blood glucose levels starting at 7 days after antibody treatment and at the other subsequent time points measured compared to $Lepr^{huA409E/huA409E}$ mice injected with isotype control ($IgG4^P$) antibody. Leptin-receptor deficient mice $Lepr^{huA409E/huA409E}$ that received isotype control ($IgG4^P$) antibody at 5 mg/kg, remained hyperglycemic at all time points measured.

As shown in FIG. 23B, on day 0 prior to administration of antibody, leptin receptor deficient $Lepr^{huA409E/huA409E}$ mice were significantly heavier when compared to control $Lepr^{hu/hu}$ mice. $Lepr^{huA409E/huA409E}$ mice treated with H4H17319P2 at 5 mg/kg exhibited significant reductions in body weight starting at 13 days after antibody treatment and at the other subsequent time points measured compared to leptin receptor deficient mice injected with isotype control ($IgG4^P$) antibody. $Lepr^{huA409E/huA409E}$ that received isotype control ($IgG4^P$) antibody at 5 mg/kg, did not show reductions in body weight from baseline at all time points measured.

As shown in FIG. 23C, $Lepr^{huA409E/huA409E}$ exhibited a significant reduction in cumulative food intake at 7 days post-H4H17319P2 treatment and at the other subsequent time points measured compared to leptin deficient mice injected with isotype control ($IgG4^P$) antibody.

As shown in FIG. 24, prior to antibody administration on day −1, $Lepr^{huA409E/huA409E}$ mice showed significantly increased adiposity, reduced lean mass and reduced bone mass when compared to $Lepr^{hu/hu}$ mice. On day 41, $Lepr^{huA409E/huA409E}$ mice treated with H4H17319P2 at 5 mg/kg exhibited a significant reduction in fat mass, and a gain in lean and bone mass compared to $Lepr^{huA409E/huA409E}$ mice injected with isotype control ($IgG4^P$) antibody.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for increasing bone mass in a subject in need thereof having low bone mass which is a symptom of hypoleptinemia, wherein the subject has hypoleptinemia and also has lipodystrophy, comprising administering an antibody or antigen-binding fragment thereof that binds human leptin receptor (LEPR) and activates LEPR signaling comprising:

a heavy chain variable region (HCVR) that comprises the HCDR1, HCDR2 and HCDR3 of a HCVR that comprises the amino acid sequence set forth in SEQ ID NO: 26, and a light chain variable region (LCVR) that comprises the LCDR1, LCDR2 and LCDR3 of a LCVR that comprises the amino acid sequence set forth in SEQ ID NO: 10; and a pharmaceutically acceptable carrier or diluent, to the subject.

2. The method of claim 1 wherein the lipodystrophy is selected from the group consisting of congenital lipodystrophy, generalized lipodystrophy, acquired lipodystrophy, partial lipodystrophy, congenital partial lipodystrophy, congenital generalized lipodystrophy, and acquired generalized lipodystrophy.

3. The method of claim 2 wherein the lipodystrophy is generalized lipodystrophy.

4. The method of claim 3, wherein the antibody or antigen-binding fragment thereof is a monospecific antibody that is a tetramer comprising two heavy chains that comprise heavy chain variable regions that comprise the amino acid sequence set forth in SEQ ID NO: 26, and two light chains that comprise light chain variable regions that comprise the amino acid sequence set forth in SEQ ID NO: 10, interconnected by disulfide bonds.

5. The method of claim 2 wherein the lipodystrophy is partial lipodystrophy.

6. The method of claim 5, wherein the antibody or antigen-binding fragment thereof is a monospecific antibody that is a tetramer comprising two heavy chains that comprise heavy chain variable regions that comprise the amino acid sequence set forth in SEQ ID NO: 26, and two light chains that comprise light chain variable regions that comprise the amino acid sequence set forth in SEQ ID NO: 10, interconnected by disulfide bonds.

7. The method of claim 1, wherein the antibody or antigen-binding fragment thereof comprises:

a heavy chain variable region that comprises:

an HCDR1 that comprises the amino acid sequence set forth in SEQ ID NO: 28, an HCDR2 that comprises the amino acid sequence set forth in SEQ ID NO: 30, and an HCDR3 that comprises the amino acid sequence set forth in SEQ ID NO: 32;

and a light chain variable region that comprises:

an LCDR1 that comprises the amino acid sequence set forth in SEQ ID NO: 12, an LCDR2 that comprises the amino acid sequence set forth in SEQ ID NO: 14, and an LCDR3 that comprises the amino acid sequence set forth in SEQ ID NO: 16.

8. The method of claim 1, wherein the antibody or antigen-binding fragment thereof comprises: a heavy chain variable region that comprises the amino acid sequence set forth in SEQ ID NO: 26; and a light chain variable region that comprises the amino acid sequence set forth in SEQ ID NO: 10.

9. The method of claim 1, wherein the antibody or antigen-binding fragment thereof is a monospecific antibody that is a tetramer comprising two heavy chains that comprise heavy chain variable regions that comprise the amino acid sequence set forth in SEQ ID NO: 26, and two light chains that comprise light chain variable regions that comprise the amino acid sequence set forth in SEQ ID NO: 10, interconnected by disulfide bonds.

10. The method of claim 9 wherein the heavy chain variable region is linked to a human heavy chain constant region and the light chain variable region is linked to a human kappa light chain constant region.

11. The method of claim 1, further comprising administering a second therapeutic agent to the subject.

12. The method of claim 11 wherein the second therapeutic agent is selected from the group consisting of: a recombinant human leptin, a PCSK9 inhibitor, a statin, ezetimibe, insulin, an insulin variant, an insulin secretagogue, metformin, a sulfonylurea, a sodium glucose cotransporter 2 (SGLT2) Inhibitor, a GLP-1 agonist/analogue, a glucagon (GCG) inhibitor, a glucagon receptor (GCGR) inhibitor, an angiopoietin-like protein (ANGPTL) inhibitor, phentermine, orlistat, topiramate, bupropion, topiramate/phentermine, bupropion/naltrexone, bupropion/zonisamide, pramlintide/metreleptin, lorcaserin, cetilistat, tesofensine, velneperit, an anticonvulsant, digoxin, coumadin, vitamin D, thyroxine, a thyroid supplement, a vitamin supplement, a calcium supplement, carnitine, coenzyme Q10, an anti-constipation medication, an anti-allergic medications, gabapentin, a narcotic, ketamine, lidocaine, and venlafaxine hydrochloride.

* * * * *